US010124059B2

(12) United States Patent
Lange et al.

(10) Patent No.: US 10,124,059 B2
(45) **Date of Patent: *Nov. 13, 2018**

(54) DIMERIC SCAFFOLD PEPTIDES COMPRISING HIV-1 GP120 AND GP41 EPITOPES

(71) Applicant: BIONOR IMMUNO AS, Skien (NO)

(72) Inventors: Einar Tønnes Lange, Skien (NO); Maja Sommerfelt Grønvold, Risør (NO); Birger Sørensen, Skien (NO); Karolina Lawitz, Limhamn (SE)

(73) Assignee: BIONOR IMMUNO AS, Skien (NO)

( * ) Notice: Subject to any disclaimer, the term of this patent is extended or adjusted under 35 U.S.C. 154(b) by 33 days.

This patent is subject to a terminal disclaimer.

(21) Appl. No.: 15/264,926

(22) Filed: Sep. 14, 2016

(65) Prior Publication Data

US 2016/0375129 A1 Dec. 29, 2016

Related U.S. Application Data

(62) Division of application No. 13/978,057, filed as application No. PCT/DK2012/050010 on Jan. 6, 2012, now Pat. No. 9,493,514.

(60) Provisional application No. 61/475,988, filed on Apr. 15, 2011.

(30) Foreign Application Priority Data

Jan. 6, 2011 (EP) .................................... 11150323

(51) Int. Cl.

| | |
|---|---|
| *A61K 39/21* | (2006.01) |
| *A61K 39/145* | (2006.01) |
| *C07K 14/005* | (2006.01) |
| *A61K 39/12* | (2006.01) |
| *C12N 7/00* | (2006.01) |
| *A61K 39/00* | (2006.01) |

(52) U.S. Cl.

CPC .............. *A61K 39/21* (2013.01); *A61K 39/12* (2013.01); *A61K 39/145* (2013.01); *C07K 14/005* (2013.01); *C12N 7/00* (2013.01); *A61K 2039/55505* (2013.01); *A61K 2039/55555* (2013.01); *A61K 2039/55566* (2013.01); *A61K 2039/572* (2013.01); *A61K 2039/575* (2013.01); *A61K 2039/6031* (2013.01); *A61K 2039/62* (2013.01); *C12N 2740/16122* (2013.01); *C12N 2740/16134* (2013.01); *C12N 2740/16171* (2013.01); *C12N 2760/16122* (2013.01); *C12N 2760/16134* (2013.01); *C12N 2770/24222* (2013.01); *C12N 2770/24234* (2013.01)

(58) Field of Classification Search

None

See application file for complete search history.

(56) References Cited

FOREIGN PATENT DOCUMENTS

| | | | |
|---|---|---|---|
| EP | 0 328 390 | A2 | 8/1989 |
| EP | 1 584 627 | A1 | 10/2005 |
| EP | 1 878 742 | A2 | 1/2008 |
| JP | 9-50531 | A | 5/1997 |
| JP | 2003-522961 | A | 7/2003 |
| WO | WO 95/13796 | A1 | 9/1995 |
| WO | WO 00/29008 | | 5/2000 |
| WO | WO 01/60769 | A1 | 8/2001 |
| WO | WO 2010/056796 | A1 | 5/2010 |
| WO | WO 2011/000962 | A2 | 1/2011 |
| WO | WO 2012/072088 | A1 | 6/2012 |

OTHER PUBLICATIONS

Brown, L., et al., "The conserved carboxy terminal region of HIV-1 gp120 is recognized by seronegative HIV-exposed people," *AIDS*, 1999, vol. 13, pp. 2515-2521.

Cadogan, M., et al., "HLA Homology within the C5 Domain Promotes Peptide Binding by HIV Type 1 gp120," *AIDS Res. Hum. Retroviruses*, 2008, vol. 24, No. 6, pp. 845-855.

Clerici, M., et al., "Alloactivated cytotoxic T cells recognize the carboxy-terminal domain of human immunodeficiency virus-1 gp120 envelope glycoprotein," *Eur. J. Immunol.*, 1993, vol. 23, pp. 2022-2025.

Cleveland, S.M., et al., "A region of the C-terminal tail of the gp41 envelope glycoprotein of human immunodeficiency virus type 1 contains a neutralizing epitope: evidence for its exposure on the surface of the Virion," *J. Gen. Virol.*, 2003, Vol. 84, pp. 591-602.

Cordiali, P., et al., "Convergent Evolution in the Homology Between HIV gp160 and HLA Class II Molecules," *AIDS Res. Hum. Retroviruses*, 1992, vol. 8, pp. 1561-1565.

Cruz, L., et al., "Linear Polymerization of a Synthetic Peptide of the V3 Region from HIV-1 JY1 Isolate Using Acetamidomethyl-protected Thiol Groups of Cysteine Residues," *Biotechnologia Aplicada*, 2000, vol. 17, pp. 35-38.

Cruz, L., et al., "Enhanced immunogenicity and cross-reactivity of HIV-1 V3-peptide and multiple antigen peptides conjugated to distinct carrier proteins," *International Immunopharmacology*, 2009, vol. 9(12), pp. 1452-1459.

de Santis, C., et al., "Human Antibodies to Iimmundominant C5 Region of HIV-1 gp120 Cross-React with HLA Class 1 on Activated Cells," *AIDS Res. Hum. Retroviruses*, 1994, vol. 10, No. 2, pp. 157-162.

Djordjevic, A., et al., "The Presence of Antibodies Recognizing a Peptide derived from the Second Conserved Region of HIV-1 gp120 Correlates with Non-Progressive HIV Infection," *Curr. HIV Res.*, 2007, vol. 5, pp. 443-448.

(Continued)

*Primary Examiner* — Jeffrey S Parkin

(74) *Attorney, Agent, or Firm* — Womble Bond Dickinson (US) LLP

(57) ABSTRACT

The present invention relates to novel peptides and methods for inducing an immune response in a subject against an antigen and for treatment, diagnosis and prognosis of infections or autoimmune diseases including infections with HCV, HIV, CMV and Flu. The invention further relates to methods for identifying and providing peptides useful for the treatment and diagnosis.

12 Claims, No Drawings

Specification includes a Sequence Listing.

(56) References Cited

OTHER PUBLICATIONS

Gallo, Robert C., "The end or the beginning of the drive to an HIV-preventive vaccine: a view from over 20 years," *The Lancet*, 2005, vol. 366(9500), pp. 1894-1898.

Gokulan, K., et al., "Advantage of Dimeric Peptide Antigens in Serodiagnosis of HIV-1 Infection," *Microbiol. Immunol.*, 1997, vol. 41(3), pp. 215-220.

Gokulan, K., et al., "Increase in the Immunogenicity of HIV Peptide Antigens by Chemical Linkage to Polytuftsin ($TKPR_{40}$)," *DNA And Cell Biology*, 1999, vol. 18(8), pp. 623-630.

Guilhaudis, L., et al., "Solution structure of the HIV gp120 C5 domain," *Eur. J. Biochem.*, 2002, vol. 269, pp. 4860-4867.

Habeshaw, J., et al., "Does the HIV envelope induce a chronic graft-versus-host-like disease?," *Immunology Today*, 1992, vol. 13, No. 6, pp. 207-210.

Habeshaw, J., "HLA mimicry by HIV-1 gp120 in the pathogenesis of AIDS," *Immunology Today*, 1994, vol. 15, No. 1, pp. 39-40.

Habeshaw, J., et al., "How HIV-1 lentivirus causes immune deficiency disease," *Medical Hypotheses*, 1999, vol. 52, No. 1, pp. 59-67.

Helseth, E., et al., "Human Immunodeficiency Virus Type 1 gp120 Envelope Glycoprotein Regions Important for Association with the gp41 Transmembrane Glycoprotein," *J. Virol.*, 1991, vol. 65, No. 4, pp. 2119-2123.

Hollier, M.J. and Dimmock, N.J., "The C-terminal tail of the gp41 transmembrane envelope glycoprotein of HIV-1 clades A, B, C, and D may exist in two conformations: An analysis of sequence, structure, and function," *Virology*, 2005, vol. 337, pp. 284-296.

Hoshino, M., et al., "Design and Characterization of the anion-sensitive coiled-coil peptide," *Protein Science*, 1997, vol. 6(7), pp. 1396-1404.

Hounsell, E.F., et al., "A Proposed Molecular Model for the Carboxyt Terminus of HIV-1 gp120 Showing Structural Features Consistent with the Presence of a T-cell Alloepitope," *Molecular Aspects of Medicine*, 1991, vol. 12, pp. 283-296.

Kennedy, R.C., et al., "Antiserum to a Synthetic Peptide Recognizes the HTLV-III Envelope Glycoprotein," *Science*, 1986, vol. 231, pp. 1556-1559.

Kiepiela, P., et al., "T-Cell responses to different HIV proteins have discordant associations with Viral load," *Nat. Med.*, 2007, vol. 13, No. 1, pp. 46-53.

Lifson, A.R., et al., "Long-Term Human Immunodeficiency Virus Infection in Asymptomatic Homosexual and Bisexual Men with Normal CD4+ Lymphocyte Counts: Immunologic and Virologic Characteristics," *J. Infect. Dis*, 1991, vol. 163, pp. 959-965.

Loomis-Price, L.D., et al., "Correlation between Humoral Responses to Human Immunodeficiency Virus Type 1 Envelope and Disease Progression in Early-Stage Infection," *J. Infect. Dis*, 1998, vol. 178, pp. 1306-1316.

Lopalco, L., et al., "Human immunodeficiency virus type 1 gp120 C5 region mimics the HLA class I α1 peptide-binding domain," *Eur. J. Immunology*, 1993, vol. 23, pp. 2016.2021.

"Notice of Reason for Refusal" for JP Application No. 2013-547811, dated 2015, pp. 1-4

Pancera, M., et al., "Structure of HIV-1 gp120 with gp41-interactive region reveals layerd envelope architecture and basis of conformational mobility," *PNAS*, 2010, vol. 107, No. 3, pp. 1166-1171.

Postler, T.S. and Desrosier, R.C., "The Tale of the Long Tail: the Cytoplasmic Domain of HIV-1 gp41," *J. Virol.*, 2013, vol. 87, No. 1, pp. 2-15.

Robey, F. A, et al., "A Helical Epitope in the C4 Domain of HIV Glycoprotein 120," The Journal of Biological Chemistry, 1995, vol. 270, pp. 23918-23921.

Sen, J., et al., "Role of the HIV gp120 Conserved Domain 5 in Processing and Viral Entry," *Biochemistry*, 2008 vol. 47, pp. 7788-7795

Sheikh, M.J., et al., "The gp120 envelope of HIV-1 binds peptides in a similar manner to human leukocyte antigens," *AIDS*, 1995, vol. 9, pp. 1229-1235.

Schulz, A., et al., "Preparation of Disulfide-Bonded Polypeptic Heterodimers by Titration of Thio-Activated Peptides with Thiol-Containing Peptides," *Tetrahedron*, 2000, vol. 56, pp. 3889-3891.

Steckbeck, J.D., et al., "Topology of the C-terminal Tail of HIV-1 gp41: Differential Exposure of the Kennedy Epitope on Cell and Viral Membranes," *PLoS ONE*, 2010, vol. 5, e15261.

Walker, Bruce, et al, "Toward an AIDS Vaccine," *Science*, 2008, vol. 320, pp. 760-764.

Warren, R.Q., et al., "Patterns of Antibody Reactivity to Selected Human Immunodeficiency Virus Type 1 (HIV-1) gp160 Epitopes in Infected Individuals Grouped According to CD4+ Cell Levels," *J. Clin. Immunol.*, 1991, vol. 11, No. 1, pp. 13-21.

Wilson, S.E., et al., "Type 1 Envelope Glycoprotein 120 Carboxy-Terminal Peptide-Induced Human T Cell Lines Selectively Suppress Heterogeneous Proliferative T Cell Responses to Soluble Antigens," *AIDS Res. Hum. Retroviruses*, 1997, vol. 13, No. 15, pp. 1313-1324.

Wong, M.T., et al., "Longitudinal Analysis of the Humoral Immune Response to Human Immunodeficiency Virus Type 1 (HIV-1) gp160 Epitopes in Rapidly Progressing and Nonprogressing HIV-1-Infected Subjects," *J. Infect. Dis.*, 1993, vol. 168, pp. 1523-1527.

Zhu, P., et al., "Electron tomography analysis of envelope glycoprotein trimers on HIV and simian immunodeficiency virus virions," *PNAS*, 2003, vol. 100, No. 26, pp. 15812-15817.

Sequences Uniprot, Accession C9E989, submitted Nov. 3, 2009.

DIMERIC SCAFFOLD PEPTIDES COMPRISING HIV-1 GP120 AND GP41 EPITOPES

CROSS-REFERENCE TO RELATED APPLICATIONS

This application is a divisional of U.S. application Ser. No. 13/978,057, filed Oct. 19, 2013 which is a national stage filing under 35 U.S.C. 371 of PCT/DK2012/050010, filed Jan. 6, 2012, which International Application was published by the International Bureau in English on Jul. 12, 2012, and application claims priority from U.S. Provisional Application No. 61/475,988, filed on Apr. 15, 2011, which applications are hereby incorporated in their entirety by reference in this application.

FIELD OF THE INVENTION

The present invention relates to novel peptides and methods for stimulating humoral or B-cell immunity, such as in the treatment, diagnosis and prognosis of infections with pathogens associated with infectious diseases including infections with HCV, HIV, CMV and Flu as well as antigens associated with autoimmune diseases. The invention further relates to methods for identifying and providing peptides useful in stimulating humoral or B-cell immunity, such as in the treatment and diagnosis of such diseases.

BACKGROUND OF THE INVENTION

Vaccination aims to stimulate the immune response to a specific pathogen in advance of infection. When an individual is exposed to that pathogen, a memory response is triggered which prevents the establishment of infection. Vaccines therefore stimulate the adaptive immune response which unlike innate immunity, is long lived and has memory. There are two major arms to the adaptive immune system; the humoral immunity which involves the development of antibodies that can bind virus particles and certain antibodies that can neutralize infection, and the cell mediated immunity that leads to the development of cytotoxic T-cells that kill infected cells exposing viral epitopes in the context of HLA class I, in this way eliminating infected cells.

The only disease which has been eliminated by virtue of a successful vaccination campaign is smallpox. A campaign is currently in progress to eradicate polio. Features of virus infections that can be eliminated by vaccination are that they; are caused by viruses with stable virus antigens (i.e. very low mutation frequency, few subtypes), lack a reservoir in other animal species, do not persist in the body once the infection is over, and where vaccination leads to long lasting immunity. Viruses such as polio and measles fulfill these criteria whereas viruses such as influenza virus, HCV, and HIV that vary their protein sequences do not. It is for this reason that new and alternate approaches are required to develop vaccines for these diseases.

Hepatitis C is a liver disease that results from infection with the hepatitis C virus (HCV). It can range in severity from a mild illness lasting a few weeks to a serious, lifelong illness. Hepatitis C is spread via blood; the most common form of transmission is through sharing needles or other equipment used to inject drugs. The infection can be either "acute" or "chronic". Acute HCV infection is an asymptomatic, short-term illness that occurs within the first 6 months after someone is exposed to the hepatitis C virus. For most people, acute infection leads to chronic infection, which can result in long-term complications and even death.

It is estimated that 170 million people are infected with HCV worldwide, equating to approximately 3% of the global population. There are also approximately 3-4 million people who are infected every year; with an estimated 80% of these newly infected patients progressing to chronic infection.

HCV is an enveloped positive stranded ribonucleic acid (RNA) virus with a diameter of about 50 nm, belonging to the genus Hepacivirus in the family Flaviviridae that replicate in the cytoplasm of infected cells. The only known reservoir for HCV is humans, although the virus has experimentally been transmitted to chimpanzees. The natural targets of HCV are hepatocytes and possibly B-lymphocytes. As of 2008, six different genotypes and more than 100 subtypes of the virus are known. Replication occurs through an RNA-dependent RNA polymerase that lacks a proofreading function, which results in a very high rate of mutations. Rapid mutations in a hypervariable region of the HCV genome coding for the envelope proteins enable the virus to escape immune surveillance by the host. As a consequence, most HCV-infected people proceed to chronic infection.

The 6 genotypes of HCV have different geographical spread. The disease in the early stages is generally asymptomatic; the majority of patients with chronic infection eventually progress to complications such as liver fibrosis and cirrhosis, and, in 1-5% of cases, hepatocellular carcinoma.

HCV is the major cause of non-A, non-B hepatitis worldwide. Acute infection with HCV frequently leads to chronic hepatitis and end-stage cirrhosis. It is estimated that up to 20% of HCV chronic carriers may develop cirrhosis over a time period of about 20 years and that of those with cirrhosis between 1 to 5% is at risk to develop liver carcinoma.

Influenza remains a significant cause of mortality and morbidity worldwide. The World Health Organisation (WHO) estimates that seasonal epidemics affect 3-5 million people annually and result in 250,000-500,000 mortalities. Influenza is caused by viruses in the family Orthomyxoviridae which are negative stranded RNA viruses. The influenza virus exists as three types, A, B and C of which only A is associated with pandemics. Types A viruses are found in both humans and animals, particularly birds but also other mammals such as pigs. Type A viruses are further typed into subtypes according to different kinds and combinations of virus surface proteins. Among many subtypes, influenza A (H1N1) and A (H3N2) subtypes were circulating among humans in 2009. Influenza A and B are included in the seasonal vaccine, whereas influenza C occurs only rarely, and so it is not included in the seasonal vaccine. Type B viruses are human specific and Type C viruses cause a very mild disease. The genomes of Orthomyxoviruses are segmented. Influenzaviruses Types A and B have 8 segments whereas type C has seven. Pandemics may arise as a result of re-assortment of gene segments when two different type A viruses infect the same cell. There is no immunity in the population to this novel re-assorted virus. Three pandemics occurred in the twentieth century: "Spanish influenza" in 1918, "Asian influenza" in 1957, and "Hong Kong influenza" in 1968. The 1918 pandemic killed an estimated 40-50 million people worldwide. Subsequent pandemics were much milder, with an estimated 2 million deaths in 1957 and 1 million deaths in 1968. In June 2009 the WHO declared a pandemic from influenza virus H1N1 (swine flu) which was declared over in August 2010.

Human papillomaviruses are made up of a group of DNA viruses in the family Papillomaviridae which infect the skin and mucous membranes. Two groups which are derived from more than 100 different identified subtypes are the main cause for clinical concern: those causing warts (both benign and genital warts), and a group of 12 "high risk" subtypes that can result in cervical cancer. This latter group has been attributed as a contributory factor in the development of nearly all types of cervical cancer. Worldwide, cervical cancer remains the second most common malignancy in women, and is a leading cause of cancer-related death for females in developing countries. HPV 16 and 18 have been mainly associated with cervical cancer; however, the virus is also a cause of throat cancer in both men and women. HPV is transmitted through contact and enters the skin through abrasions. An abortive infection, where only the early proteins are expressed is associated with cancer development.

OBJECT OF THE INVENTION

It is an object of embodiments of the invention to provide peptides, including multimeric, such as dimeric peptides, that may be used as immunogens to stimulate the humoral immunity in a subject.

In particular, it is an object of embodiments of the invention to provide peptides including multimeric, such as dimeric peptides comprising epitopes of an antigen that stimulates cells of the B lymphocyte lineage (B-cells) to secrete antibodies against this antigen.

The B-cell activation provided by the peptides according to the present invention may be both T cell-independent and T cell-dependent. Accordingly, the peptides according to the present invention or parts thereof may interact with B-cell receptors to activate the B-cells either through a T helper cell dependent or independent manner leading to the production of specific antibodies. Furthermore, the peptides may be taken up by antigen presenting cells (macrophages and/or dendritic cells) such that epitopes within the peptides are correctly processed and presented to T-lymphocytes, such as a helper T cell, which in turn helps to activate the B cells in order to stimulate an effective immune response. The peptides may also be taken up by activated B-cells which can also act as antigen presenting cells. Peptides interact with the B-cells through the B-cell receptor and are then internalised into the cell. The epitopes within the peptides will be processed and presented to T-lymphocytes such as helper cells.

However, in some important aspects of the present invention, the peptides according to the present invention are designed to not effectively penetrate and be taken up by antigen presenting cells. Accordingly, in these aspects of the invention, the peptides according to the present invention may provide B-cell activation through interaction at the cell surface via the B-cell receptor. It is to be understood that in order to provide sustained B-cell stimulation, it is preferred that the peptides according to the present invention are designed to comprise a helper epitope that may be taken up by antigen presenting cells in order to stimulate CD4+T-helper cells that can sustain effective humoral immunity in a subject.

Further, it is an object of embodiments of the invention to provide peptides that may be used as antigens, to provide immunogenic compositions and methods for inducing an immune response in a subject against an antigen.

Further, it is an object of embodiments of the invention to provide peptides that may be used as antigens that can serve as targets in diagnostic assays.

SUMMARY OF THE INVENTION

The present invention pertains to a peptide design promoting efficient activation of a humoral immune response against antigens contained within this peptide design.

It has been found by the present inventor(s) that peptide constructs—amino acid sequences with a particular pattern or scaffold design, and in particular multimeric, such as dimeric peptides of this design—have the ability to effectively elicit a humoral immune response in a subject in response to the administration of these peptides.

The peptide constructs according to the present invention have been designed to be able to attach or bind to the cell surface. The peptide constructs or parts thereof may then be taken up by the antigen presenting cells (such as macrophages and dendritic cells) and stimulate helper T-cells in order to elicit efficient and long lasting T-cell dependent B-cell activation. Alternatively the B-cells themselves may provide for the induction of help to activate the B-cells.

Accordingly the peptides according to the present invention may penetrate the cells and may be used to load cells with an immunogenically effective amount of a peptide or fragments of this peptide that can be presented by macrophages and dendritic cells. Accordingly these peptide constructs may elicit both a Cytotoxic T-lymphocyte immune (CTL) response and/or a humoral immune response.

So, in a first aspect the present invention relates to isolated monomeric peptides consisting of not more than 60 amino acids with the following structure $$X^1\text{-}X^2\text{-}X^3\text{-}X^4\text{-}X^5\text{-}X^6 \qquad \text{(formula I)},$$

wherein $X^1$, $X^3$ and optional moiety $X^5$ each independently defines a linear sequence of any 1, 2, 3, 4, or 5 amino acid independently selected from glycine, arginine, norleucine, glutamine, serine, lysine, tryptophan, cysteine, or a derivative thereof; $X^2$, $X^4$, and optional moiety $X^6$ each independently defines a linear sequence of 5-17 amino acids, each having more than 50% sequence identity to a specific natural antigen.

In a second aspect the present invention relates to an isolated multimeric peptide comprising two or more monomeric peptides, each monomeric peptide independently consisting of not more than 60 amino acids with the following structure $$X^1\text{-}X^2\text{-}X^3\text{-}X^4\text{-}X^5\text{-}X^6 \qquad \text{(formula I)},$$

wherein $X^1$, $X^3$ and optional moiety $X^5$ independently defines a linear sequence of any 1, 2, 3, 4, or 5 amino acid independently selected from glycine, arginine, norleucine, glutamine, serine, lysine, tryptophan, cysteine, or a derivative thereof; $X^2$, $X^4$, and optional moiety $X^6$ each independently defines a linear sequence of 5-17 amino acids, each having more than 50% sequence identity to a specific natural antigen, said monomeric peptides being covalently joined by one or more intermolecular bond.

In a third aspect the present invention relates to isolated monomeric peptides consisting of not more than 60 amino acids with the following structure $$X^1\text{-}X^2\text{-}X^3\text{-}X^4\text{-}X^5\text{-}X^6 \qquad \text{(formula I)},$$

wherein $X^1$, $X^3$ and optional moiety $X^5$ each independently defines a linear sequence of any 1, 2, 3, 4, or 5 amino acid independently selected from glycine, arginine, norleucine, aspartic acid, glutamic acid, glutamine, serine, lysine, tryptophan, cysteine, ornithine, diaminopropionic acid or a derivative thereof; $X^2$, $X^4$, and optional moiety $X^6$ each independently defines a linear sequence of 5-17 amino acids, each having 50% or more sequence identity to a specific natural antigen.

In a further aspect the present invention relates to an isolated multimeric peptide comprising two or more monomeric peptides, each monomeric peptide independently consisting of not more than 60 amino acids with the following structure

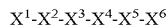 (formula I), wherein $X^1$, $X^3$ and optional moiety $X^5$ independently defines a linear sequence of any 1, 2, 3, 4, or 5 amino acid independently selected from glycine, arginine, norleucine, aspartic acid, glutamic acid, glutamine, serine, lysine, tryptophan, cysteine, ornithine, diaminopropionic acid or a derivative thereof; $X^2$, $X^4$, and optional moiety $X^6$ each independently defines a linear sequence of 5-17 amino acids, each having 50% or more sequence identity to a specific natural antigen, said monomeric peptides being covalently joined by one or more intermolecular bond.

In a further aspect the present invention relates to a composition comprising two or more compounds selected from a monomeric peptide according to the present invention, and an isolated multimeric peptide according to the present invention.

In a further aspect the present invention relates to the use of a peptide selected from a monomeric peptide according to the present invention, and an isolated multimeric peptide according to the present invention for inducing a humoral immune response in a subject.

In a further aspect the present invention relates to an isolated nucleic acid or polynucleotide encoding a peptide according to the invention.

In a further aspect the present invention relates to a vector comprising the nucleic acid or polynucleotide encoding a peptide according to the invention.

In a further aspect the present invention relates to a host cell comprising the vector comprising the nucleic acid or polynucleotide encoding a peptide according to the invention.

In a further aspect the present invention relates to an immunogenic composition comprising at least one monomeric peptide, an isolated multimeric peptide according to the invention, a peptide composition, the nucleic acid or polynucleotide, or the vector according the invention; in combination with a pharmaceutically acceptable diluent or vehicle and optionally an immunological adjuvant. In some embodiments this immunogenic composition is in the form of a vaccine composition.

In a further aspect the present invention relates to a method for inducing an immune response in a subject against an antigen which comprises administration of at least one monomeric peptide, an isolated multimeric peptide, a peptide composition, the nucleic acid or polynucleotide, or the vector, or the composition of the invention.

In a further aspect the present invention relates to a method for reducing and/or delaying the pathological effects of a disease antigen, such as an infectious agent in a subject infected with said agent or having said disease caused by said antigen, the method comprising administering an effective amount of at least one monomeric peptide, an isolated multimeric peptide, a peptide composition, the nucleic acid or polynucleotide, or the vector, or the composition according to the invention.

In a further aspect the present invention relates to a peptide according to the invention for use as a medicament, or for treating the pathological effects of a disease antigen, such as an infectious agent in a subject infected with said agent or having said disease caused by said antigen.

In a further aspect the present invention relates to a peptide according to the invention for use in a diagnostic assay. In a further aspect the present invention relates to a peptide according to the invention for use in an in vitro assay.

DETAILED DISCLOSURE OF THE INVENTION

Definitions

When terms such as "one", "a" or "an" are used in this disclosure they mean "at least one", or "one or more" unless otherwise indicated. Further, the term "comprising" is intended to mean "including" and thus allows for the presence of other constituents, features, conditions, or steps than those explicitly recited.

As used herein a "multimeric peptide" or "oligomeric peptide" refers to an assembly of two or more different or identical linear peptide sequences or subunits, preferably interconnected or assembled by one or more chemical bond of a linker. Preferably the peptide sequences are interconnected by one or more, such as one covalent bond, such as an intermolecular disulfide (S—S) bond between two Cys residues, a methylated peptide bond between a N-ε-methylated Lys side-chain and the side-chain of an Asp or Glu residue, an oxime bond, or a thioether bond. The term includes a dimeric (or dimer) peptide suitably formed by a chemical linking of two linear peptide sequences. The term "multimeric peptide" further includes an assembly of 2, 3, 4, 5, 6, 7, 8, 9 or 10 different or identical peptide sequences. In some embodiments, the multimeric peptide is a dimeric peptide.

As used herein a "linker" refers to any compound suitable for assembly of the two or more different or identical linear peptide sequences or subunits into a multimeric peptide. The term includes any linker found useful in peptide chemistry. Since the multimeric peptide may be assembled or connected by standard peptide bonds in a linear way, the term linker also includes a "peptide spacer", also referred to as a "spacer".

In some embodiments, the linker is not a peptide sequence. In some embodiments, the linker is not a branched peptide sequence.

In some embodiments, the linker does not itself contain a peptide sequence derived from or identical to a natural antigen.

In some embodiments, the linker has a molecular weight of less than 10 kDa, such as less than 9 kDa, such as less than 8 kDa, such as less than 7 kDa, such as less than 6 kDa, such as less than 5 kDa, such as less than 4 kDa, such as less than 3 kDa, such as less than 2 kDa, such as less than 1.5 kDa, such as less than 1 kDa, such as less than 0.5 kDa, such as less than 0.2 kDa. In some embodiments, wherein the multimeric peptide is a dimeric peptide, the linker is not linking the two peptide sequences from one terminal cysteine in the first peptide to a second terminal cysteine in the second peptide.

In some embodiments, the linker is not linking the two or more peptide sequences through a terminal cysteine in any one of the peptides.

In some embodiments, the linker is not linking from a cysteine residue.

In some embodiments, in the peptide according to the present invention, $X^1$, $X^3$ and optional moiety $X^5$ in the same peptide is not identical in sequence.

In some embodiments, in the peptide according to the present invention, $X^2$, $X^4$ and optional moiety $X^6$ in the same peptide is not identical in sequence.

In some embodiments, in the multimeric peptide according to the present invention, $X^1$, $X^3$ and optional moiety $X^5$ in one peptide is not identical in sequence with $X^1$, $X^3$ and optional moiety $X^5$ in any other peptide.

In some embodiments, in the multimeric peptide according to the present invention, $X^2$, $X^4$ and optional moiety $X^6$ in one peptide is not identical in sequence with $X^2$, $X^4$ and optional moiety $X^6$ in any other peptide.

"HIV" generally denotes human immunodeficiency virus I.

"HIV disease" is composed of several stages including the acute HIV infection which often manifests itself as a flu-like infection and the early and medium stage symptomatic disease, which has several non-characteristic symptoms such as skin rashes, fatigue, night sweats, slight weight loss, mouth ulcers, and fungal skin and nail infections. Most HIV infected will experience mild symptoms such as these before developing more serious illnesses. It is generally believed that it takes five to seven years for the first mild symptoms to appear. As HIV disease progresses, some individuals may become quite ill even if they have not yet been diagnosed with AIDS (see below), the late stage of HIV disease. Typical problems include chronic oral or vaginal thrush (a fungal rash or spots), recurrent herpes blisters on the mouth (cold sores) or genitals, ongoing fevers, persistent diarrhea, and significant weight loss. "AIDS" is the late stage HIV disease and is a condition which progressively reduces the effectiveness of the immune system and leaves individuals susceptible to opportunistic infections and tumors.

The term "cell-penetrating peptide" as used herein refers to a peptide with the capability to translocate across the plasma membrane into either cytoplasmic and/or nuclear compartments of eukaryotic and/or prokaryotic cells, such as into cytoplasm, nucleus, lysosome, endoplasmatic reticulum, golgi apparatus, mitocondria and/or chloroplast, seemingly energy-independently. This capability to translocate across the plasma membrane of a "cell-penetrating peptide" may be non-invasive, energy-independent, non-saturable, and/or receptor independent. In one embodiment the term "cell-penetrating peptide" refers to a peptide, which is demonstrated to translocate across a plasma membrane as determined by the assay provided in the examples. The term "non-cell-penetrating peptide" as used herein refers to a peptide, which is not a cell-penetrating peptide.

The term "derived from an antigen" when in reference to a peptide derived from a source (such as a virus etc.) as used herein is intended to refer to a peptide which has been obtained (e.g., isolated, purified, etc.) from the source. Usually the peptide has been adapted or modified from the original source. Preferably, the peptide may be genetically engineered and/or chemically synthesized to be essentially identical to the native peptide of the source. The term includes the use of variants of known native peptide sequences, such as peptide sequences, where 1, 2, 3, 4, 5, 6, or 7 amino acids of the native peptide sequence have been substituted with any other amino acid, such as conservative substitutions. Alternatively, 1, 2, 3, 4, 5, 6, or 7 amino acids have been removed or added to the native peptide sequence. Accordingly, in some embodiments, the peptides according to the present invention comprises the sequences $X^2$ and/or $X^4$, and/or $X^6$, that is defined as a sequence of 5-17 amino acids derived from an antigen, wherein the peptide sequence of the antigen comprises 1, 2, 3, 4, 5, 6, or 7 substitutions, additions or deletions relative to the antigen, such as the addition of an arginine in the N- or C-terminal of the amino acid sequence of $X^2$ and/or $X^4$ and/or $X^6$. The amino acids used in the amino acid sequences according to the invention may be in both L- and/or D-form. It is to be understood that both L- and D-forms may be used for different amino acids within the same peptide sequence. In some embodiments the amino acids within the peptide sequence are in L-form, such as natural amino acids. It is to be understood that any known antigen may be used in the constructs according to the present invention.

In some specific embodiments, the first 1, 2, or 3 amino acids in the N-terminal of the amino acid sequences according to the invention are in the D-form. It is assumed that the N-terminal trimming and thereby degradation of the peptides are somewhat delayed by having amino acids of the D-form in the N-terminal of these cell-penetrating peptides. Alternatively and in some embodiments, the first 1, 2, or 3 amino acids in the N-terminal of the amino acid sequences according to the invention are amino acids in beta or gamma forms. Beta amino acids have their amino group bonded to the beta carbon rather than the alpha carbon as in the 20 standard natural amino acids. A capital D-letter subscript after the letter representing the amino acid residue designate herein amino acids specified to be in D-form, such as $W_D$ referring to a tryptophan in D-form. A capital L-letter subscript after the letter representing the amino acid residue designate herein amino acids specified to be in L-form, such as $W_L$ referring to a tryptophan in L-form.

Alternatively, the first 1, 2, or 3 amino acids in the N-terminal of the amino acid sequences according to the invention may be modified by incorporation of fluorine, or alternatively cyclic amino acids or other suitable non-natural amino acids are used.

It is to be understood that for a multimeric peptide one or more, such as all peptide strands may have modified amino acids in the N-terminal of the amino acid sequences. The linker linking two or more peptide strands may be placed anywhere within the peptide strand, in particular if one or more of the peptide strands have modified amino acids in the N-terminal of the amino acid sequences. The linker may also serve to protect the peptide from degradation, which often is degradation from the N-terminal. Accordingly, the linker may be more freely placed if one or both peptide strands are protected from degradation.

A "variant" or "analogue" of a peptide refers to a peptide having an amino acid sequence that is substantially identical to a reference peptide, typically a native or "parent" polypeptide. The peptide variant may possess one or more amino acid substitutions, deletions, and/or insertions at certain positions within the native amino acid sequence.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). A particular form of conservative amino acid substitutions include those with amino acids, which are not among the normal 20 amino acids encoded by the genetic code. Since preferred embodiments of the present invention entail use of synthetic peptides, it is unproblematic to provide such "non-naturally occurring" amino acid residues in the peptides disclosed herein, and thereby it is possible to exchange the natural saturated carbon chains in the side chains of amino acid residues with shorter or longer saturated carbon chains—for instance, lysine may be substituted with an amino acid having a side chain —$(CH_2)_n NH_3$, where n is different from 4, and arginine may be substituted with an amino acid having the side chain —$(CH_2)_n NHC(=NH_2)NH_2$, where n is different from 3, etc. Similarly, the acidic amino acids aspartic acid and glutamic acid may be substituted with amino acid residues having the side chains —$(CH_2)_n COOH$, where n>2.

The term "substantially identical" in the context of two amino acid sequences means that the sequences, when optimally aligned, such as by the programs GAP or BEST-FIT using default gap weights, share at least about 50, at least about 60, at least about 70, at least about 80, at least about 90, at least about 95, at least about 98, or at least about 99 percent sequence identity. In some embodiments, when measuring the sequence identity between two different peptide sequences, a gap of one or two amino acids is allowed when the two peptide sequences are aligned without having any influence on the value of sequence identity. In some embodiments, a residue position that is not identical differ by only a conservative amino acid substitution. Sequence identity is typically measured using sequence analysis software. Protein analysis software matches similar sequences using measures of similarity assigned to various substitutions, deletions and other modifications, including conservative amino acid substitutions. For instance, the publicly available GCG software contains programs such as "Gap" and "BestFit" which can be used with default parameters to determine sequence homology or sequence identity between closely related polypeptides, such as homologous polypeptides from different species of organisms or between a wild-type protein and a mutein thereof. See, e.g., GCG Version 6.1. Polypeptide sequences can also be compared using FASTA or ClustalW, applying default or recommended parameters. A program in GCG Version 6.1., FASTA (e.g., FASTA2 and FASTA3) provides alignments and percent sequence identity of the regions of the best overlap between the query and search sequences (Pearson, Methods Enzymol. 1990; 183:63-98; Pearson, Methods Mol. Biol. 2000; 132:185-219). Another preferred algorithm when comparing a sequence to a database containing a large number of sequences from various organisms is the computer program BLAST, especially blastp, using default parameters. See, e.g., Altschul et al., J. Mol. Biol. 1990; 215:403-410; Altschul et al., Nucleic Acids Res. 1997; 25:3389-402 (1997); each herein incorporated by reference. "Corresponding" amino acid positions in two substantially identical amino acid sequences are those aligned by any of the protein analysis software mentioned herein, typically using default parameters.

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of a specific peptide sequence will exhibit 98%-99% homogeneity for peptides in the context of all present peptide species in the composition or at least with respect to substantially active peptide species in the context of proposed use.

The term "linear sequence" as used herein refers to the specific sequence of amino acids connected by standard peptide bonds in standard N- to C-terminal direction. The peptide may contain only peptide bonds. In some embodiments however, a second part of a peptide sequence may be bound to and continue from the side chain of a terminal amino acid in a first part of an amino acid sequence. Also the term does not exclude that an amino acid within a sequence, such as within $X^1$, $X^2$, $X^3$, $X^4$, and/or $X^5$, may be connected, such as through the side chains, with another amino acid at a distant location within the peptide sequence, such as a distant location within $X^1$, $X^2$, $X^3$, $X^4$, and/or $X^5$.

In the context of the present invention, "treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas "treatment" of a patient in whom symptoms or clinically relevant manifestations of a disease or disorder have been identified generally does not constitute preventive or prophylactic therapy.

The term "antigen" denotes a substance of matter which is recognized by the immune system's specifically recognizing components (antibodies, T-cells).

The term "immunogen" is in the present context intended to denote a substance of matter, which is capable of inducing an adaptive immune response in an individual, where said adaptive immune response targets the immunogen. In relation to the present invention, an immunogen will induce a humoral and/or cell-mediated immune response. In other words, an immunogen is an antigen, which is capable of inducing immunity.

The terms "epitope", "antigenic determinant" and "antigenic site" are used interchangeably herein and denotes the region in an antigen or immunogen which is recognized by antibodies (in the case of antibody binding epitopes, also known as "B-cell epitopes") or by T-cell receptors when the epitope is complexed to an MHC molecule (in the case of T-cell receptor binding epitopes, i.e. "T-cell epitopes").

"B cell antigen" means any antigen that naturally is or could be engineered to be recognized by a B cell, and that triggers an immune response in a B cell (e.g., an antigen that is specifically recognized by a B cell receptor on a B cell).

The term "immunogenically effective amount" has its usual meaning in the art, i.e. an amount of an immunogen, which is capable of inducing an immune response, which significantly engages pathogenic agents, which share immunological features with the immunogen.

The term "vaccine" is used for a composition comprising an immunogen and which is capable of inducing an immune response which is either capable of reducing the risk of developing a pathological condition or capable of inducing a therapeutically effective immune response which may aid in the cure of (or at least alleviate the symptoms of) a pathological condition.

The term "pharmaceutically acceptable" has its usual meaning in the art, i.e. it is used for a substance that can be accepted as part of a medicament for human use when treating the disease in question and thus the term effectively excludes the use of highly toxic substances that would worsen rather than improve the treated subject's condition.

A "T helper lymphocyte epitope" (a $T_H$ epitope), "T helper epitope" or "helper epitope" is peptide, which binds an MHC Class II molecule and can be presented on the surface of an antigen presenting cell (APC) bound to the MHC Class II molecule. An "immunological carrier" is generally a substance of matter which includes one or many $T_H$ epitopes, and which increase the immune response against an antigen to which it is coupled by ensuring that T-helper lymphocytes are activated and proliferate. Examples of known immunological carriers are the tetanus and diphtheria toxoids and keyhole limpet hemocyanin (KLH).

In the scaffold design according to the present invention, $X^2$, $X^4$, and $X^6$ defines a sequence of 5-17 amino acids derived from the antigen. This sequence of amino acids derived from an antigen may herein be referred to as an epitope.

The peptides according to the present invention may be a helper T lymphocyte (HTL) inducing peptide comprising HTL epitopes. A "HTL inducing peptide" is a HLA Class II binding peptide that is capable of inducing a HTL response. Also the peptides according to the present invention may in other embodiments be CTL inducing peptides comprising CTL epitopes in addition to or as an alternative to being a HTL inducing peptide. A "CTL inducing peptide" is a HLA Class I binding peptide that is capable of inducing a CTL response.

In other alternative embodiments, tryptophan or tryptophan derivatives are used in the sequence defined by $X^1$, $X^3$, or $X^5$. Any suitable tryptophan derivatives may be used. As used herein "tryptophan derivatives" means an unnatural modified tryptophan amino acid residue including those disclosed in U.S. Pat. No. 7,232,803, such as tri tert.-butyltryptophan, di-tert-butyl tryptophan, 7-benzyloxytryptophan, homotryptophan, 5'-aminoethyltryptophan (available as side chain Boc and N-alpha FMOC derivative from RSP Amino Acids Analogues Inc, Boston, Mass., USA), N-Acetylhomotryptophan (Toronto Research), 7-Benzyloxytryptophan (Toronto Research), Homotryptophan (Toronto Research), and tryptophan residues which have been substituted at the 1-, 2-, 5- and/or 7-position of the indole ring, positions 1- or 2- being preferred e.g. 5' hydroxy tryptophan.

The term "amino acid derivative", sometimes used in the context of a "derivative thereof" referring to a specific amino acid, means an amino acid compound, wherein one or more chemical groups has been modified, added or removed as compared to the amino acid to which the amino acid compound is a derivative of, while still having an amine group and a carboxylic acid group, as well as a side chain of an amino acid and still being able to form peptide bonds. In some embodiments an amino acid derivative is a standard amino acid that has only been modified in the side chain of the amino acid. In some embodiments an amino acid derivative is a non-natural amino acid such as Dpr. In some embodiments an amino acid is a modified moiety which is incorporated into the chemically synthesized peptide or polypeptide and that comprises an activatable group that is linkable, after activation, to another peptide, such as Dpr (Ser), Lys(Ser), or Ornithine(Ser).

The term "antibody response" refers to the production of antibodies (e.g., IgM, IgA, IgG) which bind to an antigen of interest, this response is measured for instance by assaying sera by antigen ELISA.

The term "adjuvant" as used herein refers to any compound which, when delivered together or simultaneously with an antigen, non-specifically enhances the immune response to that antigen. Exemplary adjuvants include but are not limited to oil in water and water in oil adjuvants, aluminum-based adjuvants (e.g., AlOH, AlPO4, etc), and Montanide ISA 720.

The terms "patient" and "subject" refer to any human or animal that may be treated using the methods of the present invention.

As used herein, the term "immune response" refers to the reactivity of an organism's immune system in response to an antigen. In vertebrates, this may involve antibody production, induction of cell-mediated immunity, and/or complement activation (e.g., phenomena associated with the vertebrate immune system's prevention and resolution of infection by microorganisms). In preferred embodiments, the term immune response encompasses but is not limited to one or more of a "lymphocyte proliferative response," a "cytokine response," and an "antibody response."

The term "net charge" as used herein with reference to a peptide sequence refers to the total electric charge of the peptide sequence represented by the sum of charges of each individual amino acid in the peptide sequence, wherein each basic amino acid are given a charge of +1, each acidic amino acid a charge of −1, and each neutral amino acid a charge of 0. Accordingly, the net charge will depend on the number and identities of charged amino acids.

The term "basic amino acid" as used herein refers to any amino acid including both natural and non-natural amino acids that has an isoelectric point above 6.3 (such as above 7.4) as measured according to Kice & Marvell "Modern Principles of organic Chemsitry" (Macmillan, 1974) or Matthews and van Holde "Biochemistry" Cummings Publishing Company, 1996.

Included within this definition are Arginine, Lysine, Homoarginine (Har), and Histidine as well as derivatives thereof. Suitable non-naturally basic amino acids are e.g. as described in U.S. Pat. No. 6,858,396. Suitable positively charged amino acids includes un-natural alpha amino acids available from Bachem AG and includes alpha-amino-glycine, alpha,gamma-diaminobutyric acid, ornithine, alpha, beta-diaminoproprionic acid, alpha-difluoromethyl-ornithine, 4-amino-piperidine-4carboxylic acid, 2,6-diamino-4-hexynoic acid, beta-(1-piperazinyl)-alanine, 4,5-dehydro-lysine, delta-hydroxy-lysine, omega-hydroxy-norarginine, homoarginine, omega-amino-arginine, omega-methyl-arginine, alpha-methyl-histidine, 2,5-diiodo-histidine, 1-methyl-histidine, 3-methyl-histidine, beta-(2-pyridyl)-alanine, beta-(3-pyridyl)-alanine, beta-(2-quinolyl)-alanine, 3-amino-tyrosine, 4-amino-phenylalanine, and spinacine.

The term "neutral amino acid" as used herein refers to an amino acid that has an isoelectric point between 4.8 and 6.3 as measured according to Kice & Marvell "Modern Principles of organic Chemistry" (Macmillan, 1974). The term "acidic amino acid" as used herein refers to an amino acid that has an isoelectric point below 4.8 as measured according to Kice & Marvell "Modern Principles of organic Chemsitry" (Macmillan, 1974).

Antigens

The specific natural antigen used in the peptide constructs according to the present invention may be a protein or peptide sequence derived from any B cell antigen, such as from any disease antigen, such as an infectious agent. Suitable antigens to be used according to the present invention include antigens derived from a bacteria, a *mycobacterium*, a virus, a parasite such as protozoa, a fungus, a cancer antigen, such as an oncogene, a prion, an atopic disease antigen, an addictive or abused substance or a toxin or an antigen of an autoimmune disease, such as rheumatoid arthritis, insulin dependent diabetes, multiple sclerosis and the like.

As used herein a "disease antigen" refers to any antigen confirmed or suspected to be involved in a specific disease.

In some embodiments, the antigen is an abused or addictive substance or a portion thereof, including, but are not limited to, nicotine, a narcotic, a cough suppressant, a tranquilizer, and a sedative. In some embodiments, the antigen is a toxin, such as a toxin from a chemical weapon or natural sources, or a pollutant.

Examples of bacteria for which antigens may be provided include, but are not limited to, *M. tuberculosis, Mycobacterium, mycoplasma, neisseria* and *legionella*. Examples of parasites include, but are not limited to, *rickettsia* and *chlamydia*.

Examples of an infectious disease antigen is TbH9 (also known as Mtb 39A), a tuberculosis antigen. Other tuberculosis antigens include, but are not limited to DPV (also known as Mtb8.4), 381, Mtb41, Mtb40, Mtb32A, M\/9.9A, Mtb9.8, Mtb16, Mtb72f, Mtb59f, Mtb88f, Mtb71f, Mtb46f and Mtb31f ("f" indicates that it is a fusion or two or more proteins).

Examples of cancer antigens may be a tumor associated antigen such as HER2, HER3 or HER4 receptor or one or more tumor-associated antigens or cell-surface receptors disclosed in US Publication No. 20080171040 or US Publication No. 20080305044 and are incorporated in their entirety by reference.

Other suitable cancer antigens that may be used by the present invention include CD proteins such as CD2, CD3, CD4, CD5, CD6, CD8, CD11, CD14, CD18, CD19, CD20, CD21, CD22, CD25, CD26, CD27, CD28, CD30, CD33, CD36, CD37, CD38, CD40, CD44, CD52, CD55, CD56, CD70, CD79, CD80, CD81, CD103, CD105, CD134, CD137, CD138, and CD152; members of the ErbB receptor family such as the EGF receptor, HER2, HER3 or HER4 receptor; cell adhesion molecules such as LFA-I, Mac1, pi 50.95, VLA-4, ICAM-I, VCAM, EpCAM, alpha4/beta7 integrin, and alpha v/beta3 integrin including either alpha or beta subunits thereof (e.g. anti-CD11a, anti-CD18 or anti-CD11b antibodies); growth factors such as VEGF; tissue factor (TF); TGF-β; alpha interferon (alpha-IFN); an interleukin, such as IL-8; IgE; blood group antigens Apo2, death receptor; flk2/flt3 receptor; obesity (OB) receptor; mpl receptor; CTLA-4; protein C etc. In some embodiment the antigen is selected from IGF-IR, CanAg, EphA2, MUC1, MUC16, VEGF, TF, CD19, CD20, CD22, CD27, CD33, CD37, CD38, CD40, CD44, CD56, CD138, CA6, Her2/neu, EpCAM, CRIPTO (a protein produced at elevated levels in a majority of human breast cancer cells), darpins, alpha$_v$/beta$_3$ integrin, alpha$_v$/beta$_5$ integrin, alpha γ/beta integrin, TGF-β, CD11a, CD18, Apo2 and C242. In some embodiment the antigen is selected from a CD proteins such as CD3, CD4, CD8, CD19, CD20, CD27, CD34, CD37, CD38, CD46, CD56, CD70 and CD138; members of the ErbB receptor family such as the EGF receptor, HER2, HER3 or HER4 receptor; cell adhesion molecules such as LFA-I, Mac1, pI50.95, VLA-4, ICAM-I, VCAM, EpCAM, alpha4/beta7 integrin, and alpha v/beta3 integrin including either alpha or beta subunits thereof (e.g. anti-CD11a, anti-CD18 or anti-CD11b antibodies); growth factors such as VEGF; tissue factor (TF); TGF-β; alpha interferon (alpha-IFN); an interleukin, such as IL-8; IgE; blood group antigens Apo2, death receptor; flk2/flt3 receptor; obesity (OB) receptor; mpl receptor; CTLA-4; protein C, etc. The most preferred targets herein are IGF-IR, CanAg, EGF-R, EGF-RvIII, EphA2, MUC1, MUC16, VEGF, TF, CD19, CD20, CD22, CD27, CD33, CD37, CD38, CD40, CD44, CD56, CD70, CD138, CA6, Her2/neu, CRIPTO (a protein produced at elevated levels in a majority of human breast cancer cells), alpha$_v$/beta$_3$ integrin, alpha$_v$/beta$_5$ integrin, TGF-β, CD11a, CD18, Apo2, EpCAM and C242. In some embodiment the antigen is selected from a cellular oncogene, such as ras or myc.

Examples of viral antigens for use with the present invention include, but are not limited to, e.g., HIV, HCV, CMV, HPV, Flu, adenoviruses, retroviruses, picornaviruses, etc. Non-limiting example of retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NSI, NSI, NS1-NS2A, 80% E, and other Japanese encephalitis viral antigen components; rabies viral antigens such as rabies glycoprotein, rabies nucleoprotein and other rabies viral antigen components. See Fundamental Virology, Second Edition, eds. Fields, B. N. and Knipe, D. M. (Raven Press, New York, 1991) for additional examples of viral antigens.

The epitopes to be incorporated into the scaffold design according to the present invention may be derived from viruses in virus families such as adenoviridae, retroviridae, picornaviridae, herpesviridae, rotaviruses (reoviridae), hantaviruses (Bunyaviridae), coronaviridiae, togaviridae, flaviviridae, rhabdoviridae, paramyxoviridae, orthomyxoviridae, bunyaviridae, arenaviridae, reoviridae, papilomaviridae, parvoviridae, poxviridae, hepadnaviridae, or spongiform virus. In certain specific, non-limiting examples, the viral antigen are peptides obtained from at least one of HIV, CMV, hepatitis A, B, and C, influenza, measles, polio, smallpox, rubella; respiratory syncytial, herpes simplex, varicella zoster, Epstein-Barr, Japanese encephalitis, rabies, flu, and/or cold viruses.

HCV:

Peptides according to the present invention may comprise a known antigen. For antigens derived from HCV these antigens may be derived from the Core, E1, E2, P7, NS2, NS3, NS4 (NS4A and NS4B) and NS5 (NS5A and NS5B) protein of the Hepatitis C Virus (HCV). The epitopes are those which elicit a HLA class I and/or class II restricted T lymphocyte response in an immunized host. More specific, the HLA class I restricted peptides of the present invention may bind to at least one HLA molecule of the following HLA class I groups: HLA-A*01, HLA-A*02, HLA-A*03, HLA-A*11, HLA-A*24, HLA-B*07, HLA-B*08, HLA-B*35, HLA-B*40, HLA-B*44, HLA-Cw3, HLA-Cw4, HLA-Cw6 or HLA-Cw7. The HLA class II restricted peptides of the present invention bind to at least one HLA molecule of the following HLA class II groups: HLA-DRB1, -DRB2, -DRB3, -DRB4, -DRB5, -DRB6, -DRB7, -DRB8 or -DRB9.

MHC binding HCV peptides that may be used according to the present invention as epitopes are disclosed in e.g. WO02/34770 (Imperial College Innovations Ltd), WO01/21189 and WO02/20035 (Epimmune), WO04/024182 (Intercell), WO95/25122 (The Scripps Research Institute), WO95/27733 (Government of the USA, Department of Health and Human Services), EP 0935662 (Chiron), WO02/26785 (Immusystems GmbH), WO95/12677 (Innogenetics N.V), WO97/34621 (Cytel Corp), and EP 1652858 (Innogenetics N.V.).

In other embodiments, the scaffold design according to the present invention comprises a PADRE peptide, such as the universal T cell epitope called PADRE as disclosed in WO95/07707 (Epimmune) the content of which are enclosed herein by reference. A 'PanDR binding peptide or PADRE peptide" is a member of a family of molecules that binds more than one HLA class II DR molecule. PADRE binds to most HLA-DR molecules and stimulates in vitro and in vivo human helper T lymphocyte (HTL) responses. Alternatively T-help epitopes can be used from universally used vaccines such as tetanus toxoid.

In a further embodiment, the peptides in the composition or polyepitopic peptide are characterized in that they are derived from a HCV protein, and more specifically from at least one of the following HCV regions selected from the group consisting of Core, E1, E2/NS1, NS2, NS3, NS4A, NS4B, NS5A and NS5B. Even more preferred is that peptides are characterized in that they are present in the HCV consensus sequence of genotype 1a, 1b and/or 3a.

Other HLA class I and II binding peptides that may be used according to the invention may be identified by the method as described in WO03/105058—Algonomics, by the method as described by Epimmune in WO01/21189 and/or by three public database prediction servers, respectively Syfpeithi, BIMAS and nHLAPred. It is also an aspect of this present invention that each peptide may be used within the scaffold design of the invention in combination with the same peptide as multiple repeats, or with any other peptide(s) or epitope(s).

CMV:
The epitopes to be incorporated into the scaffold design according to the present invention may be derived from cytomegalovirus (CMV) including CMV glycoproteins gB and gH.

Flu:
The epitopes to be incorporated into the scaffold design according to the present invention may be derived from fragments or portions of Influenza hemagglutinin (HA) or Influenza neuraminidase (NA), nucleoprotein (NP), M1, M2, NS1, NEP, PA, PB1, PB1-F2, PB2 for each of the subgroups, such as H1N1, H2N2 og H3N2.

Suitable epitopes may be derived from an HA protein of one, or more than one subtype, including H1, H2, H3, H4, H5, H6, H7, H8, H9, H10, H11, H12, H13, H14, H15 or H16 or fragment or portion thereof. Examples of subtypes comprising such HA proteins include A/New Caledonia/20/99 (H1N1) A/Indonesia/5/2006 (H5N1), A/chicken/New York/1995, A/herring gull/DE/677/88 (H2N8), A/Texas/32/2003, A/mallard/MN/33/00, A/duck/Shanghai/1/2000, A/northern pintail/TX/828189/02, A/Turkey/Ontario/6118/68 (H8N4), A/shoveler/Iran/G54/03, A/chicken/Germany/N/1949 (H10N7), A/duck/England/56 (H11N6), A/duck/Alberta/60/76 (H12N5), A/Gull/Maryland/704/77 (H13N6), A/Mallard/Gurjev/263/82, A/duck/Australia/341/83 (H15N8), A/black-headed gull/Sweden/5/99 (H16N3), B/Lee/40, C/Johannesburg/66, A/PuertoRico/8/34 (H1N1), A/Brisbane/59/2007 (H1N1), A/Solomon Islands 3/2006 (H1N1), A/Brisbane 10/2007 (H3N2), A/Wisconsin/67/2005 (H3N2), B/Malaysia/2506/2004, B/Florida/4/2006, A/Singapore/1/57 (H2N2), A/Anhui/1/2005 (H5N1), A/Vietnam/1194/2004 (H5N1), A/Teal/HongKong/W312/97 (H6N1), A/Equine/Prague/56 (H7N7), A/HongKong/1073/99 (H9N2)).

In some embodiments of the invention, the HA protein may be an H1, H2, H3, H5, H6, H7 or H9 subtype. In other embodiments, the H1 protein may be from the A/New Caledonia/20/99 (H1N1), A/PuertoRico/8/34 (H1N1), A/Brisbane/59/2007 (H1N1), or A/Solomon Islands 3/2006 (H1N1) strain. The H3 protein may also be from the A/Brisbane 10/2007 (H3N2) or A/Wisconsin/67/2005 (H3N2) strain. In other embodiments, the H2 protein may be from the A/Singapore/1/57 (H2N2) strain. The H5 protein may be from the A/Anhui/1/2005 (H5N1), A/Vietnam/1194/2004 (H5N1), or A/Indonesia/5/2005 strain. In other embodiments, the H6 protein may be from the A/Teal/HongKong/W312/97 (H6N1) strain. The H7 protein may be from the A/Equine/Prague/56 (H7N7) strain. In other embodiments, the H9 protein is from the A/HongKong/1073/99 (H9N2) strain. In other embodiments, the HA protein may be from an influenza virus may be a type B virus, including B/Malaysia/2506/2004 or B/Florida/4/2006. The influenza virus HA protein may be H5 Indonesia.

Human immunodeficiency virus (HIV):
For HIV, the epitopes to be incorporated into the scaffold design according to the present invention may be derived from viral proteins consisting of gp120, gp160, gp41, p24gag or p55gag the regulatory proteins (such as Tat, Rev, Nef) as well as the viral enzymes (such as polymerase, integrase or protease) derived from HIV, including members of the various genetic subtypes.

Human Papillomavirus (HPV):
For HPV, the epitopes to be incorporated into the scaffold design according to the present invention may be derived from the group consisting E1, E2, E3, E4, E6 and E7, L1 and L2 proteins. The epitopes may be derived from any type including types 8, 11, 16, 18, 31, 33, 35, 39, 45, 51, 52, 56, 58, and 59.

Carriers, Adjuvants and Vehicles—Delivery
The peptides according to the invention may be delivered by various means and within various compositions, herein referred to as "compositions", "vaccine compositions" or "pharmaceutical compositions". The peptides of the present invention and pharmaceutical and vaccine compositions of the invention are useful for administration to both animals, such as mammals, and, in particular, to humans, to treat and/or prevent virus infection. Vaccine compositions containing the peptides of the invention are administered to a patient infected with the virus in question or to an individual susceptible to, or otherwise at risk for, virus infection to elicit an immune response against the specific antigens and thus enhance the patient's own immune response capabilities.

Various art-recognized delivery systems may be used to deliver the peptides, into appropriate cells. The peptides can be delivered in a pharmaceutically acceptable carrier or as colloidal suspensions, or as powders, with or without diluents. They can be "naked" or associated with delivery vehicles and delivered using delivery systems known in the art, such as recombinant virus particles, nanoparticles, such as nanogold, or cyclotides.

A "pharmaceutically acceptable carrier" or "pharmaceutically acceptable adjuvant" is any suitable excipient, diluent, carrier and/or adjuvant which, by themselves, do not induce the production of antibodies harmful to the individual receiving the composition nor do they elicit protection. Preferably, a pharmaceutically acceptable carrier or adjuvant enhances the immune response elicited by an antigen. Suitable carriers or adjuvant typically comprise one or more of the compounds included in the following non-exhaustive list: large slowly metabolized macromolecules such as proteins, polysaccharides, polylactic acids, polyglycolic acids, polymeric amino acids, amino acid copolymers and inactive virus particles; aluminium hydroxide, aluminium phosphate (see International Patent Application Publication No. WO93/24148), alum (KAl(SO4)2.12H2O), or one of these in combination with 3-0-deacylated monophosphoryl lipid A (see International Patent Application Publication No. WO93/19780); N-acetyl-muramyl-L-threonyl-D-isoglutamine (see U.S. Pat. No. 4,606,918), N-acetyl-normuramyl-L-alanyl-D-isoglutamine, N-acetylmuramyl-L-alanyl-D-isoglutamyl-L-alanine2-(1',2'-dipalmitoyl-sn-glycero-3-hydroxyphosphoryloxy) ethylamine; RIBI (ImmunoChem Research Inc., Hamilton, Mont., USA) which contains monophosphoryl lipid A (i.e., a detoxified endotoxin), trehalose-6,6-dimycolate, and cell wall skeleton (MPL+TDM+CWS) in a 2% squalene/Tween 80 emulsion. Any of the three components MPL, TDM or CWS may also be used alone or combined 2 by 2; adjuvants such as Stimulon (Cambridge Bioscience, Worcester, Mass., USA), SAF-1 (Syntex); adjuvants such as combinations between QS21 and 3-de-O-acetylated monophosphoryl lipid A (see International Application No. WO94/00153), which may be further supplemented with an oil-in-water emulsion (see, e.g., International Application Nos. WO95/17210, WO97/01640 and WO9856414) in which the oil-in-water emulsion comprises a metabolisable oil and a saponin, or a metabolisable oil, a saponin, and a sterol, or which may be further supplemented with a cytokine (see International Application No. WO98/57659); adjuvants such as MF-59 (Chiron), or poly[di(carboxylatophenoxy) phosphazene] based adjuvants (Virus Research Institute); blockcopolymer based adjuvants such as Optivax (Vaxcel, Cytrx) or inulin-based adjuvants, such as Algammulin and Gammalnulin (Anutech); Complete or Incomplete Freund's Adjuvant (CFA or IFA, respectively) or Gerbu preparations (Gerbu Biotechnik); a saponin such as QuilA, a purified saponin such as QS21, QS7 or QS17, -escin or digitonin; immunostimulatory oligonucleotides comprising unmethylated CpG dinucleotides such as [purine-purine-CG-pyrimidine-pyrimidine] oligonucleotides. These immunostimulatory oligonucleotides include CpG class A, B, and C molecules (Coley Pharmaceuticals), ISS (Dynavax), Immunomers (Hybridon). Immunostimulatory oligonucleotides may also be combined with cationic peptides as described, e.g., by Riedl et al. (2002); Immune Stimulating Complexes comprising saponins, for example Quil A (ISCOMS); excipients and diluents, which are inherently non-toxic and non-therapeutic, such as water, saline, glycerol, ethanol, isopropyl alcohol, DMSO, wetting or emulsifying agents, pH buffering substances, preservatives, and the like; a biodegradable and/or biocompatible oil such as squalane, squalene, eicosane, tetratetracontane, glycerol, peanut oil, vegetable oil, in a concentration of, e.g., 1 to 10% or 2.5 to 5%; vitamins such as vitamin C (ascorbic acid or its salts or esters), vitamin E (tocopherol), or vitamin A; carotenoids, or natural or synthetic flavanoids; trace elements, such as selenium; any Toll-like receptor ligand as reviewed in Barton and Medzhitov (2002).

Any of the afore-mentioned adjuvants comprising 3-de-O-acetylated monophosphoryl lipid A, said 3-de-O-acetylated monophosphoryl lipid A may be forming a small particle (see International Application No. WO94/21292).

In any of the aforementioned adjuvants MPL or 3-de-O-acetylated monophosphoryl lipid A can be replaced by a synthetic analogue referred to as RC-529 or by any other amino-alkyl glucosaminide 4-phosphate (Johnson et al. 1999, Persing et al. 2002). Alternatively it can be replaced by other lipid A analogues such as OM-197 (Byl et al. 2003).

A "pharmaceutically acceptable vehicle" includes vehicles such as water, saline, physiological salt solutions, glycerol, ethanol, etc. Auxiliary substances such as wetting or emulsifying agents, pH buffering substances, preservatives may be included in such vehicles. Delivery systems known in the art are e.g. lipopeptides, peptide compositions encapsulated in poly-DL-lactide-co-glycolide ("PLG"), microspheres, peptide compositions contained in immune stimulating complexes (ISCOMS), multiple antigen peptide systems (MAPs), viral delivery vectors, particles of viral or synthetic origin, adjuvants, liposomes, lipids, microparticles or microcapsules, gold particles, nanoparticles, polymers, condensing agents, polysaccharides, polyamino acids, dendrimers, saponins, QS21, adsorption enhancing materials, fatty acids or, naked or particle absorbed cDNA.

The peptides may be delivered in oils such as Endocine™ and Montanide™ (Eurocine)-Montanide™ ISA 51 VG or Montanide™ ISA 720 VG (Seppic).

The adjuvant may be stimulators of the innate immune system that can be given separately from the peptide such as Leukotriene B4 (LTB4) and granulocyte macrophage colony stimulating factor (GM-CSF), such as Sargramostim/Leukine (glycosylated GM-CSF) and Molgramostim (nonglycosylated GM-CSF).

Typically, a vaccine or vaccine composition is prepared as an injectable, either as a liquid solution or suspension. Injection may be subcutaneous, intramuscular, intravenous, intraperitoneal, intrathecal, intradermal, or intraepidermal. Other types of administration comprise electroporation, implantation, suppositories, oral ingestion, enteric application, inhalation, aerosolization or nasal spray or drops. Solid forms, suitable for dissolving in, or suspension in, liquid vehicles prior to injection may also be prepared. The preparation may also be emulsified or encapsulated in liposomes for enhancing adjuvant effect.

A liquid formulation may include oils, polymers, vitamins, carbohydrates, amino acids, salts, buffers, albumin, surfactants, or bulking agents. Preferable carbohydrates include sugar or sugar alcohols such as mono-, di-, tri-, oligo- or polysaccharides, or water-soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. Sucrose is most preferred. "Sugar alcohol" is defined as a C4 to C8 hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to the amount used as long as the sugar or sugar alcohol is soluble in the aqueous preparation. Preferably, the sugar or sugar alcohol concentration is between 1.0% (w/v) and 7.0% (w/v), more preferable between 2.0 and 6.0%

(w/v). Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Any physiological buffer may be used, but citrate, phosphate, succinate, and glutamate buffers or mixtures thereof are preferred. Most preferred is a citrate buffer. Preferably, the concentration is from 0.01 to 0.3 molar. Surfactants that can be added to the formulation are shown in EP patent applications No. EP 0 270 799 and EP 0 268 110.

Additionally, polypeptides can be chemically modified by covalent conjugation to a polymer to increase their circulating half-life, for example. Preferred polymers, and methods to attach them to peptides, are shown in U.S. Pat. Nos. 4,766,106; 4,179,337; 4,495,285; and 4,609,546. Preferred polymers are polyoxyethylated polyols and polyethylene glycol (PEG). PEG is soluble in water at room temperature and has the general formula:

R(O—CH2-CH2)$_n$O—R where R can be hydrogen, or a protective group such as an alkyl or alkanol group. Preferably, the protective group has between 1 and 8 carbons, more preferably it is methyl. The symbol n is a positive integer, preferably between 1 and 1.000, more preferably between 2 and 500. The PEG has a preferred average molecular weight between 1000 and 40.000, more preferably between 2000 and 20.000, most preferably between 3.000 and 12.000. Preferably, PEG has at least one hydroxy group, more preferably it is a terminal hydroxy group. It is this hydroxy group which is preferably activated. However, it will be understood that the type and amount of the reactive groups may be varied to achieve a covalently conjugated PEG/polypeptide of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al., 1988, and a discussion of POG/IL-2 conjugates is found in U.S. Pat. No. 4,766,106.

Another drug delivery system for increasing circulatory half-life is the liposome. The peptides and nucleic acids of the invention may also be administered via liposomes, which serve to target a particular tissue, such as lymphoid tissue, or to target selectively infected cells, as well as to increase the half-life of the peptide and nucleic acids composition. Liposomes include emulsions, foams, micelles, insoluble monolayers, liquid crystals, phospholipid dispersions, lamellar layers and the like. In these preparations, the peptide or nucleic acids to be delivered is incorporated as part of a liposome or embedded, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide or nucleic acids of the invention can be directed to the site of lymphoid cells, where the liposomes then deliver the peptide and nucleic acids compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al, 1980, and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated. For example, liposomes carrying either immunogenic polypeptides are known to elicit CTL responses in vivo (Reddy et al., 1992; Collins et al., 1992; Fries et al., 1992; Nabel et al., 1992).

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

Use of the Peptides for Evaluating Immune Responses:

The peptides according to the present invention may be used as diagnostic reagents. For example, a peptide of the invention may be used to determine the susceptibility of a particular individual to a treatment regimen which employs the peptide or related peptides, and thus may be helpful in modifying an existing treatment protocol or in determining a prognosis for an affected individual. In addition, the peptides may also be used to predict which individuals will be at substantial risk for developing a chronic virus infection.

Accordingly, the present invention relates to a method of determining the outcome for a subject exposed to a disease antigen, such as an infectious agent, such as a pathogen, comprising the steps of determining whether the subject has an immune response to one or more peptides according to the present invention.

In a preferred embodiment of the invention, the peptides as described herein can be used as reagents to evaluate an immune response. The immune response to be evaluated can be induced by using as an immunogen any agent that may result in the production of antigen-specific CTLs or HTLs that recognize and bind to the peptide(s) to be employed as the reagent. The peptide reagent need not be used as the immunogen. Assay systems that can be used for such an analysis include relatively recent technical developments such as tetramers, staining for intracellular lymphokines and interferon release assays, or ELISPOT assays.

For example, a peptide of the invention may be used in a tetramer staining assay to assess peripheral blood mononuclear cells (PBMC) for the presence of antigen-specific CTLs following exposure to an antigen or an immunogen. The HLA-tetrameric complex is used to directly visualize antigen-specific CTLS (see, e.g., Ogg et al., 1998; and Altman et al., 1996) and determine the frequency of the antigen-specific CTL population in a sample of peripheral blood mononuclear cells. A tetramer reagent using a peptide of the invention may be generated as follows: a peptide that binds to an HLA molecule is reconstituted in the presence of the corresponding HLA heavy chain and beta2-microglobulin to generate a trimolecular complex. The complex is biotinylated at the carboxyl terminal end of the heavy chain at a site that was previously engineered into the protein. Tetramer formation is then induced by the addition of streptavidin. By means of fluorescently labeled streptavidin, the tetramer can be used to stain antigen-specific cells. The cells may then be identified, for example, by flow cytometry. Such an analysis may be used for diagnostic or prognostic purposes. Cells identified by the procedure can also be used for therapeutic purposes. As an alternative to tetramers also pentamers or dimers can be used (Current Protocols in Immunology (2000) unit 17.2 supplement 35)

Peptides of the invention may also be used as reagents to evaluate immune recall responses. (see, e.g., Bertoni et al., 1997 and Perna et al., 1991.). For example, patient PBMC samples from individuals with HCV infection may be analyzed for the presence of antigen-specific CTLs or HTLs using specific peptides. A blood sample containing mononuclear cells may be evaluated by cultivating the PBMCs and stimulating the cells with a peptide of the invention.

After an appropriate cultivation period, the expanded cell population may be analyzed, for example, for cytotoxic activity (CTL) or for HTL activity.

The peptides may also be used as reagents to evaluate the efficacy of a vaccine.

PBMCs obtained from a patient vaccinated with an immunogen may be analyzed using, for example, either of the methods described above. The patient is HLA typed, and peptide epitope reagents that recognize the allele-specific molecules present in that patient are selected for the analysis. The immunogenicity of the vaccine is indicated by the presence of epitope-specific CTLs and/or HTLs in the PBMC sample.

The peptides of the invention may also be used to make antibodies, using techniques well known in the art (see, e.g. CURRENT PROTOCOLS IN IMMUNOLOGY, Wiley/Greene, NY; and Antibodies, A Laboratory Manual, Harlow and Lane, Cold Spring Harbor Laboratory Press, 1989). Such antibodies include those that recognize a peptide in the context of an HLA molecule, i.e., antibodies that bind to a peptide-MHC complex.

In certain embodiments a first monomeric peptide and the at least one second monomeric peptide are associated via a linker; the linker may comprise any peptide linker, or peptide spacer, such as a glycine, a lysine or an arginine linker/spacer, a polyhistidinyl tag, Protein G, and Protein A but it is also possible to use a bis-maleimide linker/spacer, a disulfide linker, or a polyethylene glycol (PEG) linker. In practice, any linker found useful in peptide chemistry is also useful as a linker according to the present invention. Thus, the invention contemplates the use of "simple" linear peptides which are conjugated or fused to each other, but also peptide combinations where the individual peptides derived from a natural antigen are linked via non-peptide linkers. Use of multiple linker types are also within the scope of the present invention, and it is e.g. also a part of the invention to utilise linear peptides which include intrachain disulphide linkers.

Particularly interesting peptide combinations of the invention are set forth in the preamble to the examples.

In certain embodiments, at least one of the first and at least one second peptides in the peptide combination comprises an N- or C-terminal modification, such as an amidation, acylation, or acetylation.

Since the peptide combinations are contemplated as vaccine agents or diagnostic agents, they are in certain embodiments coupled to a carrier molecule, such as an immunogenic carrier. The peptides of the peptide combinations may thus be linked to other molecules either as recombinant fusions (e.g. via CLIP technology) or through chemical linkages in an oriented (e.g. using heterobifunctional cross-linkers) or nonoriented fashion. Linking to carrier molecules such as for example diphtheria toxin, latex beads (convenient in diagnostic and prognostic embodiments), and magnetic beads (also convenient in diagnostic and prognostic embodiments), polylysine constructs etc, are all possible according to the invention.

The immunogenic carrier is conveniently selected from carrier proteins such as those conventionally used in the art (e.g. diphtheria or tetanus toxoid, KLH etc.), but it is also possible to use shorter peptides (T-helper epitopes) which can induce T-cell immunity in larger proportions of a population. Details about such T-helper epitopes can e.g. be found in WO 00/20027, which is hereby incorporated by reference herein—all immunolgic carriers and "promiscuous" (i.e. universal) T-helper epitopes discussed therein are useful as immunogenic carriers in the present invention.

In certain embodiments, the carrier is a virus like particle, i.e. a particle sharing properties with virions without being infectious. Such virus-like particles may be provided chemically (e.g. Jennings and Bachmann Ann Rev Pharmacol. Toxicol. 2009. 49:303-26 Immunodrugs: Therapeutic VLP-based vaccines for chronic diseases) or using cloning techniques to generate fusion proteins (e.g. Peabody et al. J. Mol. Biol. 2008; 380: 252-63. Immunogenic display of diverse peptides on virus-like particles of RNA phage MS2). Another example is "Remune", an HIV vaccine originally made by Immune Response Corporation, which consists of formalin inactivated HIV that has been irradiated to destroy the viral genome.

In an embodiment, a nucleic acid is encoding one or more monomeric peptide of the multimeric, such as dimeric peptide according to the invention, where the encoded first peptide and the encoded at least one second peptide of a multimeric peptide are associated via a peptide linker, including a peptide spacer, and/or a disulphide bridge. The peptide linker/spacer is typically selected from the group consisting of a glycine, an arginine, a lysine linker/spacer, or a glycine-lysine linker/spacer, but any peptide linker known in the art may be useful. The term peptide linker thus also is intended to denote coupling between the first and second peptide via a peptide bond. A peptide linker that links a first and second peptide by standard peptide bonds may also be referred to as a peptide spacer. Also, the first and second peptides may be linked via a peptide linker and a disulphide bond, as is the case when an intrachain disulphide bond is established.

In one embodiment, the nucleic acid according to the invention encodes the peptide combination, which is coupled (by fusion) to a carrier molecule, such as an immunogenic carrier; useful carriers are discussed above.

In some embodiments the linker is selected from the group consisting of a bis-maleimide linker, a disulfide linker, a polyethylene glycol (PEG) linker, a glycine linker/spacer, a lysine linker/spacer, and an arginine linker/spacer.

In some embodiments the multimeric peptide, such as a dimeric peptide contain a linker in the free amino group of the N-terminal of a monomeric peptide linking said monomeric peptide to another monomeric peptide.

In some embodiments the multimeric peptide, such as a dimeric peptide contain a linker in the free carboxyl group of the C-terminal of a monomeric peptide linking said monomeric peptide to another monomeric peptide.

At least two options for such linkers are described in A. R Jacobson et al, J. Med. Chem. 1989, 32, 1708-1717 and in D Giannotti et al, Journal of Medicinal Chemistry, 2000, Vol. 43, No. 22, the disclosures of which is hereby incorporated by reference.

Alternatively a link between the N-termini of peptides may be established by reacting with Br—$(CH_2)_n$—Br.

The length of the linker may be varied by the addition of glycine residues, for example Fmoc-NH—$CH_2CH_2$—NH-Gly-$NH_2$ may be used.

An example of such a synthesis, wherein a dimeric peptide is prepared by conjugation through succinic acid, may be as follows:

(H-Gly-Gly-Ala-Lys-Arg-Arg-Val-Val-Gln-Arg-Glu-Lys-Arg-Ala-Gly-Glu-Arg-Glu-Lys-Arg-Ala-$NH_2$)E(H-Gly-Gly-Ile-Glu-Glu-Glu-Gly-Gly-Arg-Asp-Arg-Asp-Arg-Gly-Gly-Glu-Gln-Asp-Arg-Asp-Arg-$NH_2$)F (Succinic acid linker between $Gly^1E$ and $Gly^1F$)

This dimer was produced from the reaction of the following 2 monomers

Monomer E

H-Gly-Gly-Ala-Lys-Arg-Arg-Val-Val-Gln-Arg-Glu-Lys-Arg-Ala-Gly-Glu-Arg-Glu-Lys-Arg-Ala-$NH_2$ (SEQ ID NO:143)

Monomer F

H-Gly-Gly-Ile-Glu-Glu-Glu-Gly-Gly-Arg-Asp-Arg-Asp-Arg-Gly-Gly-Glu-Gln-Asp-Arg-Asp-Arg-$NH_2$ (SEQ ID NO:144).

The two monomers are reacted to give a heterodimer according to the reaction scheme outlined below; where the link is between N-terminal on Gly' of on chain E and the N-terminal on Gly' in chain F.

Monomers E and F are synthesized separately on a Sieber Amid resin. The Fmoc-groups on N-terminal Gly are removed while the peptides are still on resin. The peptides are cleaved from resin. The resulting protected peptide E is reacted with succinic acid anhydride and thereafter reacted with the protected peptide F. Protective groups are subsequently removed with 95% TFA. The formed heterodimer may be purified from un-reacted monomers by conventional purification methods known to the person skilled in the art.

An example of a synthesis, wherein a dimeric peptide is prepared by conjugation through di-amino propane, may be as follows:

(H-Gly-Gly-Ala-Lys-Arg-Arg-Val-Val-Gln-Arg-Glu-

Lys-Arg-Ala-Gly-Glu-Arg-Glu-Lys-Arg-Ala-Gly-Gly)

G(H-Gly-Gly-Ile-Glu-Glu-Glu-Gly-Gly-Arg-Asp-Arg-

Asp-Arg-Gly-Gly-Glu-Gln-Asp-Arg-Asp-Arg-Gly-Gly)H trifluoroacetate salt (Diamino propane linker between $Gly^{23}$ and $Gly^{23}$)

This dimer was produced from the reaction of the following 2 protected monomers

Monomer G
(SEQ ID NO: 145)
H-Gly-Gly-Ala-Lys-Arg-Arg-Val-Val-Gln-Arg-Glu-Lys-

Arg-Ala-Gly-Glu-Arg-Glu-Lys-Arg-Ala-Gly-Gly-COOH

Monomer H
(SEQ ID NO: 146)
H-Gly-Gly-Ile-Glu-Glu-Glu-Gly-Gly-Arg-Asp-Arg-Asp-

Arg-Gly-Gly-Glu-Gln-Asp-Arg-Asp-Arg-Gly-Gly-COOH

The two monomers G and H are reacted to give a heterodimer according to the reaction scheme outlined below; where the link is between C-terminal on $Gly^{23}$ of on chain G and the C-terminal on $Gly^{23}$ in chain H.

Monomers G and H are synthesized separately on a 2-chlorotrityl resin. Boc-Gly-OH is coupled to the peptides on the resin before cleaving them of the resin. The resulting peptides are then Boc-protected, alternatively they may me acetylated before being cleaved of the resin. The resulting protected peptide G is reacted with Fmoc-diaminopropane, Fmoc is deprotected and G is coupled to the C-terminal of the protected peptide H via a peptide bond. Protective groups are subsequently removed with 95% TFA. The formed heterodimer may be purified from un-reacted monomers by conventional purification methods known to the person skilled in the art.

Method for Synthesis of Cys-Lys Bridge:

Exemplified with the preparation of BI400-B trifluoroacetate salt (H-Gly-Ala-Lys-Arg-Arg-Val-Val-Gly-Gly-Cys(2-oxoethyl)-Gly-Gly-Ala-Lys-Arg-Arg-Val-Val-Gln-Arg- Glu-Lys-Arg-Ala-Gly-Glu-Arg-Glu-Lys-Arg-Ala-NH₂)

A(H-Gly-Lys-Gly-Gly-Ile-Glu-Glu-Glu-Gly-Gly-Arg-

Asp-Arg-Asp-Arg-Gly-Gly-Glu-Gln-Asp-Arg-Asp-Arg-

NH₂)B trifluoroacetate salt (Thioether bond between Cys(2-oxo-ethyl)⁹A and Lys²B)

This dimer was produced from the reaction of the following 2 protected monomers

Monomer A
(SEQ ID NO: 121)
H-Gly-Ala-Lys-Arg-Arg-Val-Val-Gly-Gly-Cys-Gly-Gly-

Ala-Lys-Arg-Arg-Val-Val-Gln-Arg-Glu-Lys-Arg-Ala-

Gly-Glu-Arg-Glu-Lys-Arg-Ala-NH₂

Monomer B
(SEQ ID NO: 122)
H-Gly-Lys(bromoacetyl)-Gly-Gly-Ile-Glu-Glu-Glu-

Gly-Gly-Arg-Asp-Arg-Asp-Arg-Gly-Gly-Glu-Gln-Asp-

Arg-Asp-Arg-NH₂;

Or with the preparation of 400-Seq B trifluoroacetate salt (H-Gly-Ala-Lys-Arg-Arg-Val-Val-Gly-Gly-Cys(2-oxo-ethyl)-Gly-Gly-Ala-Lys-Arg-Arg-Val-Val-Gln-Arg-Glu-Lys-Arg-Ala-Gly-Glu-Arg-Glu-Lys-Arg-Ala-NH₂)
A(H-Gly-Lys-Gly-Gly-Ile-Glu-Glu-Glu-Gly-Gly-Arg-Asp-Arg-Asp-Arg-Gly-Gly-Gln-Asp-Arg-Asp-Arg-NH₂)
B trifluoroacetate salt (Thioether bond between Cys(2-oxo-ethyl)⁹A and Lys²B)

This dimer was produced from the reaction of the following 2 protected monomers

Monomer A
(SEQ ID NO: 121)
H-Gly-Ala-Lys-Arg-Arg-Val-Val-Gly-Gly-Cys-Gly-Gly-Ala-Lys-Arg-Arg-Val-Val-Gln-Arg-Glu-Lys-Arg-Ala-Gly-Glu-Arg-Glu-Lys-Arg-Ala-NH₂

Monomer B
(SEQ ID NO: 147)
H-Gly-Lys(bromoacetyl)-Gly-Gly-Ile-Glu-Glu-Glu-Gly-Gly-Arg-Asp-Arg-Asp-Arg-Gly-Gly-Gln-Asp-Arg-Asp-Arg-NH₂

The 2 monomers are reacted to give a heterodimer according to the reaction scheme outlined below; where the link is created between Lys 2 (bromoacetyl) side chain on chain B and Cys in chain A.

At neutral pH and room temperature, bromoacetyl moieties in buffered aqueous solutions are very reactive towards SH-containing moieties, such as the thiol group in cysteine. Thus, if a cysteine is present on the other peptide sequence, the SH will attack the bromoacetyl to form a intermolecular thioether bridge. When the reaction is buffered with a sodium-containing buffer, such as NaHCO₃, the only byproduct of the reaction is NaBr, an innocuous salt.

The formed heterodimer may be purified from un-reacted monomers by conventional purification methods known to the person skilled in the art.

Method for synthesis of oxime bond between two peptide sequences, an intermolecular bond:

Exemplified with the preparation of 400-Seq B* trifluoroacetate salt (H-Gly-Ala-Lys-Arg-Arg-Val-Val-Gly-Gly-Dpr(COCHO)-Gly-Gly-Ala-Lys-Arg-Arg-Val-Val-Gln-Arg-Glu-Lys-Arg-Ala-Gly-Glu-Arg-Glu-Lys-Arg-Ala-NH₂)D(H-Gly-Lys(aminooxyacerylated)--Gly-Gly-Ile-Glu-Glu-Glu-Gly-Gly-Arg-Asp-Arg-Asp-Arg-Gly-Gly-Gln-Asp-Arg-Asp-Arg-NH₂)C trifluoroacetate salt
(oxime is created between Dpr(COCHO)-)⁹D and Lys(aminooxyacerylated)²C)

This dimer is produced from the reaction of the following two monomers:

Monomer C
(SEQ ID NO: 148)
H-Gly-Lys(aminooxyacerylated)-Gly-Gly-Ile-Glu-Glu-Glu-Gly-Gly-Arg-Asp-Arg-Asp-Arg-Gly-Gly-Gln-Asp-Arg-Asp-Arg-NH₂

Monomer D
(SEQ ID NO: 149)
H-Gly-Ala-Lys-Arg-Arg-Val-Val-Gly-Gly-Dpr(Ser)-Gly-Gly-Ala-Lys-Arg-Arg-Val-Val-Gln-Arg-Glu-Lys-Arg-Ala-Gly-Glu-Arg-Glu-Lys-Arg-Ala-NH₂.

The two monomers are reacted to give a heterodimer according to the reaction scheme outlined below; where the link is created between Lys² (aminooxyacetylated) side chain on chain C and oxidized Dpr(Ser) in chain D.

After removal of the Mtt group from Lys and while the peptide was still attached to the resin aminooxyacetylated (AoA) monomer C was synthesized by coupling aminooxyacetic acid to Lys.

The peptide was then cleaved from the solid phase support and purified by conventional purification methods. The monomer D was, after cleavage from resin and purification, created by oxidation of the serinyl diaminopropionic acid residue (Dpr(Ser)) with periodate to the aldehyde function. Equimolar amounts of monomer A and B were dissolved in acetonitrile and acetate buffer (pH 4). After reaction for 16 h at room temperature, the product C-oxime-D was isolated by conventional purification methods known to the person skilled in the art.

Dpr=diaminopropionic acid

Fmoc-Dpr (Boc-Ser(tBu))—OH Merck 04-12-1186

Method for Synthesis of Dimers with PEG-Linker:

A multimeric, such as dimeric peptide, such as a heterodimeric peptide may be synthesized by, but are not restricted to the following protocol:

To the peptidyl resin containing deblocked Asp or Glu residue (monomer 1) is added HBTU, DIPEA and Trt-amino PEG amine in DMF. The mixture is allowed to couple over night. The resin is filtered from the solution and washed by standard protocol. The Trt group is removed from the Trt-PEGylated peptide. The monomer 2 containing deblocked Asp or Glu residue is then coupled to the exposed amino group using HBTU and DIPEA. After cleavage the desired product is purified using any suitable technique to give the desired multimeric peptide.

In some embodiments the isolated monomeric peptide contain intramolecular bonds, such as in the form of intramolecular Cys-Cys bonds. It is to be understood that the "intramolecular bond", used interchangeably with "intrachain bond", is a bond between two different amino acids within the same peptide chain, which however is not necessarily adjacent to each other in the peptide sequence. Accordingly, in some embodiments, the isolated multimeric peptide according to the invention may contain both intramolecular bonds within one or more of the monomers, as well as an intermolecular bond between two chains of the multimeric peptide, such as a dimer. This intramolecular bond may be in the form of Cys-Cys bonds formed with cysteine residues within the same peptide sequence. In some embodiments the monomer contains an intramolecular bond derived from a Lys residue or other amino acid residue, such as a Ser, Cys, Asp or Glu that make the bond, such as a thioether bond or an oxime bond or through a PEG linker, to an amino acid residue on the other monomer peptide sequence.

Method for synthesis of multimeric peptides with PolyLys or MAPS:

PolyLys or MAPS (multiple antigen peptides)—has been extensively used over the last 20 years as a carrier protein to produce strong immunogenic response. The MAP system utilizes a peptidyl core of three or more radially branched lysine core to form a backbone for which the epitope sequences of interest can be built parallel using standard solid-phase chemistry.

The MAP system is a commercial product available from several companies such as AnaSpec, Bio-synthesis Inc. and others. The product, as offered in the catalogue only allows attachment of two (identical) peptide sequence to the polyLys core. It is however possible also to link two different peptide sequences by using different protecting groups for alfa- and epsylon-amino functional groups of lysine on the two different peptide sequences.

Use of the MAP system has been described in references including: Wang, C. Y et al. "Long-term high-titer neutralizing activity induced by octameric synthetic HIV antigen" Science 254, 285-288 (1991). Posnett, D. et al. "A novel method for producing anti-peptide antibodies" J. Biol. Chem. 263, 1719-1725 (1988), and in Tam, J. P. "Synthetic peptide vaccine design: synthesis and properties of a high-density multiple antigenic peptide system" PNAS USA 85, 5409-5413 (1988).

The MAP system could also be prepared by chemical (thioether, oxime, hydrazone) ligation of appropriately functionalized tetra- or octavalent polylysine constructs with the peptide antigen. By the use of this chemical ligation, the two peptide sequences being linked together would not have to be identical as they are synthesized separately.

Additionally a novel application of the MAP-based system is to synthesize on solid support a "probe" containing a poly(ethylene glycol) (PEG) chain in the dendritic arms of MAP.

Use of the MAP system will increase the size of a multimeric complex and may increase the immunogenic response.

Methods for the Synthesis of Multimeric Peptides Using PEG:

Suitable Multi-Arm Activated PEG to be used for a PEG linker are commercially available, e.g. a compound with the following structure:

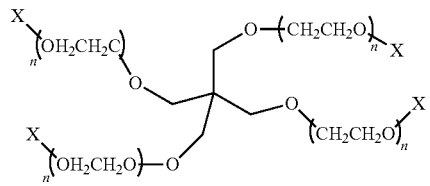

Wherein X may be ethanethiol —CH2CH2SH (could be used to form S—S bridge with the epitope or a thioether link) or propylamine —CH2CH2CH2NH2, among others. These handles preferably allows for the linking of two identical peptide sequences and may be seen as a poly-monomeric epitope presenting construct. One could, however, anchor a dimer (two epitopes linked together) to the PEG above.

Method for synthesis of peptide-poly-L-Lys (PLL)-polyethylene glycol (PEG) construct:

Peptide-PLL-PEG constructs, may be synthesized by, but are not restricted to the following protocol:

Fmoc-Poly-L-Lys-resin (a commercial product) is de-protected with 20% piperifine-DMF.

Fmoc-NH-PEG$_4$-COOH, in a mixed solvent of CH$_2$Cl$_2$-NMP is added followed by HBTU and DIPEA and the reaction is allowed to proceed for 24 h. The resultant pegylated poly-L-Lys-resin is washed and the pegylation step is repeated. The reaction is monitored by Kaiser's ninhydrin test until a negative reading is obtained. After de-protection of Fmoc group, four identical peptide chains are synthesized directly on the branched poly-L-Lys-polyethylene glycol core by a stepwise solid-phase procedure. All residues activated with HBTU and DIPEA are allowed to couple for 2 h. The coupling is monitored by Kaiser's ninhydrin test and is repeated if needed. After cleavage the desired product is purified using any suitable technique to give the desired peptide-construct.

TABLE 1

(Amino acids underlined refers to place of linker in dimeric molecules; Letter C in a large font refers to a cysteine residue optionally involved in an intramolecular bond with another cysteine residue in the same peptide sequence. Homoarginine is abbreviated Har, Norleucine is abbreviated as Nle or alternatively with the single letter "Z", N-ε-methylated Lys is abbreviated Lys(Me), Citrulline is abbreviated with the single letter "B", diaminopropionic acid is abbreviated with Dpr and serinyl diaminopropionic acid is abbreviated Dpr(Ser). Flu; abbreviation for Influenza)

| Chain | Antigen | Reference ID | X1 | X2 | X3 | X4 | X5 | X6 | Position with reference to positions in SEQ ID NO: 1 SEQ ID NO: 3, and SEQ ID NO: 4 | | | |
|---|---|---|---|---|---|---|---|---|---|---|---|---|
| | | | | | | | | | X2-SEQ | X4-SEQ | X6-SEQ | Protein |
| | Flu | BI100_CGn at | RR | SLLTEVETP | GCG | VETPIR | G | TPIRNEWG | 2-10 | 7-12 | 9-16 | M2 |
| | Flu | BI100_CG | RR | SLZTDIETP | GCG | IDTPIR | G | TPIBQDWG | 2-10 | 7-12 | 9-16 | M2 |
| | Flu | BI100-CGcyc | WWGC | TDIET | CG | I TABLE 1-continued (Amino acids underlined refers to place of linker in dimeric molecules; Letter C in a large font refers to a cysteine residue optionally involved in an intramolecular bond with another cysteine residue in the same peptide sequence. Homoarginine is abbreviated Har, Norleucine is abbreviated as Nle or alternatively with the single letter "Z", N-ε-methylated Lys is abbreviated Lys(Me), Citrulline is abbreviated with the single letter "B", diaminopropionic acid is abbreviated with Dpr and serinyl diaminopropionic acid is abbreviated Dpr(Ser). Flu; abbreviation for Influenza)

| Chain | Antigen | Reference ID | X1 | X2 | X3 | X4 | X5 | X6 | X2-SEQ | X4-SEQ | X6-SEQ | Protein |
|---|---|---|---|---|---|---|---|---|---|---|---|---|
| | HIV | | CGG | AKRRVV | GG | AKRRVV | GG | QREKR | 501-506 | 501-506 | 507-511 | gp120 |
| | HIV | | CGGG | DQQLL | GG | AEEEIV | GG | IEEEGG | 257-261 | 266-271 | 222-227 | |
| | HIV | | CGG | AEEEVV | GG | DQQLL | | | 266-271 | 257-261 | — | |
| | HIV | | GCGG | AKRRVV | GG | AKRRVV | | | 501-506 | 501-506 | — | |
| A | HIV | BI400-B (a-chain) | G | AKRRVV | GGCGG | AKRRVVQREKRA | G | EREKRA | 501-506 | 507-512 | 507-512 | gp120 |
| B | HIV | BI400-B (b-chain) | GK TABLE 1-continued (Amino acids underlined refers to place of linker in dimeric molecules; Letter C in a large font refers to a cysteine residue optionally involved in an intramolecular bond with another cysteine residue in the same peptide sequence. Homoarginine is abbreviated Har, Norleucine is abbreviated as Nle or alternatively with the single letter "Z", N-ε-methylated Lys is abbreviated Lys(Me), Citrulline is abbreviated with the single letter "B", diaminopropionic acid is abbreviated with Dpr and serinyl diaminopropionic acid is abbreviated Dpr(Ser). Flu; abbreviation for Influenza)

| Chain | Antigen | Reference ID | X1 | X2 | X3 | X4 | X5 | X6 | Position with reference to positions in SEQ ID NO: 1 SEQ ID NO: 3, and SEQ ID NO: 4. | | | | |
|---|---|---|---|---|---|---|---|---|---|---|---|---|---|
| | | | | | | | | | X2-SEQ | X4-SEQ | X6-SEQ | Protein |
| B | HIV | BI400-Bu3 (a-chain) (b-chain) | GKG | GIEEE | GG | EQDRDR | GG | ERDRD | 221-225 | 228-233 | 228-232 | gp41 |
| A | HIV | SEQ400_B (Cyc) | GC | AKRRVV | CGGKG | AKRRVVQREKRA | G | EREKRA | 501-506 | 501-512 | 507-512 | gp120 |
| B | HIV | SEQ400_B (Cyc) | GKG | GIEEE | GG | RDRDR | GG | EQDRDR | 221-225 | 229-233 | 228-233 | gp41 |
| A | HIV | SEQ400_B (Cyc) | GC | AKRRVV | CGGKG | GAKRRVVQREKRA | G | EREKRA | 501-506 | 501-512 | 506-512 | gp120 |
| B | HIV | SEQ400_B (Cyc) | GCGG | IEEEGGRDRDR | GG | QDRDR | | EREKRA | 222-233 | 229-233 | | gp41 |
| A | HIV | BI400-bu1 (Cyc) | G | CAKRRVVC | GGKGG | AKRRVVQREKRA | G | EREKRA | 501-506 | 501-512 | 507-512 | gp120 |
| B | HIV | BI400-bu1 (Cyc) | CGG | IEEEGGGERDRDR | GG | QDRDR | | EREKRA | 222-233 | 229-233 | | gp41 |
| A | HIV | BI400-bu2 (Cyc) | G | CAKRRVVC | GGKGG | AKRRVVQREKRA | G | QREKRA | 501-506 | 501-512 | 507-512 | gp120 |
| B | HIV | BI400-bu2 (Cyc) | CGG | IEEEGGQDRDR | GG | RDRDR | | EREKRA | 222-233 | 229-233 | | gp41 |
| A | HIV | BI400-bu3 (Cyc) | G | CAKRRVVC | GGKGG | AKRRVVEREKRA | G | QREKRA | 501-506 | 501-512 | 507-512 | gp120 |
| B | HIV | BI400-bu3 (Cyc) | CGG | IEEEGGEQDRDR | GG | RDRDR | | EREKRA | 222-233 | 229-233 | | gp41 |
| A | HIV | BI400-rev (Cyc) | G | CAKRRVVC | GGKGG | AKRRVVQREKRA | G | EREKRA | 501-506 | 501-512 | 507-512 | gp120 |
| B | HIV | BI400-rev (Cyc) | CGG | EEEIGGRDRD | GG | RDRDQ | | EREKRA | 222-233 | 229-233 | | gp41 |
| A | HIV | BI450-1 (a-chain) | GG | RLEPWKH FHSQV | GC | GSQPKTA FITKGLGISYGRK | G | HPGSQ | 7-13 32-36 | 15-21 38-50 | 13-17 — | Tat Tat |
| B | HIV | BI450-1 (b-chain) | GG | RLEPWKH | C | | | | | | | |
| A | HIV | BI450-1_2 | | RLEPWKH | GC | GSQPKTA | GWK | HPGSQ | 7-13 | 15-21 | 13-17 | Tat |

TABLE 1-continued (Amino acids underlined refers to place of linker in dimeric molecules; Letter C in a large font refers to a cysteine residue optionally involved in an intramolecular bond with another cysteine residue in the same peptide sequence. Homoarginine is abbreviated Har, Norleucine is abbreviated as Nle or alternatively with the single letter "Z", N-ε-methylated Lys is abbreviated Lys(Me), Citrulline is abbreviated with the single letter "B", diaminopropionic acid is abbreviated with Dpr and serinyl diaminopropionic acid is abbreviated Dpr(Ser). Flu; abbreviation for Influenza)

| Chain | Antigen | Reference ID | X1 | X2 | X3 | X4 | X5 | X6 | X2-SEQ | X4-SEQ | X6-SEQ | Protein |
|---|---|---|---|---|---|---|---|---|---|---|---|---|
| B | HIV | BI450-1_2 (a-chain) (b-chain) | C | FITKGLGISY | G | FITKGLGISYGRK | | | 38-47 | 38-50 | | Tat |
| A | HCV | BI 350-1 (a-chain) | RR | LLADARVCS | GG | LLADARVSA | | | 342-350 | 342-350 | | E2 |
| B | HCV | BI350-1 (b-chain) | R | GV(Nle)AGIAYPS | C | GVLAGIAYYS | | | 163-172 | 163-172 | | E1 |
| A | HCV | BI350-1mod1 | RR | GNWAKVL | K | NWAKVI | | | 366-372 | 367-372 | — | E1 |
| B | HCV | BI350-1mod1 | RRG | LLADARV | GCG | SGADRV | CS | | 342-348 | 342-348 | — | E2 |
| A | HCV | BI 350-1mod2 | RR | GNWAKVL | Dpr | NWAKVI | | | 366-372 | 367-372 | — | E1 |
| B | HCV | BI350-1mod2 | RRG | LLADARV | G(Dpr(Ser))G | SGADRV | CS | | 342-348 | 342-348 | — | E2 |
| A | HCV | | RR | GNWAKVL | Lys(Me) | NWAKVI | | | 366-372 | 367-372 | — | E1 |
| B | HCV | | RRG | LLADARV | GEG | SGADRV | CS | | 342-348 | 342-348 | — | E2 |
| A | HCV | | RR | GNWAKVL | Lys(Me) | NWAKVI | | | 366-372 | 367-372 | — | E1 |
| B | HCV | | RRG | LLADARV | GDG | SGADRV | CS | | 342-348 | 342-348 | — | E2 |
| A | HCV | | RR | GNWAKVL | E | NWAKVI | | | 366-372 | 367-372 | — | E1 |
| B | HCV | | RRG | LLADARV | G(Lys(Me))G | SGADRV | CS | | 342-348 | 342-348 | — | E2 |
| A | HCV | | RR | GNWAKVL | D | NWAKVI | | | 366-372 | 367-372 | — | E1 |
| B | HCV | | RRG | LLADARV | G(Lys(Me))G | SGADRV | CS | | 342-348 | 342-348 | — | E2 |

SPECIFIC EMBODIMENTS OF THE INVENTION

In some embodiments, in the peptide according to the present invention, $X^1$, $X^3$ and optional moiety $X^5$ each independently defines a linear sequence of any 1, 2, 3, 4, or 5 amino acids.

In some embodiments, in the peptide according to the present invention, $X^1$, $X^3$ and optional moiety $X^5$ consist of one or more amino acids selected from glycine, arginine, norleucine, glutamine, serine, lysine, tryptophan, cysteine, or a derivative thereof. The derivate may be a derivative on any of the specified amino acids.

In some embodiments, in the peptide according to the present invention, $X^1$, $X^3$ and optional moiety $X^5$ consist of one or more amino acids selected from glycine, arginine, norleucine, aspartic acid, glutamic acid, glutamine, serine, lysine, tryptophan, cysteine, ornithine, diaminopropionic acid (Dpr) or a derivative thereof. The derivate may be a derivative on any of the specified amino acids.

In some embodiments, in the peptide according to the present invention, $X^5$, and/or moiety $X^6$ is not present.

In some embodiments, in the peptide according to the present invention, $X^2$ and/or $X^4$ and/or $X^6$ has more than 55%, such as more than 60%, such as more than 65%, such as more than 70%, such as more than 75%, such as more than 80%, such as more than 85%, such as more than 90%, such as more than 95%, such as more than 96%, such as more than 97%, such as more than 98%, such as more than 99%, such as 100% sequence identity to a specific natural antigen.

In some embodiments, in the peptide according to the present invention, the specific natural antigen is a protein or peptide sequence derived from a disease antigen, such as an infectious agent, such as bacteria, virus, parasite, fungus, or cancer antigens such as oncogene (lung, stomach, breast cancer) or an antigen causing an autoimmune disease such as diabetes, multiple sclerosis (MS), celiac disease, Myalgic Encephalomyelitis (ME), psoriasis, and/or Crohn's Disease.

Accordingly confirmed and suspected autoimmune diseases, where relevant antigens may be derived include Achlorhydra Autoimmune Active Chronic Hepatitis, Acute Disseminated Encephalomyelitis, Acute hemorrhagic leukoencephalitis, Addison's Disease, Agammaglobulinemia, Alopecia areata, Amyotrophic Lateral Sclerosis, Ankylosing Spondylitis, Anti-GBM/TBM Nephritis, Antiphospholipid syndrome, Antisynthetase syndrome, Arthritis, Atopic allergy, Atopic Dermatitis, Autoimmune Aplastic Anemia, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome Types I, II, & III, Autoimmune progesterone dermatitis, Autoimmune thrombocytopenic purpura, Autoimmune uveitis, Balo disease/Balo concentric sclerosis, Bechets Syndrome, Berger's disease, Bickerstaff's encephalitis, Blau syndrome, Bullous Pemphigoid, Castleman's disease, Chagas disease, Chronic Fatigue Immune Dysfunction Syndrome, Chronic inflammatory demyelinating polyneuropathy, Chronic recurrent multifocal ostomyelitis, Chronic lyme disease, Chronic obstructive pulmonary disease, Churg-Strauss syndrome, Cicatricial Pemphigoid, Coeliac Disease, Cogan syndrome, Cold agglutinin disease, Complement component 2 deficiency, Cranial arteritis, CREST syndrome, Crohns Disease (one of two types of idiopathic inflammatory bowel disease "IBD"), Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Discoid lupus erythematosus, Eczema, Endometriosis, Enthesitis-related arthritis, Eosinophilic fasciitis, Epidermolysis bullosa acquisita, Erythema nodosum, Essential mixed cryoglobulinemia, Evan's syndrome, Fibrodysplasia ossificans progressiva, Fibromyalgia, Fibromyositis, Fibrosing aveolitis, Gastritis, Gastrointestinal pemphigoid, Giant cell arteritis, Glomerulonephritis, Goodpasture's syndrome, Graves' disease, Guillain-Barrě syndrome (GBS), Hashimoto's encephalitis, Hashimoto's thyroiditis, Haemolytic anaemia, Henoch-Schonlein purpura, Herpes gestationis, Hidradenitis suppurativa, Hughes syndrome (See Antiphospholipid syndrome), Hypogammaglobulinemia, Idiopathic Inflammatory Demyelinating Diseases, Idiopathic pulmonary fibrosis, Idiopathic thrombocytopenic purpura (See Autoimmune thrombocytopenic purpura), IgA nephropathy (Also Berger's disease), Inclusion body myositis, Inflammatory demyelinating polyneuopathy, Interstitial cystitis, Irritable Bowel Syndrome (IBS), Juvenile idiopathic arthritis, Juvenile rheumatoid arthritis, Kawasaki's Disease, Lambert-Eaton myasthenic syndrome, Leukocytoclastic vasculitis, Lichen planus, Lichen sclerosus, Linear IgA disease (LAD), Lou Gehrig's Disease (Also Amyotrophic lateral sclerosis), Lupoid hepatitis, Lupus erythematosus, Majeed syndrome, Meniere's disease, Microscopic polyangiitis, Miller-Fisher syndrome, Mixed Connective Tissue Disease, Morphea, Mucha-Habermann disease, Muckle-Wells syndrome, Multiple Myeloma, Multiple Sclerosis, Myasthenia gravis, Myositis, Narcolepsy, Neuromyelitis optica (Also Devic's Disease), Neuromyotonia, Occular cicatricial pemphigoid, Opsoclonus myoclonus syndrome, Ord thyroiditis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis, Pemphigus, Pemphigus vulgaris, Pernicious anaemia, Perivenous encephalomyelitis, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic Arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatoid fever, Sarcoidosis, Schizophrenia, Schmidt syndrome, Schnitzler syndrome, Scleritis, Scleroderma, Sjogren's syndrome, Spondyloarthropathy, Sticky blood syndrome, Still's Disease, Stiff person syndrome, Subacute bacterial endocarditis (SBE), Susac's syndrome, Sweet syndrome, Sydenham Chorea, Sympathetic ophthalmia, Takayasu's arteritis, Temporal arteritis (also known as "giant cell arteritis"), Tolosa-Hunt syndrome, Transverse Myelitis, Ulcerative Colitis (one of two types of idiopathic inflammatory bowel disease "IBD"), Undifferentiated connective tissue disease, Undifferentiated spondyloarthropathy, Vasculitis, Vitiligo, Wegener's granulomatosis, Wilson's syndrome, and Wiskott-Aldrich syndrome.

In some embodiments, in the peptide according to the present invention, the specific natural antigen is a viral protein, such as a structural protein, such as a capsid protein, a regulatory protein, an enzymatic protein, and a proteolytic protein.

In some embodiments, in the peptide according to the present invention, the viral protein is a protein, such as a structural protein, such as a core or envelope protein, of a virus selected from the Hepatitis C virus; influenza virus such as an M2 protein, human immunodeficiency virus (HIV), cytomegalovirus (CMV), and Human papillomavirus (HPV).

In some embodiments, in the peptide according to the present invention, the viral protein is a viral protein of Hepatitis C virus selected from any one HCV consensus sequence of a specific genotype, such as 1, such as subtypes 1a and 1b, genotype 2, such as 2a and 2b, genotype 3, such as 3a, genotype 4, genotype 5, and genotype 6.

In some embodiments, in the peptide according to the present invention, the sequence of amino acids defined by $X^1$-$X^2$-$X^3$-$X^4$-$X^5$-$X^6$ is not found in the native sequence of said natural antigen.

In some embodiments, in the peptide according to the present invention, the sequence of amino acids defined by $X^1$-$X^2$-$X^3$-$X^4$ is not found in the native sequence of said natural antigen.

In some embodiments, in the peptide according to the present invention, the sequence of amino acids defined by $X^1$-$X^2$-$X^3$ is not found in the native sequence of said natural antigen.

In some embodiments, in the peptide according to the present invention, the monomeric peptide is of 18-60 amino acids, such as of 19-60 amino acids, such as of 20-60 amino acids, such as of 21-60 amino acids, such as of 22-60 amino acids, such as of 23-60 amino acids, such as of 24-60 amino acids, such as of 25-60 amino acids, such as of 26-60 amino acids, such as of 27-60 amino acids, such as of 28-60 amino acids, such as of 29-60 amino acids, such as of 30-60 amino acids, such as of 31-60 amino acids, such as of 32-60 amino acids, such as of 33-60 amino acids, such as of 34-60 amino acids, such as of 35-60 amino acids, such as of 36-60 amino acids, such as of 37-60 amino acids, such as of 38-60 amino acids, such as of 39-60 amino acids, such as of 40-60 amino acids, such as of 42-60 amino acids, such as of 44-60 amino acids, such as of 46-60 amino acids, such as of 48-60 amino acids, such as of 50-60 amino acids, such as of 52-60 amino acids, such as of 54-60 amino acids, such as of 56-60 amino acids, such as of 58-60 amino acids.

In some embodiments, in the peptide according to the present invention, the monomeric peptide is of 18-60 amino acids, such as 18-58 amino acids, such as 18-56 amino acids, such as 18-54 amino acids, such as 18-52 amino acids, such as 18-50 amino acids, such as 18-48 amino acids, such as 18-46 amino acids, such as 18-44 amino acids, such as 18-42 amino acids, such as 18-40 amino acids, such as 18-39 amino acids, such as 18-38 amino acids, such as 18-37 amino acids, such as 18-36 amino acids, such as 18-35 amino acids, such as 18-34 amino acids, such as 18-33 amino acids, such as 18-32 amino acids, such as 18-31 amino acids, such as 18-30 amino acids, such as 18-29 amino acids, such as 18-28 amino acids, such as 18-27 amino acids, such as 18-26 amino acids, such as 18-25 amino acids, such as 18-24 amino acids, such as 18-23 amino acids, such as 18-22 amino acids, such as 18-21 amino acids, such as 18-20 amino acids, such as 18-19 amino acids.

In some embodiments, in the peptide according to the present invention, the monomeric peptide consist of not more than about 55 amino acids, such as not more than about 50 amino acids, such as not more than about 45 amino acids, such as not more than about 40 amino acids, such as not more than about 38 amino acids, such as not more than about 36 amino acids, such as not more than about 34 amino acids, such as not more than about 32 amino acids, such as not more than about 30 amino acids, such as not more than about 28 amino acids, such as not more than about 26 amino acids, such as not more than about 24 amino acids, such as not more than about 22 amino acids, such as not more than about 20 amino acids, such as not more than about 18 amino acids, such as not more than about 16 amino acids, such as not more than about 14 amino acids, such as not more than about 12 amino acids, such as not more than about 10 amino acids.

In some embodiments, in the peptide according to the present invention, the monomeric peptide consist of at least about 10 amino acids, such as at least about 12 amino acids, such as at least about 14 amino acids, such as at least about 16 amino acids, such as at least about 18 amino acids, such as at least about 20 amino acids, such as at least about 22 amino acids, such as at least about 24 amino acids, such as at least about 26 amino acids, such as at least about 28 amino acids, such as at least about 30 amino acids, such as at least about 32 amino acids, such as at least about 34 amino acids, such as at least about 36 amino acids, such as at least about 38 amino acids, such as at least about 40 amino acids, such as at least about 45 amino acids, such as at least about 50 amino acids, such as at least about 55 amino acids, such as at least about 60.

In some embodiments, in the peptide according to the present invention, $X^2$, $X^4$, and optional moiety $X^6$ each independently defines a linear sequence of 5-12 amino acids, such as 5-10 amino acids, such as 5-8 amino acids.

In some embodiments, in the peptide according to the present invention, $X^1$, $X^3$ and optional moiety $X^5$ each independently defines a linear sequence of any 1, 2, 3, 4, or 5 amino acid independently selected from glycine, arginine, tryptophan, and cysteine, and derivatives thereof. In some embodiments, in the peptide according to the present invention, the overall net charge of $X^1$-$X^2$-$X^3$-$X^4$-$X^5$-$X^6$ is equal to or above 0, such as above 1, 2, 3, 4, or 5.

In some embodiments, in the peptide according to the present invention, $X^1$, $X^3$ and optional moiety $X^5$ each independently defines a linear sequence of any 1, 2, 3, 4, or 5 amino acid independently selected from glycine, arginine, norleucine, aspartic acid, glutamic acid, glutamine, serine, lysine, tryptophan, cysteine, ornithine, diaminopropionic acid (Dpr) and derivatives thereof. In some embodiments, in the peptide according to the present invention, the overall net charge of $X^1$-$X^2$-$X^3$-$X^4$-$X^5$-$X^6$ is equal to or above 0, such as above 1, 2, 3, 4, or 5.

In some embodiments, in the peptide according to the present invention, $X^1$, $X^3$ and optional moiety $X^5$ each independently defines a linear sequence of any 1, 2, 3, 4, or 5 amino acid independently selected from glycine, arginine, tryptophan, and cysteine, and derivatives thereof. In some embodiments, in the peptide according to the present invention, the overall net charge of $X^1$-$X^2$-$X^3$-$X^4$-$X^5$-$X^6$ is equal to or above 0, such as above 1, 2, 3, 4, or 5.

In some embodiments, in the peptide according to the present invention, the overall net charge of any one sequence selected from $X^1$, $X^2$, $X^3$, $X^4$, $X^5$, and $X^6$ is equal to or above 0, such as above 1, 2, 3, 4, or 5.

It is to be understood that parts of the monomeric peptide, such as any one sequence selected from $X^1$, $X^2$, $X^3$, $X^4$, $X^5$, and $X^6$, such as $X^3$ or $X^5$, may have an overall net charge below 0, if other parts of the monomeric peptide such as any one other sequence selected from $X^1$, $X^2$, $X^3$, $X^4$, $X^5$, and $X^6$ has an overall net charge above 0.

It is essential that parts of the monomeric peptide is able to attach to a cell surface, such as a helper cell, which binding is facilitated by a positive net charge of the sequence at the place of binding to the cell membrane.

In some embodiments, in the peptide according to the present invention, the monomeric peptide is capable of inducing a humoral immune response.

In some embodiments, in the peptide according to the present invention, the sequence $X^1$ and/or $X^3$ and/or $X^5$ is selected from K, Lys(Me), RRG, G(Dpr(Ser))G, Dpr, Dpr(ser), GG(Dpr(Ser))GG (SEQ ID NO:150), GEG, CS, GDG, E, G(Lys(Me))G, D, RR, WWGC (SEQ ID NO: 54), RRG, RRZC (SEQ ID NO: 55), WWQC (SEQ ID NO: 56), WW, RR-Har, Har, WDWGC (SEQ ID NO: 57), CGG, CGGG (SEQ ID NO: 58), GCGG (SEQ ID NO: 59), G, GKG, GC, GG, C, R, GCG, CG, GRR, GGCGG (SEQ ID NO: 60), CGGKG (SEQ ID NO: 61), CGGKGG (SEQ ID NO: 62), GGKGG (SEQ ID NO: 63), KG, and GWK.

In some embodiments, in the peptide according to the present invention, the sequence $X^2$ and/or $X^4$ and/or $X^6$ is selected from SLLTEVETP (SEQ ID NO: 64), SLZTDIETP (SEQ ID NO: 65), TDIET (SEQ ID NO: 66), CSLLT (SEQ ID NO: 67), SLLTEVQTPIRN (SEQ ID NO: 68), TPIRSEWGCRSN (SEQ ID NO: 69), IDTPIR (SEQ ID NO: 70), AKRRV (SEQ ID NO: 71), IEEEG (SEQ ID NO: 72), AKRRVV (SEQ ID NO: 73), DQQLL (SEQ ID NO: 74), AEEEVV (SEQ ID NO: 75), GIEEE (SEQ ID NO: 76), IEEEGGRDRDR (SEQ ID NO: 77), CAKRRVVC (SEQ ID NO: 78), IEEEGGERDRDR (SEQ ID NO: 79), IEEEG-GQDRDR (SEQ ID NO: 80), IEEEGGEQDRDR (SEQ ID NO: 81), EEEIGGRDRD (SEQ ID NO: 82), RLEPWKH (SEQ ID NO: 83), FHSQV (SEQ ID NO: 84), FITKGL-GISY (SEQ ID NO: 85), LLADARVCS (SEQ ID NO: 86), GV(Nle)AGIAYFS (SEQ ID NO: 87), VETPIR (SEQ ID NO: 88), VETPIRN (SEQ ID NO: 89), SNDSS (SEQ ID NO: 90), TPIBQDWG (SEQ ID NO: 91), AKRRV-VQREKRA (SEQ ID NO: 92), IEEEGGERDR (SEQ ID NO: 93), AEEEIV (SEQ ID NO: 94), RDRDR (SEQ ID NO: 95), ERDRDR (SEQ ID NO: 96), AKRRVVEREKRA (SEQ ID NO: 97), QDRDR (SEQ ID NO: 98), EQDRDR (SEQ ID NO: 99), RDRDQ (SEQ ID NO: 100), GSQPKTA (SEQ ID NO: 101), FITKGLGISYGRK (SEQ ID NO: 102), LLA-DARVSA (SEQ ID NO: 103), GVLAGIAYYS (SEQ ID NO: 104), TPIRNEWG (SEQ ID NO: 105), SEWGSRSN (SEQ ID NO: 106), SLZTDIETPG (SEQ ID NO: 107), QREKRAV (SEQ ID NO: 108), QREKR (SEQ ID NO: 109), IEEEGG (SEQ ID NO: 110), EREKRA (SEQ ID NO: 111), QREKRA (SEQ ID NO: 112), ERDRD (SEQ ID NO: 113), HPGSQ (SEQ ID NO: 114), TPIXQEW (SEQ ID NO: 151), EQDRDRGG (SEQ ID NO: 152), GNWAKVL (SEQ ID NO: 153), LLADARV (SEQ ID NO: 154), NWAKVI (SEQ ID NO: 155), and SGADRV (SEQ ID NO: 156).

In some embodiments, in the peptide according to the present invention, the monomeric peptide comprises at least one, such as one, two, three, four, or five amino acids selected from a Cys, a Lys, a Ser, an Asp, and a Glu residue, or derivatives thereof.

In some embodiments, in the peptide according to the present invention, the monomeric peptide comprises at least one cysteine, such as one, two, three, four, or five cysteines.

Some cysteines may be involved in intramolecular Cys-Cys bonds, whereas others may be involved in the bonding to another peptide monomer, i.e. an intermolecular bond.

In some embodiments in the peptide according to the present invention, the sequence $X^1$ and/or $X^3$ and/or $X^5$ is as defined in table 1.

In some embodiments in the peptide according to the present invention, the sequence $X^2$ and/or $X^4$ and/or $X^6$ is as defined in table 1.

In some embodiments the peptide with the structure $X^1$-$X^2$-$X^3$-$X^4$-$X^5$-$X^6$ is as defined in table 1.

In some embodiments in the multimeric peptide according to the present invention is a dimeric peptide.

In some embodiments the multimeric, such as a dimeric peptide comprising two, three, four, five, six, seven, eight, nine or ten monomeric peptides with the structure $X^1$-$X^2$-$X^3$-$X^4$-$X^5$-$X^6$, is as defined in table 1.

In some embodiments in the peptide according to the present invention, the sequence $X^2$ and/or $X^4$ and/or $X^6$ defines a sequence of 4-17, such as 5-16, such as 5-15, such as 5-14, such as 5-13, such as 5-12, such as 5-10 amino acids.

In some embodiments in the peptide according to the present invention, the sequence $X^2$ and/or $X^4$ and/or $X^6$ defines a sequence of more than 5, such as more than 6, such as more than 7, such as more than 8, such as more than 9, such as more than 10, such as more than 11, such as more than 12, such as more than 13, such as more than 14, such as more than 15, such as more than 16 amino acids.

In some embodiments in the peptide according to the present invention, the sequence $X^2$ and/or $X^4$ and/or $X^6$ defines a sequence of less than 17, such as less than 16, such as less than 15, such as less than 14, such as less than 13, such as less than 12, such as less than 11, such as less than 10, such as less than 9, such as less than 8, such as less than 7, such as less than 6 amino acids.

In some embodiments in the peptide according to the present invention, the sequence $X^1$ and/or $X^3$ and/or $X^5$ defines a sequence that contain one or more amino acid selected from glycine (G), arginine (R), norleucine (Nle), aspartic acid (D), glutamic acid (E), glutamine (Q), serine (S), lysine (K), tryptophan (W), cysteine (C), Ornithine, diaminopropionic acid (Dpr) and a derivative thereof.

In some embodiments in the peptide according to the present invention, the monomeric peptide contain one or more intramolecular bond, such as one or more Cys-Cys bond.

In some embodiments in the peptide according to the present invention, the monomeric peptide has delayed proteolytic degradation in the N-terminal, such as by incorporation of the first 1, 2, or 3 amino acids in the N-terminal in the D-form, or by incorporation of the first 1, 2, or 3 amino acids in the N-terminal in beta or gamma form.

In some embodiments, in the multimeric, such as a dimeric peptide according to the present invention, the two or more monomeric peptides are identical in sequence.

In some embodiments, in the multimeric, such as dimeric peptide according to the present invention, the two or more monomeric peptides are different in sequence.

In some embodiments, in the multimeric, such as dimeric peptide according to the present invention, one, two or more of the peptide strands of the multimeric, such as dimeric peptide has delayed proteolytic degradation in the N-terminal, such as by incorporation of the first 1, 2, or 3 amino acids in the N-terminal in the D-form, or by incorporation of the first 1, 2, or 3 amino acids in the N-terminal in beta or gamma form.

In some embodiments, in the multimeric, such as dimeric peptide according to the present invention, the linker is placed within any sequence selected from $X^1$, $X^2$, $X^3$, $X^4$, $X^5$, and $X^6$, such as in $X^1$, $X^2$ or $X^3$ of the first monomeric peptide to anywhere on the at least one second monomeric peptide, such as within the sequence of $X^1$, $X^2$ or $X^3$.

In some embodiments, in the multimeric, such as dimeric peptide according to the present invention, the linker is placed at an amino acid position selected from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 of the first monomeric peptide to a position selected from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 of the at least one second monomeric peptide.

In some embodiments, in the multimeric, such as dimeric peptide according to the present invention, the linker is placed in $X^1$, $X^2$ or $X^3$ of the first monomeric peptide to anywhere on the at least one second monomeric peptide, such as within the sequence of $X^1$, $X^2$ or $X^3$.

In some embodiments, in the multimeric, such as dimeric peptide according to the present invention, the multimeric, such as dimeric peptide contain a helper epitope of at least 12 amino acids, such as at least 13, 14, 15 or 17 amino acids, which helper epitope consist of a combined sequence of amino acids, which is a sequence of amino acids from the first monomeric peptide, and a sequence of amino acids from the at least one second monomeric peptide, such as between 2-12 amino acids from the first monomeric peptide and 2-12 amino acids from the at least one second monomeric peptide.

It is to be understood that an epitope may not only be present within the sequence of the monomeric peptide. An epitope may also be present with a combination of amino acids of the first and the at least one second monomeric peptide in a multimeric, such as dimeric peptide sequence, wherein this combination of amino acids forms a sequence that span from the first to the at least one second monomeric peptide sequence. This epitope may be a continuous sequence of amino acids or it may be a three-dimensional epitope with amino acids found in both monomeric peptides.

In some embodiments, in the multimeric, such as dimeric peptide according to the present invention, the intermolecular bond is a disulfide (S—S) bond between two Cys residues.

In some embodiments, in the multimeric, such as dimeric peptide according to the present invention, the intermolecular bond is a methylated peptide bond between a N-ε-methylated Lys side-chain and the side-chain of an Asp or Glu residue.

In some embodiments, in the multimeric, such as dimeric peptide according to the present invention, the intermolecular bond is a thioether bond between a Cys residue in the first monomeric peptide and a modified Lys residue in the at least one second monomeric peptide.

In some embodiments, in the multimeric, such as dimeric peptide according to the present invention, the intermolecular bond is an oxime bond.

In some embodiments, in the multimeric, such as dimeric peptide according to the present invention, the intermolecular bond is an oxime bond between a derivatized Lys residue in the first monomeric peptide and a derivatized Ser residue in the at least one second monomeric peptide.

In some embodiments, in the multimeric, such as dimeric peptide according to the present invention, the intermolecular bond is an oxime bond between a derivatized lysine, ornitine or diaminopropionic acid residue in the first monomeric peptide and a derivatized serine moiety, such as a serine residue, such as in a serinyl diaminopropionic acid residue, such as in a serinyl lysin residue or such as in a serinyl ornitine residue, in the at least one second monomeric peptide.

In some embodiments, in the multimeric, such as dimeric peptide according to the present invention, the monomeric peptides are linked by a polyethylene glycol (PEG) linker, such as through an Asp or a Glu residue in the first monomeric peptide and an Asp or a Glu residue in the at least one second monomeric peptide.

In some embodiments, in the multimeric, such as dimeric peptide according to the present invention, any one of the monomeric peptides is independently as defined herein.

In some embodiments, the peptide according to the present invention is essentially a non-cell-penetrating peptide. In other embodiments, the peptide according to the present invention is a cell-penetrating peptide. In some embodiments, the peptide according to the present invention is able to attach to the cell membrane of an antigen presenting cell.

It is to be understood that when referring to the peptides ability to attach to and enter a cell, such as an antigen presenting cell, it may be with reference to the complete sequence of the peptide as well as a fragment thereof, such as a fragment representing an epitope.

Accordingly, it may be the case that the entire sequence is essentially a non-cell-penetrating peptide, whereas a fragment of the peptide is able to efficiently enter a cell, such as an antigen presenting cell.

In some embodiments, the peptide according to the present invention is not a peptide or a dimeric peptide as specifically disclosed in International Patent Application No: PCT/DK2011/050460.

In some embodiments, the peptide according to the present invention is not a peptide or a dimeric peptide as specifically disclosed in International Patent Application No: PCT/EP2010/059513, such as one selected from:

```
                                        (SEQ ID NO: 115)
CGGAKRRVVGGAKRRVVGQREKRAV (SEQ ID NO: 116)
CGGGDQQLLGGAEEEIVGGIEEEGGERDRDR (SEQ ID NO: 117)
CGGAKRRVVGGAKRRVVGGQREKR (SEQ ID NO: 118)
CGGGDQQLLGGAEEEIVGGIEEEGG (SEQ ID NO: 119)
CGGAEEEVVGGDQQLL (SEQ ID NO: 120)
GCGGAKRRVVGGAKRRVV (SEQ ID NO: 121)
GAKRRVVGGCGGAKRRVVQREKRAGEREKRA (SEQ ID NO: 122)
GKGGIEEEGGRDRDRGGEQDRDR (SEQ ID NO: 123)
GAKRRVVGGCGGAKRRVVQREKRAGEREKRA (SEQ ID NO: 124)
GKGGIEEEGGERDRDRGGQDRDR (SEQ ID NO: 125)
GAKRRVVGGCGGAKRRVVEREKRAGQREKRA (SEQ ID NO: 126)
GKGGIEEEGGQDRDRGGRDRDR (SEQ ID NO: 127)
GAKRRVVGGCGGAKRRVVEREKRAGQREKRA (SEQ ID NO: 128)
GKGGIEEEGGEQDRDRGGERDRD
```

In some embodiments, the peptide according to the present invention is not a dimeric peptide selected from (The peptides are linked via the underlined amino acid):

```
CGGAKRRVVGGAKRRVVGQREKRAV
|
CGGGDQQLLGGAEEEIVGGIEEEGGERDRDR;

CGGAKRRVVGGAKRRVVGGQREKR
|
CGGGDQQLLGGAEEEIVGGIEEEGG;

CGGAEEEVVGGDQQLL
 |
GCGGAKRRVVGGAKRRVV;

GAKRRVVGGCGGAKRRVVQREKRAGEREKRA
         |
        GKGGIEEEGGRDRDRGGEQDRDR;

GAKRRVVGGCGGAKRRVVQREKRAGEREKRA
         |
        GKGGIEEEGGERDRDRGGQDRDR;

GAKRRVVGGCGGAKRRVVEREKRAGQREKRA
         |
        GKGGIEEEGGQDRDRGGRDRDR;

GAKRRVVGGCGGAKRRVVEREKRAGQREKRA
         |
        GKGGIEEEGGEQDRDRGGERDRD;

CGGAKRRVVGGAKRRVVGQREKRAV
|
CGGGDQQLLGGAEEEIVGGIEEEGG;

CGGAKRRVVGGAKRRVVGQREKRAV
 |
GCGGAKRRVVGGAKRRVV;

CGGAKRRVVGGAKRRVVGGQREKR
|
CGGGDQQLLGGAEEEIVGGIEEEGGERDRDR;

CGGAKRRVVGGAKRRVVGGQREKR
 |
GCGGAKRRVVGGAKRRVV;

CGGAEEEVVGGDQQLL
|
CGGGDQQLLGGAEEEIVGGIEEEGGERDRDR;

CGGAEEEVVGGDQQLL
|
CGGGDQQLLGGAEEEIVGGIEEEGG;

GAKRRVVGGCGGAKRRVVQREKRAGEREKRA
         |
        GKGGIEEEGGQDRDRGGRDRDR;

GAKRRVVGGCGGAKRRVVQREKRAGEREKRA
         |
        GKGGIEEEGGEQDRDRGGERDRD;

GAKRRVVGGCGGAKRRVVEREKRAGQREKRA
         |
        GKGGIEEEGGRDRDRGGEQDRDR;
or

GAKRRVVGGCGGAKRRVVEREKRAGQREKRA
         |
        GKGGIEEEGGERDRDRGGQDRDR.
```

Numbered embodiments according to the present invention:

1. An isolated monomeric peptides consisting of not more than 60 amino acids with the following structure $$X^1\text{-}X^2\text{-}X^3\text{-}X^4\text{-}X^5\text{-}X^6 \quad \text{(formula I)},$$

wherein $X^1$, $X^3$ and optional moiety $X^5$ each independently defines a linear sequence of any 1, 2, 3, 4, or 5 amino acid independently selected from glycine, arginine, norleucine, glutamine, serine, lysine, tryptophan, cysteine, or a derivative thereof; $X^2$, $X^4$, and optional moiety $X^6$ each independently defines a linear sequence of 5-17 amino acids, each having more than 50% sequence identity to a specific natural antigen.

2. The isolated monomeric peptide according to embodiment 1, wherein $X^2$ and/or $X^4$ and/or $X^6$ has more than 55%, such as more than 60%, such as more than 65%, such as more than 70%, such as more than 75%, such as more than 80%, such as more than 85%, such as more than 90%, such as more than 95%, such as more than 96%, such as more than 97%, such as more than 98%, such as more than 99%, such as 100% sequence identity to a specific natural antigen.

3. The isolated monomeric peptide according to embodiments 1 or 2, wherein said specific natural antigen is a protein or peptide sequence derived from a disease antigen, such as an infectious agent, such as bacteria, virus, parasite, fungus, or cancer antigens such as oncogene (lung, stomach, breast cancer) or an antigen causing an autoimmune disease such as diabetes, multiple sclerosis (MS), celiac disease, Myalgic Encephalomyelitis (ME), psoriasis, and/or Crohn's Disease.

4. The isolated monomeric peptide according to any one of embodiments 1-3, wherein said specific natural antigen is a viral protein, such as a structural protein, such as a capsid protein, a regulatory protein, an enzymatic protein, and a proteolytic protein.

5. The isolated monomeric peptide according to any one of embodiments 1-4, wherein said viral protein is a protein, such as a core protein, of a virus selected from the Hepatitis C virus; influenza virus, such as an M2 protein, human immunodeficiency virus (HIV), cytomegalovirus (CMV), and Human papillomavirus (HPV).

6. The isolated monomeric peptide according to embodiment 5, wherein said viral protein is a viral protein of Hepatitis C virus selected from any one HCV consensus sequence of a specific genotype, such as 1, such as subtypes 1a and 1b, genotype 2, such as 2a and 2b, genotype 3, such as 3a, genotype 4, genotype 5, and genotype 6.

7. The isolated monomeric peptide according to any one of embodiments 1-3, wherein the sequence of amino acids defined by $X^1$-$X^2$-$X^3$-$X^4$-$X^5$-$X^6$ is not found in the native sequence of said natural antigen.

8. The isolated monomeric peptide according to any one of embodiments 1-7, which monomeric peptide is of 18-60 amino acids, such as of 19-60 amino acids, such as of 20-60 amino acids, such as of 21-60 amino acids, such as of 22-60 amino acids, such as of 23-60 amino acids, such as of 24-60 amino acids, such as of 25-60 amino acids, such as of 26-60 amino acids, such as of 27-60 amino acids, such as of 28-60 amino acids, such as of 29-60 amino acids, such as of 30-60 amino acids, such as of 31-60 amino acids, such as of 32-60 amino acids, such as of 33-60 amino acids, such as of 34-60 amino acids, such as of 35-60 amino acids, such as of 36-60 amino acids, such as of 37-60 amino acids, such as of 38-60 amino acids, such as of 39-60 amino acids, such as of 40-60 amino acids, such as of 42-60 amino acids, such as of 44-60 amino acids, such as of 46-60 amino acids, such as of 48-60 amino acids, such as of 50-60 amino acids, such as of 52-60 amino acids, such as of 54-60 amino acids, such as of 56-60 amino acids, such as of 58-60 amino acids.

9. The isolated monomeric peptide according to any one of embodiments 1-8, which monomeric peptide is of 18-60 amino acids, such as 18-58 amino acids, such as 18-56 amino acids, such as 18-54 amino acids, such as 18-52 amino acids, such as 18-50 amino acids, such as 18-48 amino acids, such as 18-46 amino acids, such as 18-44 amino acids, such as 18-42 amino acids, such as 18-40 amino acids, such as 18-39 amino acids, such as 18-38 amino acids, such as 18-37 amino acids, such as 18-36 amino acids, such as 18-35 amino acids, such as 18-34 amino acids, such as 18-33 amino acids, such as 18-32 amino acids, such as 18-31 amino acids, such as 18-30 amino acids, such as 18-29 amino acids, such as 18-28 amino acids, such as 18-27 amino acids, such as 18-26 amino acids, such as 18-25 amino acids, such as 18-24 amino acids, such as 18-23 amino acids, such as 18-22 amino acids, such as 18-21 amino acids, such as 18-20 amino acids, such as 18-19 amino acids.

10. The isolated monomeric peptide according to any one of embodiments 1-9, which monomeric peptide consist of not more than about 55 amino acids, such as not more than about 50 amino acids, such as not more than about 45 amino acids, such as not more than about 40 amino acids, such as not more than about 38 amino acids, such as not more than about 36 amino acids, such as not more than about 34 amino acids, such as not more than about 32 amino acids, such as not more than about 30 amino acids, such as not more than about 28 amino acids, such as not more than about 26 amino acids, such as not more than about 24 amino acids, such as not more than about 22 amino acids, such as not more than about 20 amino acids, such as not more than about 18 amino acids, such as not more than about 16 amino acids, such as not more than about 14 amino acids, such as not more than about 12 amino acids, such as not more than about 10 amino acids.

11. The isolated monomeric peptide according to any one of embodiments 1-10, which monomeric peptide consist of at least about 10 amino acids, such as at least about 12 amino acids, such as at least about 14 amino acids, such as at least about 16 amino acids, such as at least about 18 amino acids, such as at least about 20 amino acids, such as at least about 22 amino acids, such as at least about 24 amino acids, such as at least about 26 amino acids, such as at least about 28 amino acids, such as at least about 30 amino acids, such as at least about 32 amino acids, such as at least about 34 amino acids, such as at least about 36 amino acids, such as at least about 38 amino acids, such as at least about 40 amino acids, such as at least about 45 amino acids, such as at least about 50 amino acids, such as at least about 55 amino acids, such as at least about 60.

12. The isolated monomeric peptide according to any one of embodiments 1-11, wherein the overall net charge of $X^1$-$X^2$-$X^3$-$X^4$-$X^5$-$X^6$ is equal to or above 0, such as above 1, 2, 3, 4, or 5.

13. The isolated monomeric peptide according to any one of embodiments 1-12, wherein said monomeric peptide is capable of inducing a humoral immune response.

14. The isolated monomeric peptide according to any one of embodiments 1-13, wherein said sequence $X^1$ and/or $X^3$ and/or $X^5$ is selected from RR, WWGC (SEQ ID NO: 54), RRG, RRZC (SEQ ID NO: 55), WWQC (SEQ ID NO: 56), WW, RR-Har, Har, WDWGC (SEQ ID NO: 57), CGG, CGGG (SEQ ID NO: 58), GCGG (SEQ ID NO: 59), G, GKG, GC, GG, C, R, GCG, CG, GRR, GGCGG (SEQ ID NO: 60), CGGKG (SEQ ID NO: 61), CGGKGG (SEQ ID NO: 62), GGKGG (SEQ ID NO: 63), KG, and GWK.

15. The isolated monomeric peptide according to any one of embodiments 1-14, wherein said sequence $X^2$ and/or $X^4$ and/or $X^6$ is selected from SLLTEVETP (SEQ ID NO: 64), SLZTDIETP (SEQ ID NO: 65), TDIET (SEQ ID NO: 66), CSLLT (SEQ ID NO: 67), SLLTEVQTPIRN (SEQ ID NO: 68), TPIRSEWGCRSN (SEQ ID NO: 69), IDTPIR (SEQ ID NO: 70), AKRRV (SEQ ID NO: 71), IEEEG (SEQ ID NO: 72), AKRRVV (SEQ ID NO: 73), DQQLL (SEQ ID NO: 74), AEEEVV (SEQ ID NO: 75), GIEEE (SEQ ID NO: 76), IEEEGGRDRDR (SEQ ID NO: 77), CAKRRVVC (SEQ ID NO: 78), IEEEGGERDRDR (SEQ ID NO: 79), IEEEG-GQDRDR (SEQ ID NO: 80), IEEEGGEQDRDR (SEQ ID NO: 81), EEEIGGRDRD (SEQ ID NO: 82), RLEPWKH (SEQ ID NO: 83), FHSQV (SEQ ID NO: 84), FITKGL-GISY (SEQ ID NO: 85), LLADARVCS (SEQ ID NO: 86), GV(Nle)AGIAYFS (SEQ ID NO: 87), VETPIR (SEQ ID NO: 88), VETPIRN (SEQ ID NO: 89), SNDSS (SEQ ID NO: 90), TPIBQDWG (SEQ ID NO: 91), AKRRV-VQREKRA (SEQ ID NO: 92), IEEEGGERDR (SEQ ID NO: 93), AEEEIV (SEQ ID NO: 94), RDRDR (SEQ ID NO: 95), ERDRDR (SEQ ID NO: 96), AKRRVVEREKRA (SEQ ID NO: 97), QDRDR (SEQ ID NO: 98), EQDRDR (SEQ ID NO: 99), RDRDQ (SEQ ID NO: 100), GSQPKTA (SEQ ID NO: 101), FITKGLGISYGRK (SEQ ID NO: 102), LLA-DARVSA (SEQ ID NO: 103), GVLAGIAYYS (SEQ ID NO: 104), TPIRNEWG (SEQ ID NO: 105), SEWGSRSN (SEQ ID NO: 106), SLZTDIETPG (SEQ ID NO: 107), QREKRAV (SEQ ID NO: 108), QREKR (SEQ ID NO: 109), IEEEGG (SEQ ID NO: 110), EREKRA (SEQ ID NO: 111), QREKRA (SEQ ID NO: 112), ERDRD (SEQ ID NO: 113), and HPGSQ (SEQ ID NO: 114).

16. The isolated monomeric peptide according to any one of embodiments 1-15, wherein said monomeric peptide comprises at least one amino acid selected from a Cys, a Lys, a Ser, an Asp, and a Glu residue, or derivatives thereof.

17. The isolated monomeric peptide according to any one of embodiments 1-16, wherein said sequence $X^1$ and/or $X^3$ and/or $X^5$ is as defined in table 1.

18. The isolated monomeric peptide according to any one of embodiments 1-17, wherein said sequence $X^2$ and/or $X^4$ and/or $X^6$ is as defined in table 1.

19. The isolated monomeric peptide according to any one of embodiments 1-18, wherein said sequence $X^2$ and/or $X^4$ and/or $X^6$ defines a sequence of 4-17, such as 5-16, such as 5-15, such as 5-14, such as 5-13, such as 5-12, such as 5-10 amino acids.

20. The isolated monomeric peptide according to any one of embodiments 1-19, which monomeric peptide contain one or more intramolecular bond, such as one or more Cys-Cys bond.

21. The isolated monomeric peptide according to any one of embodiments 1-20, which monomeric peptide has delayed proteolytic degradation in the N-terminal, such as by incorporation of the first 1, 2, or 3 amino acids in the N-terminal in the D-form, or by incorporation of the first 1, 2, or 3 amino acids in the N-terminal in beta or gamma form.

22. An isolated multimeric, such as dimeric peptide comprising two or more monomeric peptides, each monomeric peptide independently consisting of not more than 60 amino acids with the following structure

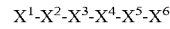

$X^1$-$X^2$-$X^3$-$X^4$-$X^5$-$X^6$ (formula I), wherein $X^1$, $X^3$ and optional moiety $X^5$ independently defines a linear sequence of any 1, 2, 3, 4, or 5 amino acid independently selected from glycine, arginine, norleucine, glutamine, serine, lysine, tryptophan, cysteine, or a derivative thereof; $X^2$, $X^4$, and optional moiety $X^6$ each independently defines a linear sequence of 5-17 amino acids, each having more than 50% sequence identity to a specific natural antigen, said monomeric peptides being covalently joined by one or more intermolecular bond.

23. The isolated dimeric peptide according to embodiment 22, wherein two or more monomeric peptides are identical in sequence.

24. The isolated dimeric peptide according to embodiment 22, wherein two or more monomeric peptides are different in sequence.

25. The isolated multimeric, such as dimeric peptide according to any one of embodiments 22-24, wherein one or more peptide strands of the multimeric, such as dimeric peptide has delayed proteolytic degradation in the N-terminal, such as by incorporation of the first 1, 2, or 3 amino acids in the N-terminal in the D-form, or by incorporation of the first 1, 2, or 3 amino acids in the N-terminal in beta or gamma form.

26. The isolated multimeric, such as dimeric peptide according to any one of embodiments 22-25, wherein the linker is placed within any sequence selected from $X^1$, $X^2$, $X^3$, $X^4$, $X^5$, and $X^6$, such as in $X^1$, $X^2$ or $X^3$ of the first monomeric peptide to anywhere on the at least one second monomeric peptide, such as within the sequence of $X^1$, $X^2$ or $X^3$.

27. The isolated multimeric, such as dimeric peptide according to any one of embodiments 22-26, which multimeric, such as dimeric peptide contain a helper epitope of at least 12 amino acids, such as at least 13, 14, 15 or 17 amino acids, which helper epitope consist of a combined sequence of amino acids, which is a sequence of amino acids from the first monomeric peptide, and a sequence of amino acids from the at least one second monomeric peptide, such as between 2-12 amino acids from the first monomeric peptide and 2-12 amino acids from the at least one second monomeric peptide.

28. The isolated multimeric, such as dimeric peptide according to any one of embodiments 22-27, wherein said intermolecular bond is selected from a disulfide (S—S) bond between two Cys residues.

29. The isolated multimeric, such as dimeric peptide according to any one of embodiments 22-28, wherein said intermolecular bond is a thioether bond between a Cys residue in the first monomeric peptide and a modified Lys residue in the at least one second monomeric peptide.

30. The isolated multimeric, such as dimeric peptide according to any one of embodiments 22-29, wherein said intermolecular bond is an oxime bond between a derivatized Lys residue in the first monomeric peptide and a derivatized Ser residue in the at least one second monomeric peptide.

31. The isolated multimeric, such as dimeric peptide according to any one of embodiments 22-30, wherein said intermolecular bond is a methylated peptide bond between a N-ε-methylated Lys side-chain in the first monomeric peptide and the side-chain of an Asp or Glu residue in the at least one second monomeric peptide.

32. The isolated multimeric, such as dimeric peptide according to any one of embodiments 22-31, wherein said monomeric peptides are linked by a polyethylene glycol (PEG) linker, such as through an Asp or a Glu residue in the first monomeric peptide and an Asp or a Glu residue in the at least one second monomeric peptide, or by a polyLys core.

33. The isolated multimeric, such as dimeric peptide according to any one of embodiments 22-31, wherein any one of said monomeric peptide is independently as defined in any one of embodiments 1-21.

34. Composition comprising two or more compounds selected from a monomeric peptide as defined in any one of embodiments 1-21, and an isolated multimeric, such as dimeric peptide as defined in any one of embodiments 22-33.

35. Use of a peptide selected from a monomeric peptide as defined in any one of embodiments 1-21, and an isolated multimeric, such as dimeric peptide as defined in any one of embodiments 22-33 for inducing a humoral immune response in a subject.

36. An isolated nucleic acid or polynucleotide encoding a peptide according to any one of embodiments 1-33.

37. A vector comprising the nucleic acid or polynucleotide according to embodiment 36.

38. A host cell comprising the vector according to embodiment 37.

39. An immunogenic composition comprising at least one monomeric peptide according to any one of embodiments 1-21, an isolated multimeric, such as dimeric peptide according to any one of embodiments 22-33, a peptide composition according to embodiment 34, the nucleic acid or polynucleotide according to embodiment 36, or the vector according to embodiment 37; in combination with a pharmaceutically acceptable diluent or vehicle and optionally an immunological adjuvant.

40. The immunogenic composition according to embodiment 39 in the form of a vaccine composition.

41. A method for inducing an immune response in a subject against an antigen which comprises administration of at least one monomeric peptide according to any one of embodiments 1-21, an isolated multimeric, such as dimeric peptide according to any one of embodiments 22-33, a peptide composition according to embodiment 34, the nucleic acid or polynucleotide according to embodiment 36, or the vector according to embodiment 37; or the composition according to any one of embodiments 39-40.

42. A method for reducing and/or delaying the pathological effects of a disease antigen, such as an infectious agent in a subject infected with said agent or having said disease caused by said antigen, the method comprising administering an effective amount of at least one monomeric peptide according to any one of embodiments 1-21, an isolated multimeric, such as dimeric peptide according to any one of embodiments 22-33, a peptide composition according to embodiment 34, the nucleic acid or polynucleotide according to embodiment 36, or the vector according to embodiment 37; or the composition according to any one of embodiments 39-40.

43. A peptide according to any one of embodiments 1-33 for use as a medicament.

44. A peptide according to any one of embodiments 1-33 for treating the pathological effects of a disease antigen, such as an infectious agent in a subject infected with said agent or having said disease caused by said antigen.

45. A peptide according to any one of embodiments 1-33 for use in an in vitro assay, such as an ELISA assay, such as for diagnostic purposes.

46. Use of a peptide according to any one of embodiments 1-33 for in vitro assay, such as an ELISA assay, such as for diagnostic purposes.

Sequence list (amino acids in bold represents suitable antigenic sequences that may be used as any of $X^2$ and/or $X^4$ and/or $X^6$ as defined in formula I of the present invention)

SEQ ID NO: 1: Flu M2
>gi|21693176|gb|AAM75162|/Human/M2/H1N1/Puerto Rico/1934/// matrix protein M2 [Influenza A virus (A/Puerto Rico/8/34/Mount Sinai(H1N1))]
MSLLTEVETPIRNEWGCRCNGSSDPLAIAANIIGILHLTLWILDRLFFKCIYRRFKYGLKGGPSTEGVPK

SMREEYRKEQQSAVDADDGHFVSIELE

SEQ ID NO: 2: >gi|1906383|gb|AAB50256.1|tat protein [Human immunodeficiency virus
1]MEPVDPRLEPWKHPGSQPKTACTNCYCKKCCFHCQVCFITKALGISYGRKKRRQRRRAHQNSQTHQASLS

KQPTSQPRGDPTGPKE

SEQ ID NO: 3: >B.FR.1983.HXB2-LAI-IIIB-BRU (gp120)
MRVKEKYQHLWRWGWRWGTMLLGMLMICSATEKLWVTVYYGVPVWKEATTTLFCASDAKAYDTEVHNVWATHACV

PTDPNPQEVVLVNVTENFNMWKNDMVEQMHEDIISLWDQSLKPCVKLTPLCVSLKCTDLKNDTNTNSSSGRMIME

KGEIKNCSFNISTSIRGKVQKEYAFFYKLDIIPIDNDTTSYKLTSCNTSVITQACPKVSFEPIPIHYCAPAGFAI

LKCNNKTFNGTGPCTNVSTVQCTHGIRPVVSTQLLLNGSLAEEEVVIRSVNFTDNAKTIIVQLNTSVEINCTRPN

NNTRKRIRIQRGPGRAFVTIGKIGNMRQAHCNISRAKWNNTLKQIASKLREQFGNNKTIIFKQSSGGDPEIVTHS

FNCGGEFFYCNSTQLFNSTWFNSTWSTEGSNNTEGSDTITLPCRIKQIINMWQKVGKAMYAPPISGQIRCSSNIT

GLLLTRDGGNSNNESEIFRPGGGDMRDNWRSELYKYKVVKIEPLGVAPTKAKRRVVQREKR

SEQ ID NO: 4: HIV gp41
>B.FR.1983.HXB2-LAI-IIIB-BRU (ACC No. K03455)
AVGIGALFLGFLGAAGSTMGAASMTLTVQARQLLSGIVQQQNNLLRAIEAQQHLLQLTVWGIKQLQARILAVERY

LKDQQLLGIWGCSGKLICTTAVPWNASWSNKSLEQIWNHTTWMEWDREINNYTSLIHSLIEESQNQQEKNEQELL

ELDKWASLWNWFNITNWLWYIKLFIMIVGGLVGLRIVFAVLSIVNRVRQGYSPLSFQTHLPTPRGPDRPEGIEEE

GGERDRDRSIRLVNGSLALIWDDLRSLCLFSYHRLRDLLLIVTRIVELLGRRGWEALKYWWNLLQYWSQELKNSA

VSLLNATAIAVAEGTDRVIEVVQGACRAIRHIPRRIRQGLERILL

SEQ ID NO: 5: >1b._._.AB016785._(HCV-E1)
YEVRNVSGVYHVTNDCSNSSIVYGAADMIMHTPGCVPCVRENNSSRCWVALTPTLAARNRSIPTTTIRRHVDLLV

GAAAFCSAMYVGDLCGSVFLVSQLFTFSPRRYETVQDCNCSLYPGHVSGHRMAWDMMMNWSPTAALVVSQLLRIP

QAVVDMVTGAHWGVLAGLAYYSMVGNWAKVLIVMLLFAGVDG

SEQ ID NO: 6: >1b._._.AB016785.AB016785
TTHVTGGQTGRTTLGITAMFAFGPHQKLQLINTNGSWHINRTALNCNDSLNTGFLAALFYARKFNSSGCPERMAS

CRPIDKFVQGWGPITHAVPDNLDQRPYCWHYAPQPCGIIPASQVCGPVYCFTPSPVVVGTTDRFGAPTYTWGENE

TDVLLLNNTRPPQGNWFGCTWMNGTGFAKTCGGPPCNIGGVGNNTLTCPTDCFRKHPEATYTKCGSGPWLTPRCM

VDYPYRLWHYPCTVNFTIFKVRMYVGGVEHRLTAACNWTRGERCDLEDRDRSELSPLLLSTTEWQVLPCSFTTLP

ALSTGLIHLHQNIVDVQYLYGVGSAVVSIVIKWEYILLLFLLLADARVCACLWMMLLIAQAEA

SEQ ID NO: 7: Accession no AF009606; Hepatitis C virus subtype 1a polyprotein gene, complete cds.
MSTNPKPQRKTKRNTNRRPQDVKFPGGGQIVGGVYLLPRRGPRL

GVRATRKTSERSQPRGRRQPIPKARRPEGRTWAQPGYPWPLYGNEGCGWAGWLLSPRG

SRPSWGPTDPRRRSRNLGKVIDTLTCGFADLMGYIPLVGAPLGGAARALAHGVRVLED

GVNYATGNLPGCSFSIFLLALLSCLTVPASAYQVRNSSGLYHVTNDCPNSSIVYEAAD

AILHTPGCVPCVREGNASRCWVAVTPTVATRDGKLPTTQLRRHIDLLVGSATLCSALY

VGDLCGSVFLVGQLFTFSPRRHWTTQDCNCSIYPGHITGHRMAWDMMMNWSPTAALVV

AQLLRIPQAIMDMIAGAHWGVLAGIAYFSMVGNWAKVLVVLLLFAGVDAETHVTGGSA

GRTTAGLVGLLTPGAKQNIQLINTNGSWHINSTALNCNESLNTGWLAGLFYQHKFNSS

GCPERLASCRRLTDFAQGWGPISYANGSGLDERPYCWHYPPRPCGIVPAKSVCGPVYC

FTPSPVVVGTTDRSGAPTYSWGANDTDVFVLNNTRPPLGNWFGCTWMNSTGFTKVCGA

PPCVIGGVGNNTLLCPTDCFRKHPEATYSRCGSGPWITPRCMVDYPYRLWHYPCTINY

-continued

TIFKVRMYVGGVEHRLEAACNWTRGERCDLEDRDRSELSPLLLSTTQWQVLPCSFTTL

PALSTGLIHLHQNIVDVQYLYGVGSSIASWAIKWEYVVLLFLLLADARVCSLWMMLL

ISQAEAALENLVILNAASLAGTHGLVSFLVFFCFAWYLKGRWVPGAVYAFYGMWPLLL

LLLALPQRAYALDTEVAASCGGVVLVGLMALTLSPYYKRYISWCMWWLQYFLTRVEAQ

LHVWVPPLNVRGGRDAVILLMCVVHPTLVFDITKLLLAIFGPLWILQASLLKVPYFVR

VQGLLRICALARKIAGGHYVQMAIIKLGALTGTYVYNHLTPLRDWAHNGLRDLAVAVE

PVVFSRMETKLITWGADTAACGDIINGLPVSARRGQEILLGPADGMVSKGWRLLAPIT

AYAQQTRGLLGCIITSLTGRDKNQVEGEVQIVSTATQTFLATCINGVCWTVYHGAGTR

TIASPKGPVIQMYTNVDQDLVGWPAPQGSRSLTPCTCGSSDLYLVTRHADVIPVRRRG

DSRGSLLSPRPISYLKGSSGGPLLCPAGHAVGLFRAAVCTRGVAKAVDFIPVENLETT

MRSPVFTDNSSPPAVPQSFQVAHLHAPTGSGKSTKVPAAYAAQGYKVLVLNPSVAATL

GFGAYMSKAHGVDPNIRTGVRTITTGSPITYSTYGKFLADGGCSGGAYDIIICDECHS

TDATSILGIGTVLDQAETAGARLVVLATATPPGSVTVSHPNIEEVALSTTGEIPFYGK

AIPLEVIKGGRHLIFCHSKKKCDELAAKLVALGINAVAYYRGLDVSVIPTSGDVVVVS

TDALMTGFTGDFDSVIDCNTCVTQTVDFSLDPTFTIETTTLPQDAVSRTQRRGRTGRG

KPGIYRFVAPGERPSGMFDSSVLCECYDAGCAWYELTPAETTVRLRAYMNTPGLPVCQ

DHLEFWEGVFTGLTHIDAHFLSQTKQSGENFPYLVAYQATVCARAQAPPPSWDQMWKC

LIRLKPTLHGPTPLLYRLGAVQNEVTLTHPITKYIMTCMSADLEVVTSTWVLVGGVLA

ALAAYCLSTGCVVIVGRIVLSGKPAIIPDREVLYQEFDEMEECSQHLPYIEQGMMLAE

QFKQKALGLLQTASRQAEVITPAVQTNWQKLEVFWAKHMWNFISGIQYLAGLSTLPGN

PAIASLMAFTAAVTSPLTTGQTLLFNILGGWVAAQLAAPGAATAFVGAGLAGAAIGSV

GLGKVLVDILAGYGAGVAGALVAFKIMSGEVPSTEDLVNLLPAILSPGALVVGVVCAA

ILRRHVGPGEGAVQWMNRLIAFASRGNHVSPTHYVPESDAAARVTAILSSLTVTQLLR

RLHQWISSECTTPCSGSWLRDIWDWICEVLSDFKTWLKAKLMPQLPGIPFVSCQRGYR

GVWRGDGIMHTRCHCGAEITGHVKNGTMRIVGPRTCRNMWSGTFPINAYTTGPCTPLP

APNYKFALWRVSAEEYVEIRRVGDFHYVSGMTTDNLKCPCQIPSPEFFTELDGVRLHR

FAPPCKPLLREEVSFRVGLHEYPVGSQLPCEPEPDVAVLTSMLTDPSHITAEAAGRRL

ARGSPPSMASSSASQLSAPSLKATCTANHDSPDAELIEANLLWRQEMGGNITRVESEN

KVVILDSFDPLVAEEDEREVSVPAEILRKSRRFARALPVWARPDYNPPLVETWKKPDY

EPPVVHGCPLPPPRSPPVPPPRKKRTVVLTESTLSTALAELATKSFGSSSTSGITGDN

TTTSSEPAPSGCPPDSDVESYSSMPPLEGEPGDPDLSDGSWSTVSSGADTEDVVCCSM

SYSWTGALVTPCAAEEQKLPINALSNSLLRHHNLVYSTTSRSACQRQKKVTFDRLQVL

DSHYQDVLKEVKAAASKVKANLLSVEEACSLTPPHSAKSKFGYGAKDVRCHARKAVAH

INSVWKDLLEDSVTPIDTTIMAKNEVFCVQPEKGGRKPARLIVFPDLGVRVCEKMALY

DVVSKLPLAVMGSSYGFQYSPGQRVEFLVQAWKSKKTPMGFSYDTRCFDSTVTESDIR

TEEAIYQCCDLDPQARVAIKSLTERLYVGGPLTNSRGENCGYRRCRASGVLTTSCGNT

LTCYIKARAACRAAGLQDCTMLVCGDDLVVICESAGVQEDAASLRAFTEAMTRYSAPP

GDPPQPEYDLELITSCSSNVSVAHDGAGKRVYYLTRDPTTPLARAAWETARHTPVNSW

LGNIIMFAPTLWARMILMTHFFSVLIARDQLEQALNCEIYGACYSIEPLDLPPIIQRL

HGLSAFSLHSYSPGEINRVAACLRKLGVPPLRAWRHRARSVRARLLSRGGRAAICGKY

-continued

LFNWAVRTKLKLTPIAAAGRLDLSGWFTAGYSGGDIYHSVSHARPRWFWFCLLLLAAG

VGIYLLPNR

SEQ ID NO: 8: HCV core protein, H77, Accession AF009606
Genbank number: 2316097
>gi|2316098|gb|AAB66324.1|polyprotein [Hepatitis C virus subtype 1a]
MSTNPKPQRKTKRNTNRRPQDVKFPGGGQIVGGVYLLPRRGPRLGVRATRKTSERSQPRGRRQPIPKARR

PEGRTWAQPGYPWPLYGNEGCGWAGWLLSPRGSRPSWGPTDPRRRSRNLGKVIDTLTCGFADLMGYIPLVGAPLGGAAR

ALAHGVRVLEDGVNYATGNLPGCSFSIFLLALLSCLTVPASA

SEQ ID NO: 9:
Hepatitis C virus mRNA, complete cds; ACCESSION M96362 M72423; Hepatitis C
virus subtype 1b
MSTNPKPQRKTKRNTNRRPQDIKFPGGGQIVGGVYLLPRRGPRL

GVRATRKTSERSQPRGRRQPIPKARRPEGRAWAQPGYPWPLYGNEGLGWAGWLLSPRG

SRPSWGPTDPRRKSRNLGKVIDTLTCGFADLMGYIPLVGAPLGGVARALAHGVRVLED

GVNYATGNLPGCSFSIFLLALLSCLTTPVSAYEVRNASGMYHVTNDCSNSSIVYEAAD

MIMHTPGCVPCVREDNSSRCWVALTPTLAARNASVPTTTLRRHVDLLVGAAFCSAMY

VGDLCGSVFLVSQLFTFSPRRHETVQDCNCSIYPGRVSGHRMAWDMMMNWSPTTALVV

SQLLRIPQAVVDMVTGSHWGILAGLAYYSMVGNWAKVLIAMLLFAGVDGTTHVTGGAQ

GRAASSLTSLFSPGPVQHLQLINTNGSWHINRTALSCNDSLNTGFVAALFYKYRFNAS

GCPERLATCRPIDTFAQGWGPITYTEPHDLDQRPYCWHYAPQPCGIVPTLQVCGPVYC

FTPSPVAVGTTDRFGAPTYRWGANETDVLLLNNAGPPQGNWFGCTWMNGTGFTKTCGG

PPCNIGGVGNNTLTCPTDCFRKHPGATYTKCGSGPWLTPRCLVDYPYRLWHYPCTVNF

TIFKVRMYVGGAEHRLDAACNWTRGERCDLEDRDRSELSPLLLSTTEWQVLPCSFTTL

PALSTGLIHLHQNIVDIQYLYGIGSAVVSFAIKWEYIVLLFLLLADARVCACLWMMLL

VAQAEAALENLVVLNAASVAGAHGILSFIVFFCAAWYIKGRLVPGAAYALYGVWPLLL

LLLALPPRAYAMDREMAASCGGAVFVGLVLLTLSPHYKVFLARFIWWLQYLITRTEAH

LQVWVPPLNVRGGRDAIILLTCVVHPELIFDITKYLLAIFGPLMVLQAGITRVPYFVR

AQGLIRACMLARKVVGGHYVQMVFMKLAALAGTYVYDHLTPLRDWAHTGLRDLAVAVE

PVVFSDMETKVITWGADTAACGDIILALPASARRGKEILLGPADSLEGQGWRLLAPIT

AYSQQTRGLLGCIITSLTGRDKNQVEGEVQVVSTATQSFLATCINGVCWTVFHGAGSK

TLAGPKGPITQMYTNVDQDLVGWPAPPGARSLTPCTCGSSDLYLVTRHADVIPVRRRG

DGRGSLLPPRPVSYLKGSSGGPLLCPSGHAVGILPAAVCTRGVAMAVEFIPVESMETT

MRSPVFTDNPSPPAVPQTFQVAHLHAPTGSGKSTRVPAAYAAQGYKVLVLNPSVAATL

GFGAYMSKAHGIDPNLRTGVRTITTGAPITYSTYGKFLADGGGSGGAYDIIMCDECHS

TDSTTIYGIGTVLDQAETAGARLVVLSTATPPGSVTVPHLNIEEVALSNTGEIPFYGK

AIPIEAIKGGRHLIFCHSKKKCDELAAKLSGLGLNAVAYYRGLDVSVIPTSGDVVVVA

TDALMTGFTGDFDSVIDCNTCVTQTVDFSLDPTFTIETTTVPQDAVSRSQRRGRTGRG

RAGIYRFVTPGERPSGMFDSSVLCECYDAGCAWYELTPAETSVRLRAYLNTPGLPVCQ

DHLEFSEGVFTGLTHIDAHFLSQTKQAGENFPYLVAYQATVCARAQAPPPSWDEMWRC

LIRLKPTLHGPTPLLYRLGAVQNEVTLTHPITKFIMTCMSADLEVVTSTWVLVGGVLA

ALAAYCLTTGSVVIVGRIILSGKPAIIPDREVLYQEFDEMEECASHLPYFEQGMQLAE

QFKQKALGLLQTATKQAEAAAPVVESKWRALETFWAKHMWNFISGIQYLAGLSTLPGN

PAIRSPMAFTASITSPLTTQHTLLFNILGGWVAAQLAPPSAASAFVGAGIAGAAVGTI

GLGKVLVDILAGYGAGVAGALVAFKIMSGEMPSAEDMVNLLPAILSPGALVVGIVCAA

-continued

ILRRHVGPGEGAVQWMNRLIAFASRGNHVSPRHYVPESEPAARVTQILSSLTITQLLK

RLHQWINEDCSTPCSSSWLREIWDWICTVLTDFKTWLQSKLLPRLPGVPFFSCQRGYK

GVWRGDGIMHTTCPCGAQITGHVKNGSMRIVGPKTCSNTWYGTFPINAYTTGPCTPSP

APNYSKALWRVAAEEYVEVTRVGDFHYVTGMTTDNVKCPCQVPAPEFFTEVDGVRLHR

YAPACRPLLREEVVFQVGLHQYLVGSQLPCEPEPDVAVLTSMLTDPSHITAETAKRRL

ARGSPPSLASSSASQLSAPSLKATCTTHHDSPDADLIEANLLWRQEMGGNITRVESEN

KVVILDSFDPLRAEDDEGEISVPAEILRKSRKFPPALPIWAPPDYNPPLLESWKDPDY

VPPVVHGCPLPPTKAPPIPPPRRKRTVVLTESTVSSALAELATKTFGSSGSSAIDSGT

ATAPPDQASGDGDRESDVESFSSMPPLEGEPGDPDLSDGSWSTVSEEASEDVVCCSMS

YTWTGALITPCAAEESKLPINPLSNSLLRHHNMVYATTSRSAGLRQKKVTFDRLQVLD

DHYRDVLKEMKAKASTVKAKLLSVEEACKLTPPHSAKSKFGYGAKDVRSLSSRAVTHI

RSVWKDLLEDTETPISTTIMAKNEVFCVQPEKGGRKPARLIVFPDLGVRVCEKMALYD

VVSTLPQAVMGSSYGFQYSPKQRVEFLVNTWKSKKCPMGFSYDTRCFDSTVTENDIRV

EESIYQCCDLAPEAKLAIKSLTERLYIGGPLTNSKGQNCGYRRCRASGVLTTSCGNTL

TCYLKATAACRAAKLRDCTMLVNGDDLVVICESAGTQEDAASLRVFTEAMTRYSAPPG

DPPQPEYDLELITSCSSNVSVAHDASGKRVYYLTRDPTTPLARAAWETARHTPVNSWL

GNIIMYAPTLWARMILMTHFFSILLAQEQLEKTLDCQIYGACYSIEPLDLPQIIERLH

GLSAFSLHSYSPGEINRVASCLRKLGVPPLRAWRHRARSVRAKLLSQGGRAATCGKYL

FNWAVRTKLKLTPIPAASRLDLSGWFVAGYSGGDIYHSLSRARPRWFMLCLLLLSVGV

GIYLLPNR

SEQ ID NO: 10, nucleocapsid protein of influenza A virus
  1 MASQGTKRSY EQMETSGERQ NATEIRASVG RMVGGIGRFY IQMCTELKLS DHEGRLIQNS
 61 ITIERMVLSA FDERRNKYLE EHPSAGKDPK KTGGPIYRRR DGKWMRELIL YDKEEIRRIW
121 RQANNGEDAT AGLTHMMIWH SNLNDATYQR TRALVRTGMD PRMCSLMQGS TLPRRSGAAG
181 AAVKGVGTMV MELIRMIKRG INDRNFWRGE NGRRTRIAYE RMCNILKGKF QTAAQRAMMD
241 QVRESRNPGN AEIEDLIFLA RSALILRGSV AHKSCLPACV YGLAVASGYD FEREGYSLVG
301 IDPFRLLQNS QVFSLIRPNE NPAHKSQLVW MACHSAAFED LRVSSFIRGT RVVPRGQLST
361 RGVQIASNEN METMDSSTLE LRSRYWAIRT RSGGNTNQQR ASAGQISVQP TFSVQRNLPF
421 ERATIMAAFT GNTEGRTSDM RTEIIRMMEN ARPEDVSFQG RGVFELSDEK ATNPIVPSFD
481 MSNEGS SEQ ID NO: 11
>gi|73919153|ref|YP_308840.1|matrix protein 2 [Influenza A virus (A/New York/392/2004(H3N2))]
MSLLTEVETPIRNEWGCRCNDSSDPLVVAASIIGILHLILWILDRLFFKCVYRLFKHGLKRGPSTEGVPE      70

SMREEYRKEQQNAVDADDSHFVSIELE

SEQ ID NO: 12
>gi|73919147|ref|YP_308843.1|nucleocapsid protein [Influenza A virus (A/New York/392/2004(H3N2))]
MASQGTKRSYEQMETDGDRQNATEIRASVGKMIDGIGRFYIQMCTELKLSDHEGRLIQNSLTIEKMVLSA      70

FDERRNKYLEEHPSAGKDPKKTGGPIYRRVDGKWMRELVLYDKEEIRRIWRQANNGEDATAGLTHIMIWH     140

SNLNDATYQRTRALVRTGMDPRMCSLMQGSTLPRRSGAAGAAVKGIGTMVMELIRMVKRGINDRNFWRGE     210

NGRKTRSAYERMCNILKGKFQTAAQRAMVDQVRESRNPGNAEIEDLIFLARSALILRGSVAHKSCLPACA     280

YGPAVSSGYDFEKEGYSLVGIDPFKLLQNSQIYSLIRPNENPAHKSQLVWMACHSAAFEDLRLLSFIRGT     350

KVSPRGKLSTRGVQIASNENMDNMGSSTLELRSGYWAIRTRSGGNTNQQRASAGQTSVQPTFSVQRNLPF     420

```
EKSTIMAAFTGNTEGRTSDMRAEIIRMMEGAKPEEVSFRGRGVFELSDEKATNPIVPSFDMSNEGSYFFG        490

DNAEEYDN

SEQ ID NO: 13
>gi|56583270|ref|NP_040979.2|matrix protein 2 [Influenza A virus (A/Puerto
Rico/8/34(H1N1))]
MSLLTEVETPIRNEWGCRCNGSSDPLAIAANIIGILHLILWILDRLFFKCIYRRFKYGLKGGPSTEGVPK

SMREEYRKEQQSAVDADDGHFVSIELE

SEQ ID NO: 14
>gi|8486130|ref|NP_040982.1|nucleocapsid protein [Influenza A virus (A/Puerto
Rico/8/34(H1N1))]
MASQGTKRSYEQMETDGERQNATEIRASVGKMIGGIGRFYIQMCTELKLSDYEGRLIQNSLTIERMVLSA

FDERRNKYLEEHPSAGKDPKKTGGPIYRRVNGKWMRELILYDKEEIRRIWRQANNGDDATAGLTHMMIWH

SNLNDATYQRTRALVRTGMDPRMCSLMQGSTLPRRSGAAGAAVKGVGTMVMELVRMIKRGINDRNFWRGE

NGRKTRIAYERMCNILKGKFQTAAQKAMMDQVRESRDPGNAEFEDLTFLARSALILRGSVAHKSCLPACV

YGPAVASGYDFEREGYSLVGIDPFRLLQNSQVYSLIRPNENPAHKSQLVWMACHSAAFEDLRVLSFIKGT

KVVPRGKLSTRGVQIASNENMETMESSTLELRSRYWAIRTRSGGNTNQQRASAGQISIQPTFSVQRNLPF

DRTTVMAAFTGNTEGRTSDMRTEIIRMMESARPEDVSFQGRGVFELSDEKAASPIVPSFDMSNEGSYFFG

DNAEEYDN

SEQ ID NO: 15
>gi|73912687|ref|YP_308853.1|membrane protein M2 [Influenza A virus
(A/Korea/426/68(H2N2))]
MSLLTEVETPIRNEWGCRCNDSSDPLVVAASIIGILHFILWILDRLFFKCIYRFFKHGLKRGPSTEGVPE

SMREEYRKEQQSAVDADDSHFVSIELE

SEQ ID NO: 16
>gi|73921307|ref|YP_308871.1|nucleoprotein [Influenza A virus
(A/Korea/426/68(H2N2))]
MASQGTKRSYEQMETDGERQNATEIRASVGKMIDGIGRFYIQMCTELKLSDYEGRLIQNSLTIERMVLSA

FDERRNKYLEEHPSAGKDPKKTGGPIYKRVDGKWMRELVLYDKEEIRRIWRQANNGDDATAGLTHMMIWH

SNLNDTTYQRTRALVRTGMDPRMCSLMQGSTLPRRSGAAGAAVKGVGTMVMELIRMIKRGINDRNFWRGE

NGRKTRSAYERMCNILKGKFQTAAQRAMMDQVRESRNPGNAEIEDLIFLARSALILRGSVAHKSCLPACV

YGPAIASGYNFEKEGYSLVGIDPFKLLQNSQVYSLIRPNENPAHKSQLVWMACNSAAFEDLRVLSFIRGT

KVSPRGKLSTRGVQIASNENMDTMESSTLELRSRYWAIRTRSGGNTNQQRASAGQISVQPAFSVQRNLPF

DKPTIMAAFTGNTEGRTSDMRAEIIRMMEGAKPEEMSFQGRGVFELSDEKATNPIVPSFDMSNEGSYFFG

DNAEEYDN

SEQ ID NO: 17
>gi|330647|gb|AAA45994.1|pp65 [Human herpesvirus 5]
MASVLGPISGHVLKAVFSRGDTPVLPHETRLLQTGIHVRSVQPSLILVSQYTPDSTPCHRGDNQLQVQHT        70

YFTGSEVENVSVNVHNPTGRSICPSQEPMSIYVYALPLKMLNIPSINVHHYPSAAERKHRHLPVADAVIH       140

ASGKQMWQARLTVSGLAWTRQQNQWKEPDVYYTSAFVFPTKDVALRHVVCAHELVCSMENTRATKMQVIG       210

DQYVKVYLESFCEDVPSGKLFMHVTLGSDVEEDLTMTRNPQPFMRPHERNGFTVLCPKNMIIKPGKISHI       280

MLDVAFTSHEHFGLLCPKSIPGLSISGNLLMNGQQIFLEVQAIRETVELRQYDPVAALFFFDIDLLLQRG       350

PQYSEHPTFTSQYRIQGKLEYRHTWDRHDEGAAQGDDDVWTSGSDSDEELVTTERKTPRVTGGGAMAGAS       420

TSAGRKRKSASSATACTAGVMTRGRLKAESTVAPEEDTDEDSDNEIHNPAVFTWPPWQAGILARNLVPMV      490

ATVQGQNLKYQEFFWDANDIYRIFAELEGVWQPAAQPKRRRHRQDALPGPCIASTPKKHRG               541

SEQ ID NO: 18
>gi|33330937|gb|AAQ10712.1|putative transforming protein E6 [Human
papillomavirus type 16]
MHQKRTAMFQDPQERPGKLPQLCTELQTTIHDIILECVYCKQQLLRREVYDFAFRDLCIVYRDGNPYAVC        70
```

DKCLKFYSKISEYRHYCYSVYGTTLEQQYNKPLCDLLIRCINCQKPLCPEEKQRHLDKKQRFHNIRGRWT    140

GRCMSCCRSSRTRRETQL

SEQ ID NO: 19
>gi|56583270|ref|NP_040979.2|matrix protein 2 [Influenza A virus (A/Puerto
Rico/8/34(H1N1))]
MSLLTEVETPIRNEWGCRCNGSSDPLAIAANIIGILHLILWILDRLFFKCIYRRFKYGLKGGPSTEGVPK

SMREEYRKEQQSAVDADDGHFVSIELE

SEQ ID NO: 20
>gi|8486139|ref|NP_040987.1|PB2 protein [Influenza A virus (A/Puerto
Rico/8/34(H1N1))]
MERIKELRNLMSQSRTREILTKTTVDHMAIIKKYTSGRQEKNPALRMKWMMAMKYPITADKRITEMIPER

NEQGQTLWSKMNDAGSDRVMVSPLAVTWWNRNGPMTNTVHYPKIYKTYFERVERLKHGTFGPVHFRNQVK

IRRRVDINPGHADLSAKEAQDVIMEVVFPNEVGARILTSESQLTITKEKKEELQDCKISPLMVAYMLERE

LVRKTRFLPVAGGTSSVYIEVLHLTQGTCWEQMYTPGGEVKNDDVDQSLIIAARNIVRRAAVSADPLASL

LEMCHSTQIGGIRMVDILKQNPTEEQAVGICKAAMGLRISSSFSFGGFTFKRTSGSSVKREEEVLTGNLQ

TLKIRVHEGYEEFTMVGRRATAILRKATRRLIQLIVSGRDEQSIAEAIIVAMVFSQEDCMIKAVRGDLNF

VNRANQRLNPMHQLLRHFQKDAKVLFQNWGVEPIDNVMGMIGILPDMTPSIEMSMRGVRISKMGVDEYSS

TERVVVSIDRFLRVRDQRGNVLLSPEEVSETQGTEKLTITYSSSMMWEINGPESVLVNTYQWIIRNWETV

KIQWSQNPTMLYNKMEFEPFQSLVPKAIRGQYSGFVRTLFQQMRDVLGTFDTAQIIKLLPFAAAPPKQSR

MQFSSFTVNVRGSGMRILVRGNSPVFNYNKATKRLTVLGKDAGTLTEDPDEGTAGVESAVLRGFLILGKE

DRRYGPALSINELSNLAKGEKANVLIGQGDVVLVMKRKRDSSILTDSQTATKRIRMAIN

SEQ ID NO: 21
>gi|8486137|ref|NP_040986.1|polymerase PA [Influenza A virus (A/Puerto
Rico/8/34(H1N1))]
MEDFVRQCFNPMIVELAEKTMKEYGEDLKIETNKFAAICTHLEVCFMYSDFHFINEQGESIIVELGDPNA

LLKHRFEIIEGRDRTMAWTVVNSICNTTGAEKPKFLPDLYDYKENRFIEIGVTRREVHIYYLEKANKIKS

EKTHIHIFSFTGEEMATKADYTLDEESRARIKTRLFTIRQEMASRGLWDSFRQSERGEETIEERFEITGT

MRKLADQSLPPNFSSLENFRAYVDGFEPNGYIEGKLSQMSKEVNARIEPFLKTTPRPLRLPNGPPCSQRS

KFLLMDALKLSIEDPSHEGEGIPLYDAIKCMRTFFGWKEPNVVKPHEKGINPNYLLSWKQVLAELQDIEN

EEKIPKTKNMKKTSQLKWALGENMAPEKVDFDDCKDVGDLKQYDSDEPELRSLASWIQNEFNKACELTDS

SWIELDEIGEDVAPIEHIASMRRNYFTSEVSHCRATEYIMKGVYINTALLNASCAAMDDFQLIPMISKCR

TKEGRRKTNLYGFIIKGRSHLRNDTDVVNFVSMEFSLTDPRLEPHKWEKYCVLEIGDMLLRSAIGQVSRP

MFLYVRTNGTSKIKMKWGMEMRRCLLQSLQQIESMIEAESSVKEKDMTKEFFENKSETWPIGESPKGVEE

SSIGKVCRTLLAKSVFNSLYASPQLEGFSAESRKLLLIVQALRDNLEPGTFDLGGLYEAIEECLINDPWV

LLNASWFNSFLTHALS

SEQ ID NO: 22
>gi|8486133|ref|NP_040984.1|nonstructural protein NS1 [Influenza A virus
(A/Puerto Rico/8/34(H1N1))]
MDPNTVSSFQVDCFLWHVRKRVADQELGDAPFLDRLRRDQKSLRGRGSTLGLDIETATRAGKQIVERILK

EESDEALKMTMASVPASRYLTDMTLEEMSREWSMLIPKQKVAGPLCIRMDQAIMDKNIILKANFSVIFDR

LETLILLRAFTEEGAIVGEISPLPSLPGHTAEDVKNAVGVLIGGLEWNDNTVRVSETLQRFAWRSSNENG

RPPLTPKQKREMAGTIRSEV

SEQ ID NO: 23
>gi|8486132|ref|NP_040983.1|nonstructural protein NS2 [Influenza A virus
(A/Puerto Rico/8/34(H1N1))]
MDPNTVSSFQDILLRMSKMQLESSSEDLNGMITQFESLKLYRDSLGEAVMRMGDLHSLQNRNEKWREQLG

QKFEEIRWLIEEVRHKLKVTENSFEQITFMQALHLLLEVEQEIRTFSFQLI

SEQ ID NO: 24
>gi|8486128|ref|NP_040981.1|neuraminidase [Influenza A virus (A/Puerto -continued Rico/8/34(H1N1))]
MNPNQKIITIGSICLVVGLISLILQIGNIISIWISHSIQTGSQNHTGICNQNIITYKNSTWVKDTTSVIL

TGNSSLCPIRGWAIYSKDNSIRIGSKGDVFVIREPFISCSHLECRTFFLTQGALLNDRHSNGTVKDRSPY

RALMSCPVGEAPSPYNSRFESVAWSASACHDGMGWLTIGISGPDNGAVAVLKYNGIITETIKSWRKKILR

TQESECACVNGSCFTIMTDGPSDGLASYKIFKIEKGKVTKSIELNAPNSHYEECSCYPDTGKVMCVCRDN

WHGSNRPWVSFDQNLDYQIGYICSGVFGDNPRPKDGTGSCGPVYVDGANGVKGFSYRYGNGVWIGRTKSH

SSRHGFEMIWDPNGWTETDSKFSVRQDVVAMTDWSGYSGSFVQHPELTGLDCIRPCFWVELIRGRPKEKT

IWTSASSISFCGVNSDTVDWSWPDGAELPFTIDK

SEQ ID NO: 25
>gi|8486126|ref|NP_040980.1|haemagglutinin [Influenza A virus (A/Puerto Rico/8/34(H1N1))]
MKANLLVLLCALAAADADTICIGYHANNSTDTVDTVLEKNVTVTHSVNLLEDSHNGKLCRLKGIAPLQLG

KCNIAGWLLGNPECDPLLPVRSWSYIVETPNSENGICYPGDFIDYEELREQLSSVSSFERFEIFPKESSW

PNHNTTKGVTAACSHAGKSSFYRNLLWLTEKEGSYPKLKNSYVNKKGKEVLVLWGIHHPSNSKDQQNIYQ

NENAYVSVVTSNYNRRFTPEIAERPKVRDQAGRMNYYWTLLKPGDTIIFEANGNLIAPRYAFALSRGFGS

GIITSNASMHECNTKCQTPLGAINSSLPFQNIHPVTIGECPKYVRSAKLRMVTGLRNIPSIQSRGLFGAI

AGFIEGGWTGMIDGWYGYHHQNEQGSGYAADQKSTQNAINGITNKVNSVIEKMNIQFTAVGKEFNKLEKR

MENLNKKVDDGFLDIWTYNAELLVLLENERTLDFHDSNVKNLYEKVKSQLKNNAKEIGNGCFEFYHKCDN

ECMESVRNGTYDYPKYSEESKLNREKVDGVKLESMGIYQILAIYSTVASSLVLLVSLGAISFWMCSNGSL

QCRICI

SEQ ID NO: 26
>gi|8486123|ref|NP_040978.1|matrix protein 1 [Influenza A virus (A/Puerto Rico/8/34(H1N1))]
MSLLTEVETYVLSIIPSGPLKAEIAQRLEDVFAGKNTDLEVLMEWLKTRPILSPLTKGILGFVFTLTVPS

ERGLQRRRFVQNALNGNGDPNNMDKAVKLYRKLKREITFHGAKEISLSYSAGALASCMGLIYNRMGAVTT

EVAFGLVCATCEQIADSQHRSHRQMVTTTNPLIRHENRMVLASTTAKAMEQMAGSSEQAAEAMEVASQAR

QMVQAMRTIGTHPSSSAGLKNDLLENLQAYQKRMGVQMQRFK

SEQ ID NO: 27
>gi|83031685|ref|YP_418248.1|PB1-F2 protein [Influenza A virus (A/Puerto Rico/8/34(H1N1))]
MGQEQDTPWILSTGHISTQKRQDGQQTPKLEHRNSTRLMGHCQKTMNQVVMPKQIVYWKQWLSLRNPILV

FLKTRVLKRWRLFSKHE

SEQ ID NO: 28
>gi|8486135|ref|NP_040985.1|polymerase 1 PB1 [Influenza A virus (A/Puerto Rico/8/34(H1N1))]
MDVNPTLLFLKVPAQNAISTTFPYTGDPPYSHGTGTGYTMDTVNRTHQYSEKARWTTNTETGAPQLNPID

GPLPEDNEPSGYAQTDCVLEAMAFLEESHPGIFENSCIETMEVVQQTRVDKLTQGRQTYDWTLNRNQPAA

TALANTIEVFRSNGLTANESGRLIDFLKDVMESMKKEEMGITTHFQRKRRVRDNMTKKMITQRTIGKRKQ

RLNKRSYLIRALTLNTMTKDAERGKLKRRAIATPGMQIRGFVYFVETLARSICEKLEQSGLPVGGNEKKA

KLANVVRKMMTNSQDTELSLTITGDNTKWNENQNPRMFLAMITYMTRNQPEWFRNVLSIAPIMFSNKMAR

LGKGYMFESKSMKLRTQIPAEMLASIDLKYFNDSTRKKIEKIRPLLIEGTASLSPGMMMGMFNMLSTVLG

VSILNLGQKRYTKTTYWWDGLQSSDDFALIVNAPNHEGIQAGVDRFYRTCKLHGINMSKKKSYINRTGTF

EFTSFFYRYGFVANFSMELPSFGVSGSNESADMSIGVTVIKNNMINNDLGPATAQMALQLFIKDYRYTYR

CHRGDTQIQTRRSFEIKKLWEQTRSKAGLLVSDGGPNLYNIRNLHIPEVCLKWELMDEDYQGRLCNPLNP

FVSHKEIESMNNAVMMPAHGPAKNMEYDAVATTHSWIPKRNRSILNTSQRGVLEDEQMYQRCCNLFEKFF

PSSSYRRPVGISSMVEAMVSRARIDARIDFESGRIKKEEFTEIMKICSTIEELRRQK

SEQ ID NO: 29
>gi|8486130|ref|NP_040982.1|nucleocapsid protein [Influenza A virus -continued (A/Puerto Rico/8/34(H1N1))]
MASQGTKRSYEQMETDGERQNATEIRASVGKMIGGIGRFYIQMCTELKLSDYEGRLIQNSLTIERMVLSA

FDERRNKYLEEHPSAGKDPKKTGGPIYRRVNGKWMRELILYDKEEIRRIWRQANNGDDATAGLTHMMIWH

SNLNDATYQRTRALVRTGMDPRMCSLMQGSTLPRRSGAAGAAVKGVGTMVMELVRMIKRGINDRNFWRGE

NGRKTRIAYERMCNILKGKFQTAAQKAMMDQVRESRDPGNAEFEDLTFLARSALILRGSVAHKSCLPACV

YGPAVASGYDFEREGYSLVGIDPFRLLQNSQVYSLIRPNENPAHKSQLVWMACHSAAFEDLRVLSFIKGT

KVVPRGKLSTRGVQIASNENMETMESSTLELRSRYWAIRTRSGGNTNQQRASAGQISIQPTFSVQRNLPF

DRTTVMAAFTGNTEGRTSDMRTEIIRMMESARPEDVSFQGRGVFELSDEKAASPIVPSFDMSNEGSYFFG

DNAEEYDN

SEQ ID NO: 30
>gi|73918826|ref|YP_308855.1|polymerase 2 [Influenza A virus
(A/Korea/426/1968(H2N2))]
MERIKELRNLMSQSRTREILTKTTVDHMAIIKKYTSGRQEKNPSLRMKWMMAMKYPITADKRITEMVPER

NEQGQTLWSKMSDAGSDRVMVSPLAVTWWNRNGPMTSTVHYPKIYKTYFEKVERLKHGTFGPVHFRNQVK

IRRRVDINPGHADLSAKEAQDVIMEVVFPNEVGARILTSESQLTITKEKKEELQDCKISPLMVAYMLERE

LVRKTRFLPVAGGTSSVYIEVLHLTQGTCWEQMYTPGGEVRNDDVDQSLIIAARNIVRRAAVSADPLASL

LEMCHSTQIGGTRMVDILRQNPTEEQAVDICKAAMGLRISSSFSFGGFTFKRTSGSSIKREEEVLTGNLQ

TLKIRVHEGYEEFTMVGKRATAILRKATRRLVQLIVSGRDEQSIAEAIIVAMVFSQEDCMIKAVRGDLNF

VNRANQRLNPMHQLLRHFQKDAKVLFQNWGIEHIDNVMGMIGVLPDMTPSTEMSMRGIRVSKMGVDEYSS

TERVVVSIDRFLRVRDQRGNVLLSPEEVSETQGTEKLTITYSSSMMWEINGPESVLVNTYQWIIRNWETV

KIQWSQNPTMLYNKMEFEPFQSLVPKAIRGQYSGFVRTLFQQMRDVLGTFDTTQIIKLLPFAAAPPKQSR

MQFSSLTVNVRGSGMRILVRGNSPVFNYNKTTKRLTILGKDAGTLTEDPDEGTSGVESAVLRGFLILGKE

DRRYGPALSINELSTLAKGEKANVLIGQGDVVLVMKRKRDSSILTDSQTATKRIRMAIN

SEQ ID NO: 31
>gi|73919145|ref|YP_308850.1|hemagglutinin [Influenza A virus
(A/Korea/426/68(H2N2))]
MAIIYLILLFTAVRGDQICIGYHANNSTEKVDTILERNVTVTHAKDILEKTHNGKLCKLNGIPPLELGDC

SIAGWLLGNPECDRLLSVPEWSYIMEKENPRYSLCYPGSFNDYEELKHLLSSVKHFEKVKILPKDRWTQH

TTTGGSWACAVSGKPSFFRNMVWLTRKGSNYPVAKGSYNNTSGEQMLIIWGVHHPNDEAEQRALYQNVGT

YVSVATSTLYKRSIPEIAARPKVNGLGRRMEFSWTLLDMWDTINFESTGNLVAPEYGFKISKRGSSGIMK

TEGTLENCETKCQTPLGAINTTLPFHNVHPLTIGECPKYVKSEKLVLATGLRNVPQIESRGLFGAIAGFI

EGGWQGMVDGWYGYHHSNDQGSGYAADKESTQKAFNGITNKVNSVIEKMNTQFEAVGKEFSNLEKRLENL

NKKMEDGFLDVWTYNAELLVLMENERTLDFHDSNVKNLYDKVRMQLRDNVKELGNGCFEFYHKCDNECMD

SVKNGTYDYPKYEEESKLNRNEIKGVKLSSMGVYQILAIYATVAGSLSLAIMMAGISFWMCSNGSLQCRI

CI

SEQ ID NO: 32
>gi|73912688|ref|YP_308854.1|membrane protein M1 [Influenza A virus
(A/Korea/426/68(H2N2))]
MSLLTEVETYVLSIVPSGPLKAEIAQRLEDVFAGKNTDLEALMEWLKTRPILSPLTKGILGFVFTLTVPS

ERGLQRRRFVQNALNGNGDPNNMDRAVKLYRKLKREITFHGAKEVALSYSAGALASCMGLIYNRMGAVTT

EVAFAVVCATCEQIADSQHRSHRQMVTTTNPLIRHENRMVLASTTAKAMEQMAGSSEQAAEAMEVASQAR

QMVQAMRAIGTPPSSSAGLKDDLLENLQAYQKRMGVQMQRFK

SEQ ID NO: 33
>gi|73912687|ref|YP_308853.1|membrane protein M2 [Influenza A virus
(A/Korea/426/68(H2N2))]
MSLLTEVETPIRNEWGCRCNDSSDPLVVAASIIGILHFILWILDRLFFKCIYRFFKHGLKRGPSTEGVPE

SMREEYRKEQQSAVDADDSHFVSIELE

-continued

SEQ ID NO: 34
>gi|73912685|ref|YP_308852.1|polymerase PA [Influenza A virus (A/Korea/426/68(H2N2))]
MEDFVRQCFNPMIVELAEKAMKEYGEDLKIETNKFAAICTHLEVCFMYSDFHFINEQGESIMVELDDPNA

LLKHRFEIIEGRDRTMAWTVVNSICNTTGAEKPKFLPDLYDYKENRFIEIGVTRREVHIYYLEKANKIKS

ENTHIHIFSFTGEEMATKADYTLDEESRARIKTRLFTIRQEMANRGLWDSFRQSERGEETIEERFEITGT

MRRLADQSLPPNFSCLENFRAYVDGFEPNGYIEGKLSQMSKEVNAKIEPFLKTTPRPIRLPDGPPCFQRS

KFLLMDALKLSIEDPSHEGEGIPLYDAIKCMRTFFGWKEPYIVKPHEKGINPNYLLSWKQVLAELQDIEN

EEKIPRTKNMKKTSQLKWALGENMAPEKVDFDNCRDISDLKQYDSDEPELRSLSSWIQNEFNKACELTDS

IWIELDEIGEDVAPIEHIASMRRNYFTAEVSHCRATEYIMKGVYINTALLNASCAAMDDFQLIPMISKCR

TKEGRRKTNLYGFIIKGRSHLRNDTDVVNFVSMEFSLTDPRLEPHKWEKYCVLEIGDMLLRSAIGQMSRP

MFLYVRTNGTSKIKMKWGMEMRPCLLQSLQQIESMVEAESSVKEKDMTKEFFENKSETWPIGESPKGVEE

GSIGKVCRTLLAKSVFNSLYASPQLEGFSAESRKLLLVVQALRDNLEPGTFDLGGLYEAIEECLINDPWV

LLNASWFNSFLTHALR

SEQ ID NO: 35
>gi|73921833|ref|YP_308877.1|PB1-F2 protein [Influenza A virus (A/Korea/426/68(H2N2))]
MGQEQDTPWTQSTEHINIQKRGSGQQTRKLERPNLTQLMDHYLRTMNQVDMHKQTASWKQWLSLRNHTQE

SLKIRVLKRWKLFNKQEWTN

SEQ ID NO: 36
>gi|73912683|ref|YP_308851.1|PB1 polymerase subunit [Influenza A virus (A/Korea/426/68(H2N2))]
MDVNPTLLFLKVPAQNAISTTFPYTGDPPYSHGTGTGYTMDTVNRTHQYSEKGKWTTNTETGAPQLNPID

GPLPEDNEPSGYAQTDCVLEAMAFLEESHPGIFENSCLETMEVIQQTRVDKLTQGRQTYDWTLNRNQPAA

TALANTIEVFRSNGLTANESGRLIDFLKDVIESMDKEEMEITTHFQRKRRVRDNMTKKMVTQRTIGKKKQ

RLNKRSYLIRALTLNTMTKDAERGKLKRRAIATPGMQIRGFVHFVETLARNICEKLEQSGLPVGGNEKKA

KLANVVRKMMTNSQDTELSFTITGDNTKWNENQNPRVFLAMITYITRNQPEWFRNVLSIAPIMFSNKMAR

LGKGYMFESKSMKLRTQIPAEMLASIDLKYFNESTRKKIEKIRPLLIDGTVSLSPGMMMGMFNMLSTVLG

VSILNLGQKKYTKTTYWWDGLQSSDDFALIVNAPNHEGIQAGVNRFYRTCKLVGINMSKKKSYINRTGTF

EFTSFFYRYGFVANFSMELPSFGVSGINESADMSIGVTVIKNNMINNDLGPATAQMALQLFIKDYRYTYR

CHRGDTQIQTRRSFELKKLWEQTRSKAGLLVSDGGSNLYNIRNLHIPEVCLKWELMDEDYQGRLCNPLNP

FVSHKEIESVNNAVVMPAHGPAKSMEYDAVATTHSWTPKRNRSILNTSQRGILEDEQMYQKCCNLFEKFF

PSSSYRRPVGISSMVEAMVSRARIDARIDFESGRIKKEEFAEIMKICSTIEELRRQK

SEQ ID NO: 37
>gi|73921567|ref|YP_308869.1|non-structural protein NS2 [Influenza A virus (A/Korea/426/68(H2N2))]
MDSNTVSSFQDILLRMSKMQLGSSSEDLNGMITQFESLKLYRDSLGEAVMRMGDLHSLQNRNGKWREQLG

QKFEEIRWLIEEVRHRLKITENSFEQITFMQALQLLFEVEQEIRTFSFQLI

SEQ ID NO: 38
>gi|73921566|ref|YP_308870.1|non-structural protein NS1 [Influenza A virus (A/Korea/426/68(H2N2))]
MDSNTVSSFQVDCFLWHVRKQVVDQELGDAPFLDRLRRDQKSLRGRGSTLDLDIEAATRVGKQIVERILK

EESDEALKMTMASAPASRYLTDMTIEELSRDWFMLMPKQKVEGPLCIRIDQAIMDKNIMLKANFSVIFDR

LETLILLRAFTEEGAIVGEISPLPSLPGHTIEDVKNAIGVLIGGLEWNDNTVRVSKTLQRFAWRSSNENG

RPPLTPKQKRKMARTIRSKVRRDKMAD

SEQ ID NO: 39
>gi|73921307|ref|YP_308871.1|nucleoprotein [Influenza A virus (A/Korea/426/68(H2N2))]
MASQGTKRSYEQMETDGERQNATEIRASVGKMIDGIGRFYIQMCTELKLSDYEGRLIQNSLTIERMVLSA

FDERRNKYLEEHPSAGKDPKKTGGPIYKRVDGKWMRELVLYDKEEIRRIWRQANNGDDATAGLTHMMIWH

-continued

SNLNDTTYQRTRALVRTGMDPRMCSLMQGSTLPRRSGAAGAAVKGVGTMVMELIRMIKRGINDRNFWRGE

NGRKTRSAYERMCNILKGKFQTAAQRAMMDQVRESRNPGNAEIEDLIFLARSALILRGSVAHKSCLPACV

YGPAIASGYNFEKEGYSLVGIDPFKLLQNSQVYSLIRPNENPAHKSQLVWMACNSAAFEDLRVLSFIRGT

KVSPRGKLSTRGVQIASNENMDTMESSTLELRSRYWAIRTRSGGNTNQQRASAGQISVQPAFSVQRNLPF

DKPTIMAAFTGNTEGRTSDMRAEIIRMMEGAKPEEMSFQGRGVFELSDEKATNPIVPSFDMSNEGSYFFG

DNAEEYDN

SEQ ID NO: 40
>gi|73921304|ref|YP_308872.1|neuraminidase [Influenza A virus
(A/Korea/426/68(H2N2))]
MNPNQKIITIGSVSLTIATVCFLMQIAILVTTVTLHFKQHECDSPASNQVMPCEPIIIERNITEIVYLNN

TTIEKEICPEVVEYRNWSKPQCQITGFAPFSKDNSIRLSAGGDIWVTREPYVSCDPGKCYQFALGQGTTL

DNKHSNDTIHDRIPHRTLLMNELGVPFHLGTRQVCVAWSSSSCHDGKAWLHVCVTGDDKNATASFIYDGR

LMDSIGSWSQNILRTQESECVCINGTCTVVMTDGSASGRADTRILFIEEGKIVHISPLSGSAQHVEECSC

YPRYPDVRCICRDNWKGSNRPVIDINMEDYSIDSSYVCSGLVGDTPRNDDRSSNSNCRNPNNERGNPGVK

GWAFDNGDDVWMGRTISKDLRSGYETFKVIGGWSTPNSKSQINRQVIVDSNNWSGYSGIFSVEGKRCINR

CFYVELIRGRQQETRVWWTSNSIVVFCGTSGTYGTGSWPDGANINFMPI

SEQ ID NO: 41
>gi|73919213|ref|YP_308844.1|nonstructural protein 2 [Influenza A virus
(A/New York/392/2004(H3N2))]
MDSNTVSSFQDILLRMSKMQLGSSSEDLNGMITQFESLKIYRDSLGEAVMRMGDLHLLQNRNGKWREQLG

QKFEEIRWLIEEVRHRLKTTENSFEQITFMQALQLLFEVEQEIRTFSFQLI

SEQ ID NO: 42
>gi|73919212|ref|YP_308845.1|nonstructural protein 1 [Influenza A virus
(A/New York/392/2004(H3N2))]
MDSNTVSSFQVDCFLWHIRKQVVDQELSDAPFLDRLRRDQRSLRGRGNTLGLDIKAATHVGKQIVEKILK

EESDEALKMTMVSTPASRYITDMTIEELSRNWFMLMPKQKVEGPLCIRMDQAIMEKNIMLKANFSVIFDR

LETIVLLRAFTEEGAIVGEISPLPSFPGHTIEDVKNAIGVLIGGLEWNDNTVRVSKNLQRFAWRSSNENG

GPPLTPKQKRKMARTARSKV

SEQ ID NO: 43
>gi|73919207|ref|YP_308839.1|hemagglutinin [Influenza A virus (A/New
York/392/2004(H3N2))]
MKTIIALSYILCLVFAQKLPGNDNSTATLCLGHHAVPNGTIVKTITNDQIEVTNATELVQSSSTGGICDS

PHQILDGENCTLIDALLGDPQCDGFQNKKWDLFVERSKAYSNCYPYDVPDYASLRSLVASSGTLEFNNES

FNWTGVTQNGTSSACKRRSNNSFFSRLNWLTHLKFKYPALNVTMPNNEKFDKLYIWGVHHPGTDNDQISL

YAQASGRITVSTKRSQQTVIPSIGSRPRIRDVPSRISIYWTIVKPGDILLINSTGNLIAPRGYFKIRSGK

SSIMRSDAPIGKCNSECITPNGSIPNDKPFQNVNRITYGACPRYVKQNTLKLATGMRNVPEKQTRGIFGA

IAGFIENGWEGMVDGWYGFRHQNSEGTGQAADLKSTQAAINQINGKLNRLIGKTNEKFHQIEKEFSEVEG

RIQDLEKYVEDTKIDLWSYNAELLVALENQHTIDLTDSEMNKLFERTKKQLRENAEDMGNGCFKIYHKCD

NACIGSIRNGTYDHDVYRDEALNNRFQIKGVELKSGYKDWILWISFAISCFLLCVALLGFIMWACQKGNI

RCNICI

SEQ ID NO: 44
>gi|73919153|ref|YP_308840.1|matrix protein 2 [Influenza A virus (A/New
York/392/2004(H3N2))]
MSLLTEVETPIRNEWGCRCNDSSDPLVVAASIIGILHLILWILDRLFFKCVYRLFKHGLKRGPSTEGVPE

SMREEYRKEQQNAVDADDSHFVSIELE

SEQ ID NO: 45
>gi|73919152|ref|YP_308841.1|matrix protein 1 [Influenza A virus (A/New
York/392/2004(H3N2))]
MSLLTEVETYVLSIVPSGPLKAEIAQRLEDVFAGKNTDLEALMEWLKTRPILSPLTKGILGFVFTLTVPS -continued

ERGLQRRRFVQNALNGNGDPNNMDKAVKLYRKLKREITFHGAKEIALSYSAGALASCMGLIYNRMGAVTT

EVAFGLVCATCEQIADSQHRSHRQMVATTNPLIKHENRMVLASTTAKAMEQMAGSSEQAAEAMEIASQAR

QMVQAMRAVGTHPSSSTGLRDDLLENLQTYQKRMGVQMQRFK

SEQ ID NO: 46
>gi|73919150|ref|YP_308848.1|PB1-F2 protein [Influenza A virus (A/New York/392/2004(H3N2))]
MEQEQDTPWTQSTEHTNIQRRGSGRQIQKLGHPNSTQLMDHYLRIMSQVDMHKQTVSWRLWPSLKNPTQV

SLRTHALKQWKSFNKQGWTN

SEQ ID NO: 47
>gi|73919149|ref|YP_308847.1|polymerase PB1 [Influenza A virus (A/New York/392/2004(H3N2))]
MDVNPTLLFLKVPAQNAISTTFPYTGDPPYSHGTGTGYTMDTVNRTHQYSEKGKWTTNTETGAPQLNPID

GPLPEDNEPSGYAQTDCVLEAMAFLEESHPGIFENSCLETMEVVQQTRVDKLTQGRQTYDWTLNRNQPAA

TALANTIEVFRSNGLTANESGRLIDFLKDVMESMDKEEMEITTHFQRKRRVRDNMTKKMVTQRTIGKKKQ

RVNKRGYLIRALTLNTMTKDAERGKLKRRAIATPGMQIRGFVYFVETLARSICEKLEQSGLPVGGNEKKA

KLANVVRKMMTNSQDTELSFTITGDNTKWNENQNPRMFLAMITYITKNQPEWFRNILSIAPIMFSNKMAR

LGKGYMFESKRMKLRTQIPAEMLASIDLKYFNESTRKKIEKIRPLLIDGTASLSPGMMMGMFNMLSTVLG

VSVLNLGQKKYTKTTYWWDGLQSSDDFALIVNAPNHEGIQAGVDRFYRTCKLVGINMSKKKSYINKTGTF

EFTSFFYRYGFVANFSMELPSFGVSGINESADMSIGVTVIKNNMINNDLGPATAQMALQLFIKDYRYTYR

CHRGDTQIQTRRSFELKKLWDQTQSRAGLLVSDGGPNLYNIRNLHIPEVCLKWELMDENYRGRLCNPLNP

FVSHKEIESVNNAVVMPAHGPAKSMEYDAVATTHSWNPKRNRSILNTSQRGILEDEQMYQKCCNLFEKFF

PSSSYRRPIGISSMVEAMVSRARIDARIDFESGRIKKEEFSEIMKICSTIEELRRQK

SEQ ID NO: 48
>gi|73919147|ref|YP_308843.1|nucleocapsid protein [Influenza A virus (A/New York/392/2004(H3N2))]
MASQGTKRSYEQMETDGDRQNATEIRASVGKMIDGIGRFYIQMCTELKLSDHEGRLIQNSLTIEKMVLSA

FDERRNKYLEEHPSAGKDPKKTGGPIYRRVDGKWMRELVLYDKEEIRRIWRQANNGEDATAGLTHIMIWH

SNLNDATYQRTRALVRTGMDPRMCSLMQGSTLPRRSGAAGAAVKGIGTMVMELIRMVKRGINDRNFWRGE

NGRKTRSAYERMCNILKGKFQTAAQRAMVDQVRESRNPGNAEIEDLIFLARSALILRGSVAHKSCLPACA

YGPAVSSGYDFEKEGYSLVGIDPFKLLQNSQIYSLIRPNENPAHKSQLVWMACHSAAFEDLRLLSFIRGT

KVSPRGKLSTRGVQIASNENMDNMGSSTLELRSGYWAIRTRSGGNTNQQRASAGQTSVQPTFSVQRNLPF

EKSTIMAAFTGNTEGRTSDMRAEIIRMMEGAKPEEVSFRGRGVFELSDEKATNPIVPSFDMSNEGSYFFG

DNAEEYDN

SEQ ID NO: 49
>gi|73919136|ref|YP_308842.1|neuraminidase [Influenza A virus (A/New York/392/2004(H3N2))]
MNPNQKIITIGSVSLTISTICFFMQIAILITTVTLHFKQYEFNSPPNNQVMLCEPTIIERNITEIVYLTN

TTIEKEMCPKLAEYRNWSKPQCDITGFAPFSKDNSIRLSAGGDIWVTREPYVSCDPDKCYQFALGQGTTL

NNVHSNDTVHDRTPYRTLLMNELGVPFHLGTKQVCIAWSSSSCHDGKAWLHVCVTGDDKNATASFIYNGR

LVDSIVSWSKKILRTQESECVCINGTCTVVMTDGSASGKADTKILFIEEGKIIHTSTLSGSAQHVEECSC

YPRYPGVRCVCRDNWKGSNRPIVDINIKDYSIVSSYVCSGLVGDTPRKNDSSSSHCLDPNNEEGGHGVK

GWAFDDGNDVWMGRTISEKLRSGYETFKVIEGWSKPNSKLQINRQVIVDRGNRSGYSGIFSVEGKSCINR

CFYVELIRGRKEETEVLWTSNSIVVFCGTSGTYGTGSWPDGADINLMPI

SEQ ID NO: 50
>gi|73919134|ref|YP_308846.1|polymerase PA [Influenza A virus (A/New York/392/2004(H3N2))]
MEDFVRQCFNPMIVELAEKAMKEYGEDLKIETNKFAAICTHLEVCFMYSDFHFINEQGESIVVELDDPNA

LLKHRFEIIEGRDRTMAWTVVNSICNTTGAEKPKFLPDLYDYKENRFIEIGVTRREVHIYYLEKANKIKS

-continued

ENTHIHIFSFTGEEIATKADYTLDEESRARIKTRLFTIRQEMANRGLWDSFRQSERGEETIEEKFEISGT

MRRLADQSLPPKFSCLENFRAYVDGFEPNGCIEGKLSQMSKEVNAKIEPFLKTTPRPIKLPNGPPCYQRS

KFLLMDALKLSIEDPSHEGEGIPLYDAIKCIKTFFGWKEPYIVKPHEKGINSNYLLSWKQVLSELQDIEN

EEKIPRTKNMKKTSQLKWALGENMAPEKVDFDNCRDISDLKQYDSDEPELRSLSSWIQNEFNKACELTDS

IWIELDEIGEDVAPIEYIASMRRNYFTAEVSHCRATEYIMKGVYINTALLNASCAAMDDFQLIPMISKCR

TKEGRRKTNLYGFIIKGRSHLRNDTDVVNFVSMEFSLTDPRLEPHKWEKYCVLEIGDMLLRSAIGQISRP

MFLYVRTNGTSKVKMKWGMEMRRCLLQSLQQIESMIEAESSIKEKDMTKEFFENKSEAWPIGESPKGVEE

GSIGKVCRTLLAKSVFNSLYASPQLEGFSAESRKLLLVVQALRDNLEPGTFDLGGLYEAIEECLINDPWV

LLNASWFNSFLTHALK

SEQ ID NO: 51
>gi|73919060|ref|YP_308849.1|polymerase PB2 [Influenza A virus (A/New
York/392/2004(H3N2))]
MERIKELRNLMSQSRTREILTKTTVDHMAIIKKYTSGRQEKNPSLRMKWMMAMKYPITADKRITEMVPER

NEQGQTLWSKMSDAGSDRVMVSPLAVTWWNRNGPVASTVHYPKVYKTYFDKVERLKHGTFGPVHFRNQVK

IRRRVDINPGHADLSAKEAQDVIMEVVFPNEVGARILTSESQLTITKEKKEELRDCKISPLMVAYMLERE

LVRKTRFLPVAGGTSSIYIEVLHLTQGTCWEQMYTPGGEVRNDDVDQSLIIAARNIVRRAAVSADPLASL

LEMCHSTQIGGTRMVDILRQNPTEEQAVDICKAAMGLRISSSFSFGGFTFKRTSGSSVKKEEEVLTGNLQ

TLKIRVHEGYEEFTMVGKRATAILRKATRRLVQLIVSGRDEQSIAEAIIVAMVFSQEDCMIKAVRGDLNF

VNRANQRLNPMHQLLRHFQKDAKVLFQNWGIEHIDSVMGMVGVLPDMTPSTEMSMRGIRVSKMGVDEYSS

TERVVVSIDRFLRVRDQRGNVLLSPEEVSETQGTERLTITYSSSMMWEINGPESVLVNTYQWIIRNWEAV

KIQWSQNPAMLYNKMEFEPFQSLVPKAIRSQYSGFVRTLFQQMRDVLGTFDTTQIIKLLPFAAAPPKQSR

MQFSSLTVNVRGSGMRILVRGNSPVFNYNKTTKRLTILGKDAGTLIEDPDESTSGVESAVLRGFLIIGKE

DRRYGPALSINELSNLAKEKANVLIGQGDVVLVMKRKRDSSILTDSQTATKRIRMAIN

SEQ ID NO: 52: CMV Protein IE122:
>gi|39841910|gb|AAR31478.1|UL122 [Human herpesvirus 5]
MESSAKRKMDPDNPDEGPSSKVPRPETPVTKATTFLQTMLRKEVNSQLSLGDPLFPELAEESLKTFEQVT

EDCNENPEKDVLAELGDILAQAVNHAGIDSSSTGHTLTTHSCSVSSAPLNKPTPTSVAVTNTPLPGASAT

PELSPRKKPRKTTRPFKVIIKPPVPPAPIMLPLIKQEDIKPEPDFTIQYRNKIIDTAGCIVISDSEEEQG

EEVETRGATASSPSTGSGTPRVTSPTHPLSQMNHPPLPDPLARPDEDSSSSSSSCSSASDSESESEEMK

CSSGGGASVTSSHHGRGGFGSAASSSLLSCGHQSSGGASTGPRKKKSKRISELDNEKVRNIMKDKNTPFCTPNVQTRRG

RVKIDEVSRMFRNTNRSLEYKNLPFTIPSMHQVLDEAIKACKTMQVNNKGIQIIYTRNHEVKSEVDAVRCRLGTMCNLA

LSTPFLMEHTMPVTHPPEVAQRTADACNEGVKAAWSLKELHTHQLCPRSSDYRNMIIHAATPVDLLGALNLCLPLMQKF

PKQVMVRIFSTNQGGFMLPIYETAAKAYAVGQFEQPTETPPEDLDTLSLAIEAAIQDLRNKSQ

SEQ ID NO: 53:
>gi|4927721|gb|AAD33253.1|AF125673_2 E7 [Human papillomavirus type 16]
MHGDTPTLHEYMLDLQPETTDLYCYEQLNDSSEEEDEIDGPAGQAEPDRAHYNIVTFCCKCDSTLRLCVQ

STHVDIRTLEDLLMGTLGIVCPICSQKP

EXAMPLE 1

The peptides according to the present invention may be synthesized by Schafer-N as c-terminal amides using the Fmoc-strategy of Sheppard, (1978) J. Chem. Soc., Chem. Commun., 539.

Cell Penetration Assay

A set of peptides is biotinylated on N-terminal, and different combinations of amino acids, with respect to length and type, are added to the sequence box $X^1$, $X^2$, $X^3$, $X^4$, $X^5$ and $X^6$ in the peptides as illustrated by the diagram below. The peptides are tested on cells grown from one individual blood donor.

Schematic diagram of amino acid sequence of the peptides according to the invention (Each X defines a sequence of amino acids):

$X^1$    $X^2$    $X^3$    $X^4$    $X^5$    $X^6$

Intracellular Staining for Biotinylated Peptides 96-well U-bottom polystyrene plates (NUNC, cat no: 163320) are used for staining of human PBMCs. Briefly, 8 ul of N- or C-terminally biotinylated peptides according to table 1 (i.e. 5 mM, 2.5 mM & 1.25 mM tested for each peptide) are incubated at 37° C. for 2 h with 40 ul of PBMC (12.5×106 cells/ml) from blood donors. Cells are then washed 3× with 150 ul of Cellwash (BD, cat no: 349524), followed by resuspension of each cell pellet with 100 ul of Trypsin-EDTA (Sigma, cat no: T4424), then incubated at 37° C. for 5 min. Trypsinated cells are then washed 3× with 150 ul of Cellwash (BD, cat no: 349524), followed by resuspension with BD Cytofix/Cytoperm™ plus (BD, cat no: 554715), then incubated at 4° C. for 20 min according to manufacturer. Cells are then washed 2× with 150 ul Perm-Wash (BD, cat no: 554715). Cells are then stained with Streptavidin-APC (BD, cat no: 554067) & Anti-hCD11c (eBioscience, cat no: 12-0116) according to manufacturer at 4° C. for 30 min aiming to visualize biotinylated peptides & dendritic cells, respectively. Cells are then washed 3× with 150 ul PermWash, followed by resuspension in staining buffer (BD, cat no: 554656) before flow cytometry. Dendritic cells are gated as CD11c+ events outside lymphocyte region (i.e. higher FSC & SSC signals than lymphocytes). 200 000 total cells are acquired on a FACSCanto II flow cytometer with HTS loader, and histograms for both total cells & dendritic cells with respect to peptide-fluorescence (i.e. GeoMean) are prepared.

Extracellular Staining for Biotinylated Peptides 96-well U-bottom polystyrene plates (NUNC, cat no: 163320) are used for staining of human PBMCs. Briefly, 8 ul of N- or C-terminally biotinylated peptides according to table 1 (i.e. 5 mM, 2.5 mM & 1.25 mM tested for each peptide; all peptides manufactured by Schafer) are incubated at 37° C. for 2 h with 40 ul of PBMC (12.5×106 cells/ml) from blood donors. Cells are then washed 3× with 150 ul of Cellwash (BD, cat no: 349524), then stained with Streptavidin-APC (BD, cat no: 554067) & Anti-hCD11c (eBioscience, cat no: 12-0116) according to manufacturer at 4° C. for 30 min aiming to visualize biotinylated peptides & dendritic cells, respectively. Cells are then washed 3× with 150 ul of Cellwash (BD, cat no: 349524), followed by resuspension in staining buffer (BD, cat no: 554656) before flow cytometry. Dendritic cells are gated as CD11c+ events outside lymphocyte region (i.e. higher FSC & SSC signals than lymphocytes). 200 000 total cells are acquired on a FACSCanto II flow cytometer with HTS loader, and histograms for both total cells & dendritic cells with respect to peptide-fluorescence (i.e. GeoMean) are prepared.

It may then be seen if the peptide has the ability to enter the cell.

EXAMPLE 2

Positive CTL Response May be Assayed by ELISPOT Assay

Human IFN-Gamma Cytotoxic T-Cell (CTL) Response by ELISPOT Assay

Briefly, at day 1, PBMC samples from HCV patients are incubated in flasks (430 000 PBMCs/cm2) for 2 h at 37° C., 5% CO2 in covering amount of culture media (RPMI 1640 Fisher Scientific; Cat No. PAAE15-039 supplemented with L-Glutamine, (MedProbe Cat. No. 13E17-605E, 10% Foetal Bovine serum (FBS), Fisher Scientific Cat. No. A15-101) and Penicillin/Streptomycin, (Fisher Scientific Cat. No. P11-010) in order to allow adherence of monocytes. Non-adherent cells are isolated, washed, and frozen in 10% V/V DMSO in FBS until further usage. Adherent cells are carefully washed with culture media, followed by incubation at 37° C. until day 3 in culture media containing 2 μg/ml final concentration of hrGM-CSF (Xiamen amoytop biotech co, cat no: 3004.9090.90) & 1 μg/ml hrIL-4 (Invitrogen, Cat no: PHC0043), and this procedure is then repeated at day 6. At day 7, cultured dendritic cells (5 000-10 000 per well) are added to ELISPOT (Millipore multiscreen HTS) plates coated with 0.5 μg/well anti-human γ Interferon together with thawed autologous non-adherent cells (200 000 per well), antigen samples (1-8 ug/ml final concentration for peptide antigens; 5 ug/ml final concentration for Concanavalin A (Sigma, Cat no: C7275) or PHA (Sigma, Cat no: L2769)) & anti-Anergy antibodies (0.03-0.05 ug/ml final concentration for both anti-PD-1 (eBioscience, cat no: 16-9989-82) & anti-PD-L1 (eBioscience, cat no: 16-5983-82)). Plates are incubated overnight and spots are developed according to manufacturer. Spots are read on ELISPOT reader (CTL-ImmunoSpot® S5 UV Analyzer).

EXAMPLE 3

The REVEAL & ProVE® Rapid Epitope Discovery System in Detail

Binding properties to HLA for the peptides according to the present invention may be tested for the following HLA-types in class I: HLA-A1, HLA-A2, HLA-A3, HLA-A11, HLA-A24, HLA-A29, HLA-B7, HLA-B8, HLA-B14, HLA-B15, HLA-B27, HLA-B35, HLA-B40, and the following HLA-types in class II: HLA-DR1, HLA-DR3, HLA-DR4, HLA-DR7, HLA-DR11, HLA-DR13, HLA-DR15. The peptides are synthesized as a Prospector PEPscreen®: Custom Peptide Library. Peptides 8-15 amino acids in length are synthesized in 0.5-2 mg quantities with high average purity. Quality control by MALDI-TOF Mass Spectrometry is carried out on 100% of samples.

The REVEAL™ binding assay determines the ability of each candidate peptide to bind to one or more MHC class I alleles and stabilizing the MHC-peptide complex. By comparing the binding to that of high and intermediate affinity T cell epitopes, the most likely immunogenic peptides in a protein sequence may be identified. Detection is based on the presence or absence of the native conformation of the MHC-peptide complex.

Each peptide is given a score relative to the positive control peptide, which is a known T cell epitope. The score of the test peptide is reported quantitatively as a percentage of the signal generated by the positive control peptide, and the peptide is indicated as having a putative pass or fail result. Assay performance is confirmed by including an intermediate control peptide that is known to bind with weaker affinity to the allele under investigation.

EXAMPLE 4

Preparation of Dimeric Peptides

Amino acids that link two monomeric peptide sequences are underlined.
Influenza (M2e):
Constructs derived from the extracellular domain on influenza protein M2 (M2e-domain)
Native Domain:

```
MSLLTEVETPIRNEWGCRCNDSSD
```

The following sequences was prepared or under preparation. The different parts, $X^1$-$X^6$, are divided by brackets.

```
BI100_CGnat
[RR][SLLTEVETP][GCG][VETPIR][G][TPIRNEWG]

BI100_CG
[RR][SL(Nle)TDIETP][GCG][IDTPIR][G][TPIBQDWG]

BI100-CGcyc
[WWGC][TDIET][CG][IDTPIR][G][TPIBQDWG]

BI100-Cyc 2
[RRGC][SLLT][C][SLLTEVQTPIRN][GRR][SEWGSRSN]

Bi150-Dimer
[RR(Nle)C][SLLTEVQTPIRN][GRR][VETPIRN]
         |
[WWQC][TPIRSEWGCRSN]GRR[SNDSSG]

BI150-new
        [WW][SL(Nle)TDIETP][GCG][IDTPIR][G][TPIBQDWG]
                             |
[RR(Har)][IDTPIR][G][TPIBQDWG][KG][SL(Nle)TDIETPG]

BI150-2mod
        [R][SLZTDIETP][Dpr(Aoa)][IDTPIR][G][TPIBQDWG]
                         |
[RR][IDTPIR][GG][TPI(Har)QEW][Dpr(Ser)][SLZTDIETPG]
```

This construct links the monomeric peptides via a Dpr (Aoa) in the first peptide to an oxidized by $NaIO_4$ Dpr(Ser) residue in the second.

Dpr(Aoa)=N-α-Fmoc-N-β-(N-t.-Boc-amino-oxyacetyl)-L-diaminopropionic acid

Explanation:

The brackets used in the sequences are meant to indicate the different parts/boxes. For BI100_CGnat/BI100_CG, the boxes will have the following amino-acid sequences:

Part $X^1$    RR

Part $X^2$    SLLTEVETP/SL(Nle)TDIETP    (aa 2-10 on M2e native domain)

Part $X^3$    GCG

Part $X^4$    VETPIR/IDTPIR    (aa 7-12 on M2e native domain)

Part $X^5$    G

Part $X^6$    TPIRNEWG/TPIBQDWG    (aa 9-16 on M2e native domain)

The boxes on part of the other sequences can be found in a similar manner

Example C5—Sequences

```
BI450-AdjBT1
W_DW_LGCAKRRVCGGAKRRVVQREKRA

BI450-AdjBT2
W_DW_LGCIEEEGCGGIEEEGGERDR

BI400-B
GAKRRVVGGCGGAKRRVVQREKRAGEREKRA
         |
         GKGGIEEEGGRDRDRGGEQDRDR
```

```
Examples of disulfide linked constructs can be,
but are not restricted to, the following linked
peptide sequences:
CGGAKRRVVGGAKRRVVGQREKRAV  (SEQ ID NO: 115)
|
CGGGDQQLLGGAEEEIVGGIEEEGGERDRDR  (SEQ ID NO: 116)

CGGAKRRVVGGAKRRVVGGQREKR  (SEQ ID NO: 117)
|
CGGGDQQLLGGAEEEIVGGIEEEGG  (SEQ ID NO: 118)

CGGAEEEVVGGDQQLL  (SEQ ID NO: 119)
|
GCGGAKRRVVGGAKRRVV  (SEQ ID NO: 120)
```

The above disulfide linked constructs may e.g. be synthesised by titration of 2-pyridinesulfenyl (SPyr)-protected cysteine-containing peptides with thiol-unprotected peptides. This has proven to be a superior procedure to selectively generate disulfide-linked peptide heterodimers preventing the formation of homodimers (Schutz A et al., Tetrahedron, Volume 56, Issue 24, 9 Jun. 2000, Pages 3889-3891). Similar constructs may be made where SEQ ID NO: 115 is disulphide linked to SEQ ID NOs 118 or 120, or where SEQ ID NO: 117 is disulphide linked to SEQ ID NOs: 116 or 120, or where SEQ ID NO: 119 is disulphide linked to SEQ ID NOs: 116 or 118.

Examples of thio-ester linked constructs can be, but are not restricted to, the following linked peptide sequences, which have all been obtained from Bachem (UK) Ltd:

```
GAKRRVVGGCGGAKRRVVQREKRAGEREKRA  (SEQ ID NO: 121)
        |
        GKGGIEEEGGRDRDRGGEQDRDR  (SEQ ID NO: 122)
```

(the peptides are linked via the underlined Cys and Lys residues; the entire construct is termed BI400-B herein).

```
GAKRRVVGGCGGAKRRVVQREKRAGEREKRA  (SEQ ID NO: 121)
        |
        GKGGIEEEGGERDRDRGGQDRDR  (SEQ ID NO: 124)
```

(the peptides are linked via the underlined Cys and Lys residues; the entire construct is termed BI400-Bu1 herein).

```
GAKRRVVGGCGGAKRRVVEREKRAGQREKRA  (SEQ ID NO: 125)
        |
        GKGGIEEEGGQDRDRGGRDRDR  (SEQ ID NO: 126)
```

(the peptides are linked via the underlined Cys and Lys residues; the entire construct is termed BI400-Bu2 herein).

```
GAKRRVVGGCGGAKRRVVEREKRAGQREKRA  (SEQ ID NO: 125)
        |
        GKGGIEEEGGEQDRDRGGERDRD  (SEQ ID NO: 128)
```

(the peptides are linked via the underlined Cys and Lys residues; the entire construct is termed BI400-Bu3 herein).

The Cys-Lys linker is typically established in the form of a thioether bond between a cysteine in one peptide and a bromoacetyl derivatized lysine in the other peptide.

Similar constructs may be made where SEQ ID NO: 121 is Cys-Lys linked to SEQ ID NOs 126 or 128, or where SEQ ID NO: 125 is Cys-Lys linked to SEQ ID NOs: 122 or 124.

Examples of other linked constructs can be, but are not restricted to, the following linked peptide sequences,

```
GAKRRVVGGSGGAKRRVVQREKRAGEREKRA  (SEQ ID NO: 129)
        |
        GKGGIEEEGGRDRDRGGEQDRDR  (SEQ ID NO: 122)
```

(the peptides are linked via the underlined Ser and Lys residues).

The Ser-Lys linker is typically established in the form of an oxime bond between oxidized (aldehyde) serine in one peptide and (aminooxyacerylated) derivatized lysine in the other peptide.

EXAMPLE 5

The Construction of HCV Dimeric Peptides

```
BI350-1mod1:
  RRGNWAKVLKNWAKVI         (SEQ ID NO: 130)
           |
  RRGLLADARVGCGSGADRVCS    (SEQ ID NO: 131)
```

This construct links the monomeric peptides via a lysine residue in the first peptide to a cysteine residue in the second peptide by using a sulpho-SMCC linker.

```
BI350-1mod2:
  RRGNWAKVL(Dpr)NWAKVI              (SEQ ID NO: 132)
           |
  RRGLLADARVG(Dpr(Ser))GSGADRVCS    (SEQ ID NO: 133)
```

This construct links the monomeric peptides via a Dpr (Aoa) in the first peptide to an oxidized by NaIO$_4$ Dpr(Ser) residue in the second peptide.

Dpr(Aoa)=N-α-Fmoc-N-β-(N-t.-Boc-amino-oxyacetyl)-L-diaminopropionic acid

Alternatively, the K or C may be substituted with an N-ε-methylated Lys, which is linked to Asp or Glu.

Accordingly, an N-ε-methylated Lys may be linked to Asp or Glu by a side-chain to side-chain peptide bond, wherein the N methylation makes the bond more stable.

The sequences would then be (Lys(Me) refers to an N-ε-methylated Lys residue):

```
RRGNWAKVL-Lys(Me)-NWAKVI       (SEQ ID NO: 134)
         |
  RRGLLADARVGEGSGADRVCS         (SEQ ID NO: 135)
or

RRGNWAKVL-Lys(Me)-NWAKVI       (SEQ ID NO: 134)
         |
  RRGLLADARVGDGSGADRVCS         (SEQ ID NO: 136)
or alternatively, if the bond is reversed:

RRGNWAKVLENWAKVI              (SEQ ID NO: 137)
           |
  RRGLLADARVG-Lys(Me)-GSGADRVCS (SEQ ID NO: 138)
or

RRGNWAKVLDNWAKVI (SEQ ID NO: 139)
           |
  RRGLLADARVG-Lys(Me)-GSGADRVCS (SEQ ID NO: 138)
```

The construction of an Influenza dimeric peptides:

```
BI150-2mod                                 (SEQ ID NO: 140)
          R-SLZTDIETP-(Dpr)-IDTPIRGTPIBQDWG
                         |                 (SEQ ID NO: 141)
  RR-IDTPIR-GG-TPI(Har)QEW-Dpr(Ser)-SLZTDIETPG
```

Dpr is diaminopropionic acid, Dpr(Ser) is serinyl diaminopropionic acid. (to form a Dpr-Dpr(Ser) oxime bond, as described elsewhere in this application)

Native sequence peptide from influenza M2e protein, which the above construct targets, used for testing:

```
             BI100-cg2
                              (SEQ ID NO: 142)
             MSLLTEVETPIRNEWGCRC
```

EXAMPLE 6

Immunological Studies

Rabbit Immunizations

New Zealand White female rabbits (n=3) was immunized intradermally at weeks 0, 2 & 6 with 1 ml of BI400-B vaccine consisting of 500 μg BI400-B in 50% V/V Freund's adjuvant (i.e. Complete Freund's adjuvant used for priming, followed by boostings with Incomplete Freund's adjuvant). Individual blood serum was isolated for ELISA.

Direct ELISA for Human or Rabbit Sera 50-100 µl of BI400-B (pre-incubated in Coating buffer—0.05M $Na_2CO_3$ pH9.6; denoted CB—in cold at 16 µg/ml for each peptide 1-3 days prior to coating) or just CB (background control) is used for coating wells in microtiter plates at 4° C. overnight. The microtiter plates are then washed 3× with washing buffer (PBS+1% v/v Triton-X100; denoted WB), followed by 2 h blocking at room temperature (RT) with 200 µl/well of blocking buffer (PBS+1% w/v BSA). Plates are then washed 3× with WB, followed by 1 h incubation at 37° C. with 50-70 ul/well of added human (or rabbit) sera (serial dilutions ranging from 1:1-1:250 in dilution buffer (PBS+1% v/v Triton-X100+1% w/v BSA; denoted DB)). Plates are then washed 6× with WB, followed by 1 h incubation at RT with 70 µl/well of Alkaline Phosphatase-conjugated Protein G (3 µg/ml in DB; Calbiochem 539305). Plates are then washed 6× with WB, followed by 10-60 min incubation at room temperature with 100 µl/well of 0.3% w/v of Phenophtalein monophosphate (Sigma P-5758). Plates are finally quenched by adding 100 µl/well of Quench solution (0.1M TRIS+0.1M EDTA+0.5M NaOH+0.01% w/v $NaN_3$; pH14), followed by ELISA reader (ASYS UVM 340) at 550 nm.

Results

The results from the immunization studies with BI400-B demonstrate that it is possible to generate peptides that elicit an efficient antibody response. The specificity of these antibody responses may be confirmed in competitive Elisa. Antibodies generated to BI400-B in animal models are comparable with antibodies elicited in natural HIV infection and associated with longterm nonprogression. These results show that these peptides are suitable for diagnostics as well as the development of a vaccine targeting HIV-induced immune activation as well as other pathogens.

EXAMPLE 7

Influenza Specific M2e Response by ELISPOT Assay

At day one, PBMC samples from blood donors were thawed, washed with warm medium and incubated in flasks (250000 PBMCs/cm2) for 24 hours at 37° C., 5% CO2 in covering amount of culture media (RPMI 1640 with ultraglutamine, Lonza, BE12-702F701; 10% Foetal Bovine serum (FBS), Fisher Scientific Cat. No. A15-101; Penicillin/Streptomycin, Fisher Scientific Cat. No. P11-010) to allow the cells to recover after thawing. At day two, the cells were added to a Falcon Microtest Tissue Culture plate, 96 well flat bottom, at 500 000 cells per well in a volume of 200 µl total medium. Parallel wells were added the indicated stimuli in duplicate or left with medium as a control for 6 days at 37° C., 5% $CO_2$. After the six day of incubation, 100 µl of the cell suspension were transferred to an ELISPOT (Millipore multiscreen HTS) plate coated with 1 µg/ml native influenza M2e protein. After a 24 hour incubation, the plate was washed four times with PBS+0.05% Tween20, and a fifth time with PBS, 200 µl/well. A mouse Anti-human IgG or IgM biotin (Southern Biotech 9040-08 and 9020-08) was diluted in PBS with 0.5% FBS and incubated for 90 minutes at 37° C. The washing was repeated as described, before 80 µl Streptavidin-Alkaline-Phosphatase (Sigma Aldrich, S289) was added each well and incubated at 60 minutes in the dark, at room temperature. The wells were then washed 2 times with PBS+0.05% Tween20 and 4 times with PBS, 200 µl/well, before the substrate, Vector Blue Alkaline Phosphatase Substrate kit III (Vector Blue, SK-5300) was added and let to develop for 7 minutes at room temperature. The reaction was stopped with running water, the plates let dry and the sport enumerated by an ELISPOT reader (CTL-ImmunoSpot® S5 UV Analyzer).

Influenza Specific M2e Response by ELISA

100 µl of antigen as indicated (pre-incubated in Coating buffer—0.05M $Na_2CO_3$ pH9.6; denoted CB—in cold at 8 µg/ml 1-3 days) or just CB (background control) was used for coating wells in microtiter plates at 4° C. The microtiter plates are then washed 3× with washing buffer (PBS+1% v/v Triton-X100; denoted WB), followed by 2 h blocking at room temperature (RT) with 200 µl/well of blocking buffer (PBS+1% w/v BSA). Plates are then washed 3× with WB, followed by 1 h incubation at 37° C. with 50-70 ul/well of added human (or rabbit or sheep) sera (serial dilutions ranging from 1:5-1:250 in dilution buffer (PBS+1% v/v Triton-X100+1% w/v BSA; denoted DB)). Plates are then washed 6× with WB, followed by 1 h incubation at RT with 70 µl/well of Alkaline Phosphatase-conjugated Protein G (3 µg/ml in DB; Calbiochem 539305) or goat anti-mouse IgG biotin (1 µg/ml, Southern Biotech, 1030-08. In case of the goat anti-mouse IgG biotin, the plates were washed one extra step as described, before addition of 100 µl Streptavidin-Alkaline-Phosphatase (1 µg/ml, Sigma Aldrich, S289) and incubated 1 hour at RT. Plates are then washed 6× with WB, followed by 10-60 min incubation at room temperature with 100 µl/well of 0.3% w/v of Phenophtalein monophosphate (Sigma P-5758). Plates are finally quenched by adding 100 µl/well of Quench solution (0.1M TRIS+0.1M EDTA+0.5M NaOH+0.01% w/v $NaN_3$; pH14), followed by a measurement with a ELISA reader (ASYS UVM 340) at 550 nm. The strength of the sera, i.e. the magnitude of the humoral immune response, is then reported as the dilution of sera that result in the described Optical Density (OD) value, or the OD value at the indicated dilution of sera.

Results

In table 2 show the relative amount of number of B-cells that proliferated compared to baseline proliferation of unstimulated PBMC. The table clearly shows that the BI150-2 mod was recognised by human memory cells as the response was IgG specific, meaning that the BI150-2 mod can stimulate class-switched B cells in a way that allow the antibodies produced to bind to the native sequence that BI150-2 mod is derived from. A large variation between individual donors is to be expected as there will be a large variation in the human population with regard to their pre-existing humoral memory towards the influenza M2 protein. From table 2 it can also be noted that the BI150-2 mod was also able to induce proliferation of IgM B cells.

TABLE 2

B cell response in human PBMC stimulated with BI150-2mod against native sequence PBMC from blood donors

|  |  | BC-39 | BC-42 | BC-28 | BC-35 | BC-31 | BC-34 | Mean | Median |
|---|---|---|---|---|---|---|---|---|---|
| IgG | Survival stimuli* | 2200% | 120% | 111% | 6625% | 300% | 100% | 1576% | 210% |
|  | Survival stimuli + BI150-2mod | 2260% | 440% | 133% | 1638% | 300% | 950% | 953% | 695% |
| IgM | Survival stimuli | 3400% | 3067% | 22900% | 300% | 400% | 3100% | 5528% | 3083% |
|  | Survival stimuli + BI150-2mod | 3400% | 6783% | 7600% | 1700% | 467% | 1300% | 3542% | 3542% |

*Surivival stimuli: rh-sCD40 Ligand, Immuno Tools, 11343345, ODN 2006 Type B CpG oligonucleotide-Human TLR9 ligand, Invivogen Sigma, Tlrl-2006, rh IL-21, Immunotools, 11340213

The vaccination of BALB/c mice was done s.c. with 100 µg peptide at weeks 1, 3, 7, serum from week 9 with 1 mg Aluminium in the form of 1.3% Alhydrogel. In table 3, the data show that the BI350-1mod1 induced a specific immune response in BALB/c mice as the vaccine antigen was recognised. It was also evident that the resulting immune response comes as a consequence of a class switching event as the immune response was IgG specific.

TABLE 3

Serum IgG response (OD) in mice vaccinated with BI350-1mod1 +Alhydrogel directed against vaccine antigen

|  | Mean (n = 6) | SEM |
|---|---|---|
| BI350-1mod1 | 0.26 | 0.09 |

The vaccination of sheep was done with 500 µg of peptide in PBS with the following adjuvants: ISA51 (vaccination week 1, 2, 3, 4, serum from week 6) and Freunds Adjuvant (vaccination weeks 1, 12, 26, serum from week 28). In table 4, the data show the dilution of serum that correspond to an OD value three times the assay background. The table clearly shows that the BI100-CG and BI100-CGcyc induced an immune response by itself or with two different standard adjuvants. This indicate that the constructs can be combined with different adjuvants and induce an IgG response, a signal that an immunological memory has been elicited in sheep.

TABLE 4

Dilution of serum three times background IgG response in sheep vaccinated with BI100 constructs directed against BI100-cg2 antigen

|  | BI100-CG | BI100CGcyc |
|---|---|---|
| Freunds | 11000 | 125 |
| ISA51 | 125 | 25 |
| None | 25 | 25 |

---

The invention claimed is:

1. A method for inducing an immune response against human immunodeficiency virus (HIV) in a subject in need thereof, said method comprising:

administering to the subject a dimeric peptide comprising the following monomeric peptides:

```
GAKRRVVGGCGGAKRRVVQREKRAGEREKRA    (SEQ ID NO: 121)
         I
         GKGGIEEEGGRDRDRGGQDRDR    (SEQ ID NO: 147)
``` wherein the peptides are linked through $C^{10}$ in SEQ ID NO: 121 and $K^2$ in SEQ ID NO: 147.

2. The method of claim 1, wherein the monomeric peptides are linked via a thio ether bond between C(2-oxo-ethyl)$^{10}$ and $K^2$.

3. The method of claim 1, wherein the N- or C-termini of the monomeric peptides are modified by amidation or acetylation.

4. The method of claim 3, wherein the C-termini of the monomeric peptides are amides.

5. A method for inducing an immune response against human immunodeficiency virus (HIV) in a subject in need thereof, said method comprising:

administering to the subject a dimeric peptide comprising the following monomeric peptides:

```
GAKRRVVGGCGGAKRRVVQREKRAGEREKRA    (SEQ ID NO: 121)
         I
         GKGGIEEEGGRDRDRGGQDRDR    (SEQ ID NO: 147)
``` wherein the monomeric peptides are linked via a thio ether bond between C(2-oxo-ethyl)$^{10}$ in SEQ ID NO: 121 and $K^2$ in SEQ ID NO: 147.

6. The method of claim 5, wherein said dimeric peptide is in the form of a trifluoroacetate salt.

7. The method of claim 1, wherein the dimeric peptide is administered as an immunogenic composition.

8. The method of claim 1, wherein the dimeric peptide is administered as an immunogenic composition in combination with a pharmaceutically acceptable diluent or vehicle.

9. The method of claim 8, wherein the dimeric peptide is administered as an immunogenic composition in combination with a pharmaceutically acceptable diluent or vehicle and an immunological adjuvant.

10. The method of claim 1, wherein the immunogenic composition is in the form of a liquid solution or suspension.

11. The method of claim 10, wherein the immunogenic composition is further emulsified or encapsulated in liposomes.

12. The method of claim 8, wherein the immunogenic composition is further emulsified or encapsulated in liposomes.

* * * * *

SEQUENCE LISTING

```
<160> NUMBER OF SEQ ID NOS: 157

<210> SEQ ID NO 1
<211> LENGTH: 97
<212> TYPE: PRT
<213> ORGANISM: Influenza A virus

<400> SEQUENCE: 1

Met Ser Leu Leu Thr Glu Val Glu Thr Pro Ile Arg Asn Glu Trp Gly
1               5                   10                  15

Cys Arg Cys Asn Gly Ser Ser Asp Pro Leu Ala Ile Ala Ala Asn Ile
                20                  25                  30

Ile Gly Ile Leu His Leu Thr Leu Trp Ile Leu Asp Arg Leu Phe Phe
            35                  40                  45

Lys Cys Ile Tyr Arg Arg Phe Lys Tyr Gly Leu Lys Gly Gly Pro Ser
        50                  55                  60

Thr Glu Gly Val Pro Lys Ser Met Arg Glu Glu Tyr Arg Lys Glu Gln
65                  70                  75                  80

Gln Ser Ala Val Asp Ala Asp Asp Gly His Phe Val Ser Ile Glu Leu
                85                  90                  95

Glu

<210> SEQ ID NO 2
```

```
<211> LENGTH: 86
<212> TYPE: PRT
<213> ORGANISM: HIV

<400> SEQUENCE: 2

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Ala His Gln Asn Ser Gln Thr
    50                  55                  60

His Gln Ala Ser Leu Ser Lys Gln Pro Thr Ser Gln Pro Arg Gly Asp
65                  70                  75                  80

Pro Thr Gly Pro Lys Glu
                85

<210> SEQ ID NO 3
<211> LENGTH: 511
<212> TYPE: PRT
<213> ORGANISM: HIV

<400> SEQUENCE: 3

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255
```

-continued

Thr Gln Leu Leu Leu Asn Gly Ser Leu Ala Glu Glu Val Val Ile
                260                 265                 270

Arg Ser Val Asn Phe Thr Asp Asn Ala Lys Thr Ile Ile Val Gln Leu
            275                 280                 285

Asn Thr Ser Val Glu Ile Asn Cys Thr Arg Pro Asn Asn Asn Thr Arg
        290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
    370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
    450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg
            500                 505                 510

<210> SEQ ID NO 4
<211> LENGTH: 345
<212> TYPE: PRT
<213> ORGANISM: HIV

<400> SEQUENCE: 4

Ala Val Gly Ile Gly Ala Leu Phe Leu Gly Phe Leu Gly Ala Ala Gly
1               5                   10                  15

Ser Thr Met Gly Ala Ala Ser Met Thr Leu Thr Val Gln Ala Arg Gln
                20                  25                  30

Leu Leu Ser Gly Ile Val Gln Gln Gln Asn Asn Leu Leu Arg Ala Ile
            35                  40                  45

Glu Ala Gln Gln His Leu Leu Gln Leu Thr Val Trp Gly Ile Lys Gln
        50                  55                  60

Leu Gln Ala Arg Ile Leu Ala Val Glu Arg Tyr Leu Lys Asp Gln Gln
65                  70                  75                  80

Leu Leu Gly Ile Trp Gly Cys Ser Gly Lys Leu Ile Cys Thr Thr Ala
                85                  90                  95

Val Pro Trp Asn Ala Ser Trp Ser Asn Lys Ser Leu Glu Gln Ile Trp
            100                 105                 110

Asn His Thr Thr Trp Met Glu Trp Asp Arg Glu Ile Asn Asn Tyr Thr

```
            115                 120                 125
Ser Leu Ile His Ser Leu Ile Glu Glu Ser Gln Asn Gln Gln Glu Lys
    130                 135                 140

Asn Glu Gln Glu Leu Leu Glu Leu Asp Lys Trp Ala Ser Leu Trp Asn
145                 150                 155                 160

Trp Phe Asn Ile Thr Asn Trp Leu Trp Tyr Ile Lys Leu Phe Ile Met
                165                 170                 175

Ile Val Gly Gly Leu Val Gly Leu Arg Ile Val Phe Ala Val Leu Ser
            180                 185                 190

Ile Val Asn Arg Val Arg Gln Gly Tyr Ser Pro Leu Ser Phe Gln Thr
        195                 200                 205

His Leu Pro Thr Pro Arg Gly Pro Asp Arg Pro Glu Gly Ile Glu Glu
    210                 215                 220

Glu Gly Gly Glu Arg Asp Arg Asp Arg Ser Ile Arg Leu Val Asn Gly
225                 230                 235                 240

Ser Leu Ala Leu Ile Trp Asp Asp Leu Arg Ser Leu Cys Leu Phe Ser
                245                 250                 255

Tyr His Arg Leu Arg Asp Leu Leu Leu Ile Val Thr Arg Ile Val Glu
            260                 265                 270

Leu Leu Gly Arg Arg Gly Trp Glu Ala Leu Lys Tyr Trp Trp Asn Leu
        275                 280                 285

Leu Gln Tyr Trp Ser Gln Glu Leu Lys Asn Ser Ala Val Ser Leu Leu
    290                 295                 300

Asn Ala Thr Ala Ile Ala Val Ala Glu Gly Thr Asp Arg Val Ile Glu
305                 310                 315                 320

Val Val Gln Gly Ala Cys Arg Ala Ile Arg His Ile Pro Arg Arg Ile
                325                 330                 335

Arg Gln Gly Leu Glu Arg Ile Leu Leu
            340                 345

<210> SEQ ID NO 5
<211> LENGTH: 192
<212> TYPE: PRT
<213> ORGANISM: HCV

<400> SEQUENCE: 5

Tyr Glu Val Arg Asn Val Ser Gly Val Tyr His Val Thr Asn Asp Cys
1               5                   10                  15

Ser Asn Ser Ser Ile Val Tyr Gly Ala Ala Asp Met Ile Met His Thr
            20                  25                  30

Pro Gly Cys Val Pro Cys Val Arg Glu Asn Asn Ser Ser Arg Cys Trp
        35                  40                  45

Val Ala Leu Thr Pro Thr Leu Ala Ala Arg Asn Arg Ser Ile Pro Thr
    50                  55                  60

Thr Thr Ile Arg Arg His Val Asp Leu Leu Val Gly Ala Ala Ala Phe
65                  70                  75                  80

Cys Ser Ala Met Tyr Val Gly Asp Leu Cys Gly Ser Val Phe Leu Val
                85                  90                  95

Ser Gln Leu Phe Thr Phe Ser Pro Arg Arg Tyr Glu Thr Val Gln Asp
            100                 105                 110

Cys Asn Cys Ser Leu Tyr Pro Gly His Val Ser Gly His Arg Met Ala
        115                 120                 125

Trp Asp Met Met Met Asn Trp Ser Pro Thr Ala Ala Leu Val Val Ser
    130                 135                 140
```

-continued

Gln Leu Leu Arg Ile Pro Gln Ala Val Val Asp Met Val Thr Gly Ala
145                 150                 155                 160

His Trp Gly Val Leu Ala Gly Leu Ala Tyr Tyr Ser Met Val Gly Asn
            165                 170                 175

Trp Ala Lys Val Leu Ile Val Met Leu Leu Phe Ala Gly Val Asp Gly
            180                 185                 190

<210> SEQ ID NO 6
<211> LENGTH: 363
<212> TYPE: PRT
<213> ORGANISM: HCV

<400> SEQUENCE: 6

Thr Thr His Val Thr Gly Gly Gln Thr Gly Arg Thr Thr Leu Gly Ile
1               5                   10                  15

Thr Ala Met Phe Ala Phe Gly Pro His Gln Lys Leu Gln Leu Ile Asn
            20                  25                  30

Thr Asn Gly Ser Trp His Ile Asn Arg Thr Ala Leu Asn Cys Asn Asp
        35                  40                  45

Ser Leu Asn Thr Gly Phe Leu Ala Ala Leu Phe Tyr Ala Arg Lys Phe
50                  55                  60

Asn Ser Ser Gly Cys Pro Glu Arg Met Ala Ser Cys Arg Pro Ile Asp
65                  70                  75                  80

Lys Phe Val Gln Gly Trp Gly Pro Ile Thr His Ala Val Pro Asp Asn
                85                  90                  95

Leu Asp Gln Arg Pro Tyr Cys Trp His Tyr Ala Pro Gln Pro Cys Gly
            100                 105                 110

Ile Ile Pro Ala Ser Gln Val Cys Gly Pro Val Tyr Cys Phe Thr Pro
        115                 120                 125

Ser Pro Val Val Val Gly Thr Thr Asp Arg Phe Gly Ala Pro Thr Tyr
130                 135                 140

Thr Trp Gly Glu Asn Glu Thr Asp Val Leu Leu Leu Asn Asn Thr Arg
145                 150                 155                 160

Pro Pro Gln Gly Asn Trp Phe Gly Cys Thr Trp Met Asn Gly Thr Gly
                165                 170                 175

Phe Ala Lys Thr Cys Gly Gly Pro Pro Cys Asn Ile Gly Gly Val Gly
            180                 185                 190

Asn Asn Thr Leu Thr Cys Pro Thr Asp Cys Phe Arg Lys His Pro Glu
        195                 200                 205

Ala Thr Tyr Thr Lys Cys Gly Ser Gly Pro Trp Leu Thr Pro Arg Cys
210                 215                 220

Met Val Asp Tyr Pro Tyr Arg Leu Trp His Tyr Pro Cys Thr Val Asn
225                 230                 235                 240

Phe Thr Ile Phe Lys Val Arg Met Tyr Val Gly Gly Val Glu His Arg
                245                 250                 255

Leu Thr Ala Ala Cys Asn Trp Thr Arg Gly Glu Arg Cys Asp Leu Glu
            260                 265                 270

Asp Arg Asp Arg Ser Glu Leu Ser Pro Leu Leu Leu Ser Thr Thr Glu
        275                 280                 285

Trp Gln Val Leu Pro Cys Ser Phe Thr Thr Leu Pro Ala Leu Ser Thr
290                 295                 300

Gly Leu Ile His Leu His Gln Asn Ile Val Asp Val Gln Tyr Leu Tyr
305                 310                 315                 320

Gly Val Gly Ser Ala Val Val Ser Ile Val Ile Lys Trp Glu Tyr Ile
                325                 330                 335

Leu Leu Leu Phe Leu Leu Leu Ala Asp Ala Arg Val Cys Ala Cys Leu
            340                 345                 350

Trp Met Met Leu Leu Ile Ala Gln Ala Glu Ala
            355                 360

<210> SEQ ID NO 7
<211> LENGTH: 3011
<212> TYPE: PRT
<213> ORGANISM: HCV

<400> SEQUENCE: 7

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His

```
                    340                 345                 350
Trp Gly Val Leu Ala Gly Ile Ala Tyr Phe Ser Met Val Gly Asn Trp
                355                 360                 365

Ala Lys Val Leu Val Val Leu Leu Phe Ala Gly Val Asp Ala Glu
        370                 375                 380

Thr His Val Thr Gly Ser Ala Gly Arg Thr Ala Gly Leu Val
385                 390                 395                 400

Gly Leu Leu Thr Pro Gly Ala Lys Gln Asn Ile Gln Leu Ile Asn Thr
                    405                 410                 415

Asn Gly Ser Trp His Ile Asn Ser Thr Ala Leu Asn Cys Asn Glu Ser
                420                 425                 430

Leu Asn Thr Gly Trp Leu Ala Gly Leu Phe Tyr Gln His Lys Phe Asn
            435                 440                 445

Ser Ser Gly Cys Pro Glu Arg Leu Ala Ser Cys Arg Arg Leu Thr Asp
        450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Pro Arg Pro Cys Gly Ile
                485                 490                 495

Val Pro Ala Lys Ser Val Cys Gly Pro Val Tyr Cys Phe Thr Pro Ser
                500                 505                 510

Pro Val Val Val Gly Thr Thr Asp Arg Ser Gly Ala Pro Thr Tyr Ser
                515                 520                 525

Trp Gly Ala Asn Asp Thr Asp Val Phe Val Leu Asn Asn Thr Arg Pro
            530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Val Gly Asn
                565                 570                 575

Asn Thr Leu Leu Cys Pro Thr Asp Cys Phe Arg Lys His Pro Glu Ala
                580                 585                 590

Thr Tyr Ser Arg Cys Gly Ser Gly Pro Trp Ile Thr Pro Arg Cys Met
            595                 600                 605

Val Asp Tyr Pro Tyr Arg Leu Trp His Tyr Pro Cys Thr Ile Asn Tyr
                610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                    645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
        690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                    725                 730                 735

Met Met Leu Leu Ile Ser Gln Ala Glu Ala Ala Leu Glu Asn Leu Val
                740                 745                 750

Ile Leu Asn Ala Ala Ser Leu Ala Gly Thr His Gly Leu Val Ser Phe
            755                 760                 765
```

-continued

Leu Val Phe Phe Cys Phe Ala Trp Tyr Leu Lys Gly Arg Trp Val Pro
    770                 775                 780

Gly Ala Val Tyr Ala Phe Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
            805                 810                 815

Ser Cys Gly Gly Val Val Leu Val Gly Leu Met Ala Leu Thr Leu Ser
                820                 825                 830

Pro Tyr Tyr Lys Arg Tyr Ile Ser Trp Cys Met Trp Trp Leu Gln Tyr
            835                 840                 845

Phe Leu Thr Arg Val Glu Ala Gln Leu His Val Trp Val Pro Pro Leu
850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Ile Cys Ala Leu Ala Arg Lys Ile
            915                 920                 925

Ala Gly Gly His Tyr Val Gln Met Ala Ile Ile Lys Leu Gly Ala Leu
        930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Arg Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Gln
            995                 1000                1005

Glu Ile Leu Leu Gly Pro Ala Asp Gly Met Val Ser Lys Gly Trp
    1010                1015                1020

Arg Leu Leu Ala Pro Ile Thr Ala Tyr Ala Gln Gln Thr Arg Gly
    1025                1030                1035

Leu Leu Gly Cys Ile Ile Thr Ser Leu Thr Gly Arg Asp Lys Asn
    1040                1045                1050

Gln Val Glu Gly Glu Val Gln Ile Val Ser Thr Ala Thr Gln Thr
    1055                1060                1065

Phe Leu Ala Thr Cys Ile Asn Gly Val Cys Trp Thr Val Tyr His
    1070                1075                1080

Gly Ala Gly Thr Arg Thr Ile Ala Ser Pro Lys Gly Pro Val Ile
    1085                1090                1095

Gln Met Tyr Thr Asn Val Asp Gln Asp Leu Val Gly Trp Pro Ala
    1100                1105                1110

Pro Gln Gly Ser Arg Ser Leu Thr Pro Cys Thr Cys Gly Ser Ser
    1115                1120                1125

Asp Leu Tyr Leu Val Thr Arg His Ala Asp Val Ile Pro Val Arg
    1130                1135                1140

Arg Arg Gly Asp Ser Arg Gly Ser Leu Leu Ser Pro Arg Pro Ile
    1145                1150                1155

Ser Tyr Leu Lys Gly Ser Ser Gly Gly Pro Leu Leu Cys Pro Ala
    1160                1165                1170

```
Gly His Ala Val Gly Leu Phe Arg Ala Ala Val Cys Thr Arg Gly
    1175                1180                1185

Val Ala Lys Ala Val Asp Phe Ile Pro Val Glu Asn Leu Glu Thr
    1190                1195                1200

Thr Met Arg Ser Pro Val Phe Thr Asp Asn Ser Pro Pro Ala
    1205                1210                1215

Val Pro Gln Ser Phe Gln Val Ala His Leu His Ala Pro Thr Gly
    1220                1225                1230

Ser Gly Lys Ser Thr Lys Val Pro Ala Ala Tyr Ala Ala Gln Gly
    1235                1240                1245

Tyr Lys Val Leu Val Leu Asn Pro Ser Val Ala Ala Thr Leu Gly
    1250                1255                1260

Phe Gly Ala Tyr Met Ser Lys Ala His Gly Val Asp Pro Asn Ile
    1265                1270                1275

Arg Thr Gly Val Arg Thr Ile Thr Thr Gly Ser Pro Ile Thr Tyr
    1280                1285                1290

Ser Thr Tyr Gly Lys Phe Leu Ala Asp Gly Gly Cys Ser Gly Gly
    1295                1300                1305

Ala Tyr Asp Ile Ile Ile Cys Asp Glu Cys His Ser Thr Asp Ala
    1310                1315                1320

Thr Ser Ile Leu Gly Ile Gly Thr Val Leu Asp Gln Ala Glu Thr
    1325                1330                1335

Ala Gly Ala Arg Leu Val Val Leu Ala Thr Ala Thr Pro Pro Gly
    1340                1345                1350

Ser Val Thr Val Ser His Pro Asn Ile Glu Glu Val Ala Leu Ser
    1355                1360                1365

Thr Thr Gly Glu Ile Pro Phe Tyr Gly Lys Ala Ile Pro Leu Glu
    1370                1375                1380

Val Ile Lys Gly Gly Arg His Leu Ile Phe Cys His Ser Lys Lys
    1385                1390                1395

Lys Cys Asp Glu Leu Ala Ala Lys Leu Val Ala Leu Gly Ile Asn
    1400                1405                1410

Ala Val Ala Tyr Tyr Arg Gly Leu Asp Val Ser Val Ile Pro Thr
    1415                1420                1425

Ser Gly Asp Val Val Val Ser Thr Asp Ala Leu Met Thr Gly
    1430                1435                1440

Phe Thr Gly Asp Phe Asp Ser Val Ile Asp Cys Asn Thr Cys Val
    1445                1450                1455

Thr Gln Thr Val Asp Phe Ser Leu Asp Pro Thr Phe Thr Ile Glu
    1460                1465                1470

Thr Thr Thr Leu Pro Gln Asp Ala Val Ser Arg Thr Gln Arg Arg
    1475                1480                1485

Gly Arg Thr Gly Arg Gly Lys Pro Gly Ile Tyr Arg Phe Val Ala
    1490                1495                1500

Pro Gly Glu Arg Pro Ser Gly Met Phe Asp Ser Ser Val Leu Cys
    1505                1510                1515

Glu Cys Tyr Asp Ala Gly Cys Ala Trp Tyr Glu Leu Thr Pro Ala
    1520                1525                1530

Glu Thr Thr Val Arg Leu Arg Ala Tyr Met Asn Thr Pro Gly Leu
    1535                1540                1545

Pro Val Cys Gln Asp His Leu Glu Phe Trp Glu Gly Val Phe Thr
    1550                1555                1560

Gly Leu Thr His Ile Asp Ala His Phe Leu Ser Gln Thr Lys Gln
```

-continued

```
            1565                1570                1575
Ser Gly Glu Asn Phe Pro Tyr Leu Val Ala Tyr Gln Ala Thr Val
            1580                1585                1590
Cys Ala Arg Ala Gln Ala Pro Pro Ser Trp Asp Gln Met Trp
            1595                1600                1605
Lys Cys Leu Ile Arg Leu Lys Pro Thr Leu His Gly Pro Thr Pro
            1610                1615                1620
Leu Leu Tyr Arg Leu Gly Ala Val Gln Asn Glu Val Thr Leu Thr
            1625                1630                1635
His Pro Ile Thr Lys Tyr Ile Met Thr Cys Met Ser Ala Asp Leu
            1640                1645                1650
Glu Val Val Thr Ser Thr Trp Val Leu Val Gly Gly Val Leu Ala
            1655                1660                1665
Ala Leu Ala Ala Tyr Cys Leu Ser Thr Gly Cys Val Val Ile Val
            1670                1675                1680
Gly Arg Ile Val Leu Ser Gly Lys Pro Ala Ile Ile Pro Asp Arg
            1685                1690                1695
Glu Val Leu Tyr Gln Glu Phe Asp Glu Met Glu Glu Cys Ser Gln
            1700                1705                1710
His Leu Pro Tyr Ile Glu Gln Gly Met Met Leu Ala Glu Gln Phe
            1715                1720                1725
Lys Gln Lys Ala Leu Gly Leu Leu Gln Thr Ala Ser Arg Gln Ala
            1730                1735                1740
Glu Val Ile Thr Pro Ala Val Gln Thr Asn Trp Gln Lys Leu Glu
            1745                1750                1755
Val Phe Trp Ala Lys His Met Trp Asn Phe Ile Ser Gly Ile Gln
            1760                1765                1770
Tyr Leu Ala Gly Leu Ser Thr Leu Pro Gly Asn Pro Ala Ile Ala
            1775                1780                1785
Ser Leu Met Ala Phe Thr Ala Ala Val Thr Ser Pro Leu Thr Thr
            1790                1795                1800
Gly Gln Thr Leu Leu Phe Asn Ile Leu Gly Gly Trp Val Ala Ala
            1805                1810                1815
Gln Leu Ala Ala Pro Gly Ala Ala Thr Ala Phe Val Gly Ala Gly
            1820                1825                1830
Leu Ala Gly Ala Ala Ile Gly Ser Val Gly Leu Gly Lys Val Leu
            1835                1840                1845
Val Asp Ile Leu Ala Gly Tyr Gly Ala Gly Val Ala Gly Ala Leu
            1850                1855                1860
Val Ala Phe Lys Ile Met Ser Gly Glu Val Pro Ser Thr Glu Asp
            1865                1870                1875
Leu Val Asn Leu Leu Pro Ala Ile Leu Ser Pro Gly Ala Leu Val
            1880                1885                1890
Val Gly Val Val Cys Ala Ala Ile Leu Arg Arg His Val Gly Pro
            1895                1900                1905
Gly Glu Gly Ala Val Gln Trp Met Asn Arg Leu Ile Ala Phe Ala
            1910                1915                1920
Ser Arg Gly Asn His Val Ser Pro Thr His Tyr Val Pro Glu Ser
            1925                1930                1935
Asp Ala Ala Ala Arg Val Thr Ala Ile Leu Ser Ser Leu Thr Val
            1940                1945                1950
Thr Gln Leu Leu Arg Arg Leu His Gln Trp Ile Ser Ser Glu Cys
            1955                1960                1965
```

```
Thr Thr Pro Cys Ser Gly Ser Trp Leu Arg Asp Ile Trp Asp Trp
1970            1975            1980

Ile Cys Glu Val Leu Ser Asp Phe Lys Thr Trp Leu Lys Ala Lys
1985            1990            1995

Leu Met Pro Gln Leu Pro Gly Ile Pro Phe Val Ser Cys Gln Arg
2000            2005            2010

Gly Tyr Arg Gly Val Trp Arg Gly Asp Gly Ile Met His Thr Arg
2015            2020            2025

Cys His Cys Gly Ala Glu Ile Thr Gly His Val Lys Asn Gly Thr
2030            2035            2040

Met Arg Ile Val Gly Pro Arg Thr Cys Arg Asn Met Trp Ser Gly
2045            2050            2055

Thr Phe Pro Ile Asn Ala Tyr Thr Thr Gly Pro Cys Thr Pro Leu
2060            2065            2070

Pro Ala Pro Asn Tyr Lys Phe Ala Leu Trp Arg Val Ser Ala Glu
2075            2080            2085

Glu Tyr Val Glu Ile Arg Arg Val Gly Asp Phe His Tyr Val Ser
2090            2095            2100

Gly Met Thr Thr Asp Asn Leu Lys Cys Pro Cys Gln Ile Pro Ser
2105            2110            2115

Pro Glu Phe Phe Thr Glu Leu Asp Gly Val Arg Leu His Arg Phe
2120            2125            2130

Ala Pro Pro Cys Lys Pro Leu Leu Arg Glu Glu Val Ser Phe Arg
2135            2140            2145

Val Gly Leu His Glu Tyr Pro Val Gly Ser Gln Leu Pro Cys Glu
2150            2155            2160

Pro Glu Pro Asp Val Ala Val Leu Thr Ser Met Leu Thr Asp Pro
2165            2170            2175

Ser His Ile Thr Ala Glu Ala Ala Gly Arg Arg Leu Ala Arg Gly
2180            2185            2190

Ser Pro Pro Ser Met Ala Ser Ser Ser Ala Ser Gln Leu Ser Ala
2195            2200            2205

Pro Ser Leu Lys Ala Thr Cys Thr Ala Asn His Asp Ser Pro Asp
2210            2215            2220

Ala Glu Leu Ile Glu Ala Asn Leu Leu Trp Arg Gln Glu Met Gly
2225            2230            2235

Gly Asn Ile Thr Arg Val Glu Ser Glu Asn Lys Val Val Ile Leu
2240            2245            2250

Asp Ser Phe Asp Pro Leu Val Ala Glu Glu Asp Glu Arg Glu Val
2255            2260            2265

Ser Val Pro Ala Glu Ile Leu Arg Lys Ser Arg Arg Phe Ala Arg
2270            2275            2280

Ala Leu Pro Val Trp Ala Arg Pro Asp Tyr Asn Pro Pro Leu Val
2285            2290            2295

Glu Thr Trp Lys Lys Pro Asp Tyr Glu Pro Pro Val Val His Gly
2300            2305            2310

Cys Pro Leu Pro Pro Pro Arg Ser Pro Pro Val Pro Pro Pro Arg
2315            2320            2325

Lys Lys Arg Thr Val Val Leu Thr Glu Ser Thr Leu Ser Thr Ala
2330            2335            2340

Leu Ala Glu Leu Ala Thr Lys Ser Phe Gly Ser Ser Ser Thr Ser
2345            2350            2355
```

```
Gly Ile Thr Gly Asp Asn Thr Thr Ser Ser Glu Pro Ala Pro
    2360            2365            2370

Ser Gly Cys Pro Pro Asp Ser Asp Val Glu Ser Tyr Ser Ser Met
2375            2380            2385

Pro Pro Leu Glu Gly Glu Pro Gly Asp Pro Asp Leu Ser Asp Gly
    2390            2395            2400

Ser Trp Ser Thr Val Ser Ser Gly Ala Asp Thr Glu Asp Val Val
2405            2410            2415

Cys Cys Ser Met Ser Tyr Ser Trp Thr Gly Ala Leu Val Thr Pro
2420            2425            2430

Cys Ala Ala Glu Glu Gln Lys Leu Pro Ile Asn Ala Leu Ser Asn
2435            2440            2445

Ser Leu Leu Arg His His Asn Leu Val Tyr Ser Thr Thr Ser Arg
2450            2455            2460

Ser Ala Cys Gln Arg Gln Lys Lys Val Thr Phe Asp Arg Leu Gln
2465            2470            2475

Val Leu Asp Ser His Tyr Gln Asp Val Leu Lys Glu Val Lys Ala
2480            2485            2490

Ala Ala Ser Lys Val Lys Ala Asn Leu Leu Ser Val Glu Glu Ala
2495            2500            2505

Cys Ser Leu Thr Pro Pro His Ser Ala Lys Ser Lys Phe Gly Tyr
2510            2515            2520

Gly Ala Lys Asp Val Arg Cys His Ala Arg Lys Ala Val Ala His
2525            2530            2535

Ile Asn Ser Val Trp Lys Asp Leu Leu Glu Asp Ser Val Thr Pro
2540            2545            2550

Ile Asp Thr Thr Ile Met Ala Lys Asn Glu Val Phe Cys Val Gln
2555            2560            2565

Pro Glu Lys Gly Gly Arg Lys Pro Ala Arg Leu Ile Val Phe Pro
2570            2575            2580

Asp Leu Gly Val Arg Val Cys Glu Lys Met Ala Leu Tyr Asp Val
2585            2590            2595

Val Ser Lys Leu Pro Leu Ala Val Met Gly Ser Ser Tyr Gly Phe
2600            2605            2610

Gln Tyr Ser Pro Gly Gln Arg Val Glu Phe Leu Val Gln Ala Trp
2615            2620            2625

Lys Ser Lys Lys Thr Pro Met Gly Phe Ser Tyr Asp Thr Arg Cys
2630            2635            2640

Phe Asp Ser Thr Val Thr Glu Ser Asp Ile Arg Thr Glu Glu Ala
2645            2650            2655

Ile Tyr Gln Cys Cys Asp Leu Asp Pro Gln Ala Arg Val Ala Ile
2660            2665            2670

Lys Ser Leu Thr Glu Arg Leu Tyr Val Gly Gly Pro Leu Thr Asn
2675            2680            2685

Ser Arg Gly Glu Asn Cys Gly Tyr Arg Arg Cys Arg Ala Ser Gly
2690            2695            2700

Val Leu Thr Thr Ser Cys Gly Asn Thr Leu Thr Cys Tyr Ile Lys
2705            2710            2715

Ala Arg Ala Ala Cys Arg Ala Ala Gly Leu Gln Asp Cys Thr Met
2720            2725            2730

Leu Val Cys Gly Asp Asp Leu Val Val Ile Cys Glu Ser Ala Gly
2735            2740            2745

Val Gln Glu Asp Ala Ala Ser Leu Arg Ala Phe Thr Glu Ala Met
```

```
                    2750               2755               2760
Thr  Arg  Tyr  Ser  Ala  Pro  Pro  Gly  Asp  Pro  Pro  Gln  Pro  Glu  Tyr
         2765                    2770                    2775

Asp  Leu  Glu  Leu  Ile  Thr  Ser  Cys  Ser  Ser  Asn  Val  Ser  Val  Ala
    2780                    2785                    2790

His  Asp  Gly  Ala  Gly  Lys  Arg  Val  Tyr  Tyr  Leu  Thr  Arg  Asp  Pro
    2795                    2800                    2805

Thr  Thr  Pro  Leu  Ala  Arg  Ala  Ala  Trp  Glu  Thr  Ala  Arg  His  Thr
    2810                    2815                    2820

Pro  Val  Asn  Ser  Trp  Leu  Gly  Asn  Ile  Ile  Met  Phe  Ala  Pro  Thr
    2825                    2830                    2835

Leu  Trp  Ala  Arg  Met  Ile  Leu  Met  Thr  His  Phe  Phe  Ser  Val  Leu
    2840                    2845                    2850

Ile  Ala  Arg  Asp  Gln  Leu  Glu  Gln  Ala  Leu  Asn  Cys  Glu  Ile  Tyr
    2855                    2860                    2865

Gly  Ala  Cys  Tyr  Ser  Ile  Glu  Pro  Leu  Asp  Leu  Pro  Pro  Ile  Ile
    2870                    2875                    2880

Gln  Arg  Leu  His  Gly  Leu  Ser  Ala  Phe  Ser  Leu  His  Ser  Tyr  Ser
    2885                    2890                    2895

Pro  Gly  Glu  Ile  Asn  Arg  Val  Ala  Ala  Cys  Leu  Arg  Lys  Leu  Gly
    2900                    2905                    2910

Val  Pro  Pro  Leu  Arg  Ala  Trp  Arg  His  Arg  Ala  Arg  Ser  Val  Arg
    2915                    2920                    2925

Ala  Arg  Leu  Leu  Ser  Arg  Gly  Gly  Arg  Ala  Ala  Ile  Cys  Gly  Lys
    2930                    2935                    2940

Tyr  Leu  Phe  Asn  Trp  Ala  Val  Arg  Thr  Lys  Leu  Lys  Leu  Thr  Pro
    2945                    2950                    2955

Ile  Ala  Ala  Ala  Gly  Arg  Leu  Asp  Leu  Ser  Gly  Trp  Phe  Thr  Ala
    2960                    2965                    2970

Gly  Tyr  Ser  Gly  Gly  Asp  Ile  Tyr  His  Ser  Val  Ser  His  Ala  Arg
    2975                    2980                    2985

Pro  Arg  Trp  Phe  Trp  Phe  Cys  Leu  Leu  Leu  Leu  Ala  Ala  Gly  Val
    2990                    2995                    3000

Gly  Ile  Tyr  Leu  Leu  Pro  Asn  Arg
    3005                    3010
```

<210> SEQ ID NO 8
<211> LENGTH: 191
<212> TYPE: PRT
<213> ORGANISM: HCV

<400> SEQUENCE: 8

```
Met  Ser  Thr  Asn  Pro  Lys  Pro  Gln  Arg  Lys  Thr  Lys  Arg  Asn  Thr  Asn
 1                  5                   10                  15

Arg  Arg  Pro  Gln  Asp  Val  Lys  Phe  Pro  Gly  Gly  Gly  Gln  Ile  Val  Gly
                20                  25                  30

Gly  Val  Tyr  Leu  Leu  Pro  Arg  Arg  Gly  Pro  Arg  Leu  Gly  Val  Arg  Ala
            35                  40                  45

Thr  Arg  Lys  Thr  Ser  Glu  Arg  Ser  Gln  Pro  Arg  Gly  Arg  Arg  Gln  Pro
    50                  55                  60

Ile  Pro  Lys  Ala  Arg  Arg  Pro  Glu  Gly  Arg  Thr  Trp  Ala  Gln  Pro  Gly
65                  70                  75                  80

Tyr  Pro  Trp  Pro  Leu  Tyr  Gly  Asn  Glu  Gly  Cys  Gly  Trp  Ala  Gly  Trp
                85                  90                  95
```

```
Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
            130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190

<210> SEQ ID NO 9
<211> LENGTH: 3010
<212> TYPE: PRT
<213> ORGANISM: HCV

<400> SEQUENCE: 9

Met Ser Thr Asn Pro Lys Pro Gln Arg Lys Thr Lys Arg Asn Thr Asn
1               5                   10                  15

Arg Arg Pro Gln Asp Ile Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Lys Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
            130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Val Ser Ala Tyr
            180                 185                 190

Glu Val Arg Asn Ala Ser Gly Met Tyr His Val Thr Asn Asp Cys Ser
            195                 200                 205

Asn Ser Ser Ile Val Tyr Glu Ala Ala Asp Met Ile Met His Thr Pro
        210                 215                 220

Gly Cys Val Pro Cys Val Arg Glu Asp Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Thr Leu Arg Arg His Val Asp Leu Leu Val Gly Val Ala Ala Phe Cys
            260                 265                 270

Ser Ala Met Tyr Val Gly Asp Leu Cys Gly Ser Val Phe Leu Val Ser
            275                 280                 285
```

```
Gln Leu Phe Thr Phe Ser Pro Arg Arg His Glu Thr Val Gln Asp Cys
    290                 295                 300

Asn Cys Ser Ile Tyr Pro Gly Arg Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Thr Gly Ser His
                340                 345                 350

Trp Gly Ile Leu Ala Gly Leu Ala Tyr Tyr Ser Met Val Gly Asn Trp
            355                 360                 365

Ala Lys Val Leu Ile Ala Met Leu Leu Phe Ala Gly Val Asp Gly Thr
        370                 375                 380

Thr His Val Thr Gly Gly Ala Gln Gly Arg Ala Ala Ser Ser Leu Thr
385                 390                 395                 400

Ser Leu Phe Ser Pro Gly Pro Val Gln His Leu Gln Leu Ile Asn Thr
                405                 410                 415

Asn Gly Ser Trp His Ile Asn Arg Thr Ala Leu Ser Cys Asn Asp Ser
            420                 425                 430

Leu Asn Thr Gly Phe Val Ala Ala Leu Phe Tyr Lys Tyr Arg Phe Asn
        435                 440                 445

Ala Ser Gly Cys Pro Glu Arg Leu Ala Thr Cys Arg Pro Ile Asp Thr
    450                 455                 460

Phe Ala Gln Gly Trp Gly Pro Ile Thr Tyr Thr Glu Pro His Asp Leu
465                 470                 475                 480

Asp Gln Arg Pro Tyr Cys Trp His Tyr Ala Pro Gln Pro Cys Gly Ile
                485                 490                 495

Val Pro Thr Leu Gln Val Cys Gly Pro Val Tyr Cys Phe Thr Pro Ser
            500                 505                 510

Pro Val Ala Val Gly Thr Thr Asp Arg Phe Gly Ala Pro Thr Tyr Arg
        515                 520                 525

Trp Gly Ala Asn Glu Thr Asp Val Leu Leu Leu Asn Asn Ala Gly Pro
        530                 535                 540

Pro Gln Gly Asn Trp Phe Gly Cys Thr Trp Met Asn Gly Thr Gly Phe
545                 550                 555                 560

Thr Lys Thr Cys Gly Gly Pro Pro Cys Asn Ile Gly Gly Val Gly Asn
                565                 570                 575

Asn Thr Leu Thr Cys Pro Thr Asp Cys Phe Arg Lys His Pro Gly Ala
            580                 585                 590

Thr Tyr Thr Lys Cys Gly Ser Gly Pro Trp Leu Thr Pro Arg Cys Leu
        595                 600                 605

Val Asp Tyr Pro Tyr Arg Leu Trp His Tyr Pro Cys Thr Val Asn Phe
    610                 615                 620

Thr Ile Phe Lys Val Arg Met Tyr Val Gly Gly Ala Glu His Arg Leu
625                 630                 635                 640

Asp Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Glu Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Ile Gln Tyr Leu Tyr Gly
    690                 695                 700
```

```
Ile Gly Ser Ala Val Val Ser Phe Ala Ile Lys Trp Glu Tyr Ile Val
705                 710                 715                 720

Leu Leu Phe Leu Leu Leu Ala Asp Ala Arg Val Cys Ala Cys Leu Trp
            725                 730                 735

Met Met Leu Leu Val Ala Gln Ala Glu Ala Ala Leu Glu Asn Leu Val
        740                 745                 750

Val Leu Asn Ala Ala Ser Val Ala Gly Ala His Gly Ile Leu Ser Phe
    755                 760                 765

Ile Val Phe Phe Cys Ala Ala Trp Tyr Ile Lys Gly Arg Leu Val Pro
770                 775                 780

Gly Ala Ala Tyr Ala Leu Tyr Gly Val Trp Pro Leu Leu Leu Leu Leu
785                 790                 795                 800

Leu Ala Leu Pro Pro Arg Ala Tyr Ala Met Asp Arg Glu Met Ala Ala
                805                 810                 815

Ser Cys Gly Gly Ala Val Phe Val Gly Leu Val Leu Leu Thr Leu Ser
            820                 825                 830

Pro His Tyr Lys Val Phe Leu Ala Arg Phe Ile Trp Trp Leu Gln Tyr
        835                 840                 845

Leu Ile Thr Arg Thr Glu Ala His Leu Gln Val Trp Val Pro Pro Leu
    850                 855                 860

Asn Val Arg Gly Gly Arg Asp Ala Ile Ile Leu Leu Thr Cys Val Val
865                 870                 875                 880

His Pro Glu Leu Ile Phe Asp Ile Thr Lys Tyr Leu Leu Ala Ile Phe
                885                 890                 895

Gly Pro Leu Met Val Leu Gln Ala Gly Ile Thr Arg Val Pro Tyr Phe
            900                 905                 910

Val Arg Ala Gln Gly Leu Ile Arg Ala Cys Met Leu Ala Arg Lys Val
        915                 920                 925

Val Gly Gly His Tyr Val Gln Met Val Phe Met Lys Leu Ala Ala Leu
    930                 935                 940

Ala Gly Thr Tyr Val Tyr Asp His Leu Thr Pro Leu Arg Asp Trp Ala
945                 950                 955                 960

His Thr Gly Leu Arg Asp Leu Ala Val Ala Val Glu Pro Val Val Phe
                965                 970                 975

Ser Asp Met Glu Thr Lys Val Ile Thr Trp Gly Ala Asp Thr Ala Ala
            980                 985                 990

Cys Gly Asp Ile Ile Leu Ala Leu Pro Ala Ser Ala Arg Arg Gly Lys
        995                 1000                1005

Glu Ile Leu Leu Gly Pro Ala Asp Ser Leu Glu Gly Gln Gly Trp
    1010                1015                1020

Arg Leu Leu Ala Pro Ile Thr Ala Tyr Ser Gln Gln Thr Arg Gly
    1025                1030                1035

Leu Leu Gly Cys Ile Ile Thr Ser Leu Thr Gly Arg Asp Lys Asn
    1040                1045                1050

Gln Val Glu Gly Glu Val Gln Val Val Ser Thr Ala Thr Gln Ser
    1055                1060                1065

Phe Leu Ala Thr Cys Ile Asn Gly Val Cys Trp Thr Val Phe His
    1070                1075                1080

Gly Ala Gly Ser Lys Thr Leu Ala Gly Pro Lys Gly Pro Ile Thr
    1085                1090                1095

Gln Met Tyr Thr Asn Val Asp Gln Asp Leu Val Gly Trp Pro Ala
    1100                1105                1110

Pro Pro Gly Ala Arg Ser Leu Thr Pro Cys Thr Cys Gly Ser Ser
```

-continued

```
            1115                1120                1125

Asp Leu Tyr Leu Val Thr Arg His Ala Asp Val Ile Pro Val Arg
            1130                1135                1140

Arg Arg Gly Asp Gly Arg Gly Ser Leu Leu Pro Arg Pro Val
            1145                1150                1155

Ser Tyr Leu Lys Gly Ser Ser Gly Gly Pro Leu Leu Cys Pro Ser
            1160                1165                1170

Gly His Ala Val Gly Ile Leu Pro Ala Ala Val Cys Thr Arg Gly
            1175                1180                1185

Val Ala Met Ala Val Glu Phe Ile Pro Val Glu Ser Met Glu Thr
            1190                1195                1200

Thr Met Arg Ser Pro Val Phe Thr Asp Asn Pro Ser Pro Pro Ala
            1205                1210                1215

Val Pro Gln Thr Phe Gln Val Ala His Leu His Ala Pro Thr Gly
            1220                1225                1230

Ser Gly Lys Ser Thr Arg Val Pro Ala Ala Tyr Ala Ala Gln Gly
            1235                1240                1245

Tyr Lys Val Leu Val Leu Asn Pro Ser Val Ala Ala Thr Leu Gly
            1250                1255                1260

Phe Gly Ala Tyr Met Ser Lys Ala His Gly Ile Asp Pro Asn Leu
            1265                1270                1275

Arg Thr Gly Val Arg Thr Ile Thr Thr Gly Ala Pro Ile Thr Tyr
            1280                1285                1290

Ser Thr Tyr Gly Lys Phe Leu Ala Asp Gly Gly Gly Ser Gly Gly
            1295                1300                1305

Ala Tyr Asp Ile Ile Met Cys Asp Glu Cys His Ser Thr Asp Ser
            1310                1315                1320

Thr Thr Ile Tyr Gly Ile Gly Thr Val Leu Asp Gln Ala Glu Thr
            1325                1330                1335

Ala Gly Ala Arg Leu Val Val Leu Ser Thr Ala Thr Pro Pro Gly
            1340                1345                1350

Ser Val Thr Val Pro His Leu Asn Ile Glu Glu Val Ala Leu Ser
            1355                1360                1365

Asn Thr Gly Glu Ile Pro Phe Tyr Gly Lys Ala Ile Pro Ile Glu
            1370                1375                1380

Ala Ile Lys Gly Gly Arg His Leu Ile Phe Cys His Ser Lys Lys
            1385                1390                1395

Lys Cys Asp Glu Leu Ala Ala Lys Leu Ser Gly Leu Gly Leu Asn
            1400                1405                1410

Ala Val Ala Tyr Tyr Arg Gly Leu Asp Val Ser Val Ile Pro Thr
            1415                1420                1425

Ser Gly Asp Val Val Val Ala Thr Asp Ala Leu Met Thr Gly
            1430                1435                1440

Phe Thr Gly Asp Phe Asp Ser Val Ile Asp Cys Asn Thr Cys Val
            1445                1450                1455

Thr Gln Thr Val Asp Phe Ser Leu Asp Pro Thr Phe Thr Ile Glu
            1460                1465                1470

Thr Thr Thr Val Pro Gln Asp Ala Val Ser Arg Ser Gln Arg Arg
            1475                1480                1485

Gly Arg Thr Gly Arg Gly Arg Ala Gly Ile Tyr Arg Phe Val Thr
            1490                1495                1500

Pro Gly Glu Arg Pro Ser Gly Met Phe Asp Ser Ser Val Leu Cys
            1505                1510                1515
```

-continued

Glu Cys Tyr Asp Ala Gly Cys Ala Trp Tyr Glu Leu Thr Pro Ala
1520             1525                1530

Glu Thr Ser Val Arg Leu Arg Ala Tyr Leu Asn Thr Pro Gly Leu
1535             1540                1545

Pro Val Cys Gln Asp His Leu Glu Phe Ser Glu Gly Val Phe Thr
1550             1555                1560

Gly Leu Thr His Ile Asp Ala His Phe Leu Ser Gln Thr Lys Gln
1565             1570                1575

Ala Gly Glu Asn Phe Pro Tyr Leu Val Ala Tyr Gln Ala Thr Val
1580             1585                1590

Cys Ala Arg Ala Gln Ala Pro Pro Pro Ser Trp Asp Glu Met Trp
1595             1600                1605

Arg Cys Leu Ile Arg Leu Lys Pro Thr Leu His Gly Pro Thr Pro
1610             1615                1620

Leu Leu Tyr Arg Leu Gly Ala Val Gln Asn Glu Val Thr Leu Thr
1625             1630                1635

His Pro Ile Thr Lys Phe Ile Met Thr Cys Met Ser Ala Asp Leu
1640             1645                1650

Glu Val Val Thr Ser Thr Trp Val Leu Val Gly Gly Val Leu Ala
1655             1660                1665

Ala Leu Ala Ala Tyr Cys Leu Thr Thr Gly Ser Val Val Ile Val
1670             1675                1680

Gly Arg Ile Ile Leu Ser Gly Lys Pro Ala Ile Ile Pro Asp Arg
1685             1690                1695

Glu Val Leu Tyr Gln Glu Phe Asp Glu Met Glu Glu Cys Ala Ser
1700             1705                1710

His Leu Pro Tyr Phe Glu Gln Gly Met Gln Leu Ala Glu Gln Phe
1715             1720                1725

Lys Gln Lys Ala Leu Gly Leu Leu Gln Thr Ala Thr Lys Gln Ala
1730             1735                1740

Glu Ala Ala Ala Pro Val Val Glu Ser Lys Trp Arg Ala Leu Glu
1745             1750                1755

Thr Phe Trp Ala Lys His Met Trp Asn Phe Ile Ser Gly Ile Gln
1760             1765                1770

Tyr Leu Ala Gly Leu Ser Thr Leu Pro Gly Asn Pro Ala Ile Arg
1775             1780                1785

Ser Pro Met Ala Phe Thr Ala Ser Ile Thr Ser Pro Leu Thr Thr
1790             1795                1800

Gln His Thr Leu Leu Phe Asn Ile Leu Gly Gly Trp Val Ala Ala
1805             1810                1815

Gln Leu Ala Pro Pro Ser Ala Ala Ser Ala Phe Val Gly Ala Gly
1820             1825                1830

Ile Ala Gly Ala Ala Val Gly Thr Ile Gly Leu Gly Lys Val Leu
1835             1840                1845

Val Asp Ile Leu Ala Gly Tyr Gly Ala Gly Val Ala Gly Ala Leu
1850             1855                1860

Val Ala Phe Lys Ile Met Ser Gly Glu Met Pro Ser Ala Glu Asp
1865             1870                1875

Met Val Asn Leu Leu Pro Ala Ile Leu Ser Pro Gly Ala Leu Val
1880             1885                1890

Val Gly Ile Val Cys Ala Ala Ile Leu Arg Arg His Val Gly Pro
1895             1900                1905

```
Gly Glu Gly Ala Val Gln Trp Met Asn Arg Leu Ile Ala Phe Ala
    1910                1915                1920

Ser Arg Gly Asn His Val Ser Pro Arg His Tyr Val Pro Glu Ser
    1925                1930                1935

Glu Pro Ala Ala Arg Val Thr Gln Ile Leu Ser Ser Leu Thr Ile
    1940                1945                1950

Thr Gln Leu Leu Lys Arg Leu His Gln Trp Ile Asn Glu Asp Cys
    1955                1960                1965

Ser Thr Pro Cys Ser Ser Ser Trp Leu Arg Glu Ile Trp Asp Trp
    1970                1975                1980

Ile Cys Thr Val Leu Thr Asp Phe Lys Thr Trp Leu Gln Ser Lys
    1985                1990                1995

Leu Leu Pro Arg Leu Pro Gly Val Pro Phe Phe Ser Cys Gln Arg
    2000                2005                2010

Gly Tyr Lys Gly Val Trp Arg Gly Asp Gly Ile Met His Thr Thr
    2015                2020                2025

Cys Pro Cys Gly Ala Gln Ile Thr Gly His Val Lys Asn Gly Ser
    2030                2035                2040

Met Arg Ile Val Gly Pro Lys Thr Cys Ser Asn Thr Trp Tyr Gly
    2045                2050                2055

Thr Phe Pro Ile Asn Ala Tyr Thr Thr Gly Pro Cys Thr Pro Ser
    2060                2065                2070

Pro Ala Pro Asn Tyr Ser Lys Ala Leu Trp Arg Val Ala Ala Glu
    2075                2080                2085

Glu Tyr Val Glu Val Thr Arg Val Gly Asp Phe His Tyr Val Thr
    2090                2095                2100

Gly Met Thr Thr Asp Asn Val Lys Cys Pro Cys Gln Val Pro Ala
    2105                2110                2115

Pro Glu Phe Phe Thr Glu Val Asp Gly Val Arg Leu His Arg Tyr
    2120                2125                2130

Ala Pro Ala Cys Arg Pro Leu Leu Arg Glu Glu Val Val Phe Gln
    2135                2140                2145

Val Gly Leu His Gln Tyr Leu Val Gly Ser Gln Leu Pro Cys Glu
    2150                2155                2160

Pro Glu Pro Asp Val Ala Val Leu Thr Ser Met Leu Thr Asp Pro
    2165                2170                2175

Ser His Ile Thr Ala Glu Thr Ala Lys Arg Arg Leu Ala Arg Gly
    2180                2185                2190

Ser Pro Pro Ser Leu Ala Ser Ser Ser Ala Ser Gln Leu Ser Ala
    2195                2200                2205

Pro Ser Leu Lys Ala Thr Cys Thr Thr His His Asp Ser Pro Asp
    2210                2215                2220

Ala Asp Leu Ile Glu Ala Asn Leu Leu Trp Arg Gln Glu Met Gly
    2225                2230                2235

Gly Asn Ile Thr Arg Val Glu Ser Glu Asn Lys Val Val Ile Leu
    2240                2245                2250

Asp Ser Phe Asp Pro Leu Arg Ala Glu Asp Glu Gly Glu Ile
    2255                2260                2265

Ser Val Pro Ala Glu Ile Leu Arg Lys Ser Arg Lys Phe Pro Pro
    2270                2275                2280

Ala Leu Pro Ile Trp Ala Pro Pro Asp Tyr Asn Pro Pro Leu Leu
    2285                2290                2295

Glu Ser Trp Lys Asp Pro Asp Tyr Val Pro Pro Val Val His Gly
```

```
              2300              2305              2310
Cys Pro Leu Pro Pro Thr Lys Ala Pro Ile Pro Pro Pro Arg
        2315              2320              2325

Arg Lys Arg Thr Val Val Leu Thr Glu Ser Thr Val Ser Ser Ala
        2330              2335              2340

Leu Ala Glu Leu Ala Thr Lys Thr Phe Gly Ser Ser Gly Ser Ser
        2345              2350              2355

Ala Ile Asp Ser Gly Thr Ala Thr Ala Pro Pro Asp Gln Ala Ser
        2360              2365              2370

Gly Asp Gly Asp Arg Glu Ser Asp Val Glu Ser Phe Ser Ser Met
        2375              2380              2385

Pro Pro Leu Glu Gly Glu Pro Gly Asp Pro Asp Leu Ser Asp Gly
        2390              2395              2400

Ser Trp Ser Thr Val Ser Glu Glu Ala Ser Glu Asp Val Val Cys
        2405              2410              2415

Cys Ser Met Ser Tyr Thr Trp Thr Gly Ala Leu Ile Thr Pro Cys
        2420              2425              2430

Ala Ala Glu Glu Ser Lys Leu Pro Ile Asn Pro Leu Ser Asn Ser
        2435              2440              2445

Leu Leu Arg His His Asn Met Val Tyr Ala Thr Thr Ser Arg Ser
        2450              2455              2460

Ala Gly Leu Arg Gln Lys Lys Val Thr Phe Asp Arg Leu Gln Val
        2465              2470              2475

Leu Asp Asp His Tyr Arg Asp Val Leu Lys Glu Met Lys Ala Lys
        2480              2485              2490

Ala Ser Thr Val Lys Ala Lys Leu Leu Ser Val Glu Glu Ala Cys
        2495              2500              2505

Lys Leu Thr Pro Pro His Ser Ala Lys Ser Lys Phe Gly Tyr Gly
        2510              2515              2520

Ala Lys Asp Val Arg Ser Leu Ser Ser Arg Ala Val Thr His Ile
        2525              2530              2535

Arg Ser Val Trp Lys Asp Leu Leu Glu Asp Thr Glu Thr Pro Ile
        2540              2545              2550

Ser Thr Thr Ile Met Ala Lys Asn Glu Val Phe Cys Val Gln Pro
        2555              2560              2565

Glu Lys Gly Gly Arg Lys Pro Ala Arg Leu Ile Val Phe Pro Asp
        2570              2575              2580

Leu Gly Val Arg Val Cys Glu Lys Met Ala Leu Tyr Asp Val Val
        2585              2590              2595

Ser Thr Leu Pro Gln Ala Val Met Gly Ser Ser Tyr Gly Phe Gln
        2600              2605              2610

Tyr Ser Pro Lys Gln Arg Val Glu Phe Leu Val Asn Thr Trp Lys
        2615              2620              2625

Ser Lys Lys Cys Pro Met Gly Phe Ser Tyr Asp Thr Arg Cys Phe
        2630              2635              2640

Asp Ser Thr Val Thr Glu Asn Asp Ile Arg Val Glu Glu Ser Ile
        2645              2650              2655

Tyr Gln Cys Cys Asp Leu Ala Pro Glu Ala Lys Leu Ala Ile Lys
        2660              2665              2670

Ser Leu Thr Glu Arg Leu Tyr Ile Gly Gly Pro Leu Thr Asn Ser
        2675              2680              2685

Lys Gly Gln Asn Cys Gly Tyr Arg Arg Cys Arg Ala Ser Gly Val
        2690              2695              2700
```

Leu Thr Thr Ser Cys Gly Asn Thr Leu Thr Cys Tyr Leu Lys Ala
    2705                2710                2715

Thr Ala Ala Cys Arg Ala Ala Lys Leu Arg Asp Cys Thr Met Leu
    2720                2725                2730

Val Asn Gly Asp Asp Leu Val Val Ile Cys Glu Ser Ala Gly Thr
    2735                2740                2745

Gln Glu Asp Ala Ala Ser Leu Arg Val Phe Thr Glu Ala Met Thr
    2750                2755                2760

Arg Tyr Ser Ala Pro Pro Gly Asp Pro Pro Gln Pro Glu Tyr Asp
    2765                2770                2775

Leu Glu Leu Ile Thr Ser Cys Ser Ser Asn Val Ser Val Ala His
    2780                2785                2790

Asp Ala Ser Gly Lys Arg Val Tyr Tyr Leu Thr Arg Asp Pro Thr
    2795                2800                2805

Thr Pro Leu Ala Arg Ala Ala Trp Glu Thr Ala Arg His Thr Pro
    2810                2815                2820

Val Asn Ser Trp Leu Gly Asn Ile Ile Met Tyr Ala Pro Thr Leu
    2825                2830                2835

Trp Ala Arg Met Ile Leu Met Thr His Phe Phe Ser Ile Leu Leu
    2840                2845                2850

Ala Gln Glu Gln Leu Glu Lys Thr Leu Asp Cys Gln Ile Tyr Gly
    2855                2860                2865

Ala Cys Tyr Ser Ile Glu Pro Leu Asp Leu Pro Gln Ile Ile Glu
    2870                2875                2880

Arg Leu His Gly Leu Ser Ala Phe Ser Leu His Ser Tyr Ser Pro
    2885                2890                2895

Gly Glu Ile Asn Arg Val Ala Ser Cys Leu Arg Lys Leu Gly Val
    2900                2905                2910

Pro Pro Leu Arg Ala Trp Arg His Arg Ala Arg Ser Val Arg Ala
    2915                2920                2925

Lys Leu Leu Ser Gln Gly Gly Arg Ala Ala Thr Cys Gly Lys Tyr
    2930                2935                2940

Leu Phe Asn Trp Ala Val Arg Thr Lys Leu Lys Leu Thr Pro Ile
    2945                2950                2955

Pro Ala Ala Ser Arg Leu Asp Leu Ser Gly Trp Phe Val Ala Gly
    2960                2965                2970

Tyr Ser Gly Gly Asp Ile Tyr His Ser Leu Ser Arg Ala Arg Pro
    2975                2980                2985

Arg Trp Phe Met Leu Cys Leu Leu Leu Ser Val Gly Val Gly
    2990                2995                3000

Ile Tyr Leu Leu Pro Asn Arg
    3005                3010

<210> SEQ ID NO 10
<211> LENGTH: 486
<212> TYPE: PRT
<213> ORGANISM: influenza A virus

<400> SEQUENCE: 10

Met Ala Ser Gln Gly Thr Lys Arg Ser Tyr Glu Gln Met Glu Thr Ser
1               5                   10                  15

Gly Glu Arg Gln Asn Ala Thr Glu Ile Arg Ala Ser Val Gly Arg Met
            20                  25                  30

Val Gly Gly Ile Gly Arg Phe Tyr Ile Gln Met Cys Thr Glu Leu Lys

-continued

```
                35                  40                  45
Leu Ser Asp His Glu Gly Arg Leu Ile Gln Asn Ser Ile Thr Ile Glu
 50                  55                  60
Arg Met Val Leu Ser Ala Phe Asp Glu Arg Arg Asn Lys Tyr Leu Glu
 65                  70                  75                  80
Glu His Pro Ser Ala Gly Lys Asp Pro Lys Thr Gly Gly Pro Ile
                 85                  90                  95
Tyr Arg Arg Arg Asp Gly Lys Trp Met Arg Glu Leu Ile Leu Tyr Asp
                100                 105                 110
Lys Glu Glu Ile Arg Arg Ile Trp Arg Gln Ala Asn Asn Gly Glu Asp
                115                 120                 125
Ala Thr Ala Gly Leu Thr His Met Met Ile Trp His Ser Asn Leu Asn
130                 135                 140
Asp Ala Thr Tyr Gln Arg Thr Arg Ala Leu Val Arg Thr Gly Met Asp
145                 150                 155                 160
Pro Arg Met Cys Ser Leu Met Gln Gly Ser Thr Leu Pro Arg Arg Ser
                165                 170                 175
Gly Ala Ala Gly Ala Ala Val Lys Gly Val Gly Thr Met Val Met Glu
                180                 185                 190
Leu Ile Arg Met Ile Lys Arg Gly Ile Asn Asp Arg Asn Phe Trp Arg
                195                 200                 205
Gly Glu Asn Gly Arg Arg Thr Arg Ile Ala Tyr Glu Arg Met Cys Asn
210                 215                 220
Ile Leu Lys Gly Lys Phe Gln Thr Ala Ala Gln Arg Ala Met Met Asp
225                 230                 235                 240
Gln Val Arg Glu Ser Arg Asn Pro Gly Asn Ala Glu Ile Glu Asp Leu
                245                 250                 255
Ile Phe Leu Ala Arg Ser Ala Leu Ile Leu Arg Gly Ser Val Ala His
                260                 265                 270
Lys Ser Cys Leu Pro Ala Cys Val Tyr Gly Leu Ala Val Ala Ser Gly
                275                 280                 285
Tyr Asp Phe Glu Arg Glu Gly Tyr Ser Leu Val Gly Ile Asp Pro Phe
                290                 295                 300
Arg Leu Leu Gln Asn Ser Gln Val Phe Ser Leu Ile Arg Pro Asn Glu
305                 310                 315                 320
Asn Pro Ala His Lys Ser Gln Leu Val Trp Met Ala Cys His Ser Ala
                325                 330                 335
Ala Phe Glu Asp Leu Arg Val Ser Ser Phe Ile Arg Gly Thr Arg Val
                340                 345                 350
Val Pro Arg Gly Gln Leu Ser Thr Arg Gly Val Gln Ile Ala Ser Asn
                355                 360                 365
Glu Asn Met Glu Thr Met Asp Ser Ser Thr Leu Glu Leu Arg Ser Arg
                370                 375                 380
Tyr Trp Ala Ile Arg Thr Arg Ser Gly Gly Asn Thr Asn Gln Gln Arg
385                 390                 395                 400
Ala Ser Ala Gly Gln Ile Ser Val Gln Pro Thr Phe Ser Val Gln Arg
                405                 410                 415
Asn Leu Pro Phe Glu Arg Ala Thr Ile Met Ala Ala Phe Thr Gly Asn
                420                 425                 430
Thr Glu Gly Arg Thr Ser Asp Met Arg Thr Glu Ile Ile Arg Met Met
                435                 440                 445
Glu Asn Ala Arg Pro Glu Asp Val Ser Phe Gln Gly Arg Gly Val Phe
                450                 455                 460
```

```
Glu Leu Ser Asp Glu Lys Ala Thr Asn Pro Ile Val Pro Ser Phe Asp
465                 470                 475                 480

Met Ser Asn Glu Gly Ser
                485

<210> SEQ ID NO 11
<211> LENGTH: 97
<212> TYPE: PRT
<213> ORGANISM: Influenza A virus

<400> SEQUENCE: 11

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Ser Ile
                20                  25                  30

Ile Gly Ile Leu His Leu Ile Leu Trp Ile Leu Asp Arg Leu Phe Phe
            35                  40                  45

Lys Cys Val Tyr Arg Leu Phe Lys His Gly Leu Lys Arg Gly Pro Ser
        50                  55                  60

Thr Glu Gly Val Pro Glu Ser Met Arg Glu Glu Tyr Arg Lys Glu Gln
65                  70                  75                  80

Gln Asn Ala Val Asp Ala Asp Ser His Phe Val Ser Ile Glu Leu
                85                  90                  95

Glu

<210> SEQ ID NO 12
<211> LENGTH: 498
<212> TYPE: PRT
<213> ORGANISM: Influenza A virus

<400> SEQUENCE: 12

Met Ala Ser Gln Gly Thr Lys Arg Ser Tyr Glu Gln Met Glu Thr Asp
1               5                   10                  15

Gly Asp Arg Gln Asn Ala Thr Glu Ile Arg Ala Ser Val Gly Lys Met
                20                  25                  30

Ile Asp Gly Ile Gly Arg Phe Tyr Ile Gln Met Cys Thr Glu Leu Lys
            35                  40                  45

Leu Ser Asp His Glu Gly Arg Leu Ile Gln Asn Ser Leu Thr Ile Glu
        50                  55                  60

Lys Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asp Gly Lys Trp Met Arg Glu Leu Val Leu Tyr Asp
                100                 105                 110

Lys Glu Glu Ile Arg Arg Ile Trp Arg Gln Ala Asn Asn Gly Glu Asp
            115                 120                 125

Ala Thr Ala Gly Leu Thr His Ile Met Ile Trp His Ser Asn Leu Asn
        130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
                180                 185                 190
```

```
Leu Ile Arg Met Val Lys Arg Gly Ile Asn Asp Arg Asn Phe Trp Arg
            195                 200                 205

Gly Glu Asn Gly Arg Lys Thr Arg Ser Ala Tyr Glu Arg Met Cys Asn
210                 215                 220

Ile Leu Lys Gly Lys Phe Gln Thr Ala Ala Gln Arg Ala Met Val Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Ala Tyr Gly Pro Ala Val Ser Ser Gly
            275                 280                 285

Tyr Asp Phe Glu Lys Glu Gly Tyr Ser Leu Val Gly Ile Asp Pro Phe
    290                 295                 300

Lys Leu Leu Gln Asn Ser Gln Ile Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Leu Leu Ser Phe Ile Arg Gly Thr Lys Val
            340                 345                 350

Ser Pro Arg Gly Lys Leu Ser Thr Arg Gly Val Gln Ile Ala Ser Asn
            355                 360                 365

Glu Asn Met Asp Asn Met Gly Ser Ser Thr Leu Glu Leu Arg Ser Gly
            370                 375                 380

Tyr Trp Ala Ile Arg Thr Arg Ser Gly Gly Asn Thr Asn Gln Gln Arg
385                 390                 395                 400

Ala Ser Ala Gly Gln Thr Ser Val Gln Pro Thr Phe Ser Val Gln Arg
                405                 410                 415

Asn Leu Pro Phe Glu Lys Ser Thr Ile Met Ala Ala Phe Thr Gly Asn
            420                 425                 430

Thr Glu Gly Arg Thr Ser Asp Met Arg Ala Glu Ile Ile Arg Met Met
            435                 440                 445

Glu Gly Ala Lys Pro Glu Glu Val Ser Phe Arg Gly Arg Gly Val Phe
450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn
```

<210> SEQ ID NO 13
<211> LENGTH: 97
<212> TYPE: PRT
<213> ORGANISM: Influenza A virus

<400> SEQUENCE: 13

```
Met Ser Leu Leu Thr Glu Val Glu Thr Pro Ile Arg Asn Glu Trp Gly
1               5                   10                  15

Cys Arg Cys Asn Gly Ser Ser Asp Pro Leu Ala Ile Ala Ala Asn Ile
            20                  25                  30

Ile Gly Ile Leu His Leu Ile Leu Trp Ile Leu Asp Arg Leu Phe Phe
        35                  40                  45

Lys Cys Ile Tyr Arg Arg Phe Lys Tyr Gly Leu Lys Gly Gly Pro Ser
    50                  55                  60
```

```
Thr Glu Gly Val Pro Lys Ser Met Arg Glu Glu Tyr Arg Lys Glu Gln
 65                  70                  75                  80

Gln Ser Ala Val Asp Ala Asp Asp Gly His Phe Val Ser Ile Glu Leu
                 85                  90                  95

Glu

<210> SEQ ID NO 14
<211> LENGTH: 498
<212> TYPE: PRT
<213> ORGANISM: Influenza A virus

<400> SEQUENCE: 14

Met Ala Ser Gln Gly Thr Lys Arg Ser Tyr Glu Gln Met Glu Thr Asp
  1               5                  10                  15

Gly Glu Arg Gln Asn Ala Thr Glu Ile Arg Ala Ser Val Gly Lys Met
                 20                  25                  30

Ile Gly Gly Ile Gly Arg Phe Tyr Ile Gln Met Cys Thr Glu Leu Lys
             35                  40                  45

Leu Ser Asp Tyr Glu Gly Arg Leu Ile Gln Asn Ser Leu Thr Ile Glu
 50                  55                  60

Arg Met Val Leu Ser Ala Phe Asp Glu Arg Arg Asn Lys Tyr Leu Glu
 65                  70                  75                  80

Glu His Pro Ser Ala Gly Lys Asp Pro Lys Lys Thr Gly Gly Pro Ile
                 85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
            115                 120                 125

Ala Thr Ala Gly Leu Thr His Met Met Ile Trp His Ser Asn Leu Asn
130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
                180                 185                 190

Leu Val Arg Met Ile Lys Arg Gly Ile Asn Asp Arg Asn Phe Trp Arg
                195                 200                 205

Gly Glu Asn Gly Arg Lys Thr Arg Ile Ala Tyr Glu Arg Met Cys Asn
            210                 215                 220

Ile Leu Lys Gly Lys Phe Gln Thr Ala Ala Gln Lys Ala Met Met Asp
225                 230                 235                 240

Gln Val Arg Glu Ser Arg Asp Pro Gly Asn Ala Glu Phe Glu Asp Leu
                245                 250                 255

Thr Phe Leu Ala Arg Ser Ala Leu Ile Leu Arg Gly Ser Val Ala His
                260                 265                 270

Lys Ser Cys Leu Pro Ala Cys Val Tyr Gly Pro Ala Val Ala Ser Gly
            275                 280                 285

Tyr Asp Phe Glu Arg Glu Gly Tyr Ser Leu Val Gly Ile Asp Pro Phe
        290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335
```

Ala Phe Glu Asp Leu Arg Val Leu Ser Phe Ile Lys Gly Thr Lys Val
            340                 345                 350

Val Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
            405                 410                 415

Asn Leu Pro Phe Asp Arg Thr Thr Val Met Ala Ala Phe Thr Gly Asn
        420                 425                 430

Thr Glu Gly Arg Thr Ser Asp Met Arg Thr Glu Ile Ile Arg Met Met
    435                 440                 445

Glu Ser Ala Arg Pro Glu Asp Val Ser Phe Gln Gly Arg Gly Val Phe
450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
            485                 490                 495

Asp Asn

<210> SEQ ID NO 15
<211> LENGTH: 97
<212> TYPE: PRT
<213> ORGANISM: Influenza A virus

<400> SEQUENCE: 15

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Ser Ile
            20                  25                  30

Ile Gly Ile Leu His Phe Ile Leu Trp Ile Leu Asp Arg Leu Phe Phe
        35                  40                  45

Lys Cys Ile Tyr Arg Phe Phe Lys His Gly Leu Lys Arg Gly Pro Ser
    50                  55                  60

Thr Glu Gly Val Pro Glu Ser Met Arg Glu Glu Tyr Arg Lys Glu Gln
65                  70                  75                  80

Gln Ser Ala Val Asp Ala Asp Asp Ser His Phe Val Ser Ile Glu Leu
                85                  90                  95

Glu

<210> SEQ ID NO 16
<211> LENGTH: 498
<212> TYPE: PRT
<213> ORGANISM: Influenza A virus

<400> SEQUENCE: 16

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

```
Arg Met Val Leu Ser Ala Phe Asp Glu Arg Arg Asn Lys Tyr Leu Glu
 65                  70                  75                  80

Glu His Pro Ser Ala Gly Lys Asp Pro Lys Thr Gly Gly Pro Ile
                 85                  90                  95

Tyr Lys Arg Val Asp Gly Lys Trp Met Arg Glu Leu Val Leu Tyr Asp
            100                 105                 110

Lys Glu Glu Ile Arg Arg Ile Trp Arg Gln Ala Asn Asn Gly Asp Asp
            115                 120                 125

Ala Thr Ala Gly Leu Thr His Met Met Ile Trp His Ser Asn Leu Asn
130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
                180                 185                 190

Leu Ile Arg Met Ile Lys Arg Gly Ile Asn Asp Arg Asn Phe Trp Arg
            195                 200                 205

Gly Glu Asn Gly Arg Lys Thr Arg Ser Ala Tyr Glu Arg Met Cys Asn
210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
                260                 265                 270

Lys Ser Cys Leu Pro Ala Cys Val Tyr Gly Pro Ala Ile Ala Ser Gly
            275                 280                 285

Tyr Asn Phe Glu Lys Glu Gly Tyr Ser Leu Val Gly Ile Asp Pro Phe
            290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys Asn Ser Ala
                325                 330                 335

Ala Phe Glu Asp Leu Arg Val Leu Ser Phe Ile Arg Gly Thr Lys Val
                340                 345                 350

Ser Pro Arg Gly Lys Leu Ser Thr Arg Gly Val Gln Ile Ala Ser Asn
            355                 360                 365

Glu Asn Met Asp Thr Met Glu Ser Ser Thr Leu Glu Leu Arg Ser Arg
            370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Ala Phe Ser Val Gln Arg
                405                 410                 415

Asn Leu Pro Phe Asp Lys Pro Thr Ile Met Ala Ala Phe Thr Gly Asn
                420                 425                 430

Thr Glu Gly Arg Thr Ser Asp Met Arg Ala Glu Ile Ile Arg Met Met
            435                 440                 445

Glu Gly Ala Lys Pro Glu Glu Met Ser Phe Gln Gly Arg Gly Val Phe
            450                 455                 460

Glu Leu Ser Asp Glu Lys Ala Thr Asn Pro Ile Val Pro Ser Phe Asp
465                 470                 475                 480
```

-continued

```
Met Ser Asn Glu Gly Ser Tyr Phe Phe Gly Asp Asn Ala Glu Glu Tyr
            485                 490                 495

Asp Asn

<210> SEQ ID NO 17
<211> LENGTH: 551
<212> TYPE: PRT
<213> ORGANISM: Human herpesvirus 5

<400> SEQUENCE: 17

Met Ala Ser Val Leu Gly Pro Ile Ser Gly His Val Leu Lys Ala Val
1               5                   10                  15

Phe Ser Arg Gly Asp Thr Pro Val Leu Pro His Glu Thr Arg Leu Leu
            20                  25                  30

Gln Thr Gly Ile His Val Arg Val Ser Gln Pro Ser Leu Ile Leu Val
        35                  40                  45

Ser Gln Tyr Thr Pro Asp Ser Thr Pro Cys His Arg Gly Asp Asn Gln
    50                  55                  60

Leu Gln Val Gln His Thr Tyr Phe Thr Gly Ser Glu Val Glu Asn Val
65                  70                  75                  80

Ser Val Asn Val His Asn Pro Thr Gly Arg Ser Ile Cys Pro Ser Gln
                85                  90                  95

Glu Pro Met Ser Ile Tyr Val Tyr Ala Leu Pro Leu Lys Met Leu Asn
            100                 105                 110

Ile Pro Ser Ile Asn Val His His Tyr Pro Ser Ala Ala Glu Arg Lys
        115                 120                 125

His Arg His Leu Pro Val Ala Asp Ala Val Ile His Ala Ser Gly Lys
    130                 135                 140

Gln Met Trp Gln Ala Arg Leu Thr Val Ser Gly Leu Ala Trp Thr Arg
145                 150                 155                 160

Gln Gln Asn Gln Trp Lys Glu Pro Asp Val Tyr Tyr Thr Ser Ala Phe
                165                 170                 175

Val Phe Pro Thr Lys Asp Val Ala Leu Arg His Val Val Cys Ala His
            180                 185                 190

Glu Leu Val Cys Ser Met Glu Asn Thr Arg Ala Thr Lys Met Gln Val
        195                 200                 205

Ile Gly Asp Gln Tyr Val Lys Val Tyr Leu Glu Ser Phe Cys Glu Asp
    210                 215                 220

Val Pro Ser Gly Lys Leu Phe Met His Val Thr Leu Gly Ser Asp Val
225                 230                 235                 240

Glu Glu Asp Leu Thr Met Thr Arg Asn Pro Gln Pro Phe Met Arg Pro
                245                 250                 255

His Glu Arg Asn Gly Phe Thr Val Leu Cys Pro Lys Asn Met Ile Ile
            260                 265                 270

Lys Pro Gly Lys Ile Ser His Ile Met Leu Asp Val Ala Phe Thr Ser
        275                 280                 285

His Glu His Phe Gly Leu Leu Cys Pro Lys Ser Ile Pro Gly Leu Ser
    290                 295                 300

Ile Ser Gly Asn Leu Leu Met Asn Gly Gln Gln Ile Phe Leu Glu Val
305                 310                 315                 320

Gln Ala Ile Arg Glu Thr Val Glu Leu Arg Gln Tyr Asp Pro Val Ala
                325                 330                 335

Ala Leu Phe Phe Phe Asp Ile Asp Leu Leu Leu Gln Arg Gly Pro Gln
            340                 345                 350
```

```
Tyr Ser Glu His Pro Thr Phe Thr Ser Gln Tyr Arg Ile Gln Gly Lys
            355                 360                 365

Leu Glu Tyr Arg His Thr Trp Asp Arg His Asp Glu Gly Ala Ala Gln
        370                 375                 380

Gly Asp Asp Asp Val Trp Thr Ser Gly Ser Asp Ser Asp Glu Glu Leu
385                 390                 395                 400

Val Thr Thr Glu Arg Lys Thr Pro Arg Val Thr Gly Gly Gly Ala Met
                405                 410                 415

Ala Gly Ala Ser Thr Ser Ala Gly Arg Lys Arg Lys Ser Ala Ser Ser
            420                 425                 430

Ala Thr Ala Cys Thr Ala Gly Val Met Thr Arg Gly Arg Leu Lys Ala
            435                 440                 445

Glu Ser Thr Val Ala Pro Glu Glu Asp Thr Asp Glu Asp Ser Asp Asn
        450                 455                 460

Glu Ile His Asn Pro Ala Val Phe Thr Trp Pro Pro Trp Gln Ala Gly
465                 470                 475                 480

Ile Leu Ala Arg Asn Leu Val Pro Met Val Ala Thr Val Gln Gly Gln
                485                 490                 495

Asn Leu Lys Tyr Gln Glu Phe Phe Trp Asp Ala Asn Asp Ile Tyr Arg
            500                 505                 510

Ile Phe Ala Glu Leu Glu Gly Val Trp Gln Pro Ala Ala Gln Pro Lys
        515                 520                 525

Arg Arg Arg His Arg Gln Asp Ala Leu Pro Gly Pro Cys Ile Ala Ser
        530                 535                 540

Thr Pro Lys Lys His Arg Gly
545                 550

<210> SEQ ID NO 18
<211> LENGTH: 158
<212> TYPE: PRT
<213> ORGANISM: Human papillomavirus type 16

<400> SEQUENCE: 18

Met His Gln Lys Arg Thr Ala Met Phe Gln Asp Pro Gln Glu Arg Pro
1               5                   10                  15

Gly Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Val Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155

<210> SEQ ID NO 19
```

```
<211> LENGTH: 97
<212> TYPE: PRT
<213> ORGANISM: Influenza A virus

<400> SEQUENCE: 19

Met Ser Leu Leu Thr Glu Val Glu Thr Pro Ile Arg Asn Glu Trp Gly
1               5                   10                  15

Cys Arg Cys Asn Gly Ser Ser Asp Pro Leu Ala Ile Ala Ala Asn Ile
                20                  25                  30

Ile Gly Ile Leu His Leu Ile Leu Trp Ile Leu Asp Arg Leu Phe Phe
            35                  40                  45

Lys Cys Ile Tyr Arg Arg Phe Lys Tyr Gly Leu Lys Gly Gly Pro Ser
50                  55                  60

Thr Glu Gly Val Pro Lys Ser Met Arg Glu Glu Tyr Arg Lys Glu Gln
65                  70                  75                  80

Gln Ser Ala Val Asp Ala Asp Asp Gly His Phe Val Ser Ile Glu Leu
                85                  90                  95

Glu

<210> SEQ ID NO 20
<211> LENGTH: 759
<212> TYPE: PRT
<213> ORGANISM: Influenza A virus

<400> SEQUENCE: 20

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
                20                  25                  30

Lys Tyr Thr Ser Gly Arg Gln Glu Lys Asn Pro Ala Leu Arg Met Lys
            35                  40                  45

Trp Met Met Ala Met Lys Tyr Pro Ile Thr Ala Asp Lys Arg Ile Thr
50                  55                  60

Glu Met Ile Pro Glu Arg Asn Glu Gln Gly Gln Thr Leu Trp Ser Lys
65                  70                  75                  80

Met Asn Asp Ala Gly Ser Asp Arg Val Met Val Ser Pro Leu Ala Val
                85                  90                  95

Thr Trp Trp Asn Arg Asn Gly Pro Met Thr Asn Thr Val His Tyr Pro
                100                 105                 110

Lys Ile Tyr Lys Thr Tyr Phe Glu Arg Val Glu Arg Leu Lys His Gly
            115                 120                 125

Thr Phe Gly Pro Val His Phe Arg Asn Gln Val Lys Ile Arg Arg Arg
130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
            195                 200                 205

Arg Glu Leu Val Arg Lys Thr Arg Phe Leu Pro Val Ala Gly Gly Thr
210                 215                 220

Ser Ser Val Tyr Ile Glu Val Leu His Leu Thr Gln Gly Thr Cys Trp
225                 230                 235                 240
```

-continued

```
Glu Gln Met Tyr Thr Pro Gly Gly Glu Val Lys Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Lys Gln Asn Pro Thr Glu
    290                 295                 300

Glu Gln Ala Val Gly Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Val Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Leu Ile Gln Leu
    370                 375                 380

Ile Val Ser Gly Arg Asp Glu Gln Ser Ile Ala Glu Ala Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Val Glu Pro Ile Asp Asn Val Met Gly Met Ile Gly Ile Leu
    450                 455                 460

Pro Asp Met Thr Pro Ser Ile Glu Met Ser Met Arg Gly Val Arg Ile
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
    610                 615                 620

Pro Pro Lys Gln Ser Arg Met Gln Phe Ser Ser Phe Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
```

```
                    660                 665                 670
Gly Thr Leu Thr Glu Asp Pro Asp Glu Gly Thr Ala Gly Val Glu Ser
                675                 680                 685

Ala Val Leu Arg Gly Phe Leu Ile Leu Gly Lys Glu Asp Arg Arg Tyr
            690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755

<210> SEQ ID NO 21
<211> LENGTH: 716
<212> TYPE: PRT
<213> ORGANISM: Influenza A virus

<400> SEQUENCE: 21

Met Glu Asp Phe Val Arg Gln Cys Phe Asn Pro Met Ile Val Glu Leu
1               5                   10                  15

Ala Glu Lys Thr Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Ile Val Glu
    50                  55                  60

Leu Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Lys Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Arg
                245                 250                 255

Ile Glu Pro Phe Leu Lys Thr Thr Pro Arg Pro Leu Arg Leu Pro Asn
            260                 265                 270
```

```
Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Arg Thr Phe Phe Gly Trp Lys Glu Pro
305                 310                 315                 320

Asn Val Val Lys Pro His Glu Lys Gly Ile Asn Pro Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Lys Thr Lys Asn Met Lys Lys Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Leu
385                 390                 395                 400

Arg Ser Leu Ala Ser Trp Ile Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ser
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Glu Ser Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Ile Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
```

```
                    690                 695                 700
Ser Trp Phe Asn Ser Phe Leu Thr His Ala Leu Ser
705                 710                 715

<210> SEQ ID NO 22
<211> LENGTH: 230
<212> TYPE: PRT
<213> ORGANISM: Influenza A virus

<400> SEQUENCE: 22

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Glu Trp Ser Met Leu Ile Pro Lys Gln Lys Val Ala
            100                 105                 110

Gly Pro Leu Cys Ile Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Asp Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asn Gly Arg Pro Pro Leu Thr Pro Lys Gln Lys Arg Glu Met Ala Gly
    210                 215                 220

Thr Ile Arg Ser Glu Val
225                 230

<210> SEQ ID NO 23
<211> LENGTH: 121
<212> TYPE: PRT
<213> ORGANISM: Influenza A virus

<400> SEQUENCE: 23

Met Asp Pro Asn Thr Val Ser Ser Phe Gln Asp Ile Leu Leu Arg Met
1               5                   10                  15

Ser Lys Met Gln Leu Glu Ser Ser Ser Glu Asp Leu Asn Gly Met Ile
            20                  25                  30

Thr Gln Phe Glu Ser Leu Lys Leu Tyr Arg Asp Ser Leu Gly Glu Ala
        35                  40                  45

Val Met Arg Met Gly Asp Leu His Ser Leu Gln Asn Arg Asn Glu Lys
    50                  55                  60

Trp Arg Glu Gln Leu Gly Gln Lys Phe Glu Glu Ile Arg Trp Leu Ile
```

```
              65                  70                  75                  80
         Glu Glu Val Arg His Lys Leu Lys Val Thr Glu Asn Ser Phe Glu Gln
                         85                  90                  95

Ile Thr Phe Met Gln Ala Leu His Leu Leu Glu Val Glu Gln Glu
                        100                 105                 110

Ile Arg Thr Phe Ser Phe Gln Leu Ile
                        115                 120

<210> SEQ ID NO 24
         <211> LENGTH: 454
         <212> TYPE: PRT
         <213> ORGANISM: Influenza A virus

<400> SEQUENCE: 24

Met Asn Pro Asn Gln Lys Ile Ile Thr Ile Gly Ser Ile Cys Leu Val
         1               5                  10                  15

Val Gly Leu Ile Ser Leu Ile Leu Gln Ile Gly Asn Ile Ile Ser Ile
                         20                  25                  30

Trp Ile Ser His Ser Ile Gln Thr Gly Ser Gln Asn His Thr Gly Ile
                         35                  40                  45

Cys Asn Gln Asn Ile Ile Thr Tyr Lys Asn Ser Thr Trp Val Lys Asp
              50                  55                  60

Thr Thr Ser Val Ile Leu Thr Gly Asn Ser Ser Leu Cys Pro Ile Arg
         65                  70                  75                  80

Gly Trp Ala Ile Tyr Ser Lys Asp Asn Ser Ile Arg Ile Gly Ser Lys
                         85                  90                  95

Gly Asp Val Phe Val Ile Arg Glu Pro Phe Ile Ser Cys Ser His Leu
                        100                 105                 110

Glu Cys Arg Thr Phe Phe Leu Thr Gln Gly Ala Leu Leu Asn Asp Arg
                        115                 120                 125

His Ser Asn Gly Thr Val Lys Asp Arg Ser Pro Tyr Arg Ala Leu Met
              130                 135                 140

Ser Cys Pro Val Gly Glu Ala Pro Ser Pro Tyr Asn Ser Arg Phe Glu
         145                 150                 155                 160

Ser Val Ala Trp Ser Ala Ser Ala Cys His Asp Gly Met Gly Trp Leu
                        165                 170                 175

Thr Ile Gly Ile Ser Gly Pro Asp Asn Gly Ala Val Ala Val Leu Lys
                        180                 185                 190

Tyr Asn Gly Ile Ile Thr Glu Thr Ile Lys Ser Trp Arg Lys Lys Ile
                        195                 200                 205

Leu Arg Thr Gln Glu Ser Glu Cys Ala Cys Val Asn Gly Ser Cys Phe
              210                 215                 220

Thr Ile Met Thr Asp Gly Pro Ser Asp Gly Leu Ala Ser Tyr Lys Ile
         225                 230                 235                 240

Phe Lys Ile Glu Lys Gly Lys Val Thr Lys Ser Ile Glu Leu Asn Ala
                        245                 250                 255

Pro Asn Ser His Tyr Glu Glu Cys Ser Cys Tyr Pro Asp Thr Gly Lys
                        260                 265                 270

Val Met Cys Val Cys Arg Asp Asn Trp His Gly Ser Asn Arg Pro Trp
                        275                 280                 285

Val Ser Phe Asp Gln Asn Leu Asp Tyr Gln Ile Gly Tyr Ile Cys Ser
              290                 295                 300

Gly Val Phe Gly Asp Asn Pro Arg Pro Lys Asp Gly Thr Gly Ser Cys
         305                 310                 315                 320
```

Gly Pro Val Tyr Val Asp Gly Ala Asn Gly Val Lys Gly Phe Ser Tyr
                    325                 330                 335

Arg Tyr Gly Asn Gly Val Trp Ile Gly Arg Thr Lys Ser His Ser Ser
                340                 345                 350

Arg His Gly Phe Glu Met Ile Trp Asp Pro Asn Gly Trp Thr Glu Thr
            355                 360                 365

Asp Ser Lys Phe Ser Val Arg Gln Asp Val Val Ala Met Thr Asp Trp
        370                 375                 380

Ser Gly Tyr Ser Gly Ser Phe Val Gln His Pro Glu Leu Thr Gly Leu
385                 390                 395                 400

Asp Cys Ile Arg Pro Cys Phe Trp Val Glu Leu Ile Arg Gly Arg Pro
                405                 410                 415

Lys Glu Lys Thr Ile Trp Thr Ser Ala Ser Ser Ile Ser Phe Cys Gly
                420                 425                 430

Val Asn Ser Asp Thr Val Asp Trp Ser Trp Pro Asp Gly Ala Glu Leu
            435                 440                 445

Pro Phe Thr Ile Asp Lys
        450

<210> SEQ ID NO 25
<211> LENGTH: 566
<212> TYPE: PRT
<213> ORGANISM: Influenza A virus

<400> SEQUENCE: 25

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Thr Lys Gly Val Thr Ala Ala Cys Ser His Ala Gly Lys Ser Ser
145                 150                 155                 160

Phe Tyr Arg Asn Leu Leu Trp Leu Thr Glu Lys Glu Gly Ser Tyr Pro
                165                 170                 175

Lys Leu Lys Asn Ser Tyr Val Asn Lys Lys Gly Lys Glu Val Leu Val
            180                 185                 190

Leu Trp Gly Ile His His Pro Ser Asn Ser Lys Asp Gln Gln Asn Ile
        195                 200                 205

Tyr Gln Asn Glu Asn Ala Tyr Val Ser Val Val Thr Ser Asn Tyr Asn
    210                 215                 220

Arg Arg Phe Thr Pro Glu Ile Ala Glu Arg Pro Lys Val Arg Asp Gln
225                 230                 235                 240

```
Ala Gly Arg Met Asn Tyr Tyr Trp Thr Leu Leu Lys Pro Gly Asp Thr
            245                 250                 255

Ile Ile Phe Glu Ala Asn Gly Asn Leu Ile Ala Pro Arg Tyr Ala Phe
        260                 265                 270

Ala Leu Ser Arg Gly Phe Gly Ser Gly Ile Ile Thr Ser Asn Ala Ser
    275                 280                 285

Met His Glu Cys Asn Thr Lys Cys Gln Thr Pro Leu Gly Ala Ile Asn
290                 295                 300

Ser Ser Leu Pro Phe Gln Asn Ile His Pro Val Thr Ile Gly Glu Cys
305                 310                 315                 320

Pro Lys Tyr Val Arg Ser Ala Lys Leu Arg Met Val Thr Gly Leu Arg
            325                 330                 335

Asn Ile Pro Ser Ile Gln Ser Arg Gly Leu Phe Gly Ala Ile Ala Gly
        340                 345                 350

Phe Ile Glu Gly Gly Trp Thr Gly Met Ile Asp Gly Trp Tyr Gly Tyr
    355                 360                 365

His His Gln Asn Glu Gln Gly Ser Gly Tyr Ala Ala Asp Gln Lys Ser
370                 375                 380

Thr Gln Asn Ala Ile Asn Gly Ile Thr Asn Lys Val Asn Ser Val Ile
385                 390                 395                 400

Glu Lys Met Asn Ile Gln Phe Thr Ala Val Gly Lys Glu Phe Asn Lys
            405                 410                 415

Leu Glu Lys Arg Met Glu Asn Leu Asn Lys Lys Val Asp Asp Gly Phe
        420                 425                 430

Leu Asp Ile Trp Thr Tyr Asn Ala Glu Leu Leu Val Leu Leu Glu Asn
    435                 440                 445

Glu Arg Thr Leu Asp Phe His Asp Ser Asn Val Lys Asn Leu Tyr Glu
450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asn Glu Cys Met Glu Ser Val
            485                 490                 495

Arg Asn Gly Thr Tyr Asp Tyr Pro Lys Tyr Ser Glu Glu Ser Lys Leu
        500                 505                 510

Asn Arg Glu Lys Val Asp Gly Val Lys Leu Glu Ser Met Gly Ile Tyr
    515                 520                 525

Gln Ile Leu Ala Ile Tyr Ser Thr Val Ala Ser Ser Leu Val Leu Leu
530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 26
<211> LENGTH: 252
<212> TYPE: PRT
<213> ORGANISM: Influenza A virus

<400> SEQUENCE: 26

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
```

```
            35                  40                  45
Arg Pro Ile Leu Ser Pro Leu Thr Lys Gly Ile Leu Gly Phe Val Phe
 50                  55                  60

Thr Leu Thr Val Pro Ser Glu Arg Gly Leu Gln Arg Arg Phe Val
 65                  70                  75                  80

Gln Asn Ala Leu Asn Gly Asn Gly Asp Pro Asn Asn Met Asp Lys Ala
                 85                  90                  95

Val Lys Leu Tyr Arg Lys Leu Lys Arg Glu Ile Thr Phe His Gly Ala
            100                 105                 110

Lys Glu Ile Ser Leu Ser Tyr Ser Ala Gly Ala Leu Ala Ser Cys Met
            115                 120                 125

Gly Leu Ile Tyr Asn Arg Met Gly Ala Val Thr Thr Glu Val Ala Phe
130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
            195                 200                 205

Ala Arg Gln Met Val Gln Ala Met Arg Thr Ile Gly Thr His Pro Ser
210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys
            245                 250

<210> SEQ ID NO 27
<211> LENGTH: 87
<212> TYPE: PRT
<213> ORGANISM: Influenza A virus

<400> SEQUENCE: 27

Met Gly Gln Glu Gln Asp Thr Pro Trp Ile Leu Ser Thr Gly His Ile
 1               5                  10                  15

Ser Thr Gln Lys Arg Gln Asp Gly Gln Gln Thr Pro Lys Leu Glu His
             20                  25                  30

Arg Asn Ser Thr Arg Leu Met Gly His Cys Gln Lys Thr Met Asn Gln
         35                  40                  45

Val Val Met Pro Lys Gln Ile Val Tyr Trp Lys Gln Trp Leu Ser Leu
 50                  55                  60

Arg Asn Pro Ile Leu Val Phe Leu Lys Thr Arg Val Leu Lys Arg Trp
 65                  70                  75                  80

Arg Leu Phe Ser Lys His Glu
                 85

<210> SEQ ID NO 28
<211> LENGTH: 757
<212> TYPE: PRT
<213> ORGANISM: Influenza A virus

<400> SEQUENCE: 28

Met Asp Val Asn Pro Thr Leu Leu Phe Leu Lys Val Pro Ala Gln Asn
 1               5                  10                  15

Ala Ile Ser Thr Thr Phe Pro Tyr Thr Gly Asp Pro Pro Tyr Ser His
```

```
               20                  25                  30
Gly Thr Gly Thr Gly Tyr Thr Met Asp Thr Val Asn Arg Thr His Gln
             35                  40                  45

Tyr Ser Glu Lys Ala Arg Trp Thr Thr Asn Thr Glu Thr Gly Ala Pro
 50                  55                  60

Gln Leu Asn Pro Ile Asp Gly Pro Leu Pro Glu Asp Asn Glu Pro Ser
 65                  70                  75                  80

Gly Tyr Ala Gln Thr Asp Cys Val Leu Glu Ala Met Ala Phe Leu Glu
             85                  90                  95

Glu Ser His Pro Gly Ile Phe Glu Asn Ser Cys Ile Glu Thr Met Glu
            100                 105                 110

Val Val Gln Gln Thr Arg Val Asp Lys Leu Thr Gln Gly Arg Gln Thr
            115                 120                 125

Tyr Asp Trp Thr Leu Asn Arg Asn Gln Pro Ala Ala Thr Ala Leu Ala
            130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Lys Lys
                165                 170                 175

Glu Glu Met Gly Ile Thr Thr His Phe Gln Arg Lys Arg Arg Val Arg
            180                 185                 190

Asp Asn Met Thr Lys Lys Met Ile Thr Gln Arg Thr Ile Gly Lys Arg
            195                 200                 205

Lys Gln Arg Leu Asn Lys Arg Ser Tyr Leu Ile Arg Ala Leu Thr Leu
        210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
            275                 280                 285

Met Met Thr Asn Ser Gln Asp Thr Glu Leu Ser Leu Thr Ile Thr Gly
            290                 295                 300

Asp Asn Thr Lys Trp Asn Glu Asn Gln Asn Pro Arg Met Phe Leu Ala
305                 310                 315                 320

Met Ile Thr Tyr Met Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
            355                 360                 365

Pro Ala Glu Met Leu Ala Ser Ile Asp Leu Lys Tyr Phe Asn Asp Ser
            370                 375                 380

Thr Arg Lys Lys Ile Glu Lys Ile Arg Pro Leu Leu Ile Glu Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Asp Phe Ala
            435                 440                 445
```

```
Leu Ile Val Asn Ala Pro Asn His Glu Gly Ile Gln Ala Gly Val Asp
    450                 455                 460

Arg Phe Tyr Arg Thr Cys Lys Leu His Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ser Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Met
625                 630                 635                 640

Asn Asn Ala Val Met Met Pro Ala His Gly Pro Ala Lys Asn Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Val Leu Glu Asp Glu Gln Met
        675                 680                 685

Tyr Gln Arg Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Thr Glu Ile Met Lys Ile Cys Ser Thr Ile Glu Glu
            740                 745                 750

Leu Arg Arg Gln Lys
        755

<210> SEQ ID NO 29
<211> LENGTH: 498
<212> TYPE: PRT
<213> ORGANISM: Influenza A virus

<400> SEQUENCE: 29

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
```

-continued

```
            50                  55                  60
Arg Met Val Leu Ser Ala Phe Asp Glu Arg Arg Asn Lys Tyr Leu Glu
 65                  70                  75                  80

Glu His Pro Ser Ala Gly Lys Asp Pro Lys Lys Thr Gly Gly Pro Ile
                     85                  90                  95

Tyr Arg Arg Val Asn Gly Lys Trp Met Arg Glu Leu Ile Leu Tyr Asp
                    100                 105                 110

Lys Glu Glu Ile Arg Arg Ile Trp Arg Gln Ala Asn Asn Gly Asp Asp
                115                     120                 125

Ala Thr Ala Gly Leu Thr His Met Met Ile Trp His Ser Asn Leu Asn
130                     135                 140

Asp Ala Thr Tyr Gln Arg Thr Arg Ala Leu Val Arg Thr Gly Met Asp
145                     150                 155                 160

Pro Arg Met Cys Ser Leu Met Gln Gly Ser Thr Leu Pro Arg Arg Ser
                    165                 170                 175

Gly Ala Ala Gly Ala Ala Val Lys Gly Val Gly Thr Met Val Met Glu
                180                 185                     190

Leu Val Arg Met Ile Lys Arg Gly Ile Asn Asp Arg Asn Phe Trp Arg
                195                 200                 205

Gly Glu Asn Gly Arg Lys Thr Arg Ile Ala Tyr Glu Arg Met Cys Asn
210                     215                 220

Ile Leu Lys Gly Lys Phe Gln Thr Ala Ala Gln Lys Ala Met Met Asp
225                     230                 235                 240

Gln Val Arg Glu Ser Arg Asp Pro Gly Asn Ala Glu Phe Glu Asp Leu
                    245                 250                 255

Thr Phe Leu Ala Arg Ser Ala Leu Ile Leu Arg Gly Ser Val Ala His
                    260                 265                 270

Lys Ser Cys Leu Pro Ala Cys Val Tyr Gly Pro Ala Val Ala Ser Gly
                275                 280                 285

Tyr Asp Phe Glu Arg Glu Gly Tyr Ser Leu Val Gly Ile Asp Pro Phe
                290                 295                 300

Arg Leu Leu Gln Asn Ser Gln Val Tyr Ser Leu Ile Arg Pro Asn Glu
305                     310                 315                 320

Asn Pro Ala His Lys Ser Gln Leu Val Trp Met Ala Cys His Ser Ala
                    325                 330                 335

Ala Phe Glu Asp Leu Arg Val Leu Ser Phe Ile Lys Gly Thr Lys Val
                340                 345                 350

Val Pro Arg Gly Lys Leu Ser Thr Arg Gly Val Gln Ile Ala Ser Asn
                355                 360                 365

Glu Asn Met Glu Thr Met Glu Ser Ser Thr Leu Glu Leu Arg Ser Arg
                370                 375                 380

Tyr Trp Ala Ile Arg Thr Arg Ser Gly Gly Asn Thr Asn Gln Gln Arg
385                     390                 395                 400

Ala Ser Ala Gly Gln Ile Ser Ile Gln Pro Thr Phe Ser Val Gln Arg
                    405                 410                 415

Asn Leu Pro Phe Asp Arg Thr Thr Val Met Ala Ala Phe Thr Gly Asn
                    420                 425                 430

Thr Glu Gly Arg Thr Ser Asp Met Arg Thr Glu Ile Ile Arg Met Met
                435                 440                 445

Glu Ser Ala Arg Pro Glu Asp Val Ser Phe Gln Gly Arg Gly Val Phe
                450                 455                 460

Glu Leu Ser Asp Glu Lys Ala Ala Ser Pro Ile Val Pro Ser Phe Asp
465                     470                 475                 480
```

Met Ser Asn Glu Gly Ser Tyr Phe Phe Gly Asp Asn Ala Glu Glu Tyr
            485                 490                 495

Asp Asn

<210> SEQ ID NO 30
<211> LENGTH: 759
<212> TYPE: PRT
<213> ORGANISM: Influenza A virus

<400> SEQUENCE: 30

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ser Leu Arg Met Lys
        35                  40                  45

Trp Met Met Ala Met Lys Tyr Pro Ile Thr Ala Asp Lys Arg Ile Thr
    50                  55                  60

Glu Met Val Pro Glu Arg Asn Glu Gln Gly Gln Thr Leu Trp Ser Lys
65                  70                  75                  80

Met Ser Asp Ala Gly Ser Asp Arg Val Met Val Ser Pro Leu Ala Val
                85                  90                  95

Thr Trp Trp Asn Arg Asn Gly Pro Met Thr Ser Thr Val His Tyr Pro
            100                 105                 110

Lys Ile Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Thr Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Ile Lys Arg Glu Glu Glu Val Leu Thr Gly Asn Leu Gln Thr Leu
            340                 345                 350

```
Lys Ile Arg Val His Glu Gly Tyr Glu Phe Thr Met Val Gly Lys
        355                 360                 365

Arg Ala Thr Ala Ile Leu Arg Lys Ala Thr Arg Arg Leu Val Gln Leu
        370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
                420                 425                 430

Gln Leu Leu Arg His Phe Gln Lys Asp Ala Lys Val Leu Phe Gln Asn
        435                 440                 445

Trp Gly Ile Glu His Ile Asp Asn Val Met Gly Met Ile Gly Val Leu
        450                 455                 460

Pro Asp Met Thr Pro Ser Thr Glu Met Ser Met Arg Gly Ile Arg Val
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Val Leu
                500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
        530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
                580                 585                 590

Ser Gly Phe Val Arg Thr Leu Phe Gln Gln Met Arg Asp Val Leu Gly
        595                 600                 605

Thr Phe Asp Thr Thr Gln Ile Ile Lys Leu Leu Pro Phe Ala Ala Ala
        610                 615                 620

Pro Pro Lys Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Thr Thr Lys Arg Leu Thr Ile Leu Gly Lys Asp Ala
                660                 665                 670

Gly Thr Leu Thr Glu Asp Pro Asp Glu Gly Thr Ser Gly Val Glu Ser
        675                 680                 685

Ala Val Leu Arg Gly Phe Leu Ile Leu Gly Lys Glu Asp Arg Arg Tyr
        690                 695                 700

Gly Pro Ala Leu Ser Ile Asn Glu Leu Ser Thr Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
                740                 745                 750

Arg Ile Arg Met Ala Ile Asn
        755
```

<210> SEQ ID NO 31
<211> LENGTH: 562
<212> TYPE: PRT
<213> ORGANISM: Influenza A virus

<400> SEQUENCE: 31

```
Met Ala Ile Ile Tyr Leu Ile Leu Leu Phe Thr Ala Val Arg Gly Asp
  1               5                  10                  15
Gln Ile Cys Ile Gly Tyr His Ala Asn Asn Ser Thr Glu Lys Val Asp
             20                  25                  30
Thr Ile Leu Glu Arg Asn Val Thr Val Thr His Ala Lys Asp Ile Leu
         35                  40                  45
Glu Lys Thr His Asn Gly Lys Leu Cys Lys Leu Asn Gly Ile Pro Pro
     50                  55                  60
Leu Glu Leu Gly Asp Cys Ser Ile Ala Gly Trp Leu Leu Gly Asn Pro
 65                  70                  75                  80
Glu Cys Asp Arg Leu Leu Ser Val Pro Glu Trp Ser Tyr Ile Met Glu
                 85                  90                  95
Lys Glu Asn Pro Arg Tyr Ser Leu Cys Tyr Pro Gly Ser Phe Asn Asp
            100                 105                 110
Tyr Glu Glu Leu Lys His Leu Leu Ser Ser Val Lys His Phe Glu Lys
        115                 120                 125
Val Lys Ile Leu Pro Lys Asp Arg Trp Thr Gln His Thr Thr Thr Gly
    130                 135                 140
Gly Ser Trp Ala Cys Ala Val Ser Gly Lys Pro Ser Phe Phe Arg Asn
145                 150                 155                 160
Met Val Trp Leu Thr Arg Lys Gly Ser Asn Tyr Pro Val Ala Lys Gly
                165                 170                 175
Ser Tyr Asn Asn Thr Ser Gly Glu Gln Met Leu Ile Ile Trp Gly Val
            180                 185                 190
His His Pro Asn Asp Glu Ala Glu Gln Arg Ala Leu Tyr Gln Asn Val
        195                 200                 205
Gly Thr Tyr Val Ser Val Ala Thr Ser Thr Leu Tyr Lys Arg Ser Ile
    210                 215                 220
Pro Glu Ile Ala Ala Arg Pro Lys Val Asn Gly Leu Gly Arg Arg Met
225                 230                 235                 240
Glu Phe Ser Trp Thr Leu Leu Asp Met Trp Asp Thr Ile Asn Phe Glu
                245                 250                 255
Ser Thr Gly Asn Leu Val Ala Pro Glu Tyr Gly Phe Lys Ile Ser Lys
            260                 265                 270
Arg Gly Ser Ser Gly Ile Met Lys Thr Glu Gly Thr Leu Glu Asn Cys
        275                 280                 285
Glu Thr Lys Cys Gln Thr Pro Leu Gly Ala Ile Asn Thr Thr Leu Pro
    290                 295                 300
Phe His Asn Val His Pro Leu Thr Ile Gly Glu Cys Pro Lys Tyr Val
305                 310                 315                 320
Lys Ser Glu Lys Leu Val Leu Ala Thr Gly Leu Arg Asn Val Pro Gln
                325                 330                 335
Ile Glu Ser Arg Gly Leu Phe Gly Ala Ile Ala Gly Phe Ile Glu Gly
            340                 345                 350
Gly Trp Gln Gly Met Val Asp Gly Trp Tyr Gly Tyr His His Ser Asn
        355                 360                 365
Asp Gln Gly Ser Gly Tyr Ala Ala Asp Lys Glu Ser Thr Gln Lys Ala
    370                 375                 380
```

```
Phe Asn Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Lys Arg
            405                 410                 415

Leu Glu Asn Leu Asn Lys Lys Met Glu Asp Gly Phe Leu Asp Val Trp
        420                 425                 430

Thr Tyr Asn Ala Glu Leu Leu Val Leu Met Glu Asn Glu Arg Thr Leu
    435                 440                 445

Asp Phe His Asp Ser Asn Val Lys Asn Leu Tyr Asp Lys Val Arg Met
450                 455                 460

Gln Leu Arg Asp Asn Val Lys Glu Leu Gly Asn Gly Cys Phe Glu Phe
465                 470                 475                 480

Tyr His Lys Cys Asp Asn Glu Cys Met Asp Ser Val Lys Asn Gly Thr
                485                 490                 495

Tyr Asp Tyr Pro Lys Tyr Glu Glu Ser Lys Leu Asn Arg Asn Glu
            500                 505                 510

Ile Lys Gly Val Lys Leu Ser Ser Met Gly Val Tyr Gln Ile Leu Ala
            515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile

<210> SEQ ID NO 32
<211> LENGTH: 252
<212> TYPE: PRT
<213> ORGANISM: Influenza A virus

<400> SEQUENCE: 32

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Ala Val Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190
```

```
Ala Gly Ser Ser Glu Gln Ala Ala Glu Ala Met Glu Val Ala Ser Gln
            195                 200                 205

Ala Arg Gln Met Val Gln Ala Met Arg Ala Ile Gly Thr Pro Pro Ser
        210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 33
<211> LENGTH: 97
<212> TYPE: PRT
<213> ORGANISM: Influenza A virus

<400> SEQUENCE: 33

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Ser Ile
            20                  25                  30

Ile Gly Ile Leu His Phe Ile Leu Trp Ile Leu Asp Arg Leu Phe Phe
        35                  40                  45

Lys Cys Ile Tyr Arg Phe Phe Lys His Gly Leu Lys Arg Gly Pro Ser
    50                  55                  60

Thr Glu Gly Val Pro Glu Ser Met Arg Glu Glu Tyr Arg Lys Glu Gln
65                  70                  75                  80

Gln Ser Ala Val Asp Ala Asp Asp Ser His Phe Val Ser Ile Glu Leu
                85                  90                  95

Glu

<210> SEQ ID NO 34
<211> LENGTH: 716
<212> TYPE: PRT
<213> ORGANISM: Influenza A virus

<400> SEQUENCE: 34

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Met Val Glu
    50                  55                  60

Leu Asp Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
                100                 105                 110

Lys Glu Asn Arg Phe Ile Glu Ile Gly Val Thr Arg Arg Glu Val His
            115                 120                 125

Ile Tyr Tyr Leu Glu Lys Ala Asn Lys Ile Lys Ser Glu Asn Thr His
        130                 135                 140

Ile His Ile Phe Ser Phe Thr Gly Glu Glu Met Ala Thr Lys Ala Asp
145                 150                 155                 160
```

```
Tyr Thr Leu Asp Glu Glu Ser Arg Ala Arg Ile Lys Thr Arg Leu Phe
            165                 170                 175
Thr Ile Arg Gln Glu Met Ala Asn Arg Gly Leu Trp Asp Ser Phe Arg
        180                 185                 190
Gln Ser Glu Arg Gly Glu Glu Thr Ile Glu Glu Arg Phe Glu Ile Thr
    195                 200                 205
Gly Thr Met Arg Arg Leu Ala Asp Gln Ser Leu Pro Pro Asn Phe Ser
210                 215                 220
Cys Leu Glu Asn Phe Arg Ala Tyr Val Asp Gly Phe Glu Pro Asn Gly
225                 230                 235                 240
Tyr Ile Glu Gly Lys Leu Ser Gln Met Ser Lys Glu Val Asn Ala Lys
                245                 250                 255
Ile Glu Pro Phe Leu Lys Thr Thr Pro Arg Pro Ile Arg Leu Pro Asp
            260                 265                 270
Gly Pro Pro Cys Phe Gln Arg Ser Lys Phe Leu Leu Met Asp Ala Leu
        275                 280                 285
Lys Leu Ser Ile Glu Asp Pro Ser His Glu Gly Glu Gly Ile Pro Leu
    290                 295                 300
Tyr Asp Ala Ile Lys Cys Met Arg Thr Phe Phe Gly Trp Lys Glu Pro
305                 310                 315                 320
Tyr Ile Val Lys Pro His Glu Lys Gly Ile Asn Pro Asn Tyr Leu Leu
                325                 330                 335
Ser Trp Lys Gln Val Leu Ala Glu Leu Gln Asp Ile Glu Asn Glu Glu
            340                 345                 350
Lys Ile Pro Arg Thr Lys Asn Met Lys Lys Thr Ser Gln Leu Lys Trp
        355                 360                 365
Ala Leu Gly Glu Asn Met Ala Pro Glu Lys Val Asp Phe Asp Asn Cys
    370                 375                 380
Arg Asp Ile Ser Asp Leu Lys Gln Tyr Asp Ser Asp Glu Pro Glu Leu
385                 390                 395                 400
Arg Ser Leu Ser Ser Trp Ile Gln Asn Glu Phe Asn Lys Ala Cys Glu
                405                 410                 415
Leu Thr Asp Ser Ile Trp Ile Glu Leu Asp Glu Ile Gly Glu Asp Val
            420                 425                 430
Ala Pro Ile Glu His Ile Ala Ser Met Arg Arg Asn Tyr Phe Thr Ala
        435                 440                 445
Glu Val Ser His Cys Arg Ala Thr Glu Tyr Ile Met Lys Gly Val Tyr
    450                 455                 460
Ile Asn Thr Ala Leu Leu Asn Ala Ser Cys Ala Ala Met Asp Asp Phe
465                 470                 475                 480
Gln Leu Ile Pro Met Ile Ser Lys Cys Arg Thr Lys Glu Gly Arg Arg
                485                 490                 495
Lys Thr Asn Leu Tyr Gly Phe Ile Ile Lys Gly Arg Ser His Leu Arg
            500                 505                 510
Asn Asp Thr Asp Val Val Asn Phe Val Ser Met Glu Phe Ser Leu Thr
        515                 520                 525
Asp Pro Arg Leu Glu Pro His Lys Trp Glu Lys Tyr Cys Val Leu Glu
    530                 535                 540
Ile Gly Asp Met Leu Leu Arg Ser Ala Ile Gly Gln Met Ser Arg Pro
545                 550                 555                 560
Met Phe Leu Tyr Val Arg Thr Asn Gly Thr Ser Lys Ile Lys Met Lys
                565                 570                 575
Trp Gly Met Glu Met Arg Pro Cys Leu Leu Gln Ser Leu Gln Gln Ile
```

```
                     580                 585                 590
        Glu Ser Met Val Glu Ala Glu Ser Ser Val Lys Glu Lys Asp Met Thr
                        595                 600                 605
        Lys Glu Phe Phe Glu Asn Lys Ser Glu Thr Trp Pro Ile Gly Glu Ser
                        610                 615                 620
        Pro Lys Gly Val Glu Gly Ser Ile Gly Lys Val Cys Arg Thr Leu
        625                 630                 635                 640
        Leu Ala Lys Ser Val Phe Asn Ser Leu Tyr Ala Ser Pro Gln Leu Glu
                        645                 650                 655
        Gly Phe Ser Ala Glu Ser Arg Lys Leu Leu Val Val Gln Ala Leu
                        660                 665                 670
        Arg Asp Asn Leu Glu Pro Gly Thr Phe Asp Leu Gly Gly Leu Tyr Glu
                        675                 680                 685
        Ala Ile Glu Glu Cys Leu Ile Asn Asp Pro Trp Val Leu Leu Asn Ala
                        690                 695                 700
        Ser Trp Phe Asn Ser Phe Leu Thr His Ala Leu Arg
        705                 710                 715

<210> SEQ ID NO 35
<211> LENGTH: 90
<212> TYPE: PRT
<213> ORGANISM: Influenza A virus

<400> SEQUENCE: 35

Met Gly Gln Glu Gln Asp Thr Pro Trp Thr Gln Ser Thr Glu His Ile
1               5                   10                  15

Asn Ile Gln Lys Arg Gly Ser Gly Gln Gln Thr Arg Lys Leu Glu Arg
                20                  25                  30

Pro Asn Leu Thr Gln Leu Met Asp His Tyr Leu Arg Thr Met Asn Gln
            35                  40                  45

Val Asp Met His Lys Gln Thr Ala Ser Trp Lys Gln Trp Leu Ser Leu
    50                  55                  60

Arg Asn His Thr Gln Glu Ser Leu Lys Ile Arg Val Leu Lys Arg Trp
65                  70                  75                  80

Lys Leu Phe Asn Lys Gln Glu Trp Thr Asn
                85                  90

<210> SEQ ID NO 36
<211> LENGTH: 757
<212> TYPE: PRT
<213> ORGANISM: Influenza A virus

<400> SEQUENCE: 36

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
```

```
                100                 105                 110
Val Ile Gln Gln Thr Arg Val Asp Lys Leu Thr Gln Gly Arg Gln Thr
            115                 120                 125
Tyr Asp Trp Thr Leu Asn Arg Asn Gln Pro Ala Ala Thr Ala Leu Ala
        130                 135                 140
Asn Thr Ile Glu Val Phe Arg Ser Asn Gly Leu Thr Ala Asn Glu Ser
145                 150                 155                 160
Gly Arg Leu Ile Asp Phe Leu Lys Asp Val Ile Glu Ser Met Asp Lys
                165                 170                 175
Glu Glu Met Glu Ile Thr Thr His Phe Gln Arg Lys Arg Arg Val Arg
            180                 185                 190
Asp Asn Met Thr Lys Lys Met Val Thr Gln Arg Thr Ile Gly Lys Lys
        195                 200                 205
Lys Gln Arg Leu Asn Lys Arg Ser Tyr Leu Ile Arg Ala Leu Thr Leu
    210                 215                 220
Asn Thr Met Thr Lys Asp Ala Glu Arg Gly Lys Leu Lys Arg Arg Ala
225                 230                 235                 240
Ile Ala Thr Pro Gly Met Gln Ile Arg Gly Phe Val His Phe Val Glu
                245                 250                 255
Thr Leu Ala Arg Asn Ile Cys Glu Lys Leu Glu Gln Ser Gly Leu Pro
            260                 265                 270
Val Gly Gly Asn Glu Lys Lys Ala Lys Leu Ala Asn Val Val Arg Lys
        275                 280                 285
Met Met Thr Asn Ser Gln Asp Thr Glu Leu Ser Phe Thr Ile Thr Gly
    290                 295                 300
Asp Asn Thr Lys Trp Asn Glu Asn Gln Asn Pro Arg Val Phe Leu Ala
305                 310                 315                 320
Met Ile Thr Tyr Ile Thr Arg Asn Gln Pro Glu Trp Phe Arg Asn Val
                325                 330                 335
Leu Ser Ile Ala Pro Ile Met Phe Ser Asn Lys Met Ala Arg Leu Gly
            340                 345                 350
Lys Gly Tyr Met Phe Glu Ser Lys Ser Met Lys Leu Arg Thr Gln Ile
        355                 360                 365
Pro Ala Glu Met Leu Ala Ser Ile Asp Leu Lys Tyr Phe Asn Glu Ser
    370                 375                 380
Thr Arg Lys Lys Ile Glu Lys Ile Arg Pro Leu Leu Ile Asp Gly Thr
385                 390                 395                 400
Val Ser Leu Ser Pro Gly Met Met Met Gly Met Phe Asn Met Leu Ser
                405                 410                 415
Thr Val Leu Gly Val Ser Ile Leu Asn Leu Gly Gln Lys Lys Tyr Thr
            420                 425                 430
Lys Thr Thr Tyr Trp Trp Asp Gly Leu Gln Ser Ser Asp Asp Phe Ala
        435                 440                 445
Leu Ile Val Asn Ala Pro Asn His Glu Gly Ile Gln Ala Gly Val Asn
    450                 455                 460
Arg Phe Tyr Arg Thr Cys Lys Leu Val Gly Ile Asn Met Ser Lys Lys
465                 470                 475                 480
Lys Ser Tyr Ile Asn Arg Thr Gly Thr Phe Glu Phe Thr Ser Phe Phe
                485                 490                 495
Tyr Arg Tyr Gly Phe Val Ala Asn Phe Ser Met Glu Leu Pro Ser Phe
            500                 505                 510
Gly Val Ser Gly Ile Asn Glu Ser Ala Asp Met Ser Ile Gly Val Thr
        515                 520                 525
```

```
Val Ile Lys Asn Asn Met Ile Asn Asn Asp Leu Gly Pro Ala Thr Ala
            530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Ala Gly Leu Leu Val Ser
            580                 585                 590

Asp Gly Gly Ser Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
            610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Thr Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
            690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ala Glu Ile Met Lys Ile Cys Ser Thr Ile Glu Glu
            740                 745                 750

Leu Arg Arg Gln Lys
            755

<210> SEQ ID NO 37
<211> LENGTH: 121
<212> TYPE: PRT
<213> ORGANISM: Influenza A virus

<400> SEQUENCE: 37

Met Asp Ser Asn Thr Val Ser Ser Phe Gln Asp Ile Leu Leu Arg Met
1               5                   10                  15

Ser Lys Met Gln Leu Gly Ser Ser Glu Asp Leu Asn Gly Met Ile
            20                  25                  30

Thr Gln Phe Glu Ser Leu Lys Leu Tyr Arg Asp Ser Leu Gly Glu Ala
        35                  40                  45

Val Met Arg Met Gly Asp Leu His Ser Leu Gln Asn Arg Asn Gly Lys
    50                  55                  60

Trp Arg Glu Gln Leu Gly Gln Lys Phe Glu Glu Ile Arg Trp Leu Ile
65                  70                  75                  80

Glu Glu Val Arg His Arg Leu Lys Ile Thr Glu Asn Ser Phe Glu Gln
                85                  90                  95

Ile Thr Phe Met Gln Ala Leu Gln Leu Leu Phe Glu Val Glu Gln Glu
            100                 105                 110

Ile Arg Thr Phe Ser Phe Gln Leu Ile
        115                 120
```

-continued

```
<210> SEQ ID NO 38
<211> LENGTH: 237
<212> TYPE: PRT
<213> ORGANISM: Influenza A virus

<400> SEQUENCE: 38
```

Met Asp Ser Asn Thr Val Ser Ser Phe Gln Val Asp Cys Phe Leu Trp
1               5                   10                  15

His Val Arg Lys Gln Val Val Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Asp Leu Asp Ile Glu Ala Ala Thr Arg Val Gly Lys Gln Ile
50                  55                  60

Val Glu Arg Ile Leu Lys Glu Glu Ser Asp Glu Ala Leu Lys Met Thr
65                  70                  75                  80

Met Ala Ser Ala Pro Ala Ser Arg Tyr Leu Thr Asp Met Thr Ile Glu
                85                  90                  95

Glu Leu Ser Arg Asp Trp Phe Met Leu Met Pro Lys Gln Lys Val Glu
            100                 105                 110

Gly Pro Leu Cys Ile Arg Ile Asp Gln Ala Ile Met Asp Lys Asn Ile
        115                 120                 125

Met Leu Lys Ala Asn Phe Ser Val Ile Phe Asp Arg Leu Glu Thr Leu
130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ile Glu Asp Val Lys Asn
                165                 170                 175

Ala Ile Gly Val Leu Ile Gly Gly Leu Glu Trp Asn Asp Asn Thr Val
            180                 185                 190

Arg Val Ser Lys Thr Leu Gln Arg Phe Ala Trp Arg Ser Ser Asn Glu
        195                 200                 205

Asn Gly Arg Pro Pro Leu Thr Pro Lys Gln Lys Arg Lys Met Ala Arg
210                 215                 220

Thr Ile Arg Ser Lys Val Arg Arg Asp Lys Met Ala Asp
225                 230                 235

```
<210> SEQ ID NO 39
<211> LENGTH: 498
<212> TYPE: PRT
<213> ORGANISM: Influenza A virus

<400> SEQUENCE: 39
```

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Lys Arg Val Asp Gly Lys Trp Met Arg Glu Leu Val Leu Tyr Asp

```
              100                 105                 110
Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Ser Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Pro Ala Ile Ala Ser Gly
        275                 280                 285

Tyr Asn Phe Glu Lys Glu Gly Tyr Ser Leu Val Gly Ile Asp Pro Phe
    290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys Asn Ser Ala
                325                 330                 335

Ala Phe Glu Asp Leu Arg Val Leu Ser Phe Ile Arg Gly Thr Lys Val
            340                 345                 350

Ser Pro Arg Gly Lys Leu Ser Thr Arg Gly Val Gln Ile Ala Ser Asn
        355                 360                 365

Glu Asn Met Asp Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Ala Phe Ser Val Gln Arg
                405                 410                 415

Asn Leu Pro Phe Asp Lys Pro Thr Ile Met Ala Ala Phe Thr Gly Asn
            420                 425                 430

Thr Glu Gly Arg Thr Ser Asp Met Arg Ala Glu Ile Ile Arg Met Met
        435                 440                 445

Glu Gly Ala Lys Pro Glu Glu Met Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 40
<211> LENGTH: 469
```

```
<212> TYPE: PRT
<213> ORGANISM: Influenza A virus

<400> SEQUENCE: 40

Met Asn Pro Asn Gln Lys Ile Ile Thr Ile Gly Ser Val Ser Leu Thr
1               5                   10                  15

Ile Ala Thr Val Cys Phe Leu Met Gln Ile Ala Ile Leu Val Thr Thr
            20                  25                  30

Val Thr Leu His Phe Lys Gln His Glu Cys Asp Ser Pro Ala Ser Asn
        35                  40                  45

Gln Val Met Pro Cys Glu Pro Ile Ile Ile Glu Arg Asn Ile Thr Glu
    50                  55                  60

Ile Val Tyr Leu Asn Asn Thr Thr Ile Glu Lys Glu Ile Cys Pro Glu
65                  70                  75                  80

Val Val Glu Tyr Arg Asn Trp Ser Lys Pro Gln Cys Gln Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Gly Lys
        115                 120                 125

Cys Tyr Gln Phe Ala Leu Gly Gln Gly Thr Thr Leu Asp Asn Lys His
    130                 135                 140

Ser Asn Asp Thr Ile His Asp Arg Ile Pro His Arg Thr Leu Leu Met
145                 150                 155                 160

Asn Glu Leu Gly Val Pro Phe His Leu Gly Thr Arg Gln Val Cys Val
                165                 170                 175

Ala Trp Ser Ser Ser Cys His Asp Gly Lys Ala Trp Leu His Val
            180                 185                 190

Cys Val Thr Gly Asp Asp Lys Asn Ala Thr Ala Ser Phe Ile Tyr Asp
        195                 200                 205

Gly Arg Leu Met Asp Ser Ile Gly Ser Trp Ser Gln Asn Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Arg Ile Leu Phe
                245                 250                 255

Ile Glu Glu Gly Lys Ile Val His Ile Ser Pro Leu Ser Gly Ser Ala
            260                 265                 270

Gln His Val Glu Glu Cys Ser Cys Tyr Pro Arg Tyr Pro Asp Val Arg
        275                 280                 285

Cys Ile Cys Arg Asp Asn Trp Lys Gly Ser Asn Arg Pro Val Ile Asp
    290                 295                 300

Ile Asn Met Glu Asp Tyr Ser Ile Asp Ser Ser Tyr Val Cys Ser Gly
305                 310                 315                 320

Leu Val Gly Asp Thr Pro Arg Asn Asp Asp Arg Ser Ser Asn Ser Asn
                325                 330                 335

Cys Arg Asn Pro Asn Asn Glu Arg Gly Asn Pro Gly Val Lys Gly Trp
            340                 345                 350

Ala Phe Asp Asn Gly Asp Asp Val Trp Met Gly Arg Thr Ile Ser Lys
        355                 360                 365

Asp Leu Arg Ser Gly Tyr Glu Thr Phe Lys Val Ile Gly Gly Trp Ser
    370                 375                 380

Thr Pro Asn Ser Lys Ser Gln Ile Asn Arg Gln Val Ile Val Asp Ser
385                 390                 395                 400
```

```
Asn Asn Trp Ser Gly Tyr Ser Gly Ile Phe Ser Val Glu Gly Lys Arg
                405                 410                 415

Cys Ile Asn Arg Cys Phe Tyr Val Glu Leu Ile Arg Gly Arg Gln Gln
            420                 425                 430

Glu Thr Arg Val Trp Trp Thr Ser Asn Ser Ile Val Val Phe Cys Gly
        435                 440                 445

Thr Ser Gly Thr Tyr Gly Thr Gly Ser Trp Pro Asp Gly Ala Asn Ile
    450                 455                 460

Asn Phe Met Pro Ile
465

<210> SEQ ID NO 41
<211> LENGTH: 121
<212> TYPE: PRT
<213> ORGANISM: Influenza A virus

<400> SEQUENCE: 41

Met Asp Ser Asn Thr Val Ser Ser Phe Gln Asp Ile Leu Leu Arg Met
1               5                   10                  15

Ser Lys Met Gln Leu Gly Ser Ser Glu Asp Leu Asn Gly Met Ile
            20                  25                  30

Thr Gln Phe Glu Ser Leu Lys Ile Tyr Arg Asp Ser Leu Gly Glu Ala
            35                  40                  45

Val Met Arg Met Gly Asp Leu His Leu Leu Gln Asn Arg Asn Gly Lys
    50                  55                  60

Trp Arg Glu Gln Leu Gly Gln Lys Phe Glu Glu Ile Arg Trp Leu Ile
65                  70                  75                  80

Glu Glu Val Arg His Arg Leu Lys Thr Thr Glu Asn Ser Phe Glu Gln
                85                  90                  95

Ile Thr Phe Met Gln Ala Leu Gln Leu Leu Phe Glu Val Glu Gln Glu
            100                 105                 110

Ile Arg Thr Phe Ser Phe Gln Leu Ile
            115                 120

<210> SEQ ID NO 42
<211> LENGTH: 230
<212> TYPE: PRT
<213> ORGANISM: Influenza A virus

<400> SEQUENCE: 42

Met Asp Ser Asn Thr Val Ser Ser Phe Gln Val Asp Cys Phe Leu Trp
1               5                   10                  15

His Ile Arg Lys Gln Val Val Asp Gln Glu Leu Ser Asp Ala Pro Phe
            20                  25                  30

Leu Asp Arg Leu Arg Arg Asp Gln Arg Ser Leu Arg Gly Arg Gly Asn
            35                  40                  45

Thr Leu Gly Leu Asp Ile Lys Ala Ala Thr His Val Gly Lys Gln Ile
    50                  55                  60

Val Glu Lys Ile Leu Lys Glu Glu Ser Asp Glu Ala Leu Lys Met Thr
65                  70                  75                  80

Met Val Ser Thr Pro Ala Ser Arg Tyr Ile Thr Asp Met Thr Ile Glu
                85                  90                  95

Glu Leu Ser Arg Asn Trp Phe Met Leu Met Pro Lys Gln Lys Val Glu
            100                 105                 110

Gly Pro Leu Cys Ile Arg Met Asp Gln Ala Ile Met Glu Lys Asn Ile
            115                 120                 125
```

```
Met Leu Lys Ala Asn Phe Ser Val Ile Phe Asp Arg Leu Glu Thr Ile
    130                 135                 140

Val Leu Leu Arg Ala Phe Thr Glu Glu Gly Ala Ile Val Gly Glu Ile
145                 150                 155                 160

Ser Pro Leu Pro Ser Phe Pro Gly His Thr Ile Glu Asp Val Lys Asn
                165                 170                 175

Ala Ile Gly Val Leu Ile Gly Gly Leu Glu Trp Asn Asp Asn Thr Val
            180                 185                 190

Arg Val Ser Lys Asn Leu Gln Arg Phe Ala Trp Arg Ser Ser Asn Glu
            195                 200                 205

Asn Gly Gly Pro Pro Leu Thr Pro Lys Gln Lys Arg Lys Met Ala Arg
            210                 215                 220

Thr Ala Arg Ser Lys Val
225                 230

<210> SEQ ID NO 43
<211> LENGTH: 566
<212> TYPE: PRT
<213> ORGANISM: Influenza A virus

<400> SEQUENCE: 43

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Gln Ser Ser Ser Thr
        50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Ser Leu Tyr Ala Gln Ala Ser Gly Arg Ile Thr Val Ser Thr Lys Arg
    210                 215                 220

Ser Gln Gln Thr Val Ile Pro Ser Ile Gly Ser Arg Pro Arg Ile Arg
225                 230                 235                 240

Asp Val Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
```

```
                260                 265                 270
Tyr Phe Lys Ile Arg Ser Gly Lys Ser Ser Ile Met Arg Ser Asp Ala
            275                 280                 285

Pro Ile Gly Lys Cys Asn Ser Glu Cys Ile Thr Pro Asn Gly Ser Ile
            290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
            325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
            355                 360                 365

Phe Arg His Gln Asn Ser Glu Gly Thr Gly Gln Ala Ala Asp Leu Lys
            370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
            405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
            450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
            485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
            530                 535                 540

Val Ala Leu Leu Gly Phe Ile Met Trp Ala Cys Gln Lys Gly Asn Ile
545                 550                 555                 560

Arg Cys Asn Ile Cys Ile
            565

<210> SEQ ID NO 44
<211> LENGTH: 97
<212> TYPE: PRT
<213> ORGANISM: Influenza A virus

<400> SEQUENCE: 44

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Ser Ile
            20                  25                  30

Ile Gly Ile Leu His Leu Ile Leu Trp Ile Leu Asp Arg Leu Phe Phe
            35                  40                  45

Lys Cys Val Tyr Arg Leu Phe Lys His Gly Leu Lys Arg Gly Pro Ser
            50                  55                  60
```

```
Thr Glu Gly Val Pro Glu Ser Met Arg Glu Tyr Arg Lys Glu Gln
 65                  70                  75                  80

Gln Asn Ala Val Asp Ala Asp Asp Ser His Phe Val Ser Ile Glu Leu
                 85                  90                  95

Glu
```

```
<210> SEQ ID NO 45
<211> LENGTH: 252
<212> TYPE: PRT
<213> ORGANISM: Influenza A virus

<400> SEQUENCE: 45
```

```
Met Ser Leu Leu Thr Glu Val Glu Thr Tyr Val Leu Ser Ile Val Pro
  1               5                  10                  15

Ser Gly Pro Leu Lys Ala Glu Ile Ala Gln Arg Leu Glu Asp Val Phe
                 20                  25                  30

Ala Gly Lys Asn Thr Asp Leu Glu Ala Leu Met Glu Trp Leu Lys Thr
                 35                  40                  45

Arg Pro Ile Leu Ser Pro Leu Thr Lys Gly Ile Leu Gly Phe Val Phe
 50                  55                  60

Thr Leu Thr Val Pro Ser Glu Arg Gly Leu Gln Arg Arg Arg Phe Val
 65                  70                  75                  80

Gln Asn Ala Leu Asn Gly Asn Gly Asp Pro Asn Asn Met Asp Lys Ala
                 85                  90                  95

Val Lys Leu Tyr Arg Lys Leu Lys Arg Glu Ile Thr Phe His Gly Ala
                100                 105                 110

Lys Glu Ile Ala Leu Ser Tyr Ser Ala Gly Ala Leu Ala Ser Cys Met
                115                 120                 125

Gly Leu Ile Tyr Asn Arg Met Gly Ala Val Thr Thr Glu Val Ala Phe
130                 135                 140

Gly Leu Val Cys Ala Thr Cys Glu Gln Ile Ala Asp Ser Gln His Arg
145                 150                 155                 160

Ser His Arg Gln Met Val Ala Thr Thr Asn Pro Leu Ile Lys His Glu
                165                 170                 175

Asn Arg Met Val Leu Ala Ser Thr Thr Ala Lys Ala Met Glu Gln Met
                180                 185                 190

Ala Gly Ser Ser Glu Gln Ala Ala Glu Ala Met Glu Ile Ala Ser Gln
                195                 200                 205

Ala Arg Gln Met Val Gln Ala Met Arg Ala Val Gly Thr His Pro Ser
210                 215                 220

Ser Ser Thr Gly Leu Arg Asp Asp Leu Leu Glu Asn Leu Gln Thr Tyr
225                 230                 235                 240

Gln Lys Arg Met Gly Val Gln Met Gln Arg Phe Lys
                245                 250
```

```
<210> SEQ ID NO 46
<211> LENGTH: 90
<212> TYPE: PRT
<213> ORGANISM: Influenza A virus

<400> SEQUENCE: 46
```

```
Met Glu Gln Glu Gln Asp Thr Pro Trp Thr Gln Ser Thr Glu His Thr
  1               5                  10                  15

Asn Ile Gln Arg Arg Gly Ser Gly Arg Gln Ile Gln Lys Leu Gly His
                 20                  25                  30

Pro Asn Ser Thr Gln Leu Met Asp His Tyr Leu Arg Ile Met Ser Gln
```

```
                35                  40                  45
Val Asp Met His Lys Gln Thr Val Ser Trp Arg Leu Trp Pro Ser Leu
 50                  55                  60

Lys Asn Pro Thr Gln Val Ser Leu Arg Thr His Ala Leu Lys Gln Trp
 65                  70                  75                  80

Lys Ser Phe Asn Lys Gln Gly Trp Thr Asn
                 85                  90

<210> SEQ ID NO 47
<211> LENGTH: 757
<212> TYPE: PRT
<213> ORGANISM: Influenza A virus

<400> SEQUENCE: 47

Met Asp Val Asn Pro Thr Leu Leu Phe Leu Lys Val Pro Ala Gln Asn
 1               5                  10                  15

Ala Ile Ser Thr Thr Phe Pro Tyr Thr Gly Asp Pro Pro Tyr Ser His
                 20                  25                  30

Gly Thr Gly Thr Gly Tyr Thr Met Asp Thr Val Asn Arg Thr His Gln
                 35                  40                  45

Tyr Ser Glu Lys Gly Lys Trp Thr Thr Asn Thr Glu Thr Gly Ala Pro
 50                  55                  60

Gln Leu Asn Pro Ile Asp Gly Pro Leu Pro Glu Asp Asn Glu Pro Ser
 65                  70                  75                  80

Gly Tyr Ala Gln Thr Asp Cys Val Leu Glu Ala Met Ala Phe Leu Glu
                 85                  90                  95

Glu Ser His Pro Gly Ile Phe Glu Asn Ser Cys Leu Glu Thr Met Glu
                100                 105                 110

Val Val Gln Gln Thr Arg Val Asp Lys Leu Thr Gln Gly Arg Gln Thr
                115                 120                 125

Tyr Asp Trp Thr Leu Asn Arg Asn Gln Pro Ala Ala Thr Ala Leu Ala
130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Met Glu Ile Thr Thr His Phe Gln Arg Lys Arg Arg Val Arg
                180                 185                 190

Asp Asn Met Thr Lys Lys Met Val Thr Gln Arg Thr Ile Gly Lys Lys
                195                 200                 205

Lys Gln Arg Val Asn Lys Arg Gly Tyr Leu Ile Arg Ala Leu Thr Leu
                210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
                260                 265                 270

Val Gly Gly Asn Glu Lys Lys Ala Lys Leu Ala Asn Val Val Arg Lys
                275                 280                 285

Met Met Thr Asn Ser Gln Asp Thr Glu Leu Ser Phe Thr Ile Thr Gly
                290                 295                 300

Asp Asn Thr Lys Trp Asn Glu Asn Gln Asn Pro Arg Met Phe Leu Ala
305                 310                 315                 320
```

```
Met Ile Thr Tyr Ile Thr Lys Asn Gln Pro Glu Trp Phe Arg Asn Ile
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Arg Met Lys Leu Arg Thr Gln Ile
        355                 360                 365

Pro Ala Glu Met Leu Ala Ser Ile Asp Leu Lys Tyr Phe Asn Glu Ser
370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Val Leu Asn Leu Gly Gln Lys Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Lys Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Asp Gln Thr Gln Ser Arg Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asn Tyr Arg Gly Arg Leu
610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Asn Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
690                 695                 700

Tyr Arg Arg Pro Ile Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ser Glu Ile Met Lys Ile Cys Ser Thr Ile Glu Glu
```

```
                    740                 745                 750
Leu Arg Arg Gln Lys
        755
```

<210> SEQ ID NO 48
<211> LENGTH: 498
<212> TYPE: PRT
<213> ORGANISM: Influenza A virus

<400> SEQUENCE: 48

```
Met Ala Ser Gln Gly Thr Lys Arg Ser Tyr Glu Gln Met Glu Thr Asp
1               5                   10                  15

Gly Asp Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp His Glu Gly Arg Leu Ile Gln Asn Ser Leu Thr Ile Glu
    50                  55                  60

Lys Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asp Gly Lys Trp Met Arg Glu Leu Val Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Ile Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
            180                 185                 190

Leu Ile Arg Met Val Lys Arg Gly Ile Asn Asp Arg Asn Phe Trp Arg
        195                 200                 205

Gly Glu Asn Gly Arg Lys Thr Arg Ser Ala Tyr Glu Arg Met Cys Asn
    210                 215                 220

Ile Leu Lys Gly Lys Phe Gln Thr Ala Ala Gln Arg Ala Met Val Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Ala Tyr Gly Pro Ala Val Ser Ser Gly
        275                 280                 285

Tyr Asp Phe Glu Lys Glu Gly Tyr Ser Leu Val Gly Ile Asp Pro Phe
    290                 295                 300

Lys Leu Leu Gln Asn Ser Gln Ile Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Leu Leu Ser Phe Ile Arg Gly Thr Lys Val
            340                 345                 350
```

Ser Pro Arg Gly Lys Leu Ser Thr Arg Gly Val Gln Ile Ala Ser Asn
            355                 360                 365

Glu Asn Met Asp Asn Met Gly Ser Ser Thr Leu Glu Leu Arg Ser Gly
        370                 375                 380

Tyr Trp Ala Ile Arg Thr Arg Ser Gly Gly Asn Thr Asn Gln Gln Arg
385                 390                 395                 400

Ala Ser Ala Gly Gln Thr Ser Val Gln Pro Thr Phe Ser Val Gln Arg
                405                 410                 415

Asn Leu Pro Phe Glu Lys Ser Thr Ile Met Ala Ala Phe Thr Gly Asn
            420                 425                 430

Thr Glu Gly Arg Thr Ser Asp Met Arg Ala Glu Ile Ile Arg Met Met
        435                 440                 445

Glu Gly Ala Lys Pro Glu Glu Val Ser Phe Arg Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 49
<211> LENGTH: 469
<212> TYPE: PRT
<213> ORGANISM: Influenza A virus

<400> SEQUENCE: 49

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Met Cys Pro Lys
65                  70                  75                  80

Leu Ala Glu Tyr Arg Asn Trp Ser Lys Pro Gln Cys Asp Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Lys Asn Ala Thr Ala Ser Phe Ile Tyr Asn
        195                 200                 205

Gly Arg Leu Val Asp Ser Ile Val Ser Trp Ser Lys Lys Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
            245                 250                 255

Ile Glu Glu Gly Lys Ile Ile His Thr Ser Thr Leu Ser Gly Ser Ala
                260                 265                 270

Gln His Val Glu Glu Cys Ser Cys Tyr Pro Arg Tyr Pro Gly Val Arg
            275                 280                 285

Cys Val Cys Arg Asp Asn Trp Lys Gly Ser Asn Arg Pro Ile Val Asp
    290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser His
                325                 330                 335

Cys Leu Asp Pro Asn Asn Glu Glu Gly Gly His Gly Val Lys Gly Trp
                340                 345                 350

Ala Phe Asp Asp Gly Asn Asp Val Trp Met Gly Arg Thr Ile Ser Glu
            355                 360                 365

Lys Leu Arg Ser Gly Tyr Glu Thr Phe Lys Val Ile Glu Gly Trp Ser
370                 375                 380

Lys Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
            435                 440                 445

Thr Ser Gly Thr Tyr Gly Thr Gly Ser Trp Pro Asp Gly Ala Asp Ile
    450                 455                 460

Asn Leu Met Pro Ile
465

<210> SEQ ID NO 50
<211> LENGTH: 716
<212> TYPE: PRT
<213> ORGANISM: Influenza A virus

<400> SEQUENCE: 50

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Val Val Glu
    50                  55                  60

Leu Asp Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

```
Ile Tyr Tyr Leu Glu Lys Ala Asn Lys Ile Lys Ser Glu Asn Thr His
130                 135                 140
Ile His Ile Phe Ser Phe Thr Gly Glu Glu Ile Ala Thr Lys Ala Asp
145                 150                 155                 160
Tyr Thr Leu Asp Glu Glu Ser Arg Ala Arg Ile Lys Thr Arg Leu Phe
                165                 170                 175
Thr Ile Arg Gln Glu Met Ala Asn Arg Gly Leu Trp Asp Ser Phe Arg
            180                 185                 190
Gln Ser Glu Arg Gly Glu Glu Thr Ile Glu Glu Lys Phe Glu Ile Ser
        195                 200                 205
Gly Thr Met Arg Arg Leu Ala Asp Gln Ser Leu Pro Pro Lys Phe Ser
210                 215                 220
Cys Leu Glu Asn Phe Arg Ala Tyr Val Asp Gly Phe Glu Pro Asn Gly
225                 230                 235                 240
Cys Ile Glu Gly Lys Leu Ser Gln Met Ser Lys Glu Val Asn Ala Lys
                245                 250                 255
Ile Glu Pro Phe Leu Lys Thr Thr Pro Arg Pro Ile Lys Leu Pro Asn
            260                 265                 270
Gly Pro Pro Cys Tyr Gln Arg Ser Lys Phe Leu Leu Met Asp Ala Leu
        275                 280                 285
Lys Leu Ser Ile Glu Asp Pro Ser His Glu Gly Glu Gly Ile Pro Leu
290                 295                 300
Tyr Asp Ala Ile Lys Cys Ile Lys Thr Phe Phe Gly Trp Lys Glu Pro
305                 310                 315                 320
Tyr Ile Val Lys Pro His Glu Lys Gly Ile Asn Ser Asn Tyr Leu Leu
                325                 330                 335
Ser Trp Lys Gln Val Leu Ser Glu Leu Gln Asp Ile Glu Asn Glu Glu
            340                 345                 350
Lys Ile Pro Arg Thr Lys Asn Met Lys Lys Thr Ser Gln Leu Lys Trp
        355                 360                 365
Ala Leu Gly Glu Asn Met Ala Pro Glu Lys Val Asp Phe Asp Asn Cys
370                 375                 380
Arg Asp Ile Ser Asp Leu Lys Gln Tyr Asp Ser Asp Glu Pro Glu Leu
385                 390                 395                 400
Arg Ser Leu Ser Ser Trp Ile Gln Asn Glu Phe Asn Lys Ala Cys Glu
                405                 410                 415
Leu Thr Asp Ser Ile Trp Ile Glu Leu Asp Glu Ile Gly Glu Asp Val
            420                 425                 430
Ala Pro Ile Glu Tyr Ile Ala Ser Met Arg Arg Asn Tyr Phe Thr Ala
        435                 440                 445
Glu Val Ser His Cys Arg Ala Thr Glu Tyr Ile Met Lys Gly Val Tyr
450                 455                 460
Ile Asn Thr Ala Leu Leu Asn Ala Ser Cys Ala Ala Met Asp Asp Phe
465                 470                 475                 480
Gln Leu Ile Pro Met Ile Ser Lys Cys Arg Thr Lys Glu Gly Arg Arg
                485                 490                 495
Lys Thr Asn Leu Tyr Gly Phe Ile Ile Lys Gly Arg Ser His Leu Arg
            500                 505                 510
Asn Asp Thr Asp Val Val Asn Phe Val Ser Met Glu Phe Ser Leu Thr
        515                 520                 525
Asp Pro Arg Leu Glu Pro His Lys Trp Glu Lys Tyr Cys Val Leu Glu
530                 535                 540
```

```
Ile Gly Asp Met Leu Leu Arg Ser Ala Ile Gly Gln Ile Ser Arg Pro
545                 550                 555                 560

Met Phe Leu Tyr Val Arg Thr Asn Gly Thr Ser Lys Val Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Ile Lys Glu Lys Asp Met Thr
        595                 600                 605

Lys Glu Phe Phe Glu Asn Lys Ser Glu Ala Trp Pro Ile Gly Glu Ser
    610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Val Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Lys
705                 710                 715

<210> SEQ ID NO 51
<211> LENGTH: 759
<212> TYPE: PRT
<213> ORGANISM: Influenza A virus

<400> SEQUENCE: 51

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
                20                  25                  30

Lys Tyr Thr Ser Gly Arg Gln Glu Lys Asn Pro Ser Leu Arg Met Lys
            35                  40                  45

Trp Met Met Ala Met Lys Tyr Pro Ile Thr Ala Asp Lys Arg Ile Thr
        50                  55                  60

Glu Met Val Pro Glu Arg Asn Glu Gln Gly Gln Thr Leu Trp Ser Lys
65                  70                  75                  80

Met Ser Asp Ala Gly Ser Asp Arg Val Met Val Ser Pro Leu Ala Val
                85                  90                  95

Thr Trp Trp Asn Arg Asn Gly Pro Val Ala Ser Thr Val His Tyr Pro
            100                 105                 110

Lys Val Tyr Lys Thr Tyr Phe Asp Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Arg Asp Cys Lys Ile Ser Pro Leu Met Val Ala Tyr Met Leu Glu
        195                 200                 205
```

```
Arg Glu Leu Val Arg Lys Thr Arg Phe Leu Pro Val Ala Gly Gly Thr
        210                 215                 220

Ser Ser Ile Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
                260                 265                 270

Ser Ala Asp Pro Leu Ala Ser Leu Leu Glu Met Cys His Ser Thr Gln
            275                 280                 285

Ile Gly Gly Thr Arg Met Val Asp Ile Leu Arg Gln Asn Pro Thr Glu
        290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Lys Glu Glu Val Leu Thr Gly Asn Leu Gln Thr Leu
                340                 345                 350

Lys Ile Arg Val His Glu Gly Tyr Glu Glu Phe Thr Met Val Gly Lys
            355                 360                 365

Arg Ala Thr Ala Ile Leu Arg Lys Ala Thr Arg Arg Leu Val Gln Leu
        370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
                420                 425                 430

Gln Leu Leu Arg His Phe Gln Lys Asp Ala Lys Val Leu Phe Gln Asn
        435                 440                 445

Trp Gly Ile Glu His Ile Asp Ser Val Met Gly Met Val Gly Val Leu
        450                 455                 460

Pro Asp Met Thr Pro Ser Thr Glu Met Ser Met Arg Gly Ile Arg Val
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Arg Leu Thr
        515                 520                 525

Ile Thr Tyr Ser Ser Met Met Trp Glu Ile Asn Gly Pro Glu Ser
        530                 535                 540

Val Leu Val Asn Thr Tyr Gln Trp Ile Ile Arg Asn Trp Glu Ala Val
545                 550                 555                 560

Lys Ile Gln Trp Ser Gln Asn Pro Ala Met Leu Tyr Asn Lys Met Glu
                565                 570                 575

Phe Glu Pro Phe Gln Ser Leu Val Pro Lys Ala Ile Arg Ser Gln Tyr
                580                 585                 590

Ser Gly Phe Val Arg Thr Leu Phe Gln Gln Met Arg Asp Val Leu Gly
            595                 600                 605

Thr Phe Asp Thr Thr Gln Ile Ile Lys Leu Leu Pro Phe Ala Ala Ala
        610                 615                 620
```

-continued

Pro Pro Lys Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
            645                 650                 655

Asn Tyr Asn Lys Thr Thr Lys Arg Leu Thr Ile Leu Gly Lys Asp Ala
        660                 665                 670

Gly Thr Leu Ile Glu Asp Pro Asp Glu Ser Thr Ser Gly Val Glu Ser
    675                 680                 685

Ala Val Leu Arg Gly Phe Leu Ile Ile Gly Lys Glu Asp Arg Arg Tyr
690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
            725                 730                 735

Arg Lys Arg Asp Ser Ser Ile Leu Thr Asp Ser Gln Thr Ala Thr Lys
        740                 745                 750

Arg Ile Arg Met Ala Ile Asn
        755

<210> SEQ ID NO 52
<211> LENGTH: 580
<212> TYPE: PRT
<213> ORGANISM: Human herpesvirus 5

<400> SEQUENCE: 52

Met Glu Ser Ser Ala Lys Arg Lys Met Asp Pro Asp Asn Pro Asp Glu
1               5                   10                  15

Gly Pro Ser Ser Lys Val Pro Arg Pro Glu Thr Pro Val Thr Lys Ala
            20                  25                  30

Thr Thr Phe Leu Gln Thr Met Leu Arg Lys Glu Val Asn Ser Gln Leu
        35                  40                  45

Ser Leu Gly Asp Pro Leu Phe Pro Glu Leu Ala Glu Glu Ser Leu Lys
    50                  55                  60

Thr Phe Glu Gln Val Thr Glu Asp Cys Asn Glu Asn Pro Glu Lys Asp
65                  70                  75                  80

Val Leu Ala Glu Leu Gly Asp Ile Leu Ala Gln Ala Val Asn His Ala
                85                  90                  95

Gly Ile Asp Ser Ser Thr Gly His Thr Leu Thr Thr His Ser Cys
            100                 105                 110

Ser Val Ser Ser Ala Pro Leu Asn Lys Pro Thr Pro Thr Ser Val Ala
        115                 120                 125

Val Thr Asn Thr Pro Leu Pro Gly Ala Ser Ala Thr Pro Glu Leu Ser
    130                 135                 140

Pro Arg Lys Lys Pro Arg Lys Thr Thr Arg Pro Phe Lys Val Ile Ile
145                 150                 155                 160

Lys Pro Pro Val Pro Ala Pro Ile Met Leu Pro Leu Ile Lys Gln
                165                 170                 175

Glu Asp Ile Lys Pro Glu Pro Asp Phe Thr Ile Gln Tyr Arg Asn Lys
            180                 185                 190

Ile Ile Asp Thr Ala Gly Cys Ile Val Ile Ser Asp Ser Glu Glu
        195                 200                 205

Gln Gly Glu Glu Val Glu Thr Arg Gly Ala Thr Ala Ser Ser Pro Ser
    210                 215                 220

Thr Gly Ser Gly Thr Pro Arg Val Thr Ser Pro Thr His Pro Leu Ser
225                 230                 235                 240

```
Gln Met Asn His Pro Pro Leu Pro Asp Pro Leu Ala Arg Pro Asp Glu
            245                 250                 255

Asp Ser Ser Ser Ser Ser Ser Cys Ser Ser Ala Ser Asp Ser
        260                 265                 270

Glu Ser Glu Ser Glu Glu Met Lys Cys Ser Ser Gly Gly Ala Ser
        275                 280                 285

Val Thr Ser Ser His His Gly Arg Gly Gly Phe Gly Ser Ala Ala Ser
        290                 295                 300

Ser Ser Leu Leu Ser Cys Gly His Gln Ser Ser Gly Gly Ala Ser Thr
305                 310                 315                 320

Gly Pro Arg Lys Lys Lys Ser Lys Arg Ile Ser Glu Leu Asp Asn Glu
                325                 330                 335

Lys Val Arg Asn Ile Met Lys Asp Lys Asn Thr Pro Phe Cys Thr Pro
                340                 345                 350

Asn Val Gln Thr Arg Arg Gly Arg Val Lys Ile Asp Glu Val Ser Arg
                355                 360                 365

Met Phe Arg Asn Thr Asn Arg Ser Leu Glu Tyr Lys Asn Leu Pro Phe
            370                 375                 380

Thr Ile Pro Ser Met His Gln Val Leu Asp Glu Ala Ile Lys Ala Cys
385                 390                 395                 400

Lys Thr Met Gln Val Asn Asn Lys Gly Ile Gln Ile Ile Tyr Thr Arg
                405                 410                 415

Asn His Glu Val Lys Ser Glu Val Asp Ala Val Arg Cys Arg Leu Gly
                420                 425                 430

Thr Met Cys Asn Leu Ala Leu Ser Thr Pro Phe Leu Met Glu His Thr
            435                 440                 445

Met Pro Val Thr His Pro Pro Glu Val Ala Gln Arg Thr Ala Asp Ala
        450                 455                 460

Cys Asn Glu Gly Val Lys Ala Ala Trp Ser Leu Lys Glu Leu His Thr
465                 470                 475                 480

His Gln Leu Cys Pro Arg Ser Ser Asp Tyr Arg Asn Met Ile Ile His
                485                 490                 495

Ala Ala Thr Pro Val Asp Leu Leu Gly Ala Leu Asn Leu Cys Leu Pro
            500                 505                 510

Leu Met Gln Lys Phe Pro Lys Gln Val Met Val Arg Ile Phe Ser Thr
            515                 520                 525

Asn Gln Gly Gly Phe Met Leu Pro Ile Tyr Glu Thr Ala Lys Ala
        530                 535                 540

Tyr Ala Val Gly Gln Phe Glu Gln Pro Thr Glu Thr Pro Pro Glu Asp
545                 550                 555                 560

Leu Asp Thr Leu Ser Leu Ala Ile Glu Ala Ala Ile Gln Asp Leu Arg
                565                 570                 575

Asn Lys Ser Gln
            580

<210> SEQ ID NO 53
<211> LENGTH: 98
<212> TYPE: PRT
<213> ORGANISM: Human papillomavirus type 16

<400> SEQUENCE: 53

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
```

20                  25                  30

Glu Glu Glu Asp Glu Ile Asp Gly Pro Ala Gly Gln Ala Glu Pro Asp
             35                  40                  45

Arg Ala His Tyr Asn Ile Val Thr Phe Cys Cys Lys Cys Asp Ser Thr
         50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                 85                  90                  95

Lys Pro

<210> SEQ ID NO 54
<211> LENGTH: 4
<212> TYPE: PRT
<213> ORGANISM: Artificial Sequence
<220> FEATURE:
<223> OTHER INFORMATION: Synthesized

<400> SEQUENCE: 54

Trp Trp Gly Cys
1

<210> SEQ ID NO 55
<211> LENGTH: 4
<212> TYPE: PRT
<213> ORGANISM: Artificial Sequence
<220> FEATURE:
<223> OTHER INFORMATION: Synthesized

<400> SEQUENCE: 55

Arg Arg Glx Cys
1

<210> SEQ ID NO 56
<211> LENGTH: 4
<212> TYPE: PRT
<213> ORGANISM: Artificial Sequence
<220> FEATURE:
<223> OTHER INFORMATION: Synthesized

<400> SEQUENCE: 56

Trp Trp Gln Cys
1

<210> SEQ ID NO 57
<211> LENGTH: 5
<212> TYPE: PRT
<213> ORGANISM: Artificial Sequence
<220> FEATURE:
<223> OTHER INFORMATION: Synthesized

<400> SEQUENCE: 57

Trp Asp Trp Gly Cys
1               5

<210> SEQ ID NO 58
<211> LENGTH: 4
<212> TYPE: PRT
<213> ORGANISM: Artificial Sequence
<220> FEATURE:
<223> OTHER INFORMATION: Synthesized

<400> SEQUENCE: 58

Cys Gly Gly Gly

-continued

```
<210> SEQ ID NO 59
<211> LENGTH: 4
<212> TYPE: PRT
<213> ORGANISM: Artificial Sequence
<220> FEATURE:
<223> OTHER INFORMATION: Synthesized

<400> SEQUENCE: 59

Gly Cys Gly Gly
1

<210> SEQ ID NO 60
<211> LENGTH: 5
<212> TYPE: PRT
<213> ORGANISM: Artificial Sequence
<220> FEATURE:
<223> OTHER INFORMATION: Synthesized

<400> SEQUENCE: 60

Gly Gly Cys Gly Gly
1               5

<210> SEQ ID NO 61
<211> LENGTH: 5
<212> TYPE: PRT
<213> ORGANISM: Artificial Sequence
<220> FEATURE:
<223> OTHER INFORMATION: Synthesized

<400> SEQUENCE: 61

Cys Gly Gly Lys Gly
1               5

<210> SEQ ID NO 62
<211> LENGTH: 6
<212> TYPE: PRT
<213> ORGANISM: Artificial Sequence
<220> FEATURE:
<223> OTHER INFORMATION: Synthesized

<400> SEQUENCE: 62

Cys Gly Gly Lys Gly Gly
1               5

<210> SEQ ID NO 63
<211> LENGTH: 5
<212> TYPE: PRT
<213> ORGANISM: Artificial Sequence
<220> FEATURE:
<223> OTHER INFORMATION: Synthesized

<400> SEQUENCE: 63

Gly Gly Lys Gly Gly
1               5

<210> SEQ ID NO 64
<211> LENGTH: 9
<212> TYPE: PRT
<213> ORGANISM: Artificial Sequence
<220> FEATURE:
<223> OTHER INFORMATION: Synthesized

<400> SEQUENCE: 64

Ser Leu Leu Thr Glu Val Glu Thr Pro
1               5
```

```
<210> SEQ ID NO 65
<211> LENGTH: 9
<212> TYPE: PRT
<213> ORGANISM: Artificial Sequence
<220> FEATURE:
<223> OTHER INFORMATION: Synthesized

<400> SEQUENCE: 65

Ser Leu Glx Thr Asp Ile Glu Thr Pro
1               5

<210> SEQ ID NO 66
<211> LENGTH: 5
<212> TYPE: PRT
<213> ORGANISM: Artificial Sequence
<220> FEATURE:
<223> OTHER INFORMATION: Synthesized

<400> SEQUENCE: 66

Thr Asp Ile Glu Thr
1               5

<210> SEQ ID NO 67
<211> LENGTH: 5
<212> TYPE: PRT
<213> ORGANISM: Artificial Sequence
<220> FEATURE:
<223> OTHER INFORMATION: Synthesized

<400> SEQUENCE: 67

Cys Ser Leu Leu Thr
1               5

<210> SEQ ID NO 68
<211> LENGTH: 12
<212> TYPE: PRT
<213> ORGANISM: Artificial Sequence
<220> FEATURE:
<223> OTHER INFORMATION: Synthesized

<400> SEQUENCE: 68

Ser Leu Leu Thr Glu Val Gln Thr Pro Ile Arg Asn
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Synthesized

<400> SEQUENCE: 69

Thr Pro Ile Arg Ser Glu Trp Gly Cys Arg Ser Asn
1               5                   10

<210> SEQ ID NO 70
<211> LENGTH: 6
<212> TYPE: PRT
<213> ORGANISM: Artificial Sequence
<220> FEATURE:
<223> OTHER INFORMATION: Synthesized

<400> SEQUENCE: 70

Ile Asp Thr Pro Ile Arg
1               5
```

```
<210> SEQ ID NO 71
<211> LENGTH: 5
<212> TYPE: PRT
<213> ORGANISM: Artificial Sequence
<220> FEATURE:
<223> OTHER INFORMATION: Synthesized

<400> SEQUENCE: 71

Ala Lys Arg Arg Val
1               5

<210> SEQ ID NO 72
<211> LENGTH: 5
<212> TYPE: PRT
<213> ORGANISM: Artificial Sequence
<220> FEATURE:
<223> OTHER INFORMATION: Synthesized

<400> SEQUENCE: 72

Ile Glu Glu Glu Gly
1               5

<210> SEQ ID NO 73
<211> LENGTH: 6
<212> TYPE: PRT
<213> ORGANISM: Artificial Sequence
<220> FEATURE:
<223> OTHER INFORMATION: Synthesized

<400> SEQUENCE: 73

Ala Lys Arg Arg Val Val
1               5

<210> SEQ ID NO 74
<211> LENGTH: 5
<212> TYPE: PRT
<213> ORGANISM: Artificial Sequence
<220> FEATURE:
<223> OTHER INFORMATION: Synthesized

<400> SEQUENCE: 74

Asp Gln Gln Leu Leu
1               5

<210> SEQ ID NO 75
<211> LENGTH: 6
<212> TYPE: PRT
<213> ORGANISM: Artificial Sequence
<220> FEATURE:
<223> OTHER INFORMATION: Synthesized

<400> SEQUENCE: 75

Ala Glu Glu Glu Val Val
1               5

<210> SEQ ID NO 76
<211> LENGTH: 5
<212> TYPE: PRT
<213> ORGANISM: Artificial Sequence
<220> FEATURE:
<223> OTHER INFORMATION: Synthesized

<400> SEQUENCE: 76

Gly Ile Glu Glu Glu
1               5
```

<210> SEQ ID NO 77
<211> LENGTH: 11
<212> TYPE: PRT
<213> ORGANISM: Artificial Sequence
<220> FEATURE:
<223> OTHER INFORMATION: Synthesized

<400> SEQUENCE: 77

Ile Glu Glu Glu Gly Gly Arg Asp Arg Asp Arg
1               5                   10

<210> SEQ ID NO 78
<211> LENGTH: 8
<212> TYPE: PRT
<213> ORGANISM: Artificial Sequence
<220> FEATURE:
<223> OTHER INFORMATION: Synthesized

<400> SEQUENCE: 78

Cys Ala Lys Arg Arg Val Val Cys
1               5

<210> SEQ ID NO 79
<211> LENGTH: 12
<212> TYPE: PRT
<213> ORGANISM: Artificial Sequence
<220> FEATURE:
<223> OTHER INFORMATION: Synthesized

<400> SEQUENCE: 79

Ile Glu Glu Glu Gly Gly Glu Arg Asp Arg Asp Arg
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Synthesized

<400> SEQUENCE: 80

Ile Glu Glu Glu Gly Gly Gln Asp Arg Asp Arg
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Synthesized

<400> SEQUENCE: 81

Ile Glu Glu Glu Gly Gly Glu Gln Asp Arg Asp Arg
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthesized

<400> SEQUENCE: 82

Glu Glu Glu Ile Gly Gly Arg Asp Arg Asp
1               5                   10

<210> SEQ ID NO 83

```
<211> LENGTH: 7
<212> TYPE: PRT
<213> ORGANISM: Artificial Sequence
<220> FEATURE:
<223> OTHER INFORMATION: Synthesized

<400> SEQUENCE: 83

Arg Leu Glu Pro Trp Lys His
1               5

<210> SEQ ID NO 84
<211> LENGTH: 5
<212> TYPE: PRT
<213> ORGANISM: Artificial Sequence
<220> FEATURE:
<223> OTHER INFORMATION: Synthesized

<400> SEQUENCE: 84

Phe His Ser Gln Val
1               5

<210> SEQ ID NO 85
<211> LENGTH: 10
<212> TYPE: PRT
<213> ORGANISM: Artificial Sequence
<220> FEATURE:
<223> OTHER INFORMATION: Synthesized

<400> SEQUENCE: 85

Phe Ile Thr Lys Gly Leu Gly Ile Ser Tyr
1               5                   10

<210> SEQ ID NO 86
<211> LENGTH: 9
<212> TYPE: PRT
<213> ORGANISM: Artificial Sequence
<220> FEATURE:
<223> OTHER INFORMATION: Synthesized

<400> SEQUENCE: 86

Leu Leu Ala Asp Ala Arg Val Cys Ser
1               5

<210> SEQ ID NO 87
<211> LENGTH: 10
<212> TYPE: PRT
<213> ORGANISM: Artificial Sequence
<220> FEATURE:
<223> OTHER INFORMATION: Synthesized

<400> SEQUENCE: 87

Gly Val Glx Ala Gly Ile Ala Tyr Phe Ser
1               5                   10

<210> SEQ ID NO 88
<211> LENGTH: 6
<212> TYPE: PRT
<213> ORGANISM: Artificial Sequence
<220> FEATURE:
<223> OTHER INFORMATION: Synthesized

<400> SEQUENCE: 88

Val Glu Thr Pro Ile Arg
1               5

<210> SEQ ID NO 89
<211> LENGTH: 7
```

```
<212> TYPE: PRT
<213> ORGANISM: Artificial Sequence
<220> FEATURE:
<223> OTHER INFORMATION: Synthesized

<400> SEQUENCE: 89

Val Glu Thr Pro Ile Arg Asn
1               5

<210> SEQ ID NO 90
<211> LENGTH: 5
<212> TYPE: PRT
<213> ORGANISM: Artificial Sequence
<220> FEATURE:
<223> OTHER INFORMATION: Synthesized

<400> SEQUENCE: 90

Ser Asn Asp Ser Ser
1               5

<210> SEQ ID NO 91
<211> LENGTH: 8
<212> TYPE: PRT
<213> ORGANISM: Artificial Sequence
<220> FEATURE:
<223> OTHER INFORMATION: Synthesized

<400> SEQUENCE: 91

Thr Pro Ile Asx Gln Asp Trp Gly
1               5

<210> SEQ ID NO 92
<211> LENGTH: 12
<212> TYPE: PRT
<213> ORGANISM: Artificial Sequence
<220> FEATURE:
<223> OTHER INFORMATION: Synthesized

<400> SEQUENCE: 92

Ala Lys Arg Arg Val Val Gln Arg Glu Lys Arg Ala
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Synthesized

<400> SEQUENCE: 93

Ile Glu Glu Glu Gly Gly Glu Arg Asp Arg
1               5                   10

<210> SEQ ID NO 94
<211> LENGTH: 6
<212> TYPE: PRT
<213> ORGANISM: Artificial Sequence
<220> FEATURE:
<223> OTHER INFORMATION: Synthesized

<400> SEQUENCE: 94

Ala Glu Glu Glu Ile Val
1               5

<210> SEQ ID NO 95
<211> LENGTH: 5
<212> TYPE: PRT
```

```
<213> ORGANISM: Artificial Sequence
<220> FEATURE:
<223> OTHER INFORMATION: Synthesized

<400> SEQUENCE: 95

Arg Asp Arg Asp Arg
1               5

<210> SEQ ID NO 96
<211> LENGTH: 6
<212> TYPE: PRT
<213> ORGANISM: Artificial Sequence
<220> FEATURE:
<223> OTHER INFORMATION: Synthesized

<400> SEQUENCE: 96

Glu Arg Asp Arg Asp Arg
1               5

<210> SEQ ID NO 97
<211> LENGTH: 12
<212> TYPE: PRT
<213> ORGANISM: Artificial Sequence
<220> FEATURE:
<223> OTHER INFORMATION: Synthesized

<400> SEQUENCE: 97

Ala Lys Arg Arg Val Val Glu Arg Glu Lys Arg Ala
1               5                   10

<210> SEQ ID NO 98
<211> LENGTH: 5
<212> TYPE: PRT
<213> ORGANISM: Artificial Sequence
<220> FEATURE:
<223> OTHER INFORMATION: Synthesized

<400> SEQUENCE: 98

Gln Asp Arg Asp Arg
1               5

<210> SEQ ID NO 99
<211> LENGTH: 6
<212> TYPE: PRT
<213> ORGANISM: Artificial Sequence
<220> FEATURE:
<223> OTHER INFORMATION: Synthesized

<400> SEQUENCE: 99

Glu Gln Asp Arg Asp Arg
1               5

<210> SEQ ID NO 100
<211> LENGTH: 5
<212> TYPE: PRT
<213> ORGANISM: Artificial Sequence
<220> FEATURE:
<223> OTHER INFORMATION: Synthesized

<400> SEQUENCE: 100

Arg Asp Arg Asp Gln
1               5

<210> SEQ ID NO 101
<211> LENGTH: 7
<212> TYPE: PRT
<213> ORGANISM: Artificial Sequence
```

```
<220> FEATURE:
<223> OTHER INFORMATION: Synthesized

<400> SEQUENCE: 101

Gly Ser Gln Pro Lys Thr Ala
1               5

<210> SEQ ID NO 102
<211> LENGTH: 13
<212> TYPE: PRT
<213> ORGANISM: Artificial Sequence
<220> FEATURE:
<223> OTHER INFORMATION: Synthesized

<400> SEQUENCE: 102

Phe Ile Thr Lys Gly Leu Gly Ile Ser Tyr Gly Arg Lys
1               5                   10

<210> SEQ ID NO 103
<211> LENGTH: 9
<212> TYPE: PRT
<213> ORGANISM: Artificial Sequence
<220> FEATURE:
<223> OTHER INFORMATION: Synthesized

<400> SEQUENCE: 103

Leu Leu Ala Asp Ala Arg Val Ser Ala
1               5

<210> SEQ ID NO 104
<211> LENGTH: 10
<212> TYPE: PRT
<213> ORGANISM: Artificial Sequence
<220> FEATURE:
<223> OTHER INFORMATION: Synthesized

<400> SEQUENCE: 104

Gly Val Leu Ala Gly Ile Ala Tyr Tyr Ser
1               5                   10

<210> SEQ ID NO 105
<211> LENGTH: 8
<212> TYPE: PRT
<213> ORGANISM: Artificial Sequence
<220> FEATURE:
<223> OTHER INFORMATION: Synthesized

<400> SEQUENCE: 105

Thr Pro Ile Arg Asn Glu Trp Gly
1               5

<210> SEQ ID NO 106
<211> LENGTH: 8
<212> TYPE: PRT
<213> ORGANISM: Artificial Sequence
<220> FEATURE:
<223> OTHER INFORMATION: Synthesized

<400> SEQUENCE: 106

Ser Glu Trp Gly Ser Arg Ser Asn
1               5

<210> SEQ ID NO 107
<211> LENGTH: 10
<212> TYPE: PRT
<213> ORGANISM: Artificial Sequence
<220> FEATURE:
```

```
<223> OTHER INFORMATION: Synthesized

<400> SEQUENCE: 107

Ser Leu Glx Thr Asp Ile Glu Thr Pro Gly
1               5                   10

<210> SEQ ID NO 108
<211> LENGTH: 7
<212> TYPE: PRT
<213> ORGANISM: Artificial Sequence
<220> FEATURE:
<223> OTHER INFORMATION: Synthesized

<400> SEQUENCE: 108

Gln Arg Glu Lys Arg Ala Val
1               5

<210> SEQ ID NO 109
<211> LENGTH: 5
<212> TYPE: PRT
<213> ORGANISM: Artificial Sequence
<220> FEATURE:
<223> OTHER INFORMATION: Synthesized

<400> SEQUENCE: 109

Gln Arg Glu Lys Arg
1               5

<210> SEQ ID NO 110
<211> LENGTH: 6
<212> TYPE: PRT
<213> ORGANISM: Artificial Sequence
<220> FEATURE:
<223> OTHER INFORMATION: Synthesized

<400> SEQUENCE: 110

Ile Glu Glu Glu Gly Gly
1               5

<210> SEQ ID NO 111
<211> LENGTH: 6
<212> TYPE: PRT
<213> ORGANISM: Artificial Sequence
<220> FEATURE:
<223> OTHER INFORMATION: Synthesized

<400> SEQUENCE: 111

Glu Arg Glu Lys Arg Ala
1               5

<210> SEQ ID NO 112
<211> LENGTH: 6
<212> TYPE: PRT
<213> ORGANISM: Artificial Sequence
<220> FEATURE:
<223> OTHER INFORMATION: Synthesized

<400> SEQUENCE: 112

Gln Arg Glu Lys Arg Ala
1               5

<210> SEQ ID NO 113
<211> LENGTH: 5
<212> TYPE: PRT
<213> ORGANISM: Artificial Sequence
<220> FEATURE:
<223> OTHER INFORMATION: Synthesized
```

```
<400> SEQUENCE: 113

Glu Arg Asp Arg Asp
1               5

<210> SEQ ID NO 114
<211> LENGTH: 5
<212> TYPE: PRT
<213> ORGANISM: Artificial Sequence
<220> FEATURE:
<223> OTHER INFORMATION: Synthesized

<400> SEQUENCE: 114

His Pro Gly Ser Gln
1               5

<210> SEQ ID NO 115
<211> LENGTH: 25
<212> TYPE: PRT
<213> ORGANISM: Artificial Sequence
<220> FEATURE:
<223> OTHER INFORMATION: Synthesized

<400> SEQUENCE: 115

Cys Gly Gly Ala Lys Arg Arg Val Val Gly Gly Ala Lys Arg Arg Val
1               5                   10                  15

Val Gly Gln Arg Glu Lys Arg Ala Val
            20                  25

<210> SEQ ID NO 116
<211> LENGTH: 31
<212> TYPE: PRT
<213> ORGANISM: Artificial Sequence
<220> FEATURE:
<223> OTHER INFORMATION: Synthesized

<400> SEQUENCE: 116

Cys Gly Gly Gly Asp Gln Gln Leu Leu Gly Gly Ala Glu Glu Glu Ile
1               5                   10                  15

Val Gly Gly Ile Glu Glu Glu Gly Gly Glu Arg Asp Arg Asp Arg
            20                  25                  30

<210> SEQ ID NO 117
<211> LENGTH: 24
<212> TYPE: PRT
<213> ORGANISM: Artificial Sequence
<220> FEATURE:
<223> OTHER INFORMATION: Synthesized

<400> SEQUENCE: 117

Cys Gly Gly Ala Lys Arg Arg Val Val Gly Gly Ala Lys Arg Arg Val
1               5                   10                  15

Val Gly Gly Gln Arg Glu Lys Arg
            20

<210> SEQ ID NO 118
<211> LENGTH: 25
<212> TYPE: PRT
<213> ORGANISM: Artificial Sequence
<220> FEATURE:
<223> OTHER INFORMATION: Synthesized

<400> SEQUENCE: 118

Cys Gly Gly Gly Asp Gln Gln Leu Leu Gly Gly Ala Glu Glu Glu Ile
1               5                   10                  15
```

Val Gly Gly Ile Glu Glu Glu Gly Gly
            20              25

<210> SEQ ID NO 119
<211> LENGTH: 16
<212> TYPE: PRT
<213> ORGANISM: Artificial Sequence
<220> FEATURE:
<223> OTHER INFORMATION: Synthesized

<400> SEQUENCE: 119

Cys Gly Gly Ala Glu Glu Glu Val Val Gly Gly Asp Gln Gln Leu Leu
1               5                   10                  15

<210> SEQ ID NO 120
<211> LENGTH: 18
<212> TYPE: PRT
<213> ORGANISM: Artificial Sequence
<220> FEATURE:
<223> OTHER INFORMATION: Synthesized

<400> SEQUENCE: 120

Gly Cys Gly Gly Ala Lys Arg Arg Val Val Gly Gly Ala Lys Arg Arg
1               5                   10                  15

Val Val

<210> SEQ ID NO 121
<211> LENGTH: 31
<212> TYPE: PRT
<213> ORGANISM: Artificial Sequence
<220> FEATURE:
<223> OTHER INFORMATION: Synthesized

<400> SEQUENCE: 121

Gly Ala Lys Arg Arg Val Val Gly Gly Cys Gly Gly Ala Lys Arg Arg
1               5                   10                  15

Val Val Gln Arg Glu Lys Arg Ala Gly Glu Arg Glu Lys Arg Ala
            20                  25                  30

<210> SEQ ID NO 122
<211> LENGTH: 23
<212> TYPE: PRT
<213> ORGANISM: Artificial Sequence
<220> FEATURE:
<223> OTHER INFORMATION: Synthesized

<400> SEQUENCE: 122

Gly Lys Gly Gly Ile Glu Glu Glu Gly Gly Arg Asp Arg Asp Arg Gly
1               5                   10                  15

Gly Glu Gln Asp Arg Asp Arg
            20

<210> SEQ ID NO 123
<211> LENGTH: 31
<212> TYPE: PRT
<213> ORGANISM: Artificial Sequence
<220> FEATURE:
<223> OTHER INFORMATION: Synthesized

<400> SEQUENCE: 123

Gly Ala Lys Arg Arg Val Val Gly Gly Cys Gly Gly Ala Lys Arg Arg
1               5                   10                  15

Val Val Gln Arg Glu Lys Arg Ala Gly Glu Arg Glu Lys Arg Ala
            20                  25                  30

```
<210> SEQ ID NO 124
<211> LENGTH: 23
<212> TYPE: PRT
<213> ORGANISM: Artificial Sequence
<220> FEATURE:
<223> OTHER INFORMATION: Synthesized

<400> SEQUENCE: 124

Gly Lys Gly Gly Ile Glu Glu Glu Gly Glu Arg Asp Arg Asp Arg
1               5                   10                  15

Gly Gly Gln Asp Arg Asp Arg
            20

<210> SEQ ID NO 125
<211> LENGTH: 31
<212> TYPE: PRT
<213> ORGANISM: Artificial Sequence
<220> FEATURE:
<223> OTHER INFORMATION: Synthesized

<400> SEQUENCE: 125

Gly Ala Lys Arg Arg Val Val Gly Gly Cys Gly Gly Ala Lys Arg Arg
1               5                   10                  15

Val Val Glu Arg Glu Lys Arg Ala Gly Gln Arg Glu Lys Arg Ala
            20                  25                  30

<210> SEQ ID NO 126
<211> LENGTH: 22
<212> TYPE: PRT
<213> ORGANISM: Artificial Sequence
<220> FEATURE:
<223> OTHER INFORMATION: Synthesized

<400> SEQUENCE: 126

Gly Lys Gly Gly Ile Glu Glu Glu Gly Gly Gln Asp Arg Asp Arg Gly
1               5                   10                  15

Gly Arg Asp Arg Asp Arg
            20

<210> SEQ ID NO 127
<211> LENGTH: 31
<212> TYPE: PRT
<213> ORGANISM: Artificial Sequence
<220> FEATURE:
<223> OTHER INFORMATION: Synthesized

<400> SEQUENCE: 127

Gly Ala Lys Arg Arg Val Val Gly Gly Cys Gly Gly Ala Lys Arg Arg
1               5                   10                  15

Val Val Glu Arg Glu Lys Arg Ala Gly Gln Arg Glu Lys Arg Ala
            20                  25                  30

<210> SEQ ID NO 128
<211> LENGTH: 23
<212> TYPE: PRT
<213> ORGANISM: Artificial Sequence
<220> FEATURE:
<223> OTHER INFORMATION: Synthesized

<400> SEQUENCE: 128

Gly Lys Gly Gly Ile Glu Glu Glu Gly Gly Glu Gln Asp Arg Asp Arg
1               5                   10                  15

Gly Gly Glu Arg Asp Arg Asp
```

20

<210> SEQ ID NO 129
<211> LENGTH: 31
<212> TYPE: PRT
<213> ORGANISM: Artificial Sequence
<220> FEATURE:
<223> OTHER INFORMATION: Synthesized

<400> SEQUENCE: 129

Gly Ala Lys Arg Arg Val Val Gly Gly Ser Gly Gly Ala Lys Arg Arg
1               5                   10                  15

Val Val Gln Arg Glu Lys Arg Ala Gly Glu Arg Glu Lys Arg Ala
            20                  25                  30

<210> SEQ ID NO 130
<211> LENGTH: 16
<212> TYPE: PRT
<213> ORGANISM: Artificial Sequence
<220> FEATURE:
<223> OTHER INFORMATION: Synthesized

<400> SEQUENCE: 130

Arg Arg Gly Asn Trp Ala Lys Val Leu Lys Asn Trp Ala Lys Val Ile
1               5                   10                  15

<210> SEQ ID NO 131
<211> LENGTH: 21
<212> TYPE: PRT
<213> ORGANISM: Artificial Sequence
<220> FEATURE:
<223> OTHER INFORMATION: Synthesized

<400> SEQUENCE: 131

Arg Arg Gly Leu Leu Ala Asp Ala Arg Val Gly Cys Gly Ser Gly Ala
1               5                   10                  15

Asp Arg Val Cys Ser
            20

<210> SEQ ID NO 132
<211> LENGTH: 16
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (10)..(10)
<223> OTHER INFORMATION: X at position 10 is Dpr

<400> SEQUENCE: 132

Arg Arg Gly Asn Trp Ala Lys Val Leu Xaa Asn Trp Ala Lys Val Ile
1               5                   10                  15

<210> SEQ ID NO 133
<211> LENGTH: 21
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (12)..(12)
<223> OTHER INFORMATION: X in position 12 is Dpr(Ser)

<400> SEQUENCE: 133

Arg Arg Gly Leu Leu Ala Asp Ala Arg Val Gly Xaa Gly Ser Gly Ala

-continued

```
1               5                   10                  15

Asp Arg Val Cys Ser
            20

<210> SEQ ID NO 134
<211> LENGTH: 16
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (10)..(10)
<223> OTHER INFORMATION: X in position 10 is an N-epsilon-methylated
      Lys residue

<400> SEQUENCE: 134

Arg Arg Gly Asn Trp Ala Lys Val Leu Xaa Asn Trp Ala Lys Val Ile
1               5                   10                  15

<210> SEQ ID NO 135
<211> LENGTH: 21
<212> TYPE: PRT
<213> ORGANISM: Artificial Sequence
<220> FEATURE:
<223> OTHER INFORMATION: Synthesized

<400> SEQUENCE: 135

Arg Arg Gly Leu Leu Ala Asp Ala Arg Val Gly Glu Gly Ser Gly Ala
1               5                   10                  15

Asp Arg Val Cys Ser
            20

<210> SEQ ID NO 136
<211> LENGTH: 21
<212> TYPE: PRT
<213> ORGANISM: Artificial Sequence
<220> FEATURE:
<223> OTHER INFORMATION: Synthesized

<400> SEQUENCE: 136

Arg Arg Gly Leu Leu Ala Asp Ala Arg Val Gly Asp Gly Ser Gly Ala
1               5                   10                  15

Asp Arg Val Cys Ser
            20

<210> SEQ ID NO 137
<211> LENGTH: 16
<212> TYPE: PRT
<213> ORGANISM: Artificial Sequence
<220> FEATURE:
<223> OTHER INFORMATION: Synthesized

<400> SEQUENCE: 137

Arg Arg Gly Asn Trp Ala Lys Val Leu Glu Asn Trp Ala Lys Val Ile
1               5                   10                  15

<210> SEQ ID NO 138
<211> LENGTH: 22
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (12)..(12)
<223> OTHER INFORMATION: X in position 12 is N-epsilon-methylated Lys
```

```
        residue
<220> FEATURE:
<221> NAME/KEY: misc_feature
<222> LOCATION: (13)..(13)
<223> OTHER INFORMATION: Xaa can be any naturally occurring amino acid

<400> SEQUENCE: 138

Arg Arg Gly Leu Leu Ala Asp Ala Arg Val Gly Lys Xaa Gly Ser Gly
1               5                   10                  15

Ala Asp Arg Val Cys Ser
            20

<210> SEQ ID NO 139
<211> LENGTH: 16
<212> TYPE: PRT
<213> ORGANISM: Artificial Sequence
<220> FEATURE:
<223> OTHER INFORMATION: Synthesized

<400> SEQUENCE: 139

Arg Arg Gly Asn Trp Ala Lys Val Leu Asp Asn Trp Ala Lys Val Ile
1               5                   10                  15

<210> SEQ ID NO 140
<211> LENGTH: 26
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (11)..(11)
<223> OTHER INFORMATION: X in position 11 is Dpr

<400> SEQUENCE: 140

Arg Ser Leu Glx Thr Asp Ile Glu Thr Pro Xaa Ile Asp Thr Pro Ile
1               5                   10                  15

Arg Gly Thr Pro Ile Asx Gln Asp Trp Gly
            20                  25

<210> SEQ ID NO 141
<211> LENGTH: 28
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (14)..(14)
<223> OTHER INFORMATION: X in position 14 is Har
<220> FEATURE:
<221> NAME/KEY: MISC_FEATURE
<222> LOCATION: (18)..(18)
<223> OTHER INFORMATION: X in position 18 is Dpr(ser)

<400> SEQUENCE: 141

Arg Arg Ile Asp Thr Pro Ile Arg Gly Gly Thr Pro Ile Xaa Gln Glu
1               5                   10                  15

Trp Xaa Ser Leu Glx Thr Asp Ile Glu Thr Pro Gly
            20                  25

<210> SEQ ID NO 142
<211> LENGTH: 19
<212> TYPE: PRT
<213> ORGANISM: Artificial Sequence
<220> FEATURE:
<223> OTHER INFORMATION: Synthesized
```

```
<400> SEQUENCE: 142

Met Ser Leu Leu Thr Glu Val Glu Thr Pro Ile Arg Asn Glu Trp Gly
1               5                   10                  15

Cys Arg Cys

<210> SEQ ID NO 143
<211> LENGTH: 21
<212> TYPE: PRT
<213> ORGANISM: Artificial Sequence
<220> FEATURE:
<223> OTHER INFORMATION: Synthesized

<400> SEQUENCE: 143

Gly Gly Ala Lys Arg Arg Val Val Gln Arg Glu Lys Arg Ala Gly Glu
1               5                   10                  15

Arg Glu Lys Arg Ala
            20

<210> SEQ ID NO 144
<211> LENGTH: 21
<212> TYPE: PRT
<213> ORGANISM: Artificial Sequence
<220> FEATURE:
<223> OTHER INFORMATION: Synthesized

<400> SEQUENCE: 144

Gly Gly Ile Glu Glu Glu Gly Gly Arg Asp Arg Asp Arg Gly Gly Glu
1               5                   10                  15

Gln Asp Arg Asp Arg
            20

<210> SEQ ID NO 145
<211> LENGTH: 23
<212> TYPE: PRT
<213> ORGANISM: Artificial Sequence
<220> FEATURE:
<223> OTHER INFORMATION: Synthesized

<400> SEQUENCE: 145

Gly Gly Ala Lys Arg Arg Val Val Gln Arg Glu Lys Arg Ala Gly Glu
1               5                   10                  15

Arg Glu Lys Arg Ala Gly Gly
            20

<210> SEQ ID NO 146
<211> LENGTH: 23
<212> TYPE: PRT
<213> ORGANISM: Artificial Sequence
<220> FEATURE:
<223> OTHER INFORMATION: Synthesized

<400> SEQUENCE: 146

Gly Gly Ile Glu Glu Glu Gly Gly Arg Asp Arg Asp Arg Gly Gly Glu
1               5                   10                  15

Gln Asp Arg Asp Arg Gly Gly
            20

<210> SEQ ID NO 147
<211> LENGTH: 22
<212> TYPE: PRT
<213> ORGANISM: Artificial Sequence
<220> FEATURE:
<223> OTHER INFORMATION: Synthesized
```

```
<400> SEQUENCE: 147

Gly Lys Gly Gly Ile Glu Glu Glu Gly Gly Arg Asp Arg Asp Arg Gly
1               5                   10                  15

Gly Gln Asp Arg Asp Arg
            20

<210> SEQ ID NO 148
<211> LENGTH: 22
<212> TYPE: PRT
<213> ORGANISM: Artificial Sequence
<220> FEATURE:
<223> OTHER INFORMATION: Synthesized

<400> SEQUENCE: 148

Gly Lys Gly Gly Ile Glu Glu Glu Gly Gly Arg Asp Arg Asp Arg Gly
1               5                   10                  15

Gly Gln Asp Arg Asp Arg
            20

<210> SEQ ID NO 149
<211> LENGTH: 31
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (10)..(10)
<223> OTHER INFORMATION: X in position 10 is Dpr(Ser)

<400> SEQUENCE: 149

Gly Ala Lys Arg Arg Val Val Gly Gly Xaa Gly Gly Ala Lys Arg Arg
1               5                   10                  15

Val Val Gln Arg Glu Lys Arg Ala Gly Glu Arg Glu Lys Arg Ala
            20                  25                  30

<210> SEQ ID NO 150
<211> LENGTH: 5
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (3)..(3)
<223> OTHER INFORMATION: X in position 3 is Dpr(Ser)

<400> SEQUENCE: 150

Gly Gly Xaa Gly Gly
1               5

<210> SEQ ID NO 151
<211> LENGTH: 7
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (4)..(4)
<223> OTHER INFORMATION: X in position 4 is Har

<400> SEQUENCE: 151

Thr Pro Ile Xaa Gln Glu Trp
1               5
```

```
<210> SEQ ID NO 152
<211> LENGTH: 8
<212> TYPE: PRT
<213> ORGANISM: Artificial Sequence
<220> FEATURE:
<223> OTHER INFORMATION: Synthesized

<400> SEQUENCE: 152

Glu Gln Asp Arg Asp Arg Gly Gly
1               5

<210> SEQ ID NO 153
<211> LENGTH: 7
<212> TYPE: PRT
<213> ORGANISM: Artificial Sequence
<220> FEATURE:
<223> OTHER INFORMATION: Synthesized

<400> SEQUENCE: 153

Gly Asn Trp Ala Lys Val Leu
1               5

<210> SEQ ID NO 154
<211> LENGTH: 7
<212> TYPE: PRT
<213> ORGANISM: Artificial Sequence
<220> FEATURE:
<223> OTHER INFORMATION: Synthesized

<400> SEQUENCE: 154

Leu Leu Ala Asp Ala Arg Val
1               5

<210> SEQ ID NO 155
<211> LENGTH: 6
<212> TYPE: PRT
<213> ORGANISM: Artificial Sequence
<220> FEATURE:
<223> OTHER INFORMATION: Synthesized

<400> SEQUENCE: 155

Asn Trp Ala Lys Val Ile
1               5

<210> SEQ ID NO 156
<211> LENGTH: 6
<212> TYPE: PRT
<213> ORGANISM: Artificial Sequence
<220> FEATURE:
<223> OTHER INFORMATION: Synthesized

<400> SEQUENCE: 156

Ser Gly Ala Asp Arg Val
1               5

<210> SEQ ID NO 157
<211> LENGTH: 22
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)...(2)
<223> OTHER INFORMATION: X in position 2 is a bromoacetyl derivatized
      Lys residue

<400> SEQUENCE: 157
```

```
Gly Xaa Gly Gly Ile Glu Glu Glu Gly Gly Arg Asp Arg Asp Arg Gly
1               5                   10                  15

Gly Gln Asp Arg Asp Arg
        20
```